US012805189B2

(12) United States Patent
Thirion et al.

(10) Patent No.: US 12,805,189 B2
(45) Date of Patent: Nov. 17, 2026

(54) ORGANIC TRIAZINE CONTAINING MOLECULES FOR USE IN OPTOELECTRONIC DEVICES

(71) Applicant: Samsung Display Co., Ltd., Yongin-si (KR)

(72) Inventors: Damien Thirion, Karlsdorf-Neuthard (DE); Damien Joly, Beinheim (FR); Michael Danz, Eggenstein-Leopoldshafen (DE)

(73) Assignee: Samsung Display Co., Ltd., Yongin-si (KR)

(*) Notice: Subject to any disclaimer, the term of this patent is extended or adjusted under 35 U.S.C. 154(b) by 970 days.

(21) Appl. No.: 18/017,662

(22) PCT Filed: Jul. 22, 2021

(86) PCT No.: PCT/EP2021/070468

§ 371 (c)(1),
(2) Date: Jan. 23, 2023

(87) PCT Pub. No.: WO2022/018175

PCT Pub. Date: Jan. 27, 2022

(65) Prior Publication Data

US 2023/0301186 A1 Sep. 21, 2023

(30) Foreign Application Priority Data

Jul. 24, 2020 (EP) .................................... 20187583

(51) Int. Cl.
*H10K 85/60* (2023.01)
*C07D 401/14* (2006.01)
(Continued)

(52) U.S. Cl.
CPC ....... *H10K 85/6572* (2023.02); *C07D 401/14* (2013.01); *C07D 403/14* (2013.01);
(Continued)

(58) Field of Classification Search
CPC .. C07D 401/14; C07D 403/14; C07D 417/14; C07D 471/04; C07D 491/048; C07D 513/04; C07D 251/24
See application file for complete search history.

(56) References Cited

U.S. PATENT DOCUMENTS 10,155,724 B2 12/2018 Jung et al.
2018/0370952 A1 12/2018 Seifermann
(Continued)

FOREIGN PATENT DOCUMENTS

CN 109134346 A 1/2019
CN 109666025 A 4/2019
(Continued)

OTHER PUBLICATIONS

International Search Report for corresponding Application No. PCT/EP2021/070468, dated Oct. 26, 2021, 2 pp.

*Primary Examiner* — Vu A Nguyen
(74) *Attorney, Agent, or Firm* — Womble Bond Dickinson (US) LLP

(57) ABSTRACT

The invention relates to an organic compound, in particular for the application in optoelectronic devices. According to the invention, the organic compound consists of a first chemical moiety with a structure of Formula I,
(Continued)

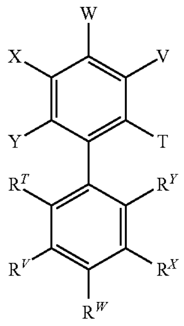

Formula I
and
two second chemical moieties, each independently with a structure of Formula II,

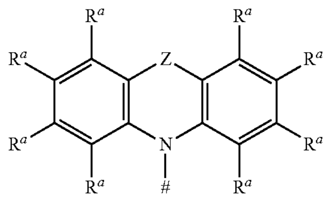

Formula II
wherein the first chemical moiety is linked to each of the two second chemical moieties via a single bond; and wherein
T and V are independently from each other selected from the group consisting of $R^A$ and $R^1$;
W is the binding site of a single bond linking the first chemical moiety to one of the two second chemical moieties or is selected from the group consisting of $R^A$ and $R^2$;
X is the binding site of a single bond linking the first chemical moiety to one of the two second chemical moieties or is $R^2$;
Y is the binding site of a single bond linking the first chemical moiety to one of the two second chemical moieties or is $R^2$;
one substituent selected from $R^T$ and $R^V$ is the binding site of a single bond linking the first chemical moiety to one of the two second chemical moieties and the other substituent selected from $R^T$ and $R^V$ is selected from the group consisting of CN and
$CF_3$;
$R^W$ is $R^I$;
$R^X$ is $R^I$; and
$R^Y$ is $R^I$.

17 Claims, 1 Drawing Sheet

(51) Int. Cl.

| | |
|---|---|
| ***C07D 403/14*** | (2006.01) |
| ***C07D 417/14*** | (2006.01) |
| ***C07D 471/04*** | (2006.01) |
| ***C07D 491/048*** | (2006.01) |
| ***C07D 513/04*** | (2006.01) |
| ***C09K 11/06*** | (2006.01) |
| ***H10K 50/11*** | (2023.01) |

(52) U.S. Cl.
CPC ......... *C07D 417/14* (2013.01); *C07D 471/04* (2013.01); *C07D 491/048* (2013.01); *C07D 513/04* (2013.01); *C09K 11/06* (2013.01); *H10K 85/654* (2023.02); *H10K 85/657* (2023.02); *C09K 2211/1018* (2013.01); *H10K 50/11* (2023.02)

(56) References Cited

U.S. PATENT DOCUMENTS

| | | | |
|---|---|---|---|
| 2019/0115544 A1 | 4/2019 | Zink et al. | |
| 2020/0203628 A1 | 6/2020 | Danz | |
| 2020/0235308 A1* | 7/2020 | Zink .................... | C07D 519/00 |

FOREIGN PATENT DOCUMENTS

| | | | |
|---|---|---|---|
| CN | 110730813 A | 1/2020 |
| CN | 110997634 A | 4/2020 |
| CN | 111032648 A | 4/2020 |
| EP | 3263569 A1 | 1/2018 |
| EP | 3672940 | 7/2020 |
| KR | 10-2020-0037361 A | 4/2020 |
| WO | WO 2018/224421 A1 | 12/2018 |
| WO | WO 2019/038376 A1 | 2/2019 |
| WO | WO 2019/038448 A1 | 2/2019 |

* cited by examiner

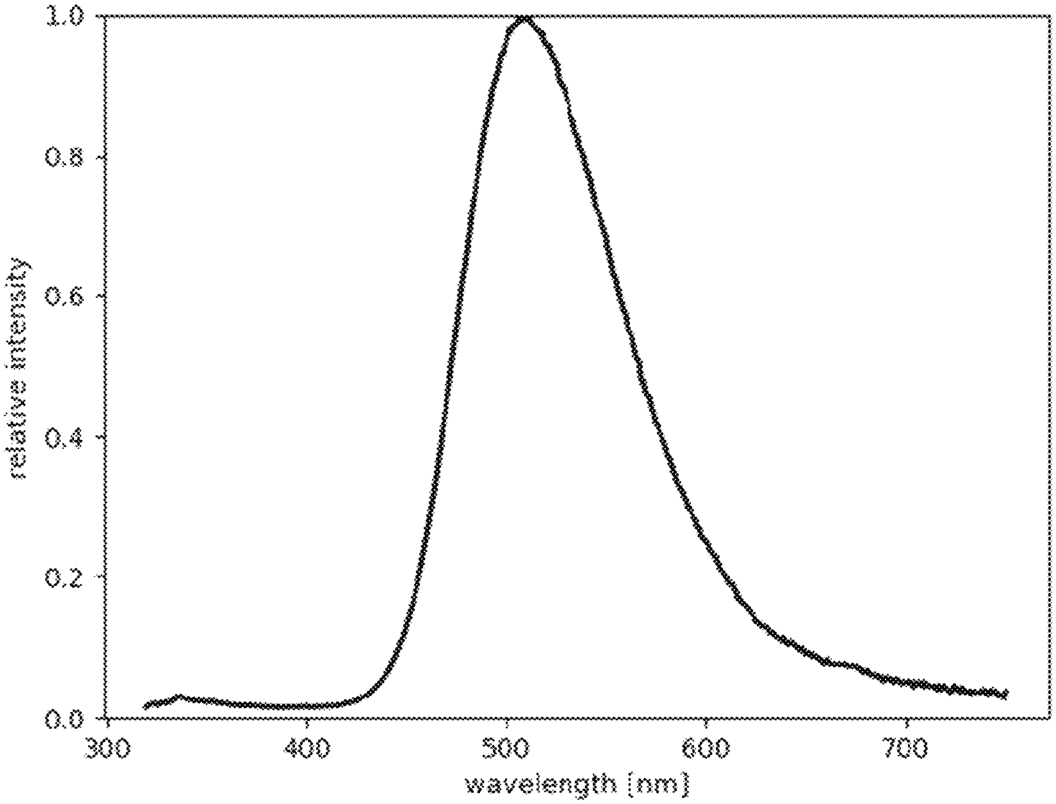
1.0
0.8
0.6
0.4
0.2
0.0
relative intensity
300
400
500
600
700
wavelength [nm]

ORGANIC TRIAZINE CONTAINING MOLECULES FOR USE IN OPTOELECTRONIC DEVICES

CROSS-REFERENCE TO RELATED APPLICATIONS

This application is a U.S. National Phase Patent Application of International Patent Application Number PCT/EP2021/070468, filed on Jul. 22, 2021, which claims priority to European Patent Application Number 20187583.8, filed on Jul. 24, 2020, the entire contents of all of which are incorporated herein by reference.

The invention relates to organic molecules and their use in organic light-emitting diodes (OLEDs) and in other optoelectronic devices.

DESCRIPTION

The object of the present invention is to provide molecules which are suitable for use in optoelectronic devices.

This object is achieved by the invention which provides a new class of organic molecules.

The organic molecules of the invention are purely organic molecules, i.e. they do not contain any metal ions in contrast to metal complexes known for use in optoelectronic devices.

The organic molecules exhibit emission maxima in the sky blue, green or yellow spectral range. The organic molecules exhibit in particular emission maxima between 490 and 600 nm, more preferably between 510 and 560 nm, and even more preferably between 520 and 540 nm. The photoluminescence quantum yields of the organic molecules according to the invention are, in particular, 10% or more. The molecules of the invention exhibit in particular thermally activated delayed fluorescence (TADF). The use of the molecules according to the invention in an optoelectronic device, for example, an organic light-emitting diode (OLED), leads to higher efficiencies of the device. Corresponding OLEDs have a higher stability than OLEDs with known emitter materials and comparable color and/or by employing the molecules according to the invention in an OLED display, a more accurate reproduction of visible colors in nature, i.e. a higher resolution in the displayed image, is achieved. In particular, the molecules can be used in combination with a fluorescence emitter to enable so-called hyper-fluorescence.

The organic molecules according to the invention include or consist of one first chemical moiety including or consisting of a structure of Formula I, Formula I

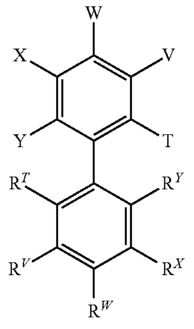

and two second chemical moieties, each independently from one another including or consisting of a structure of Formula II, Formula II

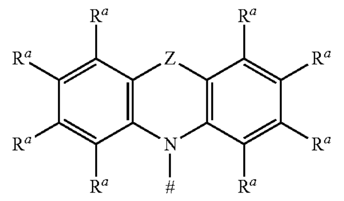

wherein the first chemical moiety is linked to each of the two second chemical moieties via a single bond.

T is selected from the group consisting of $R^A$ and $R^1$.

V is selected from the group consisting of $R^A$ and $R^1$.

W is the binding site of a single bond linking the first chemical moiety to one of the two second chemical moieties or is selected from the group consisting of $R^A$ and $R^2$.

X is the binding site of a single bond linking the first chemical moiety to one of the two second chemical moieties or is $R^2$.

Y is the binding site of a single bond linking the first chemical moiety to one of the two second chemical moieties or is $R^2$.

$R^A$ is 1,3,5-triazinyl substituted with two substituents $R^{Tz}$:

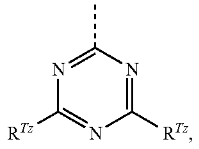

which is bonded to the structure of Formula I via the position marked by the dotted line.

$R^T$ is the binding site of a single bond linking the first chemical moiety to one of the two second chemical moieties or is selected from the group consisting of CN and $CF_3$;

$R^V$ is the binding site of a single bond linking the first chemical moiety to one of the two second chemical moieties or is selected from the group consisting of CN and $CF_3$;

$R^W$ is $R^I$.

$R^X$ is $R^I$.

$R^Y$ is $R^I$.

# represents the binding site of a single bond linking the second chemical moieties to the first chemical moiety.

Z is at each occurrence independently from one another selected from the group consisting of a direct bond, $CR^3R^4$, $C{=}CR^3R^4$, $C{=}O$, $C{=}NR^3$, $NR^3$, O, $SiR^3R^4$, S, S(O) and $S(O)_2$.

$R^1$ is at each occurrence independently from one another selected from the group consisting of:

hydrogen;

deuterium;

$C_1$-$C_5$-alkyl, wherein one or more hydrogen atoms are optionally substituted by deuterium;

$C_2$-$C_8$-alkenyl, wherein one or more hydrogen atoms are optionally substituted by deuterium;

$C_2$-$C_8$-alkynyl, wherein one or more hydrogen atoms are optionally substituted by deuterium; and $C_6$-$C_{18}$-aryl, which is optionally substituted with one or more substituents $R^6$.

$R^2$ is at each occurrence independently from one another selected from the group consisting of:

hydrogen;

deuterium;

$C_1$-$C_5$-alkyl, wherein one or more hydrogen atoms are optionally substituted by deuterium;

$C_2$-$C_8$-alkenyl, wherein one or more hydrogen atoms are optionally substituted by deuterium;

$C_2$-$C_8$-alkynyl, wherein one or more hydrogen atoms are optionally substituted by deuterium; and $C_6$-$C_{18}$-aryl, which is optionally substituted with one or more substituents $R^6$.

$R^I$ is at each occurrence independently from one another selected from the group consisting of:

hydrogen;

deuterium;

$C_1$-$C_5$-alkyl, wherein one or more hydrogen atoms are optionally substituted by deuterium;

$C_2$-$C_8$-alkenyl, wherein one or more hydrogen atoms are optionally substituted by deuterium;

$C_2$-$C_8$-alkynyl, wherein one or more hydrogen atoms are optionally substituted by deuterium; and $C_6$-$C_{18}$-aryl, which is optionally substituted with one or more substituents $R^6$.

$R^{Tz}$ is at each occurrence independently from one another selected from the group consisting of:

hydrogen;

deuterium;

$C_1$-$C_5$-alkyl, wherein one or more hydrogen atoms are optionally substituted by deuterium;

$C_6$-$C_{18}$-aryl, which is optionally substituted with one or more substituents $R^6$; and $C_3$-$C_{17}$-heteroaryl, which is optionally substituted with one or more substituents $R^6$.

$R^a$, $R^3$, and $R^4$ are at each occurrence independently from one another selected from the group consisting of hydrogen, deuterium, $N(R^5)_2$, $OR^5$, $Si(R^5)_3$, $B(OR^5)_2$, $OSO_2R^5$, $CF_3$, CN, F, Br, I;

$C_1$-$C_{40}$-alkyl, which is optionally substituted with one or more substituents $R^5$ and wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;

$C_1$-$C_{40}$-alkoxy, which is optionally substituted with one or more substituents $R^5$ and wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;

$C_1$-$C_{40}$-thioalkoxy, which is optionally substituted with one or more substituents $R^5$ and wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;

$C_2$-$C_{40}$-alkenyl, which is optionally substituted with one or more substituents $R^5$ and wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;

$C_2$-$C_{40}$-alkynyl, which is optionally substituted with one or more substituents $R^5$ and wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;

$C_6$-$C_{60}$-aryl, which is optionally substituted with one or more substituents $R^5$; and $C_3$-$C_{57}$-heteroaryl, which is optionally substituted with one or more substituents $R^5$.

$R^5$ is at each occurrence independently from one another selected from the group consisting of: hydrogen, deuterium, $N(R^6)_2$, $OR^6$, $Si(R^6)_3$, $B(OR^6)_2$, $OSO_2R^6$, $CF_3$, CN, F, Br, I;

$C_1$-$C_{40}$-alkyl, which is optionally substituted with one or more substituents $R^6$ and wherein one or more non-adjacent $CH_2$-groups are optionally substituted by $R^6C{=}CR^6$, $C{\equiv}C$, $Si(R^6)_2$, $Ge(R^6)_2$, $Sn(R^6)_2$, $C{=}O$, $C{=}S$, $C{=}Se$, $C{=}NR^6$, $P({=}O)(R^6)$, SO, $SO_2$, $NR^6$, O, S or $CONR^6$;

$C_1$-$C_{40}$-alkoxy, which is optionally substituted with one or more substituents $R^6$ and wherein one or more non-adjacent $CH_2$-groups are optionally substituted by $R^6C{=}CR^6$, $C{\equiv}C$, $Si(R^6)_2$, $Ge(R^6)_2$, $Sn(R^6)_2$, $C{=}O$, $C{=}S$, $C{=}Se$, $C{=}NR^6$, $P({=}O)(R^6)$, SO, $SO_2$, $NR^6$, O, S or $CONR^6$;

$C_1$-$C_{40}$-thioalkoxy, which is optionally substituted with one or more substituents $R^6$ and wherein one or more non-adjacent $CH_2$-groups are optionally substituted by $R^6C{=}CR^6$, $C{\equiv}C$, $Si(R^6)_2$, $Ge(R^6)_2$, $Sn(R^6)_2$, $C{=}O$, $C{=}S$, $C{=}Se$, $C{=}NR^6$, $P({=}O)(R^6)$, SO, $SO_2$, $NR^6$, O, S or $CONR^6$;

$C_2$-$C_{40}$-alkenyl, which is optionally substituted with one or more substituents $R^6$ and wherein one or more non-adjacent $CH_2$-groups are optionally substituted by $R^6C{=}CR^6$, $C{\equiv}C$, $Si(R^6)_2$, $Ge(R^6)_2$, $Sn(R^6)_2$, $C{=}O$, $C{=}S$, $C{=}Se$, $C{=}NR^6$, $P({=}O)(R^6)$, SO, $SO_2$, $NR^6$, O, S or $CONR^6$;

$C_2$-$C_{40}$-alkynyl, which is optionally substituted with one or more substituents $R^6$ and wherein one or more non-adjacent $CH_2$-groups are optionally substituted by $R^6C{=}CR^6$, $C{\equiv}C$, $Si(R^6)_2$, $Ge(R^6)_2$, $Sn(R^6)_2$, C=O, C=S, C=Se, $C{=}NR^6$, $P({=}O)(R^6)$, SO, $SO_2$, $NR^6$, O, S or $CONR^6$;

$C_6$-$C_{60}$-aryl, which is optionally substituted with one or more substituents $R^6$; and $C_3$-$C_{57}$-heteroaryl, which is optionally substituted with one or more substituents $R^6$.

$R^6$ is at each occurrence independently from one another selected from the group consisting of: hydrogen, deuterium, OPh (Ph=phenyl), $CF_3$, CN, F;

$C_1$-$C_5$-alkyl, wherein optionally one or more hydrogen atoms are independently from each other substituted by deuterium, CN, $CF_3$, or F;

$C_1$-$C_5$-alkoxy, wherein optionally one or more hydrogen atoms are independently from each other substituted by deuterium, CN, $CF_3$, or F;

$C_1$-$C_5$-thioalkoxy, wherein optionally one or more hydrogen atoms are independently from each other substituted by deuterium, CN, $CF_3$, or F;

$C_2$-$C_5$-alkenyl, wherein optionally one or more hydrogen atoms are independently from each other substituted by deuterium, CN, $CF_3$, or F;

$C_2$-$C_5$-alkynyl, wherein optionally one or more hydrogen atoms are independently from each other substituted by deuterium, CN, $CF_3$, or F;

$C_6$-$C_{18}$-aryl, which is optionally substituted with one or more $C_1$-$C_5$-alkyl or $C_6$-$C_{18}$-aryl substituents;

$C_3$-$C_{17}$-heteroaryl, which is optionally substituted with one or more $C_1$-$C_5$-alkyl or $C_6$-$C_{18}$-aryl substituents;

$N(C_6$-$C_{18}$-aryl$)_2$;

$N(C_3$-$C_{17}$-heteroaryl$)_2$; and $N(C_3$-$C_{17}$-heteroaryl$)(C_6$-$C_{18}$-aryl$)$.

The substituents $R^a$, $R^3$, $R^4$ or $R^5$ independently from each other optionally form a mono- or polycyclic, aliphatic, aromatic and/or benzo-fused ring system with one or more substituents $R^a$, $R^3$, $R^4$ or $R^5$.

According to the invention, exactly one substituent selected from the group consisting of T, V, and W is $R^A$; exactly one substituent selected from the group consisting of W, Y, and X represents the binding site of a single bond linking the first chemical moiety and one of the two second chemical moieties; exactly one substituent selected from $R^T$ and $R^V$ is the binding site of a single bond linking the first chemical moiety to one of the two second chemical moieties and exactly one substituent selected from $R^T$ and $R^V$ is selected from the group consisting of CN and CF3.

In one embodiment of the invention, the first chemical moiety includes or consists of a structure of Formula Ia:

Formula Ia

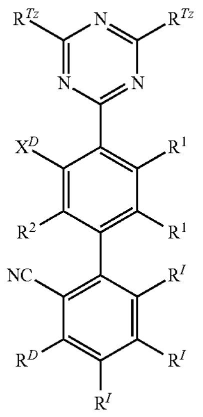

wherein $R^1$, $R^2$, $R^I$, and $R^{Tz}$ are defined as above, $X^D$ is the binding site of a single bond linking the first chemical moiety to one of the two second chemical moieties, and wherein $R^D$ is the binding site of a single bond linking the first chemical moiety to one of the two second chemical moieties.

In one embodiment, $R^1$, $R^2$, and $R^I$ are at each occurrence independently from one another selected from the group consisting of hydrogen (H), methyl, mesityl, tolyl, and phenyl. The term tolyl refers to 2-tolyl, 3-tolyl, and 4-tolyl.

In one embodiment, $R^1$, $R^2$, and $R^I$ are at each occurrence independently from one another selected from the group consisting of hydrogen (H), methyl, and phenyl.

In one embodiment, W is $R^A$.

In one embodiment, T is $R^A$.

In one embodiment, V is $R^A$.

In one embodiment, $R^T$ is CN.

In one embodiment, $R^T$ is $CF_3$.

In one embodiment, $R^V$ is CN.

In one embodiment, $R^V$ is $CF_3$.

In one embodiment, W is $R^A$ and $R^T$ is CN.

In one embodiment, W is $R^A$ and $R^T$ is $CF_3$.

In one embodiment, W is $R^A$ and $R^V$ is CN.

In one embodiment, W is $R^A$ and $R^V$ is $CF_3$.

In one embodiment, T is $R^A$ and $R^T$ is CN.

In one embodiment, T is $R^A$ and $R^T$ is $CF_3$.

In one embodiment, T is $R^A$ and $R^V$ is CN.

In one embodiment, T is $R^A$ and $R^V$ is $CF_3$.

In one embodiment, V is $R^A$ and $R^T$ is CN.

In one embodiment, V is $R^A$ and $R^T$ is $CF_3$.

In one embodiment, V is $R^A$ and $R^V$ is CN.

In one embodiment, V is $R^A$ and $R^V$ is $CF_3$.

In a further embodiment of the invention, $R^{Tz}$ is at each occurrence independently from each other selected from the group consisting of H, methyl;

phenyl, which is optionally substituted with one or more substituents $R^6$;

1,3,5-triazinyl, which is optionally substituted with one or more substituents $R^6$;

pyridinyl, which is optionally substituted with one or more substituents $R^6$; and pyrimidinyl, which is optionally substituted with one or more substituents $R^6$.

In a further embodiment of the invention, $R^{Tz}$ is at each occurrence independently from each other selected from the group consisting of H, methyl, and phenyl, wherein the phenyl-substituent may be further substituted with a nitrile group and a carbazolyl group that may again be substituted with one or more phenyl-substituents.

In a further embodiment of the invention, $R^{Tz}$ is phenyl at each occurrence.

In one embodiment of the invention, $R^3$, $R^4$, $R^5$, and $R^6$ are at each occurrence independently of each other selected from the group consisting of hydrogen, deuterium, halogen, CN, $CF_3$, $SiMe_3$, $SiPh_3$;

$C_1$-$C_5$-alkyl, wherein one or more hydrogen atoms are optionally substituted by deuterium;

$C_6$-$C_{18}$-aryl, wherein optionally one or more hydrogen atoms are independently substituted by $C_1$-$C_5$-alkyl, $C_6$-$C_{18}$-aryl, $C_3$-$C_{17}$-heteroaryl, CN or $CF_3$;

$C_3$-$C_{15}$-heteroaryl, wherein optionally one or more hydrogen atoms are independently substituted by $C_1$-$C_5$-alkyl, $C_6$-$C_{18}$-aryl, $C_3$-$C_{17}$-heteroaryl, CN or $CF_3$; and $N(Ph)_2$.

In another embodiment of the invention, $R^3$, $R^4$, $R^5$, and $R^6$ are at each occurrence independently selected from the group consisting of hydrogen, deuterium, halogen, Me, $^i$Pr, $^t$Bu, CN, $CF_3$, $SiMe_3$, $SiPh_3$, and $C_6$-$C_{18}$-aryl, wherein optionally one or more hydrogen atoms are independently substituted by $C_1$-$C_5$-alkyl, CN, $CF_3$ or Ph.

In one embodiment of the invention, $R^3$, $R^4$, $R^5$, and $R^6$ are at each occurrence independently selected from the group consisting of hydrogen, deuterium, halogen, Me, $^i$Pr, $^t$Bu, CN, $CF_3$, $SiMe_3$, $SiPh_3$, and phenyl, wherein optionally one or more hydrogen atoms are independently substituted by $C_1$-$C_5$-alkyl, CN, $CF_3$ or Ph.

In another embodiment of the invention, $R^3$, $R^4$, $R^5$, and $R^8$ are at each occurrence independently selected from the group consisting of hydrogen, deuterium, halogen, Me, $^i$Pr, $^t$Bu, CN, $CF_3$, $SiMe_3$, $SiPh_3$, and phenyl, wherein optionally one or more hydrogen atoms are independently substituted by Me, $^i$Pr, $^t$Bu, CN, $CF_3$ or Ph.

In a further embodiment of the invention, each of the two second chemical moieties at each occurrence independently from one another includes or consists of a structure of Formula IIa:

Formula IIa

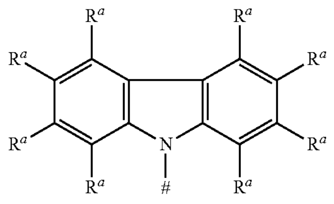

wherein # and $R^a$ are defined as above.

In a further embodiment of the invention, $R^a$ is at each occurrence independently from one another selected from the group consisting of: H, Me, $^i$Pr, $^t$Bu,

CN, $CF_3$,

Ph, which is optionally substituted with one or more substituents independently from each other selected from the group consisting of Me, $^i$Pr, $^t$Bu, CN, $CF_3$, and Ph, pyridinyl, which is optionally substituted with one or more substituents independently from each other selected from the group consisting of Me, $^i$Pr, $^t$Bu, CN, $CF_3$, and Ph, pyrimidinyl, which is optionally substituted with one or more substituents independently from each other selected from the group consisting of Me, $^i$Pr, $^t$Bu, CN, $CF_3$, and Ph, carbazolyl, which is optionally substituted with one or more substituents independently from each other selected from the group consisting of Me, $^i$Pr, $^t$Bu, CN, $CF_3$, and Ph, triazinyl, which is optionally substituted with one or more substituents independently from each other selected from the group consisting of Me, $^i$Pr, $^t$Bu, CN, $CF_3$, and Ph, and $N(Ph)_2$.

In a further embodiment of the invention, $R^a$ is at each occurrence independently from one another selected from the group consisting of: H, Me, $^i$Pr, $^t$Bu,

CN, $CF_3$,

Ph, which is optionally substituted with one or more substituents independently from each other selected from the group consisting of Me, $^i$Pr, $^t$Bu, CN, $CF_3$, and Ph, pyridinyl, which is optionally substituted with one or more substituents independently from each other selected from the group consisting of Me, $^i$Pr, $^t$Bu, CN, $CF_3$, and Ph, pyrimidinyl, which is optionally substituted with one or more substituents independently from each other selected from the group consisting of Me, $^i$Pr, $^t$Bu, CN, $CF_3$, and Ph, and triazinyl, which is optionally substituted with one or more substituents independently from each other selected from the group consisting of Me, $^i$Pr, $^t$Bu, CN, $CF_3$, and Ph.

In a further embodiment of the invention, $R^a$ is at each occurrence independently from one another selected from the group consisting of: H;

Me;

$^t$Bu;

Ph, which is optionally substituted with one or more substituents independently from each other selected from the group consisting of Me, $^i$Pr, $^t$Bu, CN, $CF_3$, and Ph; and triazinyl, which is optionally substituted with one or more substituents independently from each other selected from the group consisting of Me, $^i$Pr, $^t$Bu, CN, $CF_3$, and Ph.

In a further embodiment of the invention, $R^a$ is H at each occurrence.

In a further embodiment of the invention, the two second chemical moieties each at each occurrence independently from one another include or consist of a structure of Formula IIb, a structure of Formula IIb-2, a structure of Formula IIb-3 or a structure of Formula IIb-4:

Formula IIb

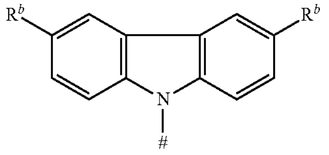

Formula IIb-2

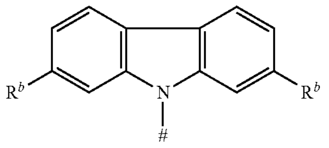

Formula IIb-3

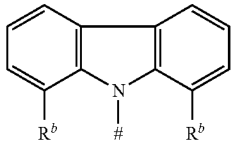

Formula IIb-4

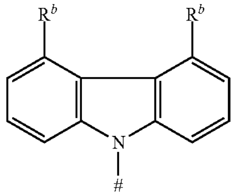

wherein $R^b$ is at each occurrence independently from one another selected from the group consisting of:

deuterium;

$N(R^5)_2$;

$OR^5$;

$Si(R^5)_3$;

$B(OR^5)_2$;

$OSO_2R^5$;

$CF_3$;

CN;

F;

Br;

I;

$C_1$-$C_{40}$-alkyl, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_1$-$C_{40}$-alkoxy, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_1$-$C_{40}$-thioalkoxy, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_2$-$C_{40}$-alkenyl, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_2$-$C_{40}$-alkynyl, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_6$-$C_{60}$-aryl, which is optionally substituted with one or more substituents $R^5$; and $C_3$-$C_{57}$-heteroaryl, which is optionally substituted with one or more substituents $R^5$.

Apart from that, the aforementioned definitions apply.

In one additional embodiment of the invention, the two second chemical moieties each at each occurrence independently from one another include or consist of a structure of Formula IIc, a structure of Formula IIc-2, a structure of Formula IIc-3, or a structure of Formula IIc-4:

Formula IIc

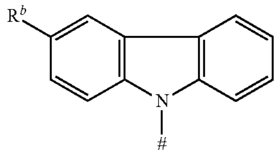

Formula IIc-2

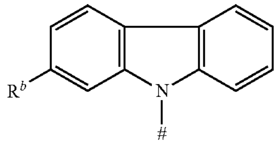

Formula IIc-3

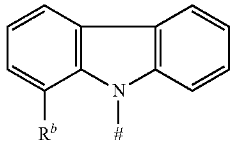

Formula IIc-4

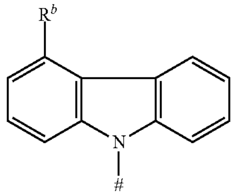

wherein the aforementioned definitions apply.

In a further embodiment of the invention, $R^b$ is at each occurrence independently from one another selected from the group consisting of:

Me;

$^i$Pr;

$^t$Bu;

CN;

$CF_3$;

Ph, which is optionally substituted with one or more substituents independently from each other selected from the group consisting of Me, $^i$Pr, $^t$Bu, CN, $CF_3$, and Ph;

pyridinyl, which is optionally substituted with one or more substituents independently from each other selected from the group consisting of Me, $^i$Pr, $^t$Bu, CN, $CF_3$, and Ph;

carbazolyl, which is optionally substituted with one or more substituents independently from each other selected from the group consisting of Me, $^i$Pr, $^t$Bu, CN, $CF_3$, and Ph;

triazinyl, which is optionally substituted with one or more substituents independently from each other selected from the group consisting of Me, $^i$Pr, $^t$Bu, CN, $CF_3$, and Ph; and $N(Ph)_2$.

In a further embodiment of the invention, $R^b$ is at each occurrence independently from one another selected from the group consisting of:

Me;

$^i$Pr;

$^t$Bu;

CN;

$CF_3$;

Ph, which is optionally substituted with one or more substituents independently from each other selected from the group consisting of Me, $^i$Pr, $^t$Bu, CN, $CF_3$, and Ph;

pyridinyl, which is optionally substituted with one or more substituents independently from each other selected from the group consisting of Me, $^i$Pr, $^t$Bu, CN, $CF_3$, and Ph;

pyrimidinyl, which is optionally substituted with one or more substituents independently from each other selected from the group consisting of Me, $^i$Pr, $^t$Bu, CN, $CF_3$, and Ph; and triazinyl, which is optionally substituted with one or more substituents independently from each other selected from the group consisting of Me, $^i$Pr, $^t$Bu, CN, $CF_3$, and Ph.

In a further embodiment of the invention, $R^b$ is at each occurrence independently from one another selected from the group consisting of:

Me;

$^t$Bu;

Ph, which is optionally substituted with one or more substituents independently from each other selected from the group consisting of Me, $^i$Pr, $^t$Bu, CN, $CF_3$, and Ph; and triazinyl, which is optionally substituted with one or more substituents independently from each other selected from the group consisting of Me, $^i$Pr, $^t$Bu, CN, $CF_3$, and Ph.

In the following, examples of the second chemical moiety are shown:

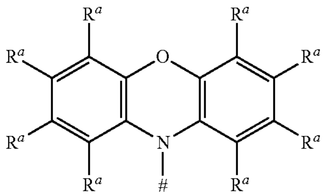

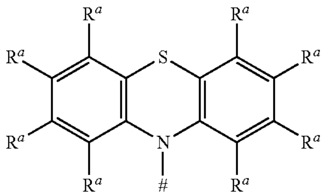

-continued

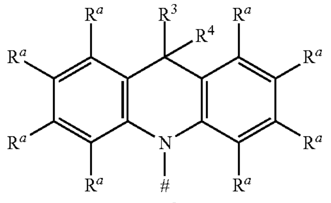

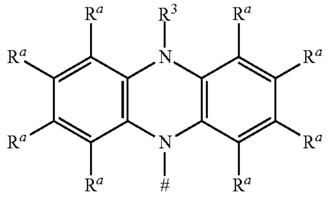

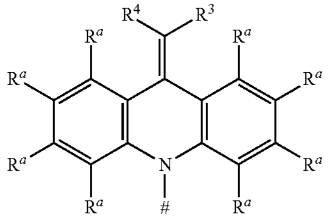

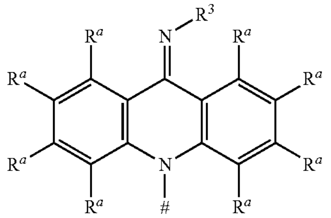

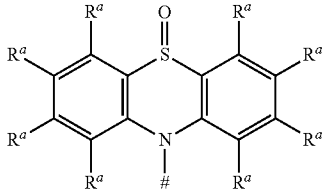

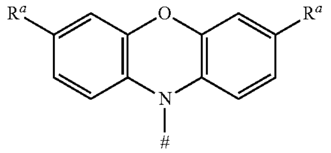

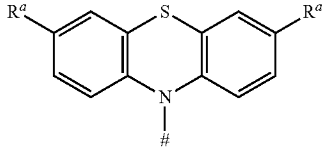

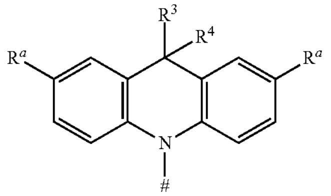

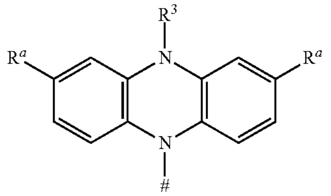

-continued
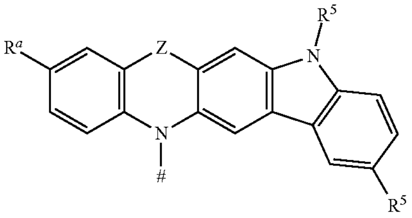
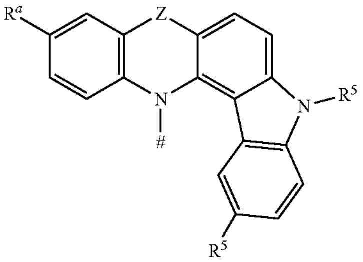
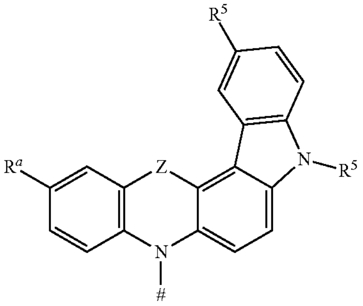
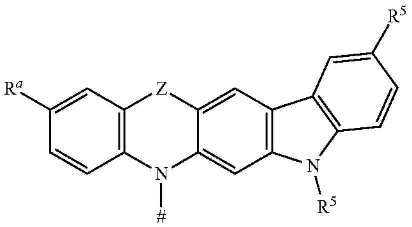
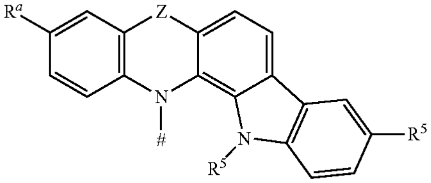
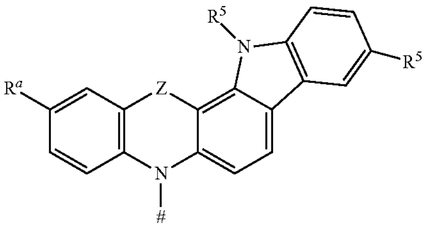
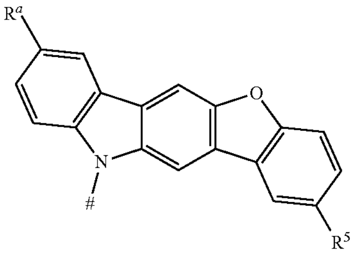
-continued
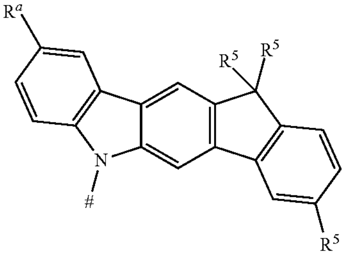
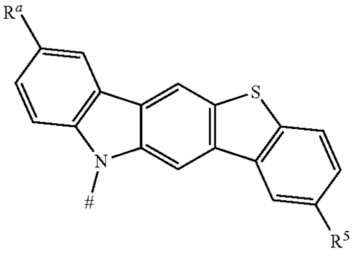
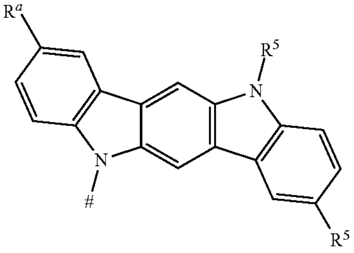
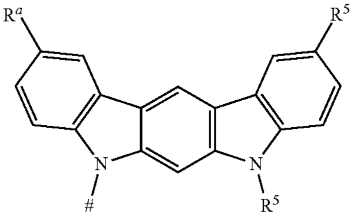
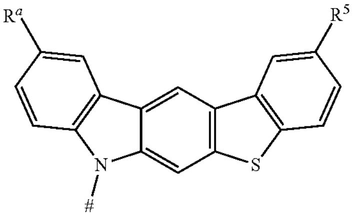
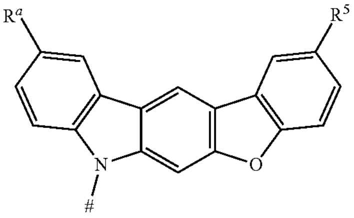
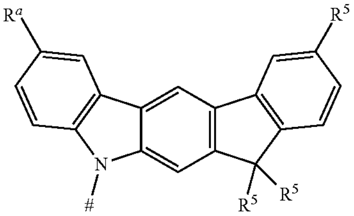

-continued
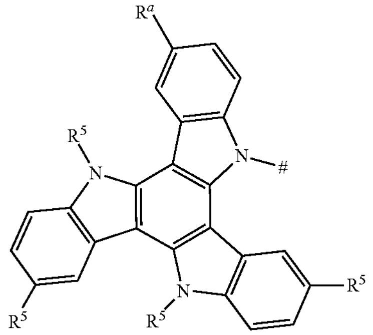
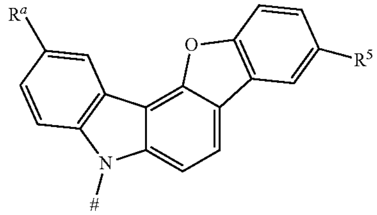
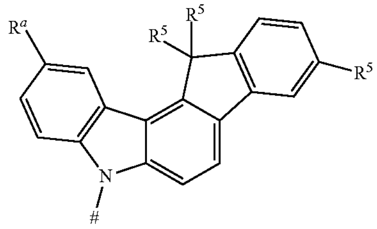
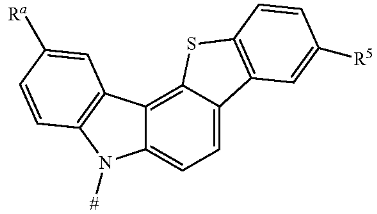
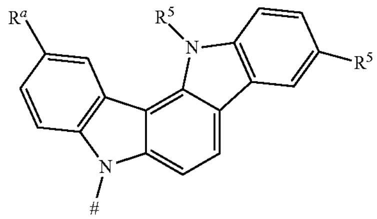
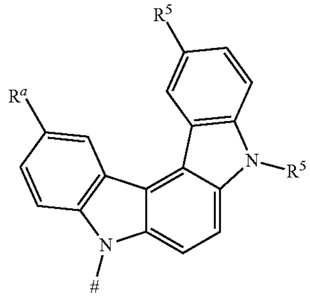
-continued
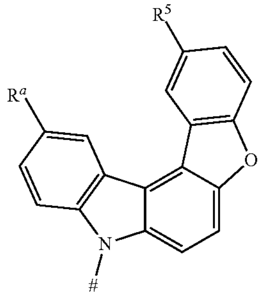
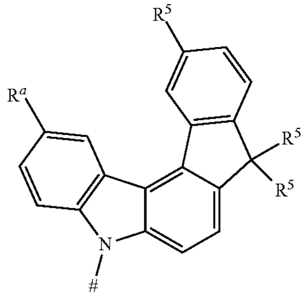
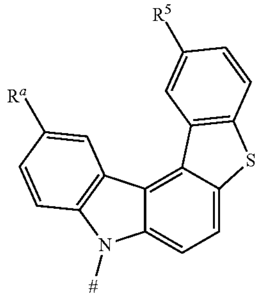
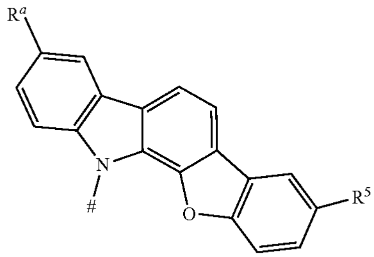
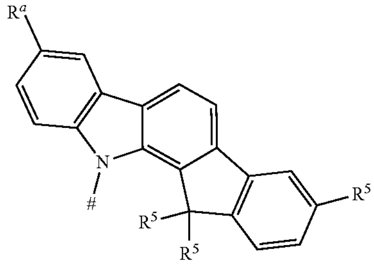
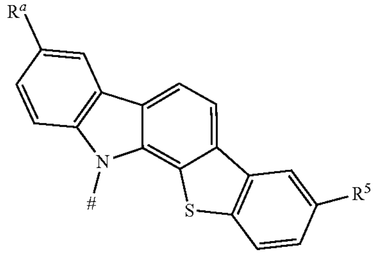

-continued

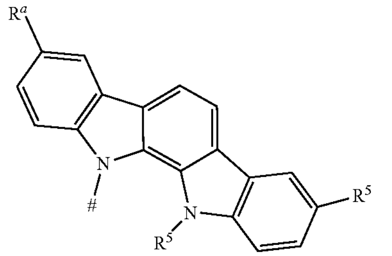

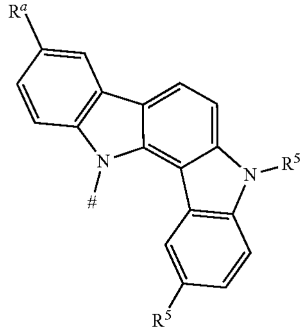

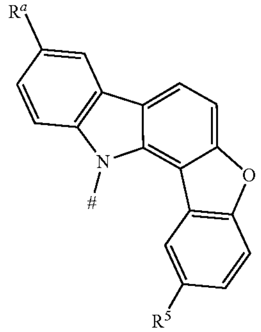

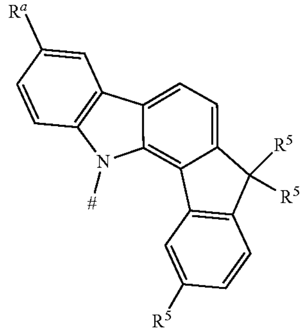

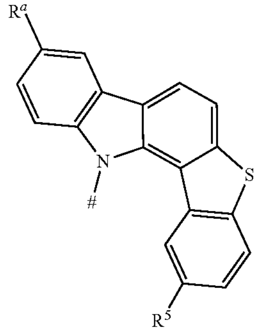

wherein for #, Z, $R^1$, $R^3$, $R^4$ and $R^5$ the aforementioned definitions apply.

In one embodiment, $R^1$ and $R^5$ are at each occurrence independently from one another selected from the group consisting of hydrogen (H), methyl (Me), i-propyl ($CH(CH_3)_2$) ($^iPr$), t-butyl ($^tBu$), phenyl (Ph), CN, $CF_3$, and diphenylamine ($NPh_2$).

In one embodiment of the invention, the organic molecules include or consist of a structure of Formula III:

Formula III

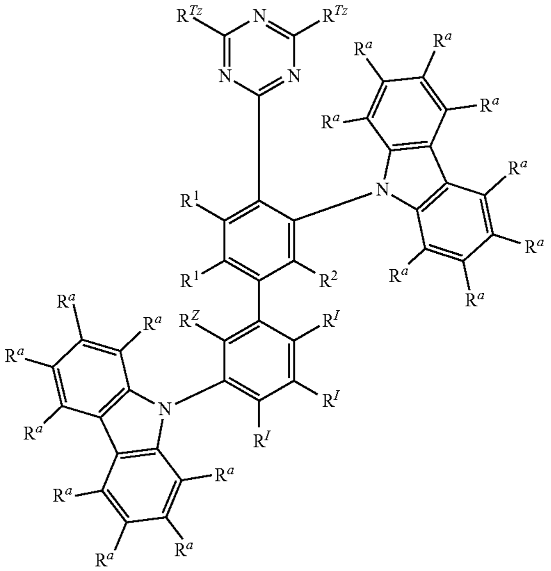

wherein $R^Z$ is selected from the group consisting of CN and $CF_3$, and wherein apart from that the aforementioned definitions apply.

In a further embodiment of the invention, the organic molecules include or consist of a structure of Formula III-1 or Formula III-2:

Formula III-1

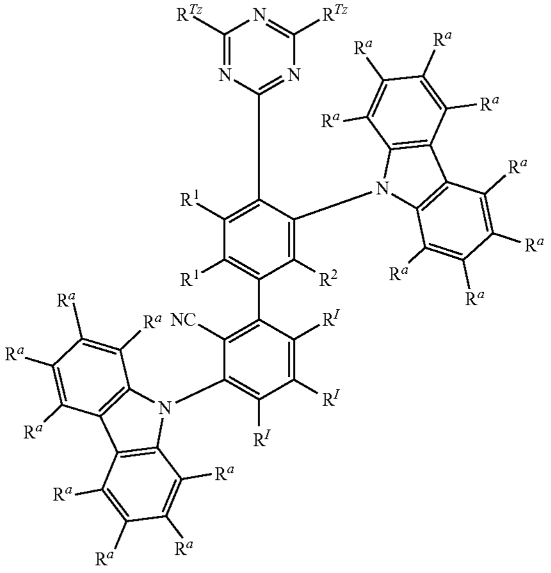

-continued

Formula III-2

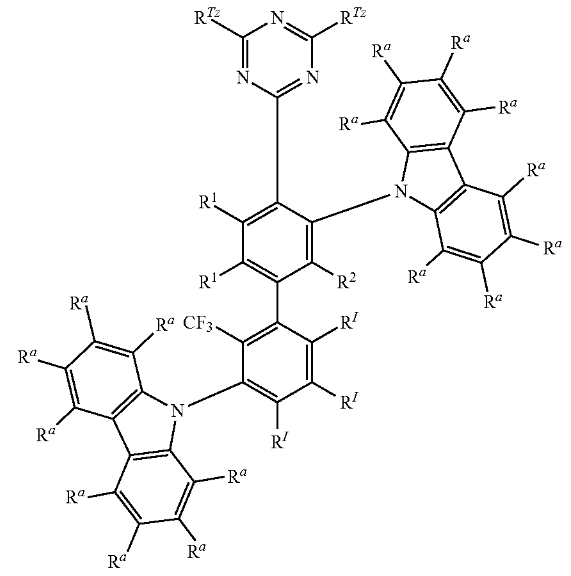

wherein the aforementioned definitions apply.

In a preferred embodiment of the invention, the organic molecules include or consist of a structure of Formula III-1.

In a further embodiment of the invention, the organic molecules include or consist of a structure of Formula IIIa-1 or IIIa-2:

Formula IIIa-1

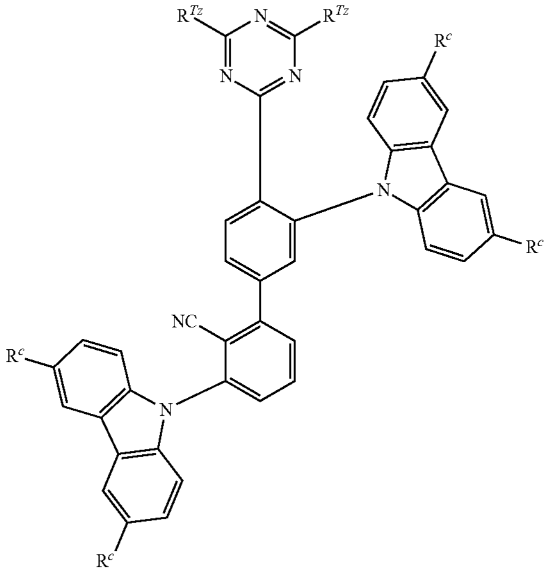

-continued

Formula IIIa-2

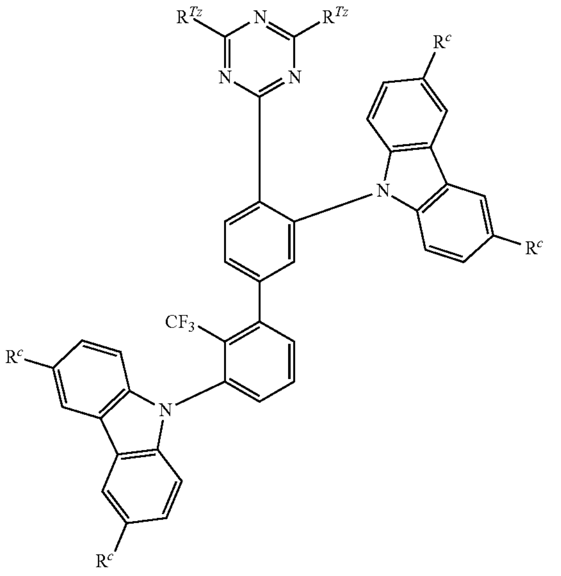

wherein $R^c$ is at each occurrence independently from one another selected from the group consisting of:

Me;

$^i$Pr;

$^t$Bu;

Ph, which is optionally substituted with one or more substituents independently from each other selected from the group consisting of Me, $^i$Pr, $^t$Bu, CN, $CF_3$, and Ph;

pyridinyl, which is optionally substituted with one or more substituents independently from each other selected from the group consisting of Me, $^i$Pr, $^t$Bu, CN, $CF_3$, and Ph;

pyrimidinyl, which is optionally substituted with one or more substituents independently from each other selected from the group consisting of Me, $^i$Pr, $^t$Bu, CN, $CF_3$, and Ph;

carbazolyl, which is optionally substituted with one or more substituents independently from each other selected from the group consisting of Me, $^i$Pr, $^t$Bu, CN, $CF_3$, and Ph;

triazinyl, which is optionally substituted with one or more substituents independently from each other selected from the group consisting of Me, $^i$Pr, $^t$Bu, CN, $CF_3$, and Ph; and $N(Ph)_2$.

In a preferred embodiment of the invention, the organic molecules include or consist of a structure of Formula IIIa-1.

In a further embodiment of the invention, the organic molecules include or consist of a structure of Formulas IIIb-1 or Formula IIIb-2:

Formula IIIb-1

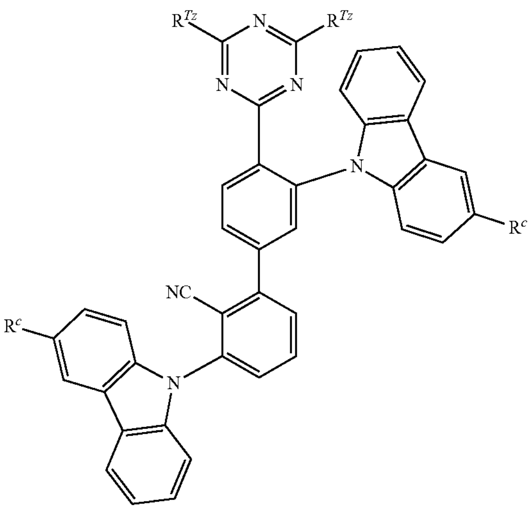

Formula IIIb-2

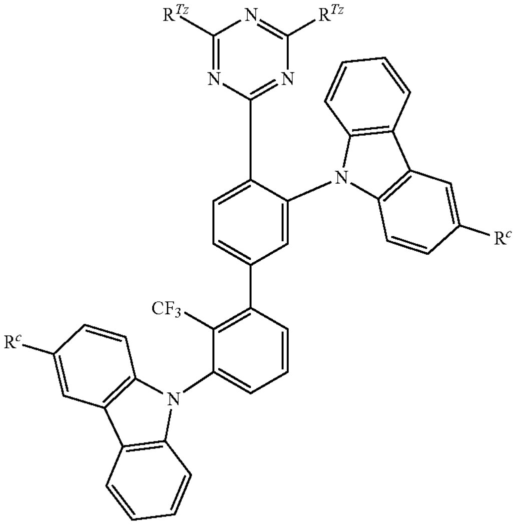

wherein the aforementioned definitions apply.

In another embodiment of the invention, the organic molecules include or consist of a structure of Formula IIIb-1.

In a further embodiment of the invention, the organic molecules include or consist of a structure of Formula IIIc-1 or IIIc-2:

Formula IIIc-1

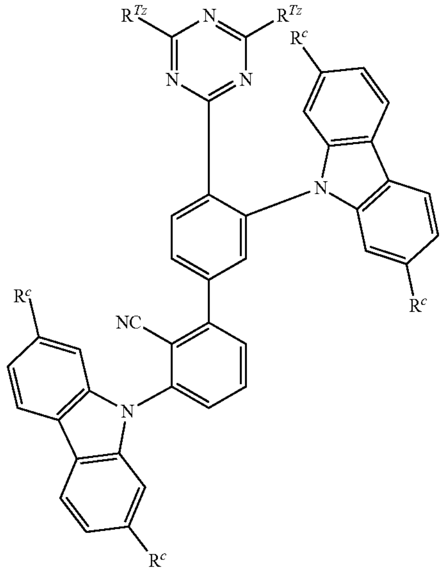

Formula IIIc-2

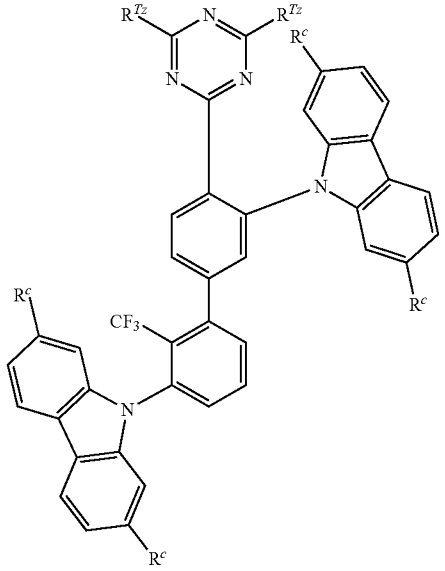

wherein the aforementioned definitions apply.

In another embodiment of the invention, the organic molecules include or consist of a structure of Formula IIIc-1.

In a further embodiment of the invention, the organic molecules include or consist of a structure of Formulas IIId-1 or IIId-2:

Formula IIId-1

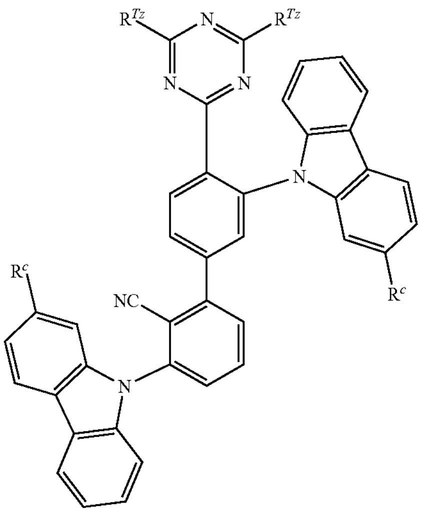

Formula IIId-2

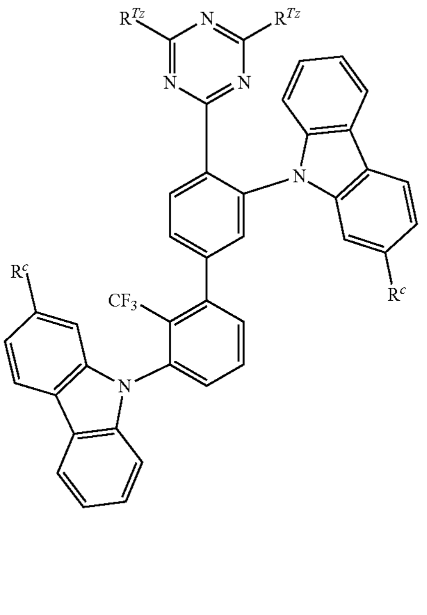

wherein the aforementioned definitions apply.

In another embodiment of the invention, the organic molecules include or consist of a structure of Formula IIId-1.

In one embodiment of the invention, the organic molecules include or consist of a structure of Formula IV:

Formula IV

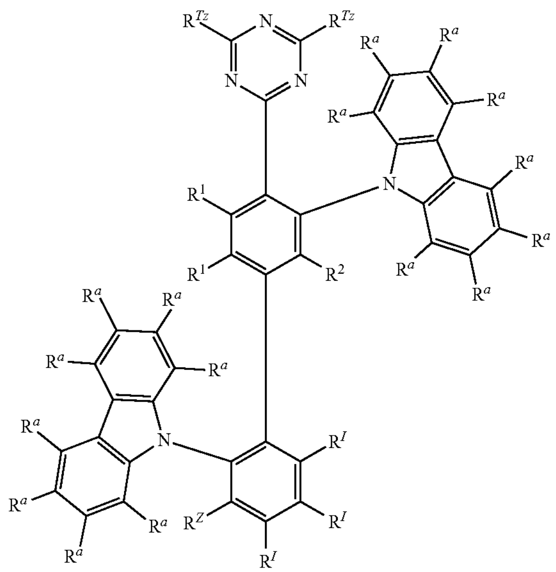

wherein the aforementioned definitions apply.

In a further embodiment of the invention, the organic molecules include or consist of a structure of Formula IV-1 or IV-2:

Formula IV-1

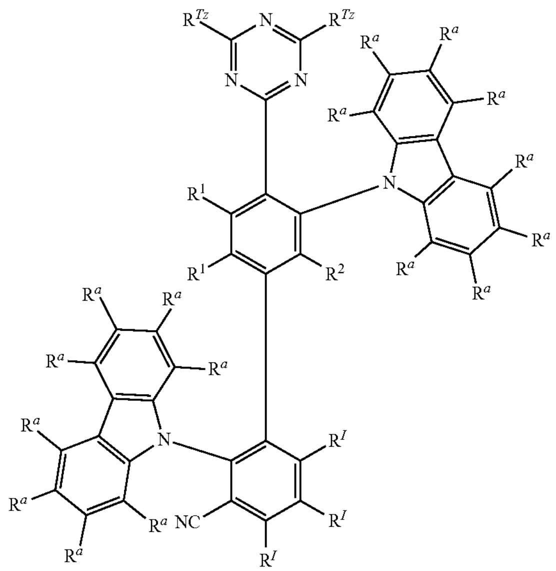

-continued

Formula IV-2

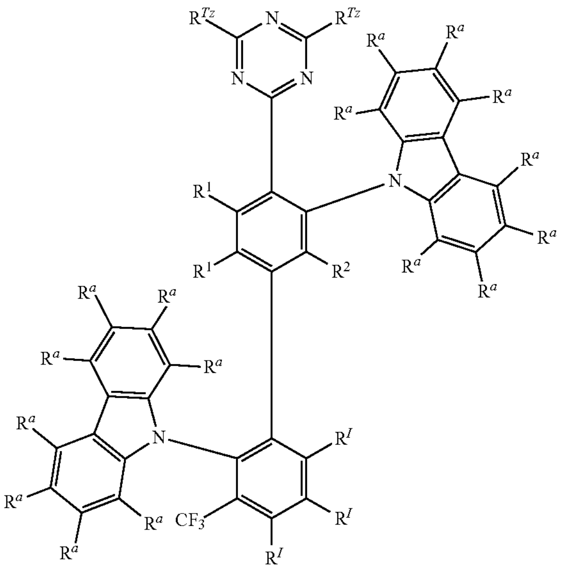

wherein the aforementioned definitions apply.

In another embodiment of the invention, the organic molecules include or consist of a structure of Formula IV-1.

In a further embodiment of the invention, the organic molecules include or consist of a structure of Formulas IVa-1 or IVa-2:

Formula IVa-1

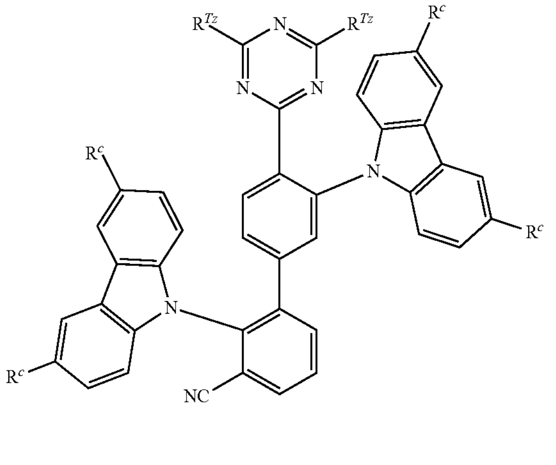

-continued

Formula IVa-2

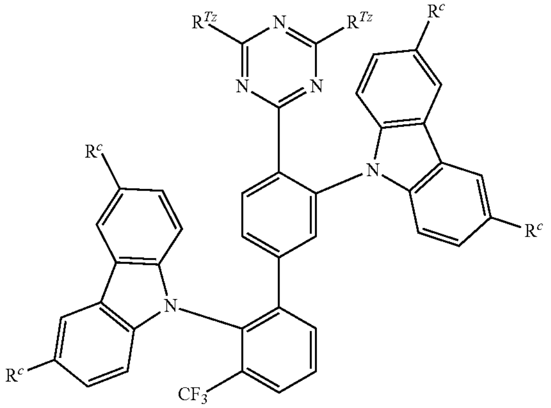

wherein the aforementioned definitions apply.

In another embodiment of the invention, the organic molecules include or consist of a structure of Formula IVa-1.

In a further embodiment of the invention, the organic molecules include or consist of a structure of Formula IVb-1 or IVb-2:

Formula IVb-1

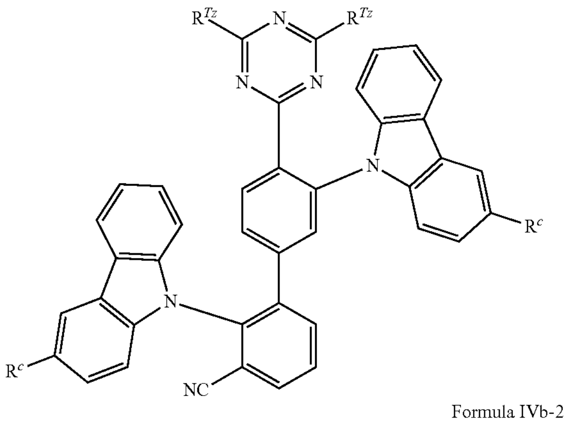

Formula IVb-2

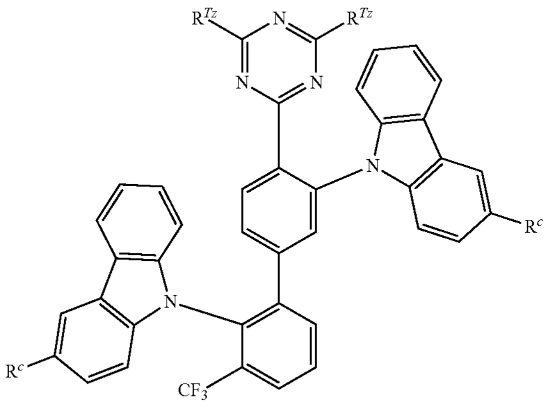

wherein the aforementioned definitions apply.

In another embodiment of the invention, the organic molecules include or consist of a structure of Formula IVb-1.

In one embodiment of the invention, the organic molecules include or consist of a structure of Formula V:

Formula V

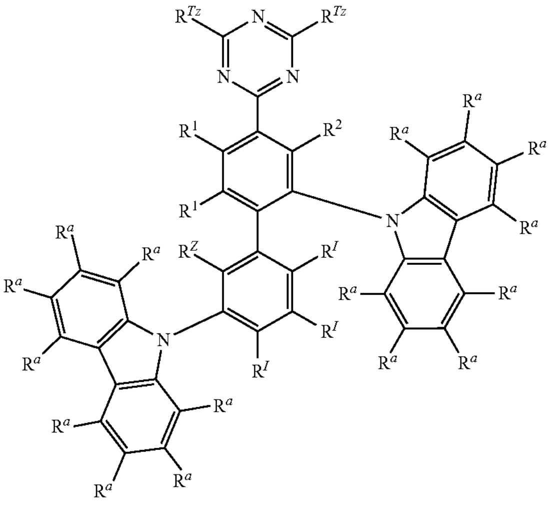

wherein the aforementioned definitions apply.

In a further embodiment of the invention, the organic molecules include or consist of a structure of Formulas V-1 or V-2:

Formula V-1

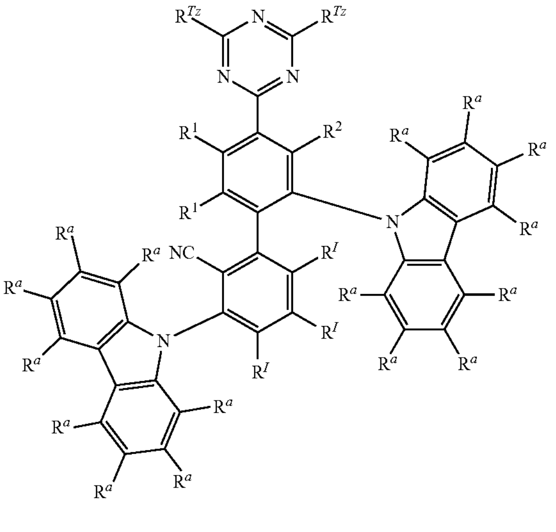

-continued

Formula V-2

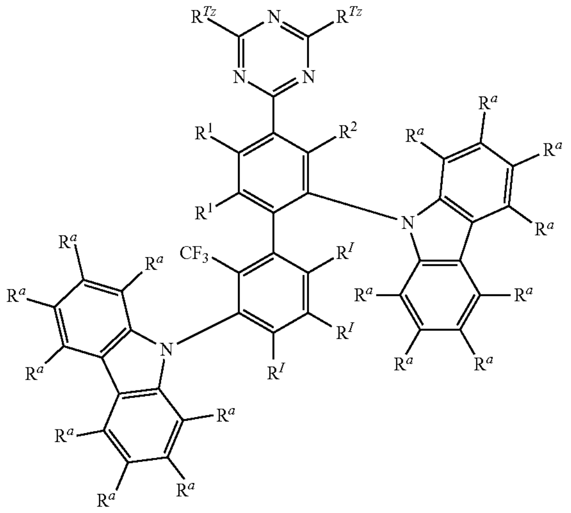

wherein the aforementioned definitions apply.

In another embodiment of the invention, the organic molecules include or consist of a structure of Formula V-1.

In one embodiment of the invention, the organic molecules include or consist of a structure of Formula VI:

Formula VI

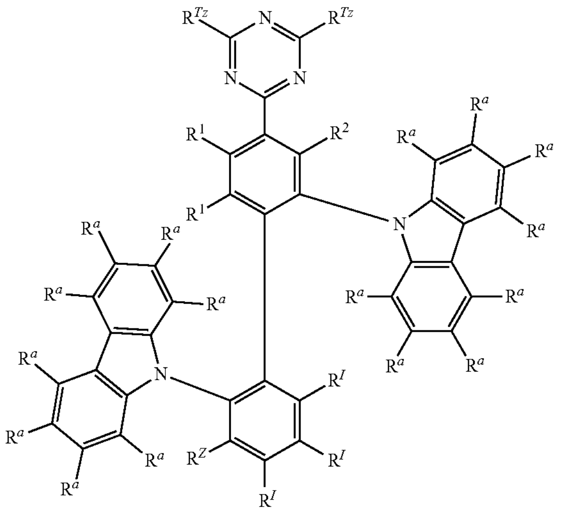

wherein the aforementioned definitions apply.

In another embodiment of the invention, the organic molecules include or consist of a structure of Formula VI wherein $R^Z$ is CN.

In one embodiment of the invention, the organic molecules include or consist of a structure of Formula VII:

Formula VII

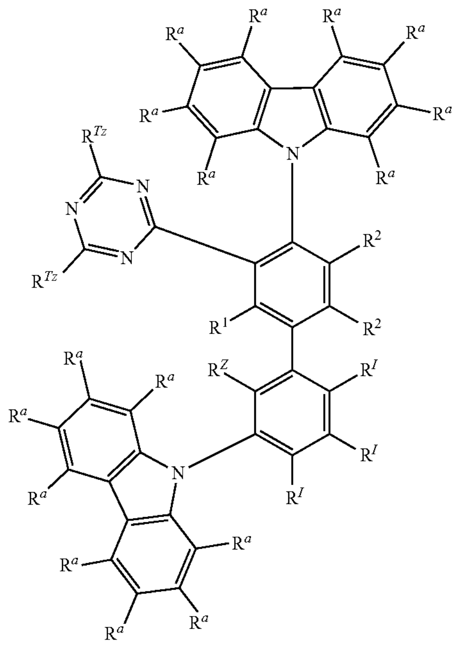

wherein the aforementioned definitions apply.

In another embodiment of the invention, the organic molecules include or consist of a structure of Formula VII wherein $R^Z$ is CN.

In one embodiment of the invention, the organic molecules include or consist of a structure of Formula VIII:

Formula VIII

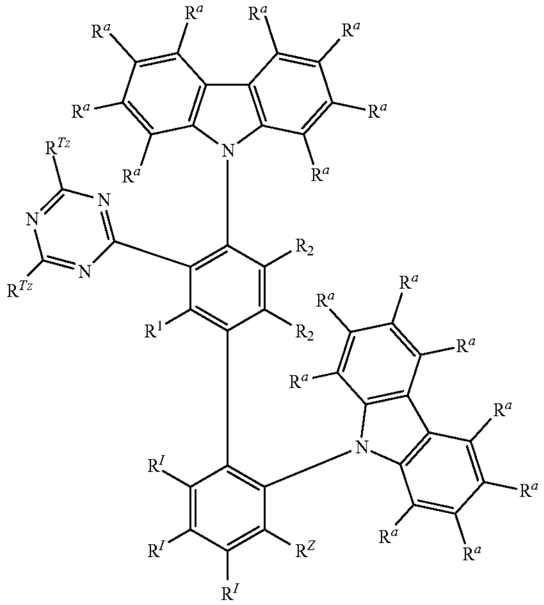

wherein the aforementioned definitions apply.

In another embodiment of the invention, the organic molecules include or consist of a structure of Formula VIII wherein $R^Z$ is CN.

In one embodiment of the invention, the organic molecules include or consist of a structure of Formula IX:

Formula IX

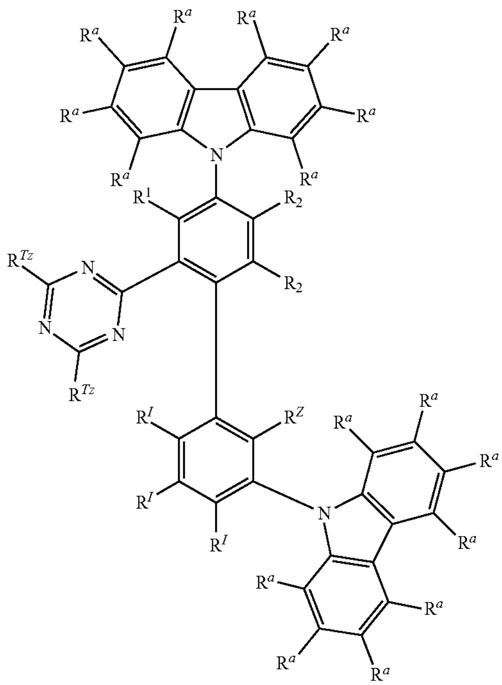

wherein the aforementioned definitions apply.

In another embodiment of the invention, the organic molecules include or consist of a structure of Formula IX wherein $R^Z$ is CN.

In one embodiment of the invention, the organic molecules include or consist of a structure of Formula X:

Formula X

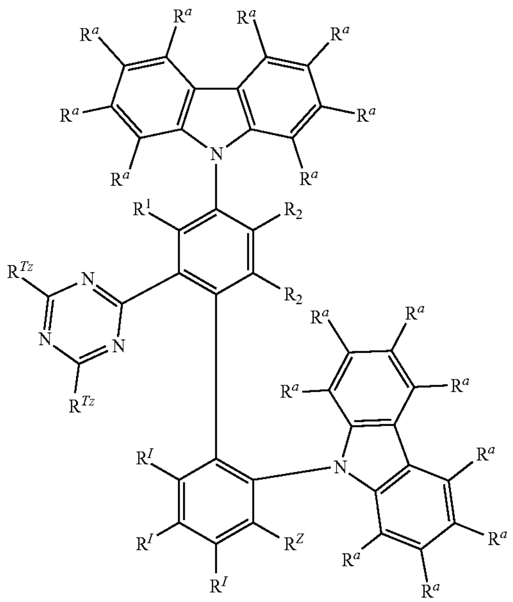

wherein the aforementioned definitions apply.

In another embodiment of the invention, the organic molecules include or consist of a structure of Formula X wherein $R^Z$ is CN.

In one embodiment of the invention, the organic molecules include or consist of a structure of Formula XI:

Formula XI

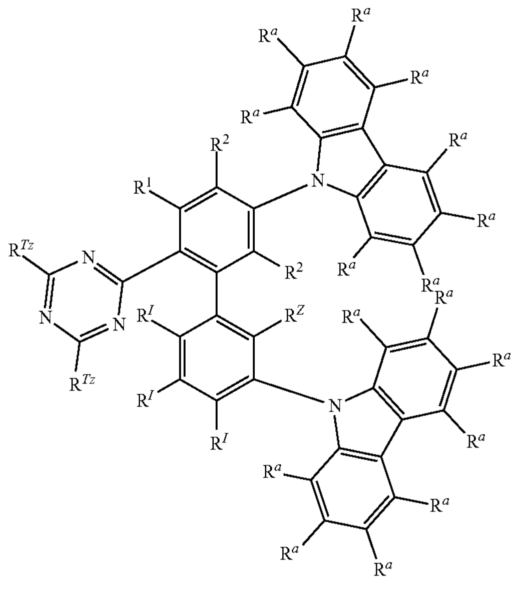

wherein the aforementioned definitions apply.

In another embodiment of the invention, the organic molecules include or consist of a structure of Formula XI wherein $R^Z$ is CN.

In one embodiment of the invention, the organic molecules include or consist of a structure of Formula XII:

Formula XII

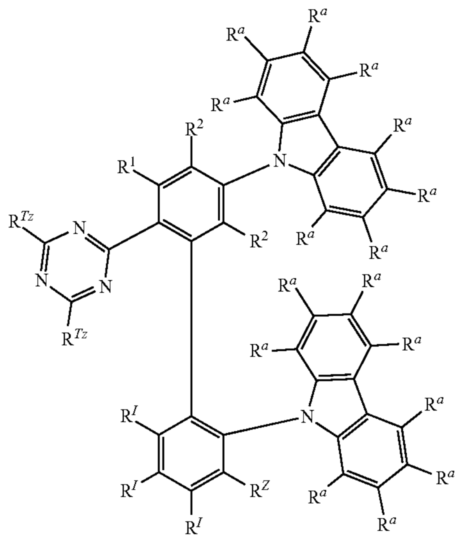

wherein the aforementioned definitions apply.

In another embodiment of the invention, the organic molecules include or consist of a structure of Formula XII wherein $R^Z$ is CN.

In one embodiment of the invention, the organic molecules include or consist of a structure of Formula XIII:

Formula XIII

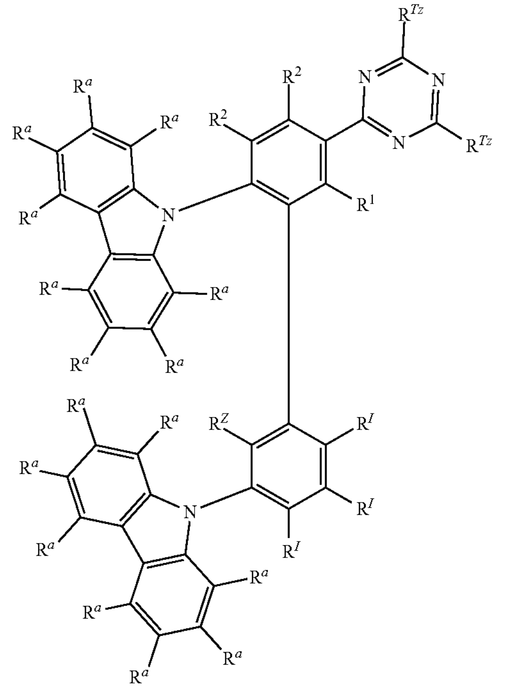

wherein the aforementioned definitions apply.

In another embodiment of the invention, the organic molecules include or consist of a structure of Formula XIII wherein $R^Z$ is CN.

In one embodiment of the invention, the organic molecules include or consist of a structure of Formula XIV:

Formula XIV

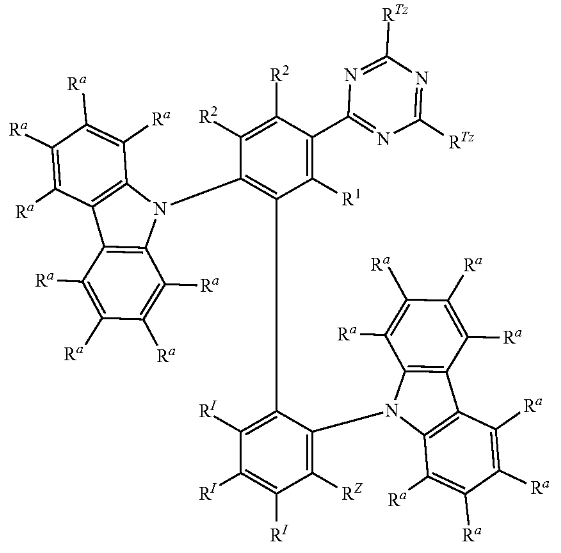

wherein the aforementioned definitions apply.

In another embodiment of the invention, the organic molecules include or consist of a structure of Formula XIV wherein $R^Z$ is CN.

As used throughout the present application, the terms "aryl" and "aromatic" may be understood in the broadest sense as any mono-, bi- or polycyclic aromatic moieties. Accordingly, an aryl group contains 6 to 60 aromatic ring atoms, and a heteroaryl group contains 5 to 60 aromatic ring atoms, of which at least one is a heteroatom. Notwithstanding, throughout the application the number of aromatic ring atoms may be given as subscripted number in the definition of certain substituents. In particular, the heteroaromatic ring includes one to three heteroatoms. Again, the terms "heteroaryl" and "heteroaromatic" may be understood in the broadest sense as any mono-, bi- or polycyclic heteroaromatic moieties that include at least one heteroatom. The heteroatoms may at each occurrence be the same or different and be individually selected from the group consisting of N, O and S. Accordingly, the term "arylene" refers to a divalent substituent that bears two binding sites to other molecular structures and thereby serving as a linker structure. In case, a group in the exemplary embodiments is defined differently from the definitions given here, for example, the number of aromatic ring atoms or number of heteroatoms differs from the given definition, the definition in the exemplary embodiments is to be applied. According to the invention, a condensed (annulated) aromatic or heteroaromatic polycycle is built of two or more single aromatic or heteroaromatic cycles, which formed the polycycle via a condensation reaction.

In particular, as used throughout the present application, the term "aryl group" or "heteroaryl group" includes groups which can be bound via any position of the aromatic or heteroaromatic group, derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthoimidazole, phenanthroimidazole, pyridoimidazole, pyrazinoimidazole, quinoxalinoimidazole, oxazole, benzoxazole, naphthooxazole, anthroxazol, phenanthroxazol, isoxazole, 1,2-thiazole, 1,3-thiazole, benzothiazole, pyridazine, benzopyridazine, pyrimidine, benzopyrimidine, 1,3,5-triazine, quinoxaline, pyrazine, phenazine, naphthyridine, carboline, benzocarboline, phenanthroline, 1,2,3-triazole, 1,2,4-triazole, benzotriazole, 1,2,3-oxadiazole, 1,2,4-oxadiazole, 1,2,5-oxadiazole, 1,2,3,4-tetrazine, purine, pteridine, indolizine and benzothiadiazole or combinations of the above mentioned groups.

As used throughout the present application, the term "cyclic group" may be understood in the broadest sense as any mono-, bi- or polycyclic moieties.

As used throughout the present application, the term biphenyl as a substituent may be understood in the broadest sense as ortho-biphenyl, meta-biphenyl, or para-biphenyl, wherein ortho, meta and para is defined in regard to the binding site to another chemical moiety.

As used throughout the present application, the term "alkyl group" may be understood in the broadest sense as any linear, branched, or cyclic alkyl substituent. In particular, examples of the term alkyl include the substituents methyl (Me), ethyl (Et), n-propyl ($^n$Pr), i-propyl ($^i$Pr), cyclopropyl, n-butyl ($^n$Bu), i-butyl ($^i$Bu), s-butyl ($^s$Bu), t-butyl ($^t$Bu), cyclobutyl, 2-methylbutyl, n-pentyl, s-pentyl, t-pentyl, 2-pentyl, neo-pentyl, cyclopentyl, n-hexyl, s-hexyl, t-hexyl, 2-hexyl, 3-hexyl, neo-hexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2,2,2]octyl, 2-bicyclo[2,2,2]-octyl, 2-(2,6-dimethyl)octyl, 3-(3,7-dimethyl)octyl, adamantyl, 2,2,2-trifluorethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)-cyclohex-1-yl, 1-(n-butyl)-cyclohex-1-yl, 1-(n-hexyl)-cyclohex-1-yl, 1-(n-octyl)-cyclohex-1-yl and 1-(n-decyl)-cyclohex-1-yl.

As used throughout the present application, examples of the term "alkenyl" include linear, branched, and cyclic alkenyl substituents. The term alkenyl group exemplarily includes the substituents ethenyl, propenyl, butenyl, pentenyl, cyclopentenyl, hexenyl, cyclohexenyl, heptenyl, cycloheptenyl, octenyl, cyclooctenyl or cyclooctadienyl.

As used throughout the present application, examples of the term "alkynyl" include linear, branched, and cyclic alkynyl substituents. The term "alkynyl group" exemplarily includes ethynyl, propynyl, butynyl, pentynyl, hexynyl, heptynyl or octynyl.

As used throughout the present application, examples of the term "alkoxy" include linear, branched, and cyclic alkoxy substituents. Examples of the term "alkoxy group" exemplarily include methoxy, ethoxy, n-propoxy, i-propoxy, n-butoxy, i-butoxy, s-butoxy, t-butoxy and 2-methylbutoxy.

As used throughout the present application, examples of the term "thioalkoxy" include linear, branched, and cyclic thioalkoxy substituents, in which the 0 of the exemplary alkoxy groups is replaced by S.

As used throughout the present application, the terms "halogen" and "halo" may be understood in the broadest sense as being preferably fluorine, chlorine, bromine or iodine.

Whenever hydrogen (H) is mentioned herein, it could also be replaced by deuterium at each occurrence.

It is understood that when a molecular fragment is described as being a substituent or otherwise attached to another moiety, its name may be written as if it were a fragment (e.g. naphthyl, dibenzofuryl) or as if it were the whole molecule (e.g. naphthalene, dibenzofuran). As used herein, these different ways of designating a substituent or attached fragment are considered to be equivalent.

In one embodiment, the organic molecules according to the invention have an excited state lifetime of not more than 25 μs, of not more than 15 μs, in particular of not more than 10 μs, more preferably of not more than 8 μs or not more than 6 μs, and even more preferably of not more than 4 μs in a film of poly(methyl methacrylate) (PMMA) with 10% by weight of the organic molecule at room temperature.

In one embodiment of the invention, the organic molecules according to the invention represent thermally-activated delayed fluorescence (TADF) emitters, which exhibit a $\Delta E_{ST}$ value, which corresponds to the energy difference between the first excited singlet state (S1) and the first excited triplet state (T1), of less than 5000 $cm^{-1}$, preferably less than 3000 $cm^{-1}$, more preferably less than 1500 $cm^{-1}$, even more preferably less than 1000 $cm^{-1}$ or even less than 500 $cm^{-1}$.

In a further embodiment of the invention, the organic molecules according to the invention have an emission peak in the visible or nearest ultraviolet range, i.e., in the range of a wavelength of from 380 to 800 nm, with a full width at half maximum of less than 0.50 eV, preferably less than 0.48 eV, more preferably less than 0.45 eV, even more preferably less than 0.43 eV or even less than 0.40 eV in a film of poly(methyl methacrylate) (PMMA) with 10% by weight of the organic molecule at room temperature.

Orbital and excited state energies can be determined either by means of experimental methods or by calculations employing quantum-chemical methods, in particular, density functional theory calculations. The energy of the highest occupied molecular orbital $E^{HOMO}$ is determined by methods known to the person skilled in the art from cyclic voltammetry measurements with an accuracy of 0.1 eV. The energy of the lowest unoccupied molecular orbital $E^{LUMO}$ is calculated as $E^{HOMO}+E^{gap}$, wherein $E^{gap}$ is determined as follows: For host compounds, the onset of the emission spectrum of a film with 10% by weight of host in poly (methyl methacrylate) (PMMA) is used as $E^{gap}$, unless stated otherwise. For emitter molecules, $E^{gap}$ is determined as the energy at which the excitation and emission spectra of a film with 10% by weight of emitter in PMMA cross.

The energy of the first excited triplet state T1 is determined from the onset of the emission spectrum at low temperature, typically at 77 K. For host compounds, where the first excited singlet state and the lowest triplet state are energetically separated by >0.4 eV, the phosphorescence is usually visible in a steady-state spectrum in 2-Me-THF. The triplet energy can thus be determined as the onset of the phosphorescence spectrum. For TADF emitter molecules, the energy of the first excited triplet state T1 is determined from the onset of the delayed emission spectrum at 77 K, if not otherwise stated measured in a film of PMMA with 10% by weight of the emitter. For both, host and emitter compounds, the energy of the first excited singlet state S1 is determined from the onset of the emission spectrum (measured as follows: TADF emitters: concentration of 10% by weight in a film of PMMA; hosts: neat film).

The onset of an emission spectrum is determined by computing the intersection of the tangent to the emission spectrum with the x-axis. The tangent to the emission spectrum is set at the high-energy side of the emission band and at the point at half maximum of the maximum intensity of the emission spectrum.

A further aspect of the invention relates to a process for preparing organic molecule (with an optional subsequent reaction) according to the invention, wherein a reactant selected from the group consisting of a 2-bromo-6-fluorobenzonitrile, a 3-bromo-2-fluorobenzonitrile, a 1-bromo-3-fluoro-2-(trifluoromethyl)benzene, and a 1-bromo-2-fluoro-3-(trifluoromethyl)benzene is used, wherein all of these reactants are optionally substituted with exactly three substituents $R^I$.

-continued

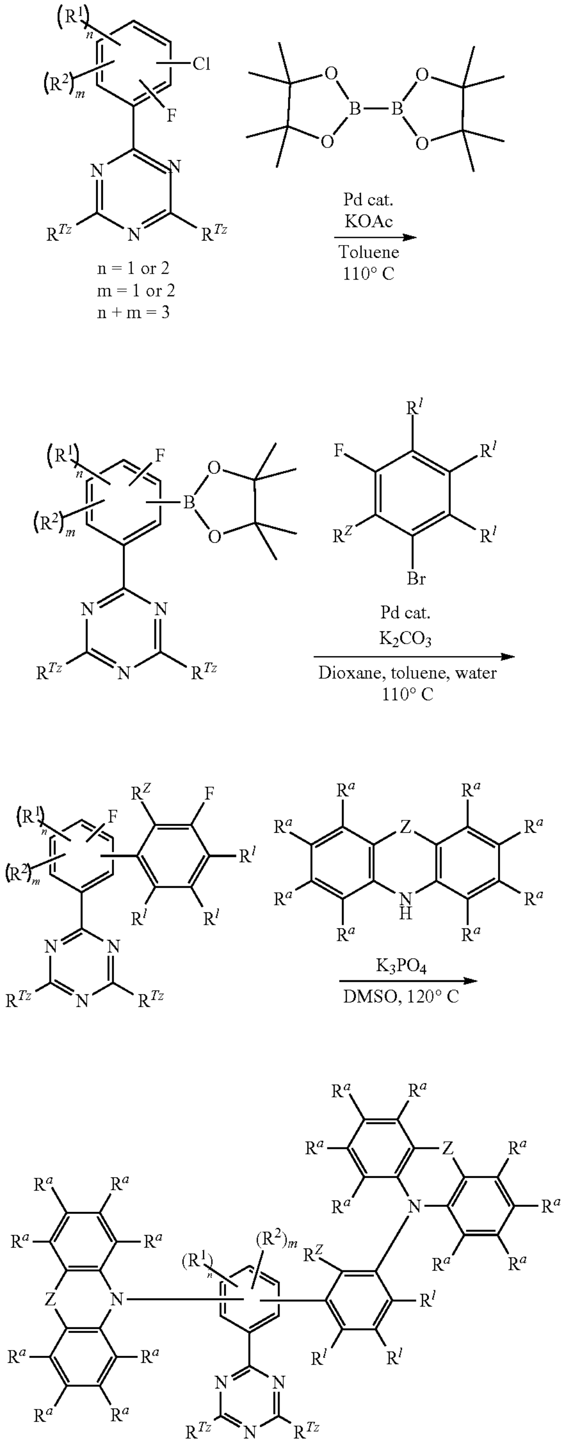

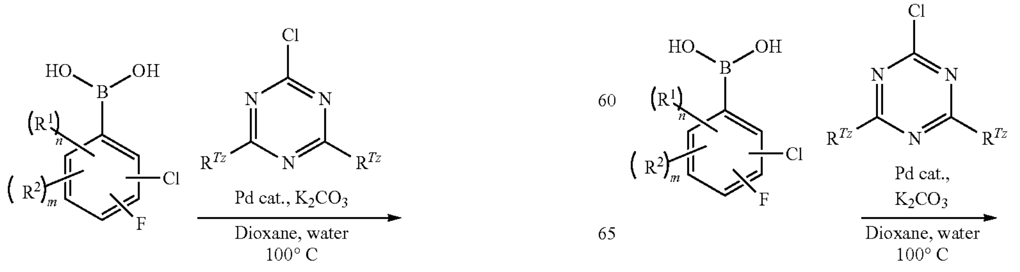

-continued

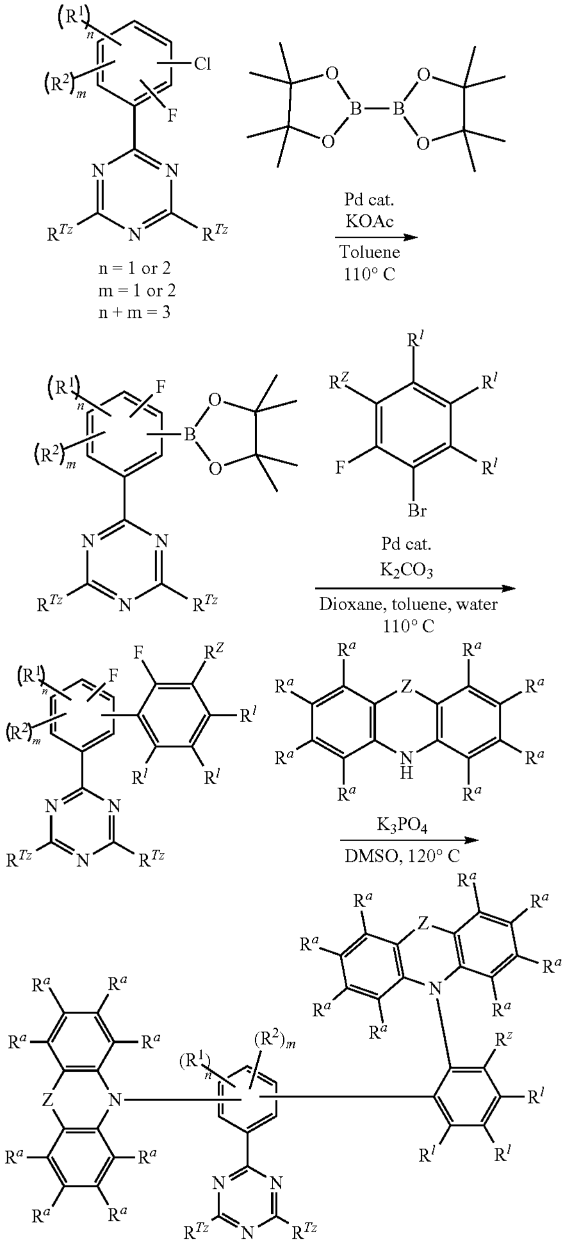

According to the invention, a boronic acid or an equivalent boronic acid ester can be used instead of a boronic pinacol ester.

For the reaction of a nitrogen heterocycle in a nucleophilic aromatic substitution with an aryl halide, preferably an aryl fluoride, typical conditions include the use of a base, such as tribasic potassium phosphate or sodium hydride, for example, in an aprotic polar solvent, such as dimethyl sulfoxide (DMSO) or N,N-dimethylformamide (DMF), for example.

An alternative synthesis route includes the introduction of a nitrogen heterocycle via copper- or palladium-catalyzed coupling to an aryl halide or aryl pseudohalide, preferably an aryl bromide, an aryl iodide, an aryl triflate or an aryl tosylate.

A further aspect of the invention relates to the use of an organic molecule according to the invention as a luminescent emitter or as an absorber, and/or as a host material and/or as an electron transport material, and/or as a hole injection material, and/or as a hole blocking material in an optoelectronic device.

The optoelectronic device, also referred to as organic optoelectronic device, may be understood in the broadest sense as any device based on organic materials that is suitable for emitting light in the visible or nearest ultraviolet (UV) range, i.e., in the range of a wavelength of from 380 nm to 800 nm. More preferably, the organic electroluminescent device may be able to emit light in the visible range, i.e., of from 400 nm to 800 nm.

In the context of such use, the optoelectronic device is more particularly selected from the group consisting of:

- organic light-emitting diodes (OLEDs),
- light-emitting electrochemical cells,
- OLED sensors, especially in gas and vapour sensors not hermetically shielded to the outside,
- organic diodes,
- organic solar cells,
- organic transistors,
- organic field-effect transistors,
- organic lasers, and
- down-conversion elements.

In a preferred embodiment in the context of such use, the organic electroluminescent device is a device selected from the group consisting of an organic light emitting diode (OLED), a light emitting electrochemical cell (LEC), and a light-emitting transistor.

In one embodiment, the light-emitting layer of an organic light-emitting diode includes the organic molecules according to the invention. In this case, the fraction of the organic molecule according to the invention in the emission layer in an optoelectronic device, more particularly in OLEDs, is 1% to 99% by weight, more particularly 5% to 80% by weight. In an alternative embodiment, the proportion of the organic molecule in the emission layer is 100% by weight.

In one embodiment, the light-emitting layer includes not only the organic molecules according to the invention but also a host material whose triplet (T1) and singlet (S1) energy levels are energetically higher than the triplet (T1) and singlet (S1) energy levels of the organic molecule.

A further aspect of the invention relates to a composition including or consisting of:

(a) at least one organic molecule according to the invention, in particular in the form of an emitter and/or a host, and (b) one or more emitter and/or host materials, which differ from the organic molecule according to the invention, and (c) optionally, one or more dyes and/or one or more solvents.

In a further embodiment of the invention, the composition has a photoluminescence quantum yield (PLQY) of more than 10%, preferably more than 20%, more preferably more than 40%, even more preferably more than 60% or even more than 70% at room temperature.

In one embodiment, the light-emitting layer includes (or essentially consists of) a composition including or consisting of:

(a) at least one organic molecule according to the invention, in particular in the form of an emitter and/or a host, and (b) one or more emitter and/or host materials, which differ from the organic molecule according to the invention, and (c) optional one or more dyes and/or one or more solvents.

Particularly preferably the light-emitting layer EML includes (or essentially consists of) a composition including or consisting of:

(i) 1-50% by weight, preferably 5-40% by weight, in particular 10-30% by weight, of one or more organic molecules according to the invention E;

(ii) 5-99% by weight, preferably 30-94.9% by weight, in particular 40-89% by weight, of at least one host compound H; and (iii) optionally 0-94% by weight, preferably 0.1-65% by weight, in particular 1-50% by weight, of at least one further host compound D with a structure differing from the structure of the molecules according to the invention; and (iv) optionally 0-94% by weight, preferably 0-65% by weight, in particular 0-50% by weight, of a solvent; and (v) optionally, 0-30% by weight, in particular 0-20% by weight, preferably 0-5% by weight, of at least one further emitter molecule F with a structure differing from the structure of the molecules according to the invention.

The components or the compositions are chosen such that the sum of the weight of the components adds up to 100%.

Preferably, energy can be transferred from the host compound H to the one or more organic molecules according to the invention (E), in particular transferred from the first excited triplet state T1(H) of the host compound H to the first excited triplet state T1(E) of the one or more organic molecules according to the invention E and/or from the first excited singlet state S1(H) of the host compound H to the first excited singlet state S1(E) of the one or more organic molecules according to the invention E.

In a further embodiment, the light-emitting layer EML includes (or (essentially) consists of) a composition including or consisting of:

(i) 1-50% by weight, preferably 5-40% by weight, in particular 10-30% by weight, of one organic molecule according to the invention E;

(ii) 5-99% by weight, preferably 30-94.9% by weight, in particular 40-89% by weight, of one host compound H; and (iii) optionally, 0-94% by weight, preferably 0.1-65% by weight, in particular 1-50% by weight, of at least one further host compound D with a structure differing from the structure of the molecules according to the invention; and (iv) optionally, 0-94% by weight, preferably 0-65% by weight, in particular 0-50% by weight, of a solvent; and (v) optionally, 0-30% by weight, in particular 0-20% by weight, preferably 0-5% by weight, of at least one further emitter molecule F with a structure differing from the structure of the molecules according to the invention.

In one embodiment, the host compound H has a highest occupied molecular orbital HOMO(H) having an energy $E^{HOMO}(H)$ in the range of from −5 to −6.5 eV and the at least one further host compound D has a highest occupied molecular orbital HOMO(D) having an energy $E^{HOMO}(D)$, wherein $E^{HOMO}(H)>E^{HOMO}(D)$.

In a further embodiment, the host compound H has a lowest unoccupied molecular orbital LUMO(H) having an energy $E^{LUMO}(H)$ and the at least one further host compound D has a lowest unoccupied molecular orbital LUMO(D) having an energy $E^{LUMO}(D)$, wherein $E^{LUMO}(H)>E^{LUMO}(D)$ In one embodiment, the host compound H has a highest occupied molecular orbital HOMO(H) having an energy $E^{HOMO}(H)$ and a lowest unoccupied molecular orbital LUMO(H) having an energy $E^{LUMO}(H)$, and the at least one further host compound D has a highest occupied molecular orbital HOMO(D) having an energy $E^{HOMO}(D)$ and a lowest unoccupied molecular orbital LUMO(D) having an energy $E^{LUMO}(D)$, the organic molecule according to the invention (E) has a highest occupied molecular orbital HOMO(E) having an energy $E^{HOMO}(E)$ and a lowest unoccupied molecular orbital LUMO(E) having an energy $E^{LUMO}(E)$, wherein $E^{HOMO}(H)>E^{HOMO}(D)$ and the difference between the energy level of the highest occupied molecular orbital HOMO(E) of the organic molecule according to the invention E ($E^{HOMO}(E)$) and the energy level of the highest occupied molecular orbital HOMO(H) of the host compound H ($E^{HOMO}(H)$) is between −0.5 eV and 0.5 eV, more preferably between −0.3 eV and 0.3 eV, even more preferably between −0.2 eV and 0.2 eV or even between −0.1 eV and 0.1 eV; and $E^{LUMO}(H)>E^{LUMO}(D)$ and the difference between the energy level of the lowest unoccupied molecular orbital LUMO(E) of the organic molecule according to the invention E ($E^{LUMO}(E)$) and the lowest unoccupied molecular orbital LUMO(D) of the at least one further host compound D ($E^{LUMO}(D)$) is between −0.5 eV and 0.5 eV, more preferably between −0.3 eV and 0.3 eV, even more preferably between −0.2 eV and 0.2 eV or even between −0.1 eV and 0.1 eV.

In a further aspect, the invention relates to an optoelectronic device including an organic molecule or a composition of the type described here, more particularly in the form of a device selected from the group consisting of organic light-emitting diode (OLED), light-emitting electrochemical cell, OLED sensor, more particularly gas and vapour sensors not hermetically externally shielded, organic diode, organic solar cell, organic transistor, organic field-effect transistor, organic laser and down-conversion element.

In a preferred embodiment, the organic electroluminescent device is a device selected from the group consisting of an organic light emitting diode (OLED), a light emitting electrochemical cell (LEC), and a light-emitting transistor.

In one embodiment of the optoelectronic device of the invention, the organic molecule according to the invention E is used as emission material in a light-emitting layer EML.

In one embodiment of the optoelectronic device of the invention the light-emitting layer EML consists of the composition according to the invention described here.

Exemplarily, when the organic electroluminescent device is an OLED, it may exhibit the following layer structure:

1. substrate
2. anode layer, A
3. hole injection layer, HIL
4. hole transport layer, HTL
5. electron blocking layer, EBL
6. emitting layer, EML
7. hole blocking layer, HBL
8. electron transport layer, ETL
9. electron injection layer, EIL
10. cathode layer, C wherein the OLED includes each layer only optionally, and different layers may be merged together into, e.g., one or more layers, and the OLED may include more than one layer of each layer type defined above.

Furthermore, the organic electroluminescent device may optionally include one or more protective layers protecting the device from damaging exposure to harmful species in the environment including, exemplarily moisture, vapor and/or gases.

In one embodiment of the invention, the organic electroluminescent device is an OLED, which exhibits the following inverted layer structure:

1. substrate
2. cathode layer, C
3. electron injection layer, EIL
4. electron transport layer, ETL
5. hole blocking layer, HBL
6. emitting layer, EML
7. electron blocking layer, EBL
8. hole transport layer, HTL
9. hole injection layer, HIL
10. anode layer A, wherein the OLED with an inverted layer structure includes each layer only optionally, and different layers may be merged together into, e.g., one or more layers, and the OLED may include more than one layer of each layer types defined above.

In one embodiment of the invention, the organic electroluminescent device is an OLED, which may exhibit stacked architecture. In this architecture, contrary to the typical arrangement, where the OLEDs are placed side by side, the individual units are stacked on top of each other. Blended light may be generated with OLEDs exhibiting a stacked architecture, in particular white light may be generated by stacking blue, green and red OLEDs. Furthermore, the OLED exhibiting a stacked architecture may optionally include a charge generation layer (CGL), which is typically located between two OLED subunits and typically consists of an n-doped layer and a p-doped layer with the n-doped layer of one CGL being typically located closer to the anode layer.

In one embodiment of the invention, the organic electroluminescent device is an OLED, which includes two or more emission layers between anode and cathode. In particular, this so-called tandem OLED includes three emission layers, wherein one emission layer emits red light, one emission layer emits green light and one emission layer emits blue light, and optionally may include further layers such as charge generation layers, blocking or transporting layers between the individual emission layers. In a further embodiment, the emission layers are adjacently stacked. In a further embodiment, the tandem OLED includes a charge generation layer between each two emission layers. In addition, adjacent emission layers or emission layers separated by a charge generation layer may be merged.

The substrate may be formed by any material or composition of materials. Most frequently, glass slides are used as substrates. Alternatively, thin metal layers (e.g., copper, gold, silver or aluminum films) or plastic films or slides may be used. This may allow for a higher degree of flexibility. The anode layer A is mostly composed of materials allowing to obtain an (essentially) transparent film. As at least one of the two electrodes should be (essentially) transparent in order to allow light emission from the OLED, either the anode layer A or the cathode layer C is transparent. Preferably, the anode layer A includes a large content or even consists of transparent conductive oxides (TCOs). Such anode layer A may, for example, include indium tin oxide, aluminum zinc oxide, fluorine doped tin oxide, indium zinc oxide, PbO, SnO, zirconium oxide, molybdenum oxide, vanadium oxide, tungsten oxide, graphite, doped Si, doped Ge, doped GaAs, doped polyaniline, doped polypyrrol and/or doped polythiophene.

The anode layer A (essentially) may consist of indium tin oxide (ITO) (e.g., $(InO_3)0.9(SnO_2)0.1$). The roughness of the anode layer A caused by the transparent conductive oxides (TCOs) may be compensated by using a hole injection layer (HIL). Further, the HIL may facilitate the injection of quasi charge carriers (i.e., holes) in that the transport of the quasi charge carriers from the TCO to the hole transport layer (HTL) is facilitated. The hole injection layer (HIL) may include poly-3,4-ethylenedioxy thiophene (PEDOT), polystyrene sulfonate (PSS), $MoO_2$, $V_2O_5$, CuPC or CuI, in particular a mixture of PEDOT and PSS. The hole injection layer (HIL) may also prevent the diffusion of metals from the anode layer A into the hole transport layer (HTL). The HIL may, for example, include PEDOT:PSS (poly-3,4-ethylenedioxy thiophene: polystyrene sulfonate), PEDOT (poly-3,4-ethylenedioxy thiophene), mMTDATA (4,4',4"-tris[phenyl(m-tolyl)amino]triphenylamine), Spiro-TAD (2,2',7,7'-tetrakis(n,n-diphenylamino)-9,9'-spirobifluorene), DNTPD (N1,N1'-(biphenyl-4,4'-diyl)bis(N1-phenyl-N4,N4-di-m-tolylbenzene-1,4-diamine), NPB (N,N'-nis-(1-naphthalenyl)-N,N'-bis-phenyl-(1,1'-biphenyl)-4,4'-diamine), NPNPB (N,N'-diphenyl-N,N'-di-[4-(N,N-diphenyl-amino)phenyl]benzidine), MeO-TPD (N,N,N',N'-tetrakis(4-methoxyphenyl)benzidine), HAT-CN (1,4,5,8,9,11-hexaazatriphenylen-hexacarbonitrile) and/or Spiro-NPD (N,N'-diphenyl-N,N'-bis-(1-naphthyl)-9,9'-spirobifluorene-2,7-diamine).

Adjacent to the anode layer A or hole injection layer (HIL), a hole transport layer (HTL) is typically located. Herein, any hole transport compound may be used. For example, electron-rich heteroaromatic compounds such as triarylamines and/or carbazoles may be used as hole transport compound. The HTL may decrease the energy barrier between the anode layer A and the light-emitting layer EML. The hole transport layer (HTL) may also be an electron blocking layer (EBL). Preferably, hole transport compounds bear comparably high energy levels of their triplet states T1. For example, the hole transport layer (HTL) may include a star-shaped heterocycle such as tris(4-carbazoyl-9-ylphenyl)amine (TCTA), poly-TPD (poly(4-butylphenyl-diphenyl-amine)), [alpha]-NPD (poly(4-butylphenyl-diphenyl-amine)), TAPC (4,4'-cyclohexyliden-bis[N,N-bis(4-methylphenyl)benzenamine]), 2-TNATA (4,4',4"-tris[2-naphthyl(phenyl)amino]triphenylamine), Spiro-TAD, DNTPD, NPB, NPNPB, MeO-TPD, HAT-CN and/or TrisPcz (9,9'-diphenyl-6-(9-phenyl-9H-carbazol-3-yl)-9H,9'H-3,3'-bicarbazole). In addition, the HTL may include a p-doped layer, which may be composed of an inorganic or organic dopant in an organic hole-transporting matrix. Transition metal oxides such as vanadium oxide, molybdenum oxide or tungsten oxide may exemplarily be used as inorganic dopant. Tetrafluorotetracyanoquinodimethane ($F_4$-TCNQ), copper-pentafluorobenzoate (Cu(I)pFBz) or transition metal complexes may exemplarily be used as the organic dopant.

The EBL may exemplarily include mCP (1,3-bis(carbazol-9-yl)benzene), TCTA, 2-TNATA, mCBP (3,3-di(9H-carbazol-9-yl)biphenyl), tris-Pcz, CzSi (9-(4-tert-Butylphenyl)-3,6-bis(triphenylsilyl)-9H-carbazole), and/or DCB (N,N'-dicarbazolyl-1,4-dimethylbenzene).

Adjacent to the hole transport layer (HTL), typically, the light-emitting layer EML is located. The light-emitting layer EML includes at least one light emitting molecule. Particularly, the EML includes at least one light emitting molecule according to the invention E. In one embodiment, the light-emitting layer includes only the organic molecules according to the invention E. Typically, the EML additionally includes one or more host materials H. Exemplarily, the host material H is selected from CBP (4,4'-Bis-(N-carbazolyl)-biphenyl), mCP, mCBP Sif87 (dibenzo[b,d]thiophen-2-yltriphenylsilane), CzSi, Sif88 (dibenzo[b,d]thiophen-2-yl)diphenylsilane), DPEPO (bis[2-(diphenylphosphino) phenyl]ether oxide), 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole, 9-[3,5-bis(2-dibenzothiophenyl)phenyl]-9H-carbazole, T2T (2,4,6-tris(biphenyl-3-yl)-1,3,5-triazine), T3T (2,4,6-tris(triphenyl-3-yl)-1,3,5-triazine) and/or TST (2,4,6-tris(9,9'-spirobifluorene-2-yl)-1,3,5-triazine). The host material H typically should be selected to exhibit first triplet (T1) and first singlet (S1) energy levels, which are energetically higher than the first triplet (T1) and first singlet (S1) energy levels of the organic molecule.

In one embodiment of the invention, the EML includes a so-called mixed-host system with at least one hole-dominant host and one electron-dominant host. In a particular embodiment, the EML includes exactly one light emitting molecule according to the invention E and a mixed-host system including T2T as the electron-dominant host and a host selected from CBP, mCP, mCBP, 9-[3-(dibenzofuran-2-yl) phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole and 9-[3,5-bis(2-dibenzothiophenyl)phenyl]-9H-carbazole as the hole-dominant host. In a further embodiment the EML includes 50-80% by weight, preferably 60-75% by weight of a host selected from CBP, mCP, mCBP, 9-[3-(dibenzofuran-2-yl)phenyl]-9H-carbazole, 9-[3-(dibenzothiophen-2-yl) phenyl]-9H-carbazole, 9-[3,5-bis(2-dibenzofuranyl)phenyl]-9H-carbazole and 9-[3,5-bis(2-dibenzothiophenyl) phenyl]-9H-carbazole; 10-45% by weight, preferably 15-30% by weight of T2T and 5-40% by weight, preferably 10-30% by weight of light emitting molecule according to the invention.

Adjacent to the light-emitting layer EML an electron transport layer (ETL) may be located. Herein, any electron transporter may be used. Exemplarily, electron-poor compounds such as, e.g., benzimidazoles, pyridines, triazoles, oxadiazoles (e.g., 1,3,4-oxadiazole), phosphinoxides and sulfone, may be used. An electron transporter may also be a star-shaped heterocycle such as 1,3,5-tri(1-phenyl-1H-benzo [d]imidazol-2-yl)phenyl (TPBi). The ETL may include NBphen (2,9-bis(naphthalen-2-yl)-4,7-diphenyl-1,10-phenanthroline), Alqa (Aluminum-tris(8-hydroxyquinoline)), TSPO1 (diphenyl-4-triphenylsilylphenyl-phosphinoxide), BPyTP2 (2,7-di(2,2'-bipyridin-5-yl)triphenyle), Sif87 (dibenzo[b,d]thiophen-2-yltriphenylsilane), Sif88 (dibenzo[b,d]thiophen-2-yl)diphenylsilane), BmPyPhB (1,3-bis[3,5-di(pyridin-3-yl)phenyl]benzene) and/or BTB (4,4'-bis-[2-(4,6-diphenyl-1,3,5-triazinyl)]-1,1'-biphenyl). Optionally, the ETL may be doped with materials such as Liq. The electron transport layer (ETL) may also block holes or a hole blocking layer (HBL) is introduced.

The HBL may, for example, include BCP (2,9-dimethyl-4,7-diphenyl-1,10-phenanthroline=Bathocuproine), BAlq (bis(8-hydroxy-2-methylquinoline)-(4-phenylphenoxy)aluminum), NBphen (2,9-bis(naphthalen-2-yl)-4,7-diphenyl-1,10-phenanthroline), Alqa (Aluminum-tris(8-hydroxyquinoline)), TSPO1 (diphenyl-4-triphenylsilylphenyl-phosphinoxide), T2T (2,4,6-tris(biphenyl-3-yl)-1,3,5-triazine), T3T (2,4,6-tris(triphenyl-3-yl)-1,3,5-triazine), TST (2,4,6-tris(9,9'-spirobifluorene-2-yl)-1,3,5-triazine), and/or TCB/TCP (1,3,5-tris(N-carbazolyl)benzol/1,3,5-tris (carbazol)-9-yl)benzene).

Adjacent to the electron transport layer (ETL), a cathode layer C may be located. For example, the cathode layer C may include or may consist of a metal (e.g., Al, Au, Ag, Pt, Cu, Zn, Ni, Fe, Pb, LiF, Ca, Ba, Mg, In, W, or Pd) or a metal alloy. For practical reasons, the cathode layer may also consist of (essentially) intransparent metals such as Mg, Ca or Al. Alternatively or additionally, the cathode layer C may also include graphite and or carbon nanotubes (CNTs). Alternatively, the cathode layer C may also consist of nanoscalic silver wires.

An OLED may further, optionally, include a protection layer between the electron transport layer (ETL) and the cathode layer C (which may be designated as electron injection layer (EIL)). This layer may include lithium fluoride, cesium fluoride, silver, Liq (8-hydroxyquinolinolatolithium), $Li_2O$, $BaF_2$, MgO and/or NaF.

Optionally, also the electron transport layer (ETL) and/or a hole blocking layer (HBL) may include one or more host compounds H.

In order to modify the emission spectrum and/or the absorption spectrum of the light-emitting layer EML further, the light-emitting layer EML may further include one or more additional emitter molecules F. Such an emitter molecule F may be any emitter molecule known in the art. Preferably such an emitter molecule F is a molecule with a structure differing from the structure of the molecules according to the invention E. The emitter molecule F may optionally be a TADF emitter. Alternatively, the emitter molecule F may optionally be a fluorescent and/or phosphorescent emitter molecule which is able to shift the emission spectrum and/or the absorption spectrum of the light-emitting layer EML. Exemplarily, the triplet and/or singlet excitons may be transferred from the emitter molecule according to the invention E to the emitter molecule F before relaxing to the ground state S0 by emitting light typically red-shifted in comparison to the light emitted by emitter molecule E. Optionally, the emitter molecule F may also provoke two-photon effects (i.e., the absorption of two photons of half the energy of the absorption maximum).

Optionally, an organic electroluminescent device (e.g., an OLED) may exemplarily be an essentially white organic electroluminescent device. Exemplarily such a white organic electroluminescent device may include at least one (deep) blue emitter molecule and one or more emitter molecules emitting green and/or red light. Then, there may also optionally be energy transmittance between two or more molecules as described above.

As used herein, if not defined more specifically in the particular context, the designation of the colors of emitted and/or absorbed light is as follows:

violet: wavelength range of >380-420 nm;
deep blue: wavelength range of >420-480 nm;
sky blue: wavelength range of >480-500 nm;
green: wavelength range of >500-560 nm;
yellow: wavelength range of >560-580 nm;
orange: wavelength range of >580-620 nm;
red: wavelength range of >620-800 nm.

With respect to emitter molecules, such colors refer to the emission maximum. Therefore, for example, a deep blue emitter has an emission maximum in the range of from >420 to 480 nm, a sky blue emitter has an emission maximum in the range of from >480 to 500 nm, a green emitter has an emission maximum in a range of from >500 to 560 nm, and a red emitter has an emission maximum in a range of from >620 to 800 nm.

A green emitter may preferably have an emission maximum between 500 and 560 nm, more preferably between 510 and 550 nm, and even more preferably between 520 and 540 nm.

A further embodiment of the present invention relates to an OLED, which emits light with CIEx and CIEy color coordinates close to the CIEx (=0.170) and CIEy (=0.797) color coordinates of the primary color green (CIEx=0.170 and CIEy=0.797) as defined by ITU-R Recommendation BT.2020 (Rec. 2020) and thus is suited for the use in Ultra High Definition (UHD) displays, e.g. UHD-TVs. In this context, the term “close to” refers to the ranges of CIEx and CIEy coordinates provided at the end of this paragraph. In commercial applications, typically top-emitting (top-electrode is transparent) devices are used, whereas test devices as used throughout the present application represent bottom-emitting devices (bottom-electrode and substrate are transparent). Accordingly, a further aspect of the present invention relates to an OLED, whose emission exhibits a CIEx color coordinate of between 0.06 and 0.34, preferably between 0.07 and 0.29, more preferably between 0.09 and 0.24 or even more preferably between 0.12 and 0.22 or even between 0.14 and 0.19 and/or a CIEy color coordinate of between 0.44 and 0.84, preferably between 0.55 and 0.83, more preferably between 0.65 and 0.82 or even more preferably between 0.70 and 0.81 or even between 0.75 and 0.8.

Accordingly, a further aspect of the present invention relates to an OLED, which exhibits an external quantum efficiency at 14500 cd/$m^2$ of more than 10%, more preferably of more than 13%, more preferably of more than 15%, even more preferably of more than 17% or even more than 20% and/or exhibits an emission maximum between 495 nm and 580 nm, preferably between 500 nm and 560 nm, more preferably between 510 nm and 550 nm, even more preferably between 515 nm and 540 nm and/or exhibits a LT97 value at 14500 cd/$m^2$ of more than 100 h, preferably more than 250 h, more preferably more than 500 h, even more preferably more than 750 h or even more than 1000 h.

A further aspect of the present invention relates to an OLED, which emits light at a distinct color point. According to the present invention, the OLED emits light with a narrow emission band (small full width at half maximum (FWHM)). In one aspect, the OLED according to the invention emits light with a FWHM of the main emission peak of less than 0.50 eV, preferably less than 0.48 eV, more preferably less than 0.45 eV, even more preferably less than 0.43 eV or even less than 0.40 eV.

In a further aspect, the invention relates to a method for producing an optoelectronic component. In this case an organic molecule of the invention is used.

The organic electroluminescent device, in particular the OLED according to the present invention can be fabricated by any means of vapor deposition and/or liquid processing. Accordingly, at least one layer is

- prepared by means of a sublimation process,
- prepared by means of an organic vapor phase deposition process,
- prepared by means of a carrier gas sublimation process, and/or
- solution processed or printed.

The methods used to fabricate the organic electroluminescent device, in particular the OLED according to the present invention are known in the art. The different layers are individually and successively deposited on a suitable substrate by means of subsequent deposition processes. The individual layers may be deposited using the same or differing deposition methods.

Vapor deposition processes may include thermal (co) evaporation, chemical vapor deposition and physical vapor deposition. For active matrix OLED display, an AMOLED backplane is used as substrate. The individual layer may be processed from solutions or dispersions employing adequate solvents. Solution deposition process exemplarily include spin coating, dip coating and jet printing. Liquid processing may optionally be carried out in an inert atmosphere (e.g., in a nitrogen atmosphere) and the solvent may optionally be completely or partially removed by means known in the state of the art.

EXAMPLES

General synthesis scheme I

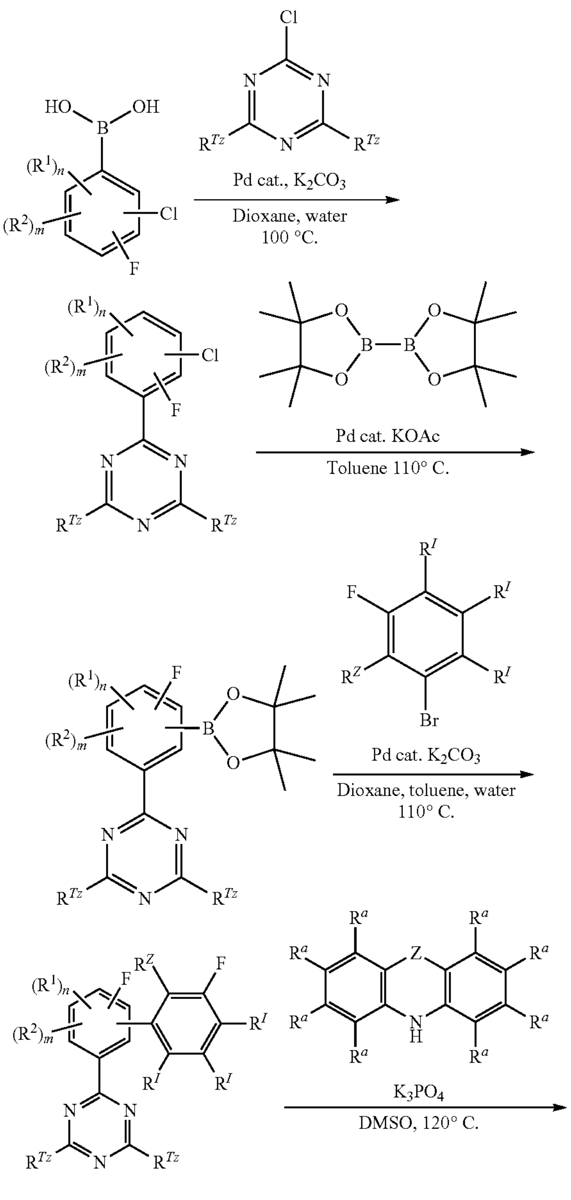

-continued
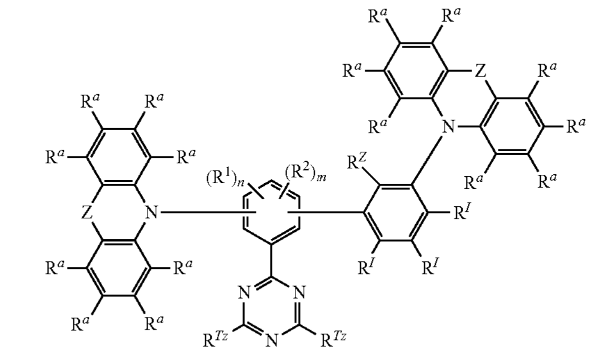
n = 1 or 2
m = 1 or 2
n + m = 3
-continued
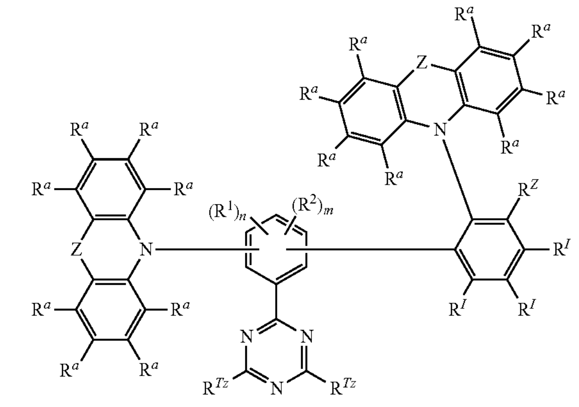
n = 1 or 2
m = 1 or 2
n + m = 3
General synthesis scheme II
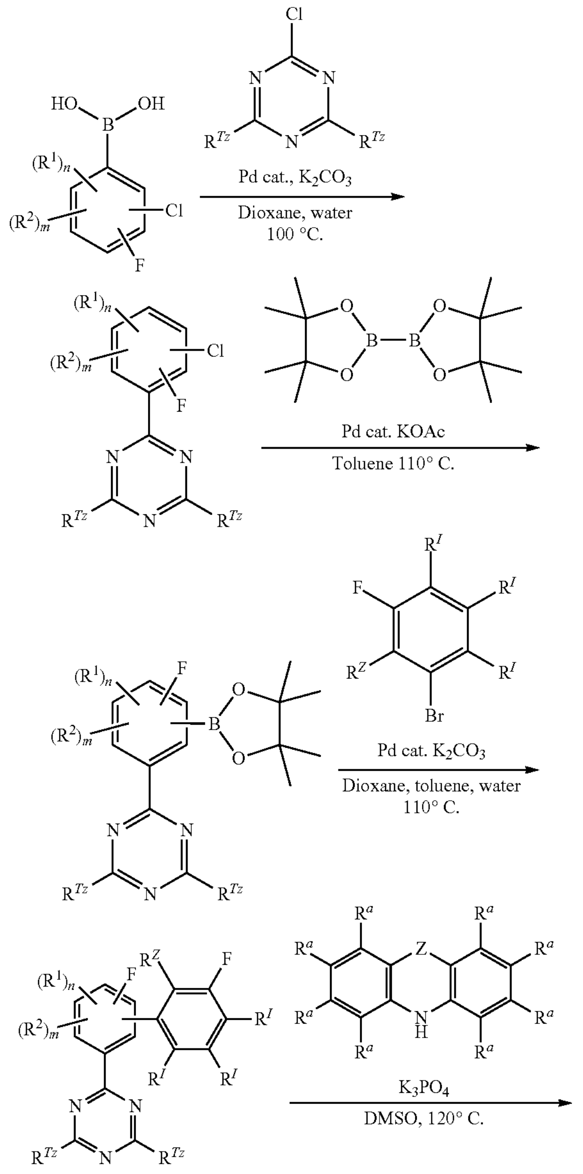
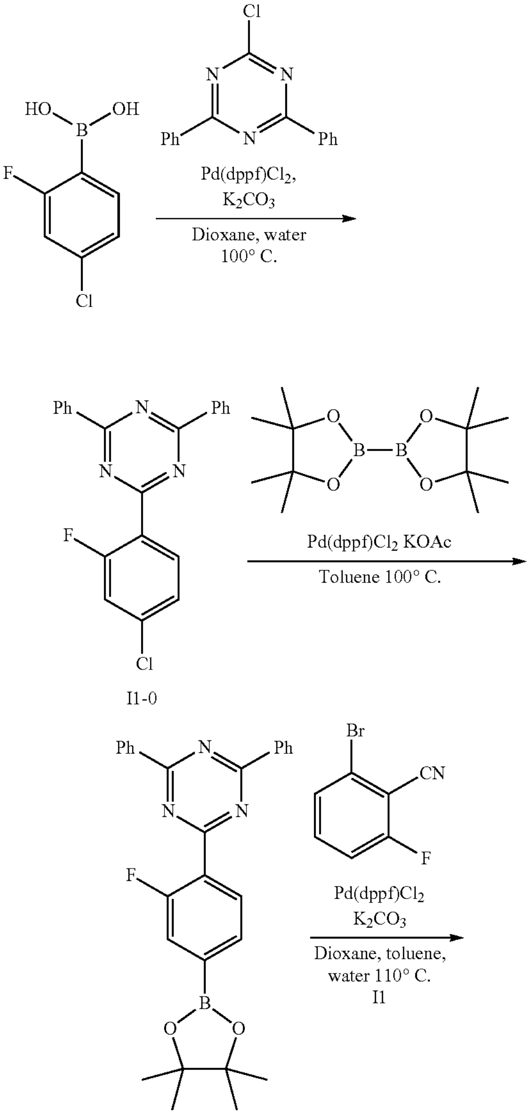
I1

-continued

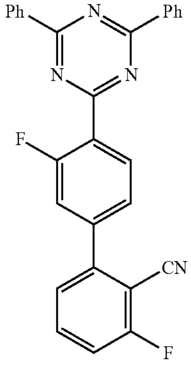

Z1

4-chloro-2-fluorophenylboronic ester (1.10 equivalents), 2-chloro-4,6-diphenyl-1,3,5-triazine (1.00 equivalents), $Pd(dppf)Cl_2$ ([1,1'-Bis(diphenylphosphino)ferrocene]dichloropalladium(II)]; 0.03 equivalents), and potassium carbonate (2.50 equivalents) were stirred under nitrogen atmosphere in a dioxane/water mixture (ratio of 9:1) at 100° C. for 16 h. The crude product was precipitated from water, filter off and washed with ethanol. The product 11-0 was obtained as a solid.

In a subsequent reaction, I1-0 (1.00 equivalents), bis (pinacolato)diboron (1.50 equivalents), $Pd(dppf)Cl_2$ ([1,1'-Bis(diphenylphosphino)ferrocene]dichloropalladium(II)]; 0.05 equivalents), and potassium acetate (6.00 equivalents) were stirred under nitrogen atmosphere in toluene at 110° C. for 20 h. Subsequently, the reaction mixture was cooled down to room temperature and extracted with ethyl acetate and water. The combined organic phases were dried over MgSO4 and the solvent was evaporated under reduced pressure. The crude product was dissolved in toluene and passed through a short silica column and the solvent was evaporated. The obtained solid was heated in ethanol under reflux for 2 h. The product was hot filtered and 11 was obtained as a solid.

In a subsequent reaction, I1 (1.00 equivalents), 2-bromo-6-fluorobenzonitrile (1.20 equivalents), $Pd(dppf)Cl_2$ ([1,1'-Bis(diphenylphosphino)ferrocene]dichloropalladium(II)]; 0.05 equivalents), and potassium carbonate (2.00 equivalents) were stirred under nitrogen atmosphere in a toluene/dioxane/water mixture (ratio of 5:5:1) at 110° C. for 16 h. Subsequently, the reaction mixture was cooled down to room temperature. The precipitated crude product was filtered off and washed with a mixture of water and methanol. The combined crude product was heated in ethanol under reflux for 1 h. The product was hot filtered, followed by washing with ethanol and Z1 was obtained as a solid.

General Procedure for Synthesis AAV2:

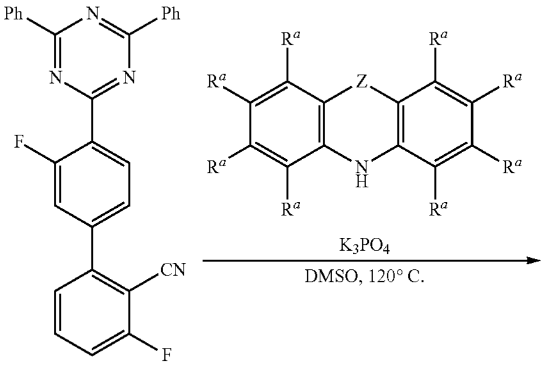

Z1

-continued

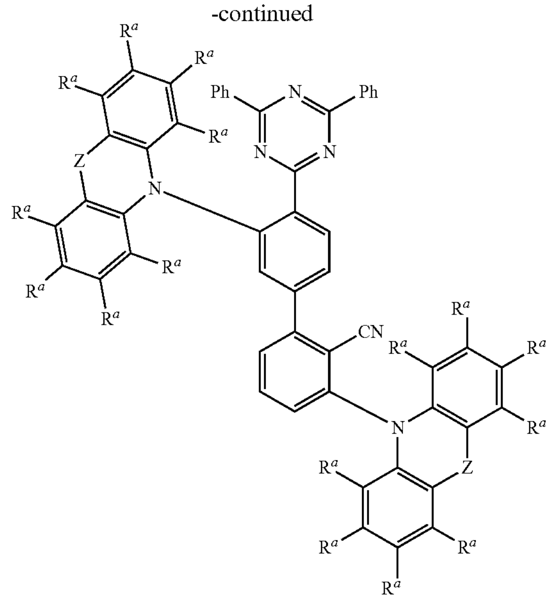

Z1 (1.00 equivalents), the corresponding donor molecule D-H (2.20 equivalents) and tribasic potassium phosphate (5.00 equivalents) were suspended under nitrogen atmosphere in DMSO and stirred at 120° C. for 20 h. Subsequently, the reaction mixture was poured into a stirred mixture of water and ice. The precipitate was filtered off, followed by washing with water and cold ethanol. The crude products was heated in ethyl acetate under reflux for 2 h. The product was hot filtered, followed by washing with ethanol. It was obtained as a solid.

In particular, the donor molecule D-H was a 3,6-substituted carbazole (e.g., 3,6-dimethylcarbazole, 3,6-diphenylcarbazole, 3,6-di-tert-butylcarbazole), a 2,7-substituted carbazole (e.g., 2,7-dimethylcarbazole, 2,7-diphenylcarbazole, 2,7-di-tert-butylcarbazole), a 1,8-substituted carbazole (e.g., 1,8-dimethylcarbazole, 1,8-diphenylcarbazole, 1,8-di-tert-butylcarbazole), a 1-substituted carbazole (e.g., 1-methylcarbazole, 1-phenylcarbazole, 1-tert-butylcarbazole), a 2-substituted carbazole (e.g., 2-methylcarbazole, 2-phenylcarbazole, 2-tert-butylcarbazole), or a 3-substituted carbazole (e.g., 3-methylcarbazole, 3-phenylcarbazole, 3-tert-butylcarbazole).

Exemplarily, a halogen-substituted carbazole, particularly 3-bromocarbazole, can be used as D-H.

In a subsequent reaction, a boronic acid ester functional group or boronic acid functional group may be, for example, introduced at the position of the one or more halogen substituents, which was introduced via D-H, to yield the corresponding carbazol-3-ylboronic acid ester or carbazol-3-ylboronic acid, e.g., via the reaction with bis(pinacolato) diboron (CAS No. 73183-34-3). Subsequently, one or more substituents $R^a$ may be introduced in place of the boronic acid ester group or the boronic acid group via a coupling reaction with the corresponding halogenated reactant $R^a$-Hal, preferably $R^a$—Cl and $R^a$—Br.

Alternatively, one or more substituents $R^a$ may be introduced at the position of the one or more halogen substituents, which was introduced via D-H, via the reaction with a boronic acid of the substituent $R^a$ [$R^a$—$B(OH)_2$] or a corresponding boronic acid ester.

Cyclic Voltammetry

Cyclic voltammograms were measured from solutions having concentration of 104 mol/L of the organic molecules in dichloromethane or a suitable solvent and a suitable supporting electrolyte (e.g. 0.1 mol/L of tetrabutylammonium hexafluorophosphate). The measurements were conducted at room temperature under nitrogen atmosphere with a three-electrode assembly (Working and counter electrodes: Pt wire, reference electrode: Pt wire) and calibrated using $FeCp_2/FeCp_2^+$ as internal standard. The HOMO data was corrected using ferrocene as internal standard against a saturated calomel electrode (SCE).

Density Functional Theory Calculation

Molecular structures were optimized employing the BP86 functional and the resolution of identity approach (RI). Excitation energies were calculated using the (BP86) optimized structures employing Time-Dependent DFT (TD-DFT) methods. Orbital and excited state energies were calculated with the B3LYP functional. Def2-SVP basis sets (and an m4-grid for numerical integration were used. The Turbomole program package was used for all calculations.

Photophysical Measurements

Sample Pretreatment: Spin-Coating

Apparatus: Spin150, SPS euro.

The sample concentration was 10 mg/ml, dissolved in a suitable solvent.

Program: 1) 3 s at 400 U/min; 2) 20 s at 1000 U/min at 1000 Upm/s. 3) 10 s at 4000 U/min at 1000 Upm/s. After coating, the films were tried at 70° C. for 1 min.

Photoluminescence Spectroscopy and TCSPC (Time-Correlated Single-Photon Counting)

Steady-state emission spectroscopy was measured by a Horiba Scientific, Modell FluoroMax-4 equipped with a 150 W Xenon-Arc lamp, excitation- and emissions monochromators and a Hamamatsu $R^{928}$ photomultiplier and a time-correlated single-photon counting option. Emissions and excitation spectra were corrected using standard correction fits.

Excited state lifetimes were determined employing the same system using the TCSPC method with FM-2013 equipment and a Horiba Yvon TCSPC hub.

Excitation Sources:

NanoLED 370 (wavelength: 371 nm, puls duration: 1.1 ns)

NanoLED 290 (wavelength: 294 nm, puls duration: <1 ns)

SpectraLED 310 (wavelength: 314 nm)

SpectraLED 355 (wavelength: 355 nm).

Data analysis (exponential fit) was done using the software suite DataStation and DAS6 analysis software. The fit was specified using the chi-squared-test.

Photoluminescence Quantum Yield Measurements

For photoluminescence quantum yield (PLQY) measurements an Absolute PL Quantum Yield Measurement C9920-03G system (Hamamatsu Photonics) was used. Quantum yields and CIE coordinates were determined using the software U6039-05 version 3.6.0.

Emission maxima were given in nm, quantum yields Φ in % and CIE coordinates as x, y values.

PLQY was determined using the following protocol:

Quality assurance: Anthracene in ethanol (known concentration) was used as reference Excitation wavelength: the absorption maximum of the organic molecule was determined and the molecule was excited using this wavelength Measurement Quantum yields were measured for sample of solutions or films under nitrogen atmosphere. The yield was calculated using the equation:

$$\Phi_{PL} = \frac{n_{photon},\ \text{emited}}{n_{photon},\ \text{absorbed}} = \frac{\int \frac{\lambda}{hc}\left[\text{Int}^{sample}_{emitted}(\lambda) - \text{Int}^{sample}_{absorbed}(\lambda)\right]d\lambda}{\int \frac{\lambda}{hc}\left[\text{Int}^{reference}_{emitted}(\lambda) - \text{Int}^{reference}_{absorbed}(\lambda)\right]d\lambda}$$

wherein $n_{photon}$ denotes the photon count and Int. denotes the intensity.

Production and Characterization of Organic Electroluminescence Devices

OLED devices including organic molecules according to the invention can be produced via vacuum-deposition methods. If a layer contains more than one compound, the weight-percentage of one or more compounds was given in %. The total weight-percentage values amount to 100%, thus if a value was not given, the fraction of this compound equals to the difference between the given values and 100%.

The (not fully optimized) OLEDs were characterized using standard methods and measuring electroluminescence spectra, the external quantum efficiency (in %) in dependency on the intensity, calculated using the light detected by the photodiode, and the current. The OLED device lifetime was extracted from the change of the luminance during operation at constant current density. The LT50 value corresponds to the time, where the measured luminance decreased to 50% of the initial luminance, analogously LT80 corresponds to the time point, at which the measured luminance decreased to 80% of the initial luminance, and LT 95 to the time point, at which the measured luminance decreased to 95% of the initial luminance etc.

Accelerated lifetime measurements were performed (e.g. applying increased current densities). Exemplarily LT80 values at 500 $cd/m^2$ were determined using the following equation:

$$LT80\left(500\frac{cd^2}{m^2}\right) = LT80(L_0)\left(\frac{L_0}{500\frac{cd^2}{m^2}}\right)^{1.6}$$

wherein Lo denotes the initial luminance at the applied current density.

The values correspond to the average of several pixels (typically two to eight), the standard deviation between these pixels was given.

HPLC-MS:

HPLC-MS spectroscopy was performed on a HPLC by Agilent (1100 series) with MS-detector (Thermo LTQ XL). A reverse phase column 4.6 mm×150 mm, particle size 5.0 μm from Waters (without pre-column) was used in the HPLC. The HPLC-MS measurements were performed at room temperature (rt) with the solvents acetonitrile, water and THF in the following concentrations:

| | | |
|---|---|---|
| solvent A: | H2O (90%) | MeCN (10%) |
| solvent B: | H2O (10%) | MeCN (90%) |
| solvent C: | THF (100%) | |

From a solution with a concentration of 0.5 mg/ml an injection volume of 15 μL was taken for the measurements. The following gradient was used:

| Flow rate [ml/min] | time [min] | A[%] | B[%] | D[%] |
|---|---|---|---|---|
| 3 | 0 | 40 | 50 | 10 |
| 3 | 10 | 10 | 15 | 75 |
| 3 | 16 | 10 | 15 | 75 |
| 3 | 16.01 | 40 | 50 | 10 |
| 3 | 20 | 40 | 50 | 10 |

Ionisation of the probe was performed by APCI (atmospheric pressure chemical ionization).

Example 1

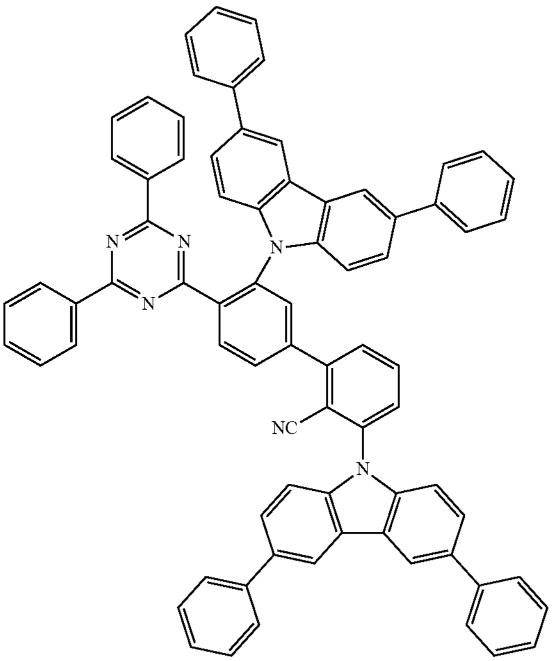 [SMILES: N#Cc1c(-c2ccc(-c3nc(-c4ccccc4)nc(-c4ccccc4)n3)c(-n3c4ccc(-c5ccccc5)cc4c4cc(-c5ccccc5)ccc43)c2)cccc1-n1c2ccc(-c3ccccc3)cc2c2cc(-c3ccccc3)ccc21]

Example 1 was synthesized according to AAV1 (41%) and AAV2 (quantitative yield).

MS (HPLC-MS):

| Molecular Formula | Retention Time | m/z calculated | m/z found |
|---|---|---|---|
| $C_{76}H_{48}N_6$ | 6.61 min | 1045.26 | 1045.80 |

The drawing depicts the emission spectrum of example 1 (10% by weight in PMMA). The emission maximum ($\lambda_{max}$) was at 509 nm. The photoluminescence quantum yield (PLQY) was 68%, the full width at half maximum (FWHM) was 0.44 eV and the emission lifetime was 16.6 μs. The resulting CIEx coordinate was determined at 0.27 and the CIEy coordinate at 0.49.

Example D1

Example 1 was tested in an optoelectronic device in the form of the OLED D1 which was fabricated with the following layer structure:

| Layer # | Thickness | D1 |
|---|---|---|
| 10 | 100 nm | Al |
| 9 | 2 nm | Liq |
| 8 | 20 nm | NBPhen |
| 7 | 10 nm | MAT1 |
| 6 | 50 nm | MAT2 (80%): Example 1 (20%) |
| 5 | 10 nm | MAT2 |
| 4 | 10 nm | TCTA |
| 3 | 50 nm | NPB |
| 2 | 5 nm | HAT-CN |
| 1 | 50 nm | ITO |
| Substrate | | Glass |

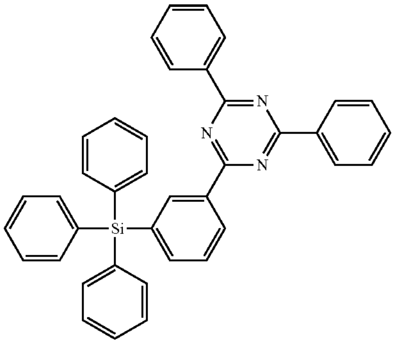

MAT1

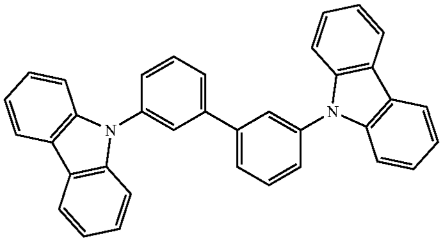

MAT2

OLED D1 yielded an external quantum efficiency (EQE) at 1000 cd/m$^2$ of 16.7%. The emission maximum was at 518 nm with a FWHM of 82 nm at 7.9 V. The corresponding CIEx value was 0.29 and the CIEy value was 0.58. A LT95-value at 1200 cd/m$^2$ of 42 h was determined.

Additional Examples of Organic Molecules of the Invention
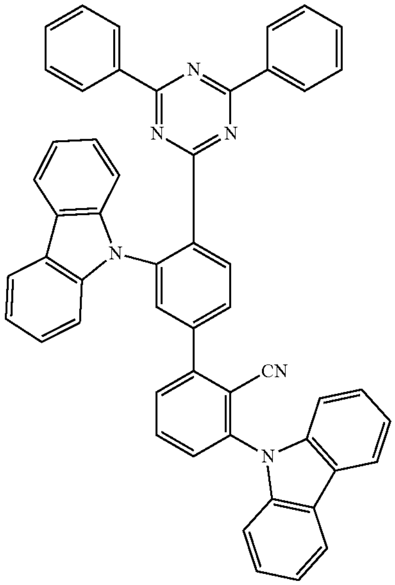
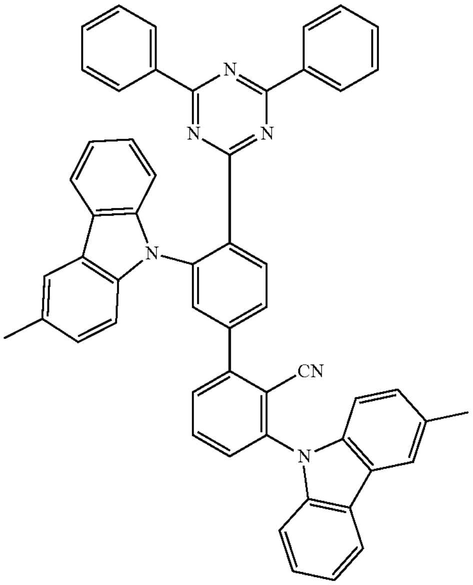
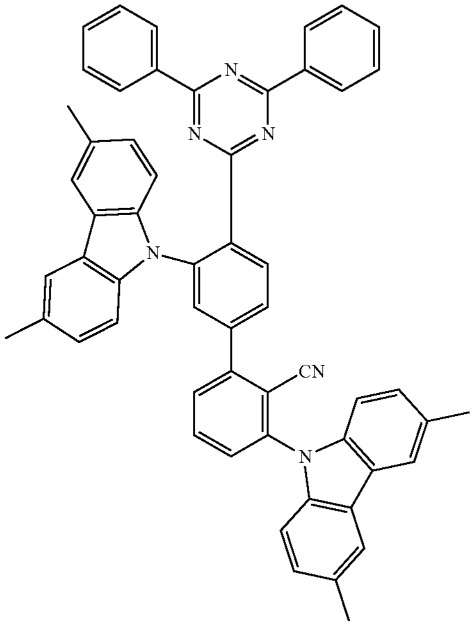
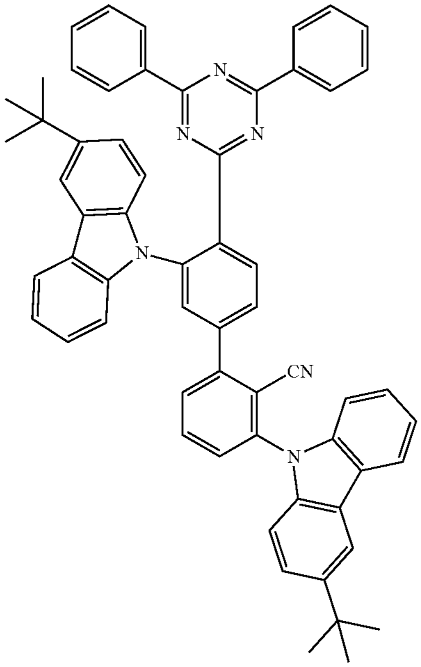

-continued
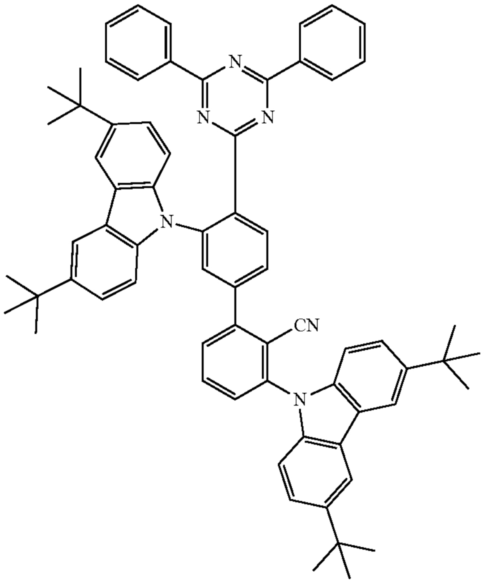
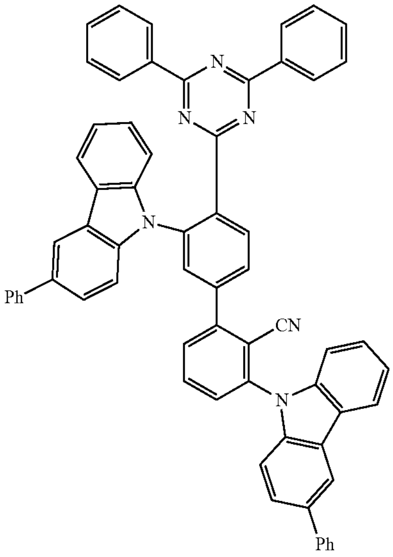
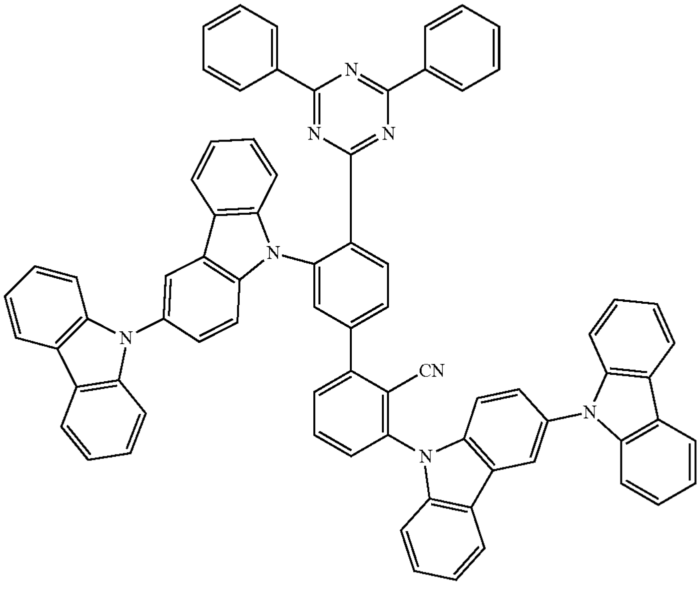

-continued
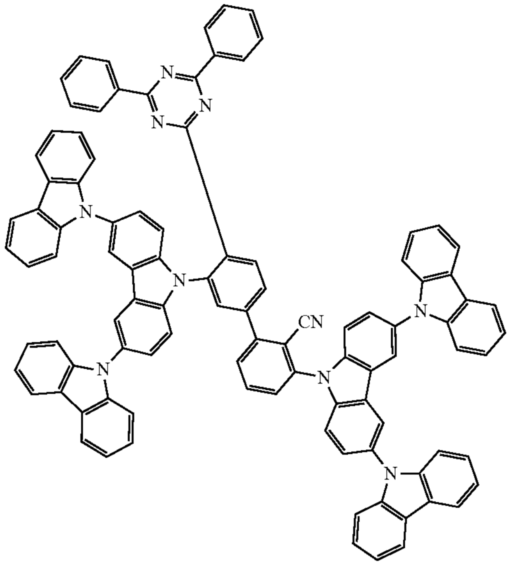
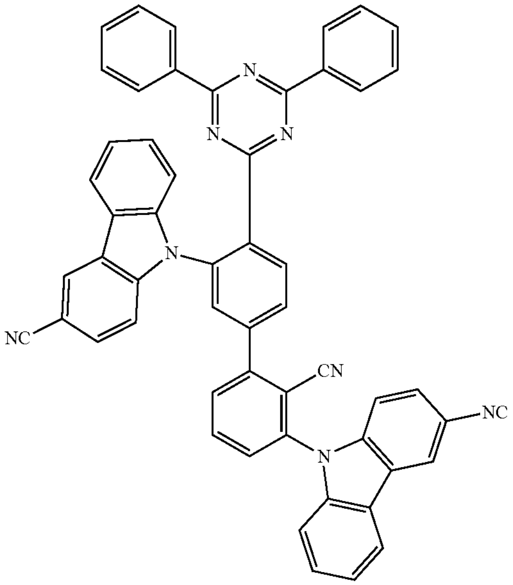
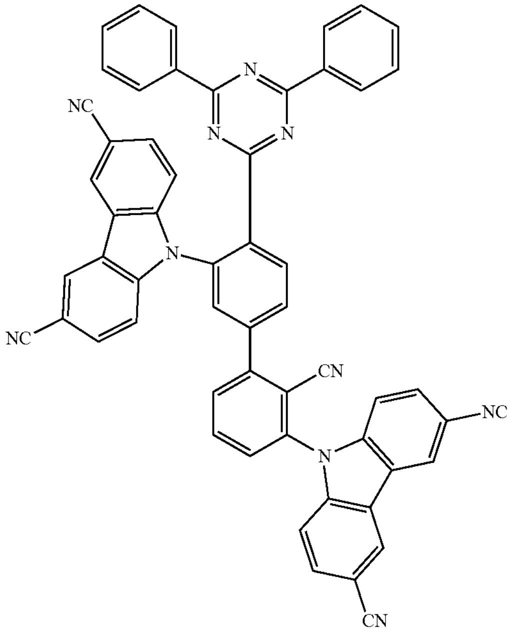
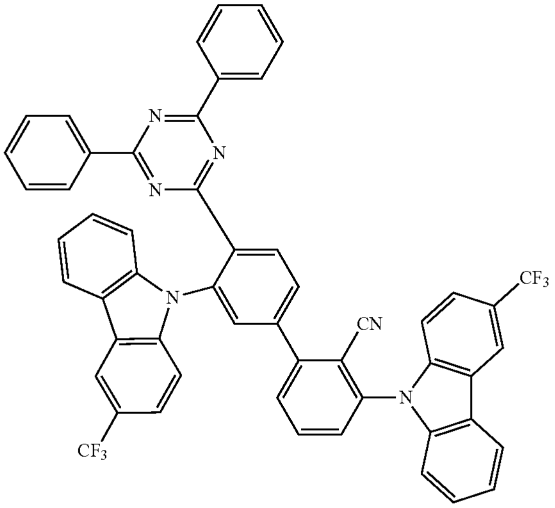

-continued
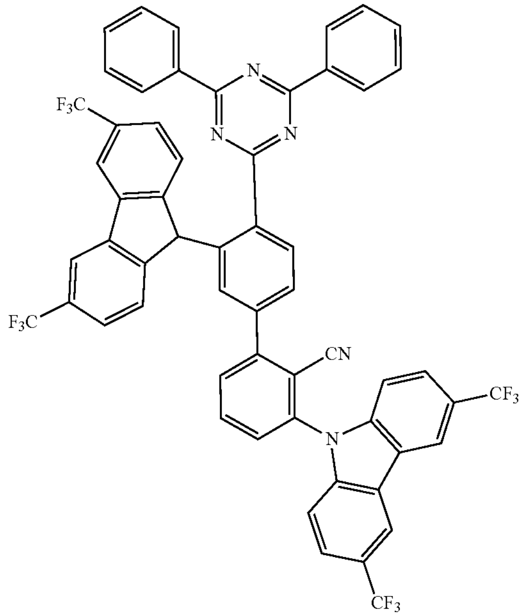
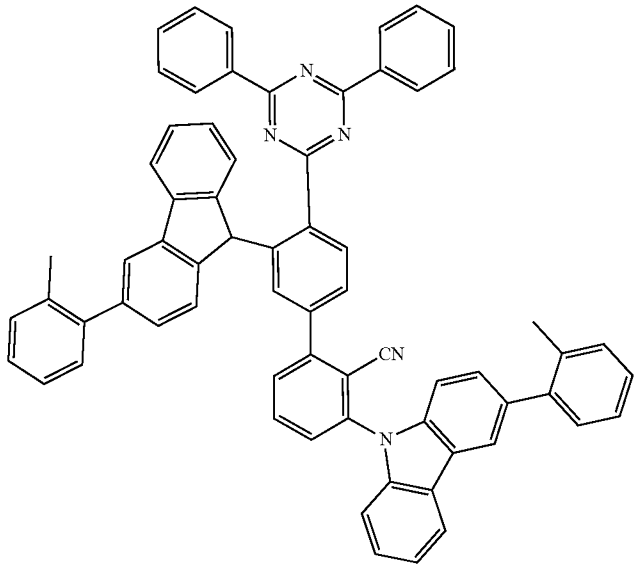
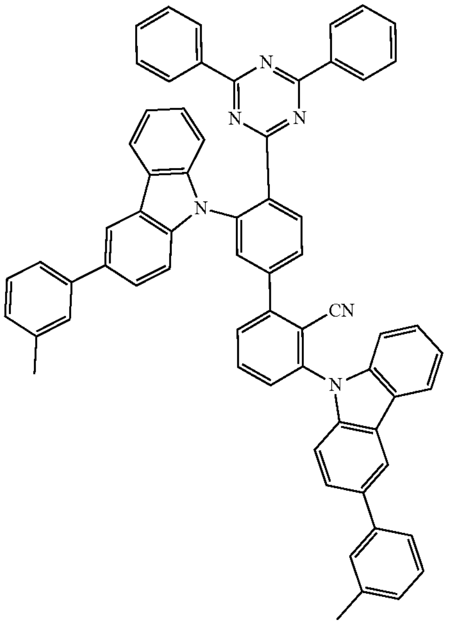

-continued
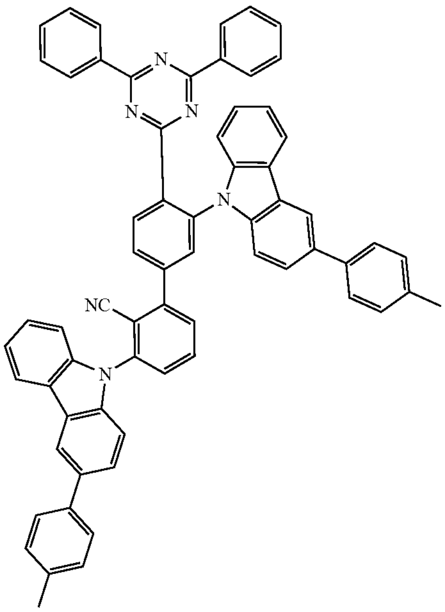
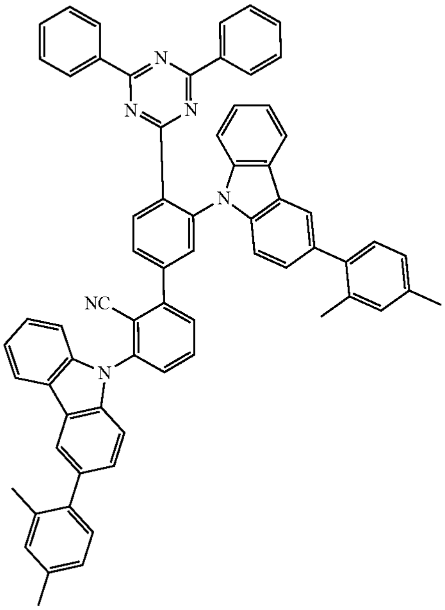
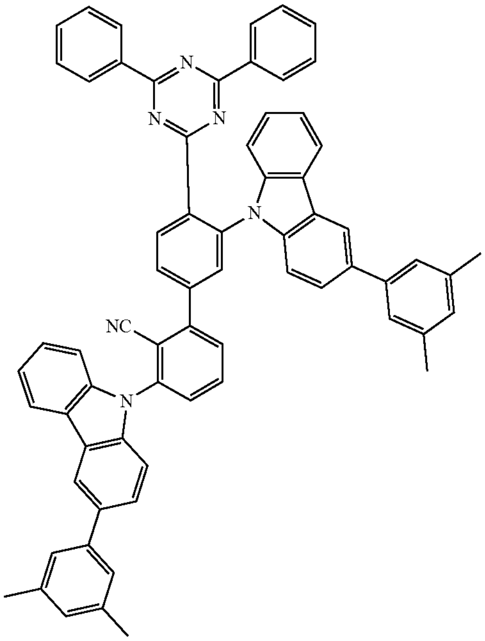
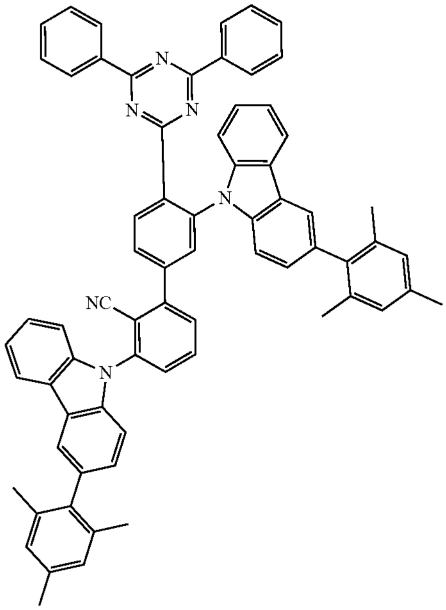

-continued
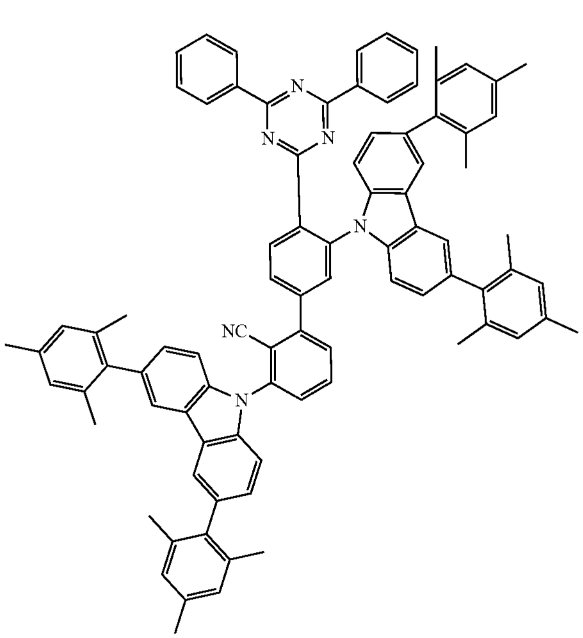
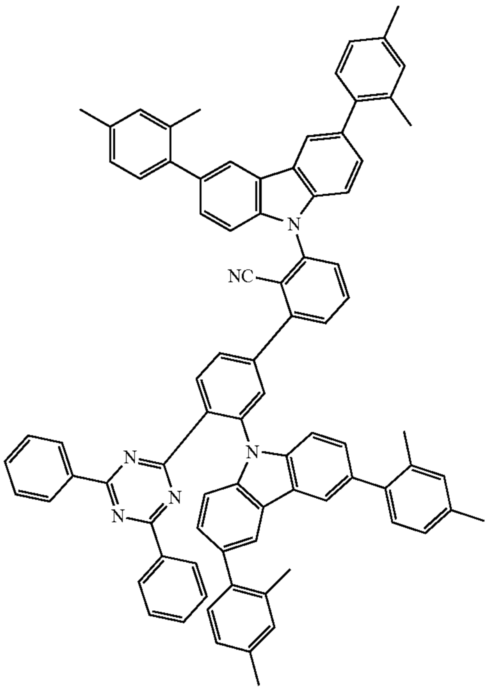
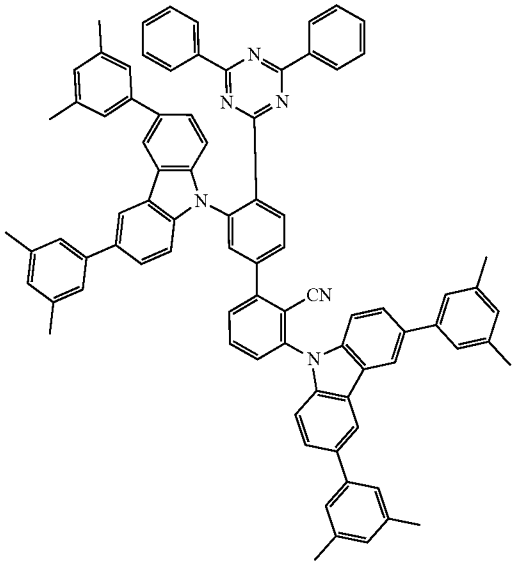
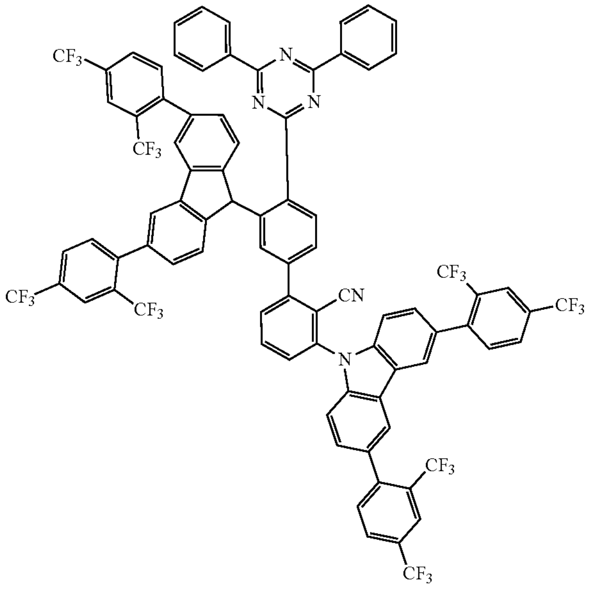

-continued
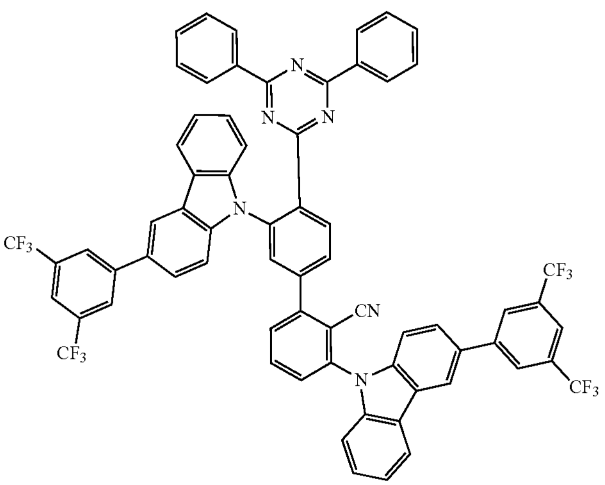
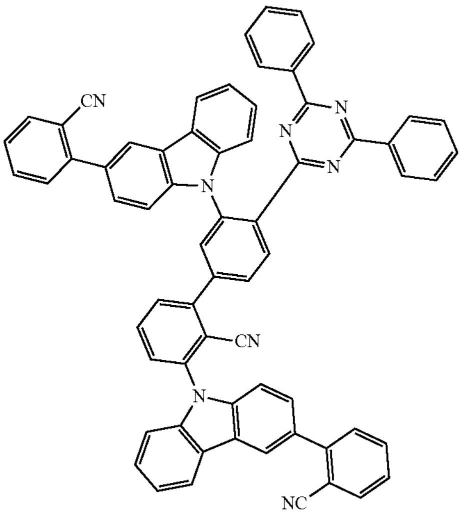
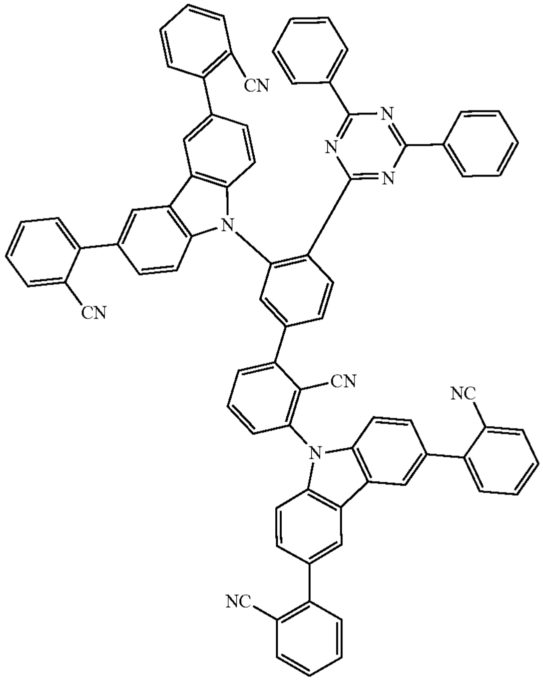
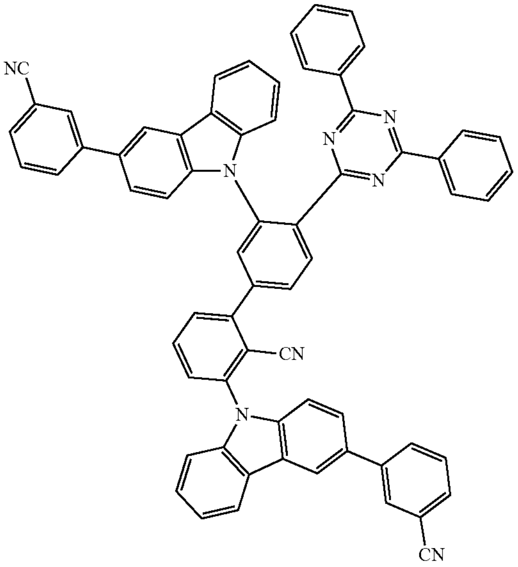

-continued
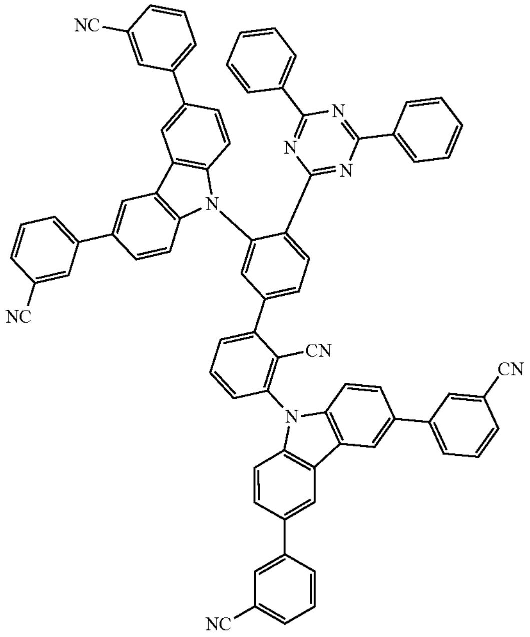
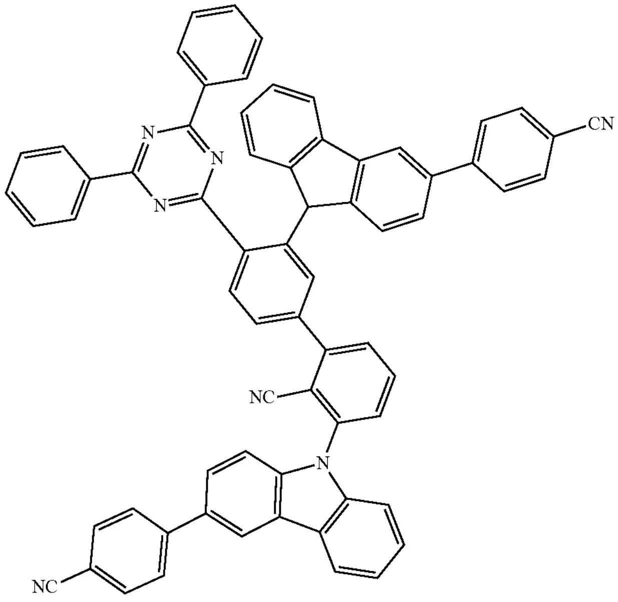

-continued
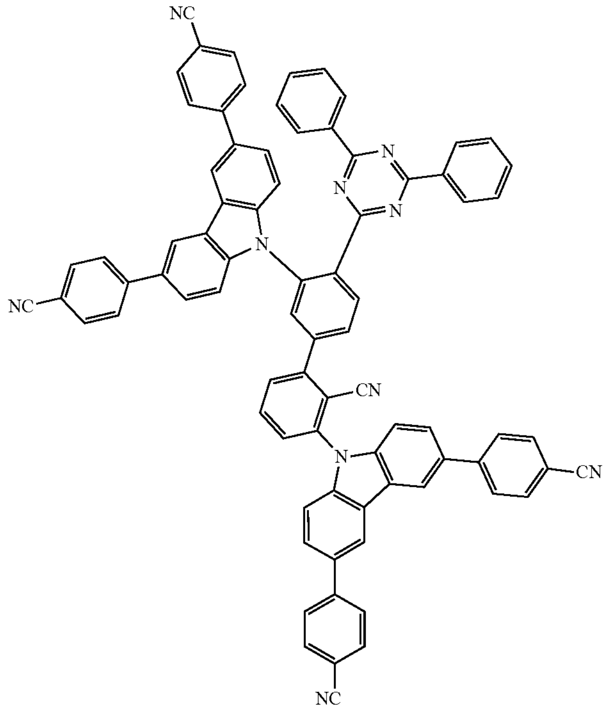
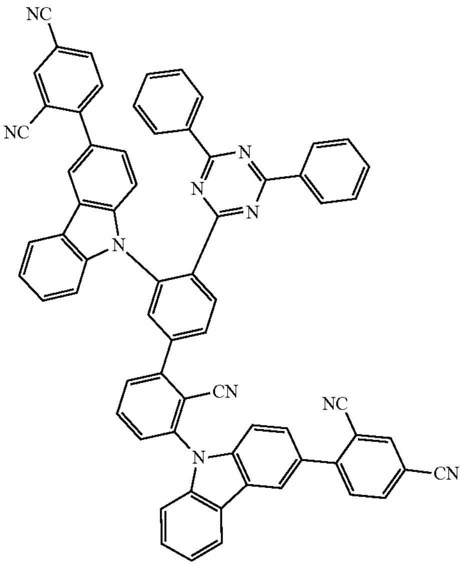
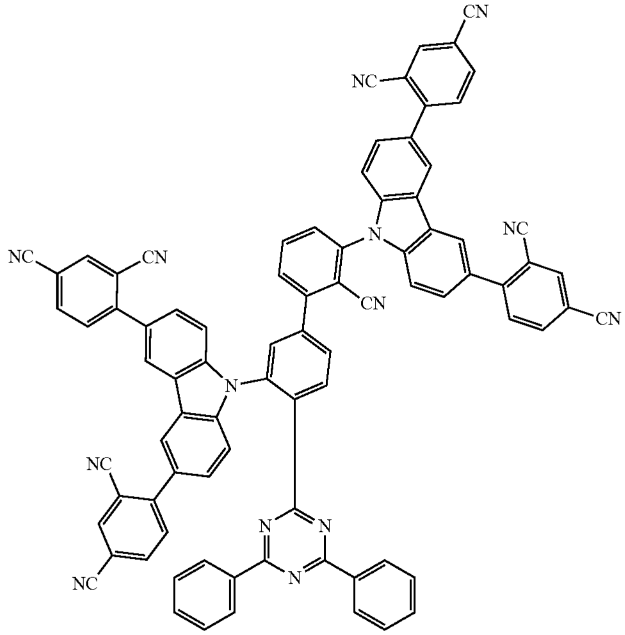

-continued
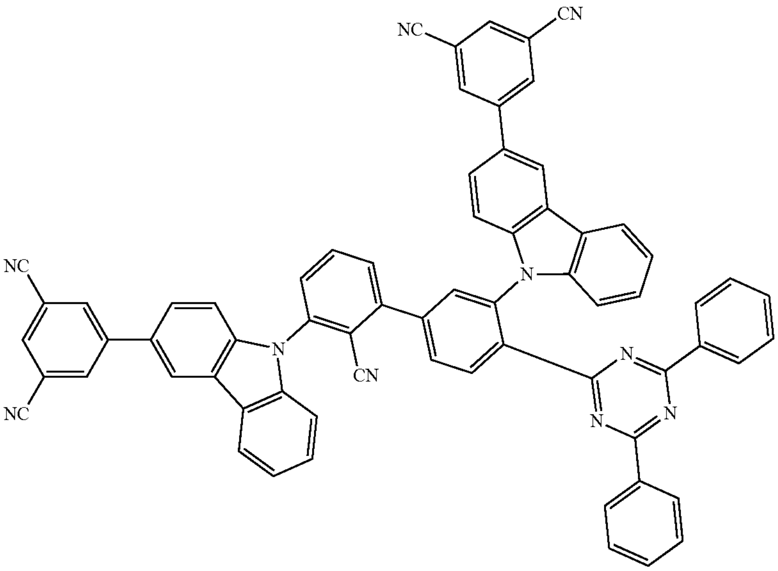
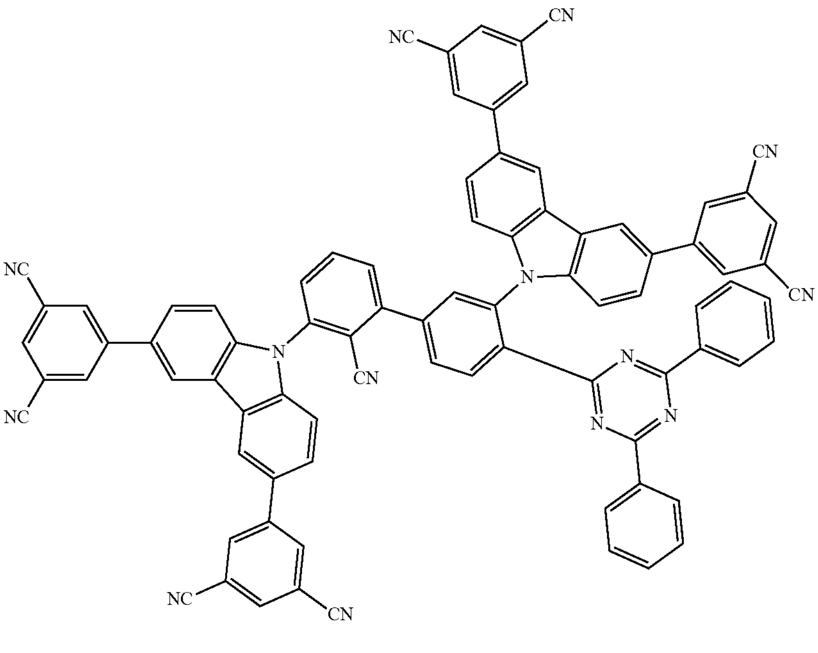

-continued
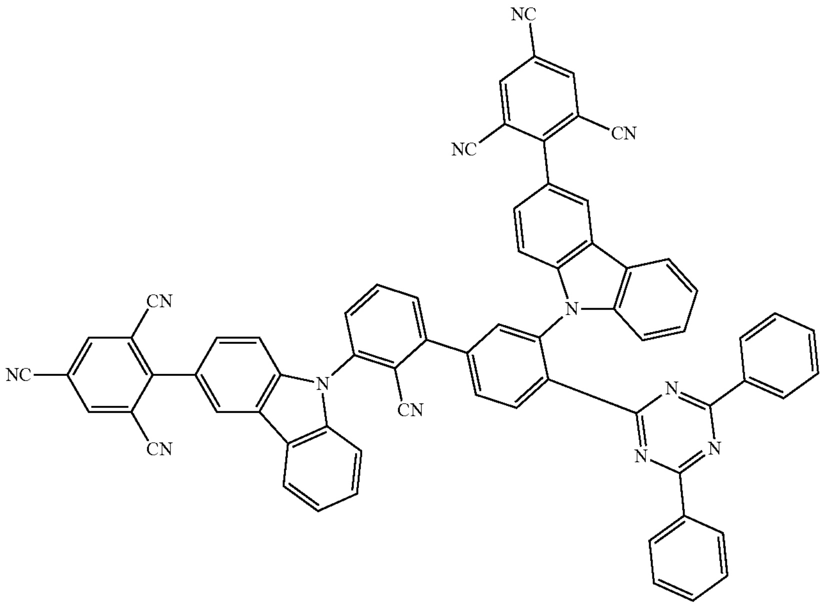
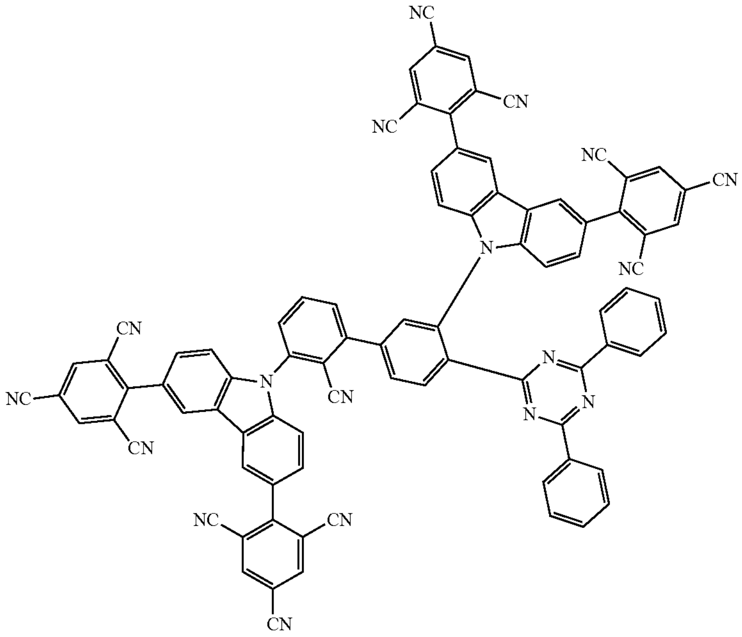

-continued
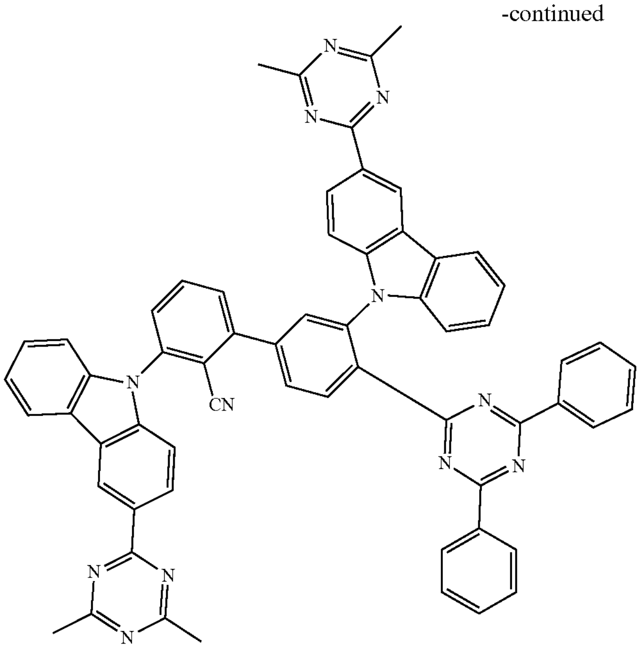
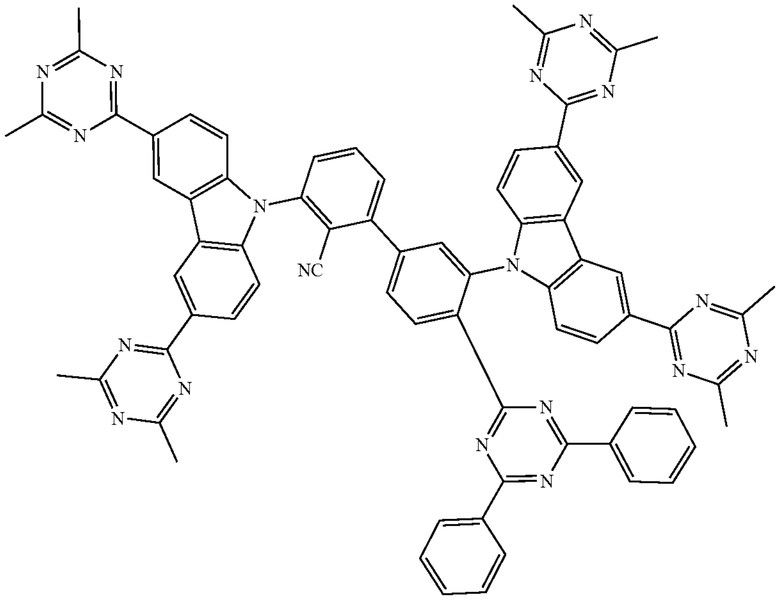

-continued
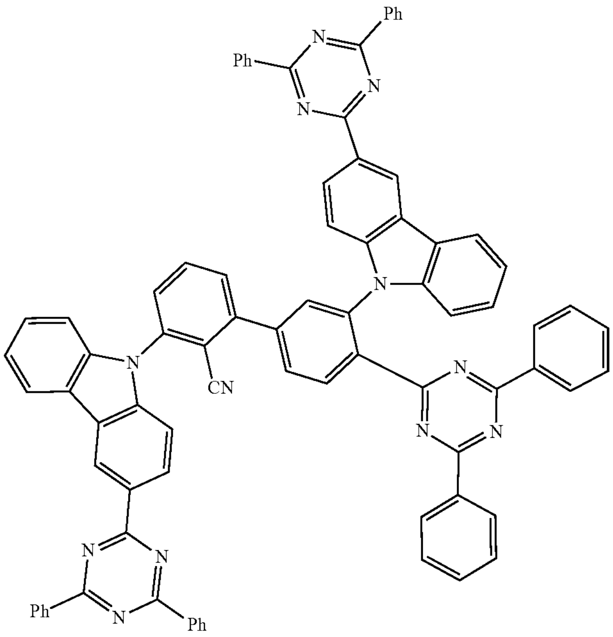
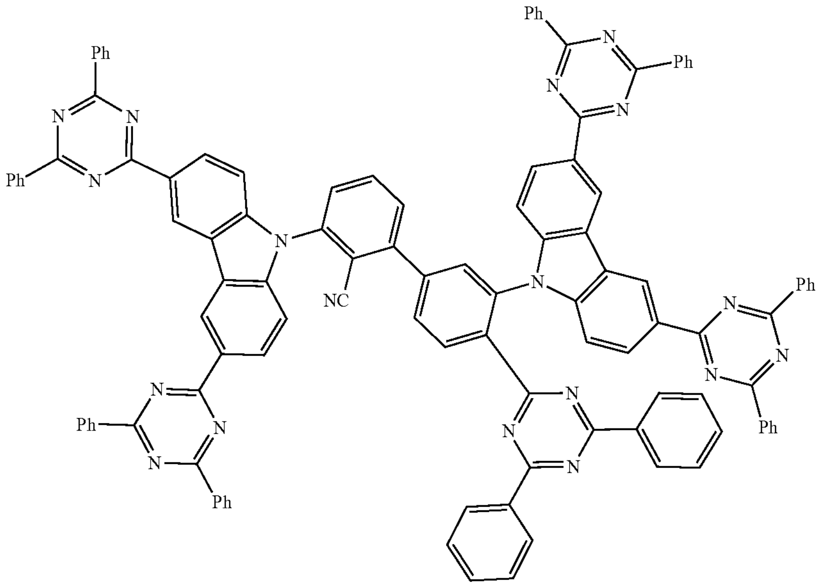

-continued
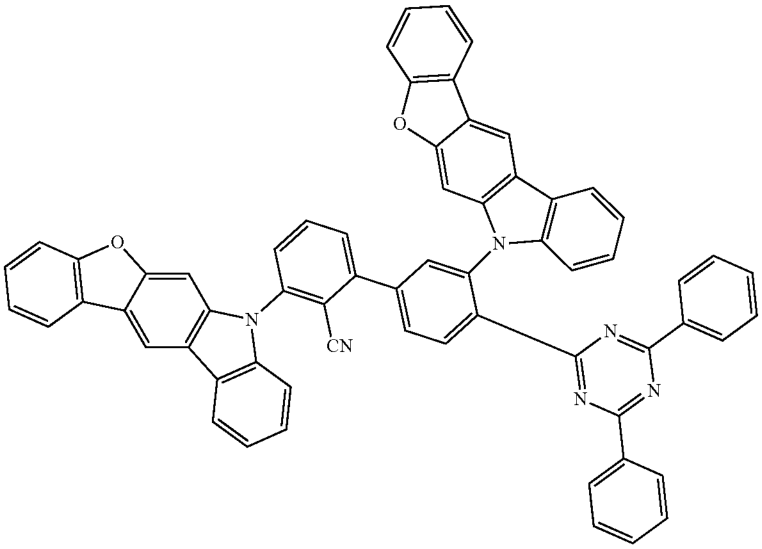
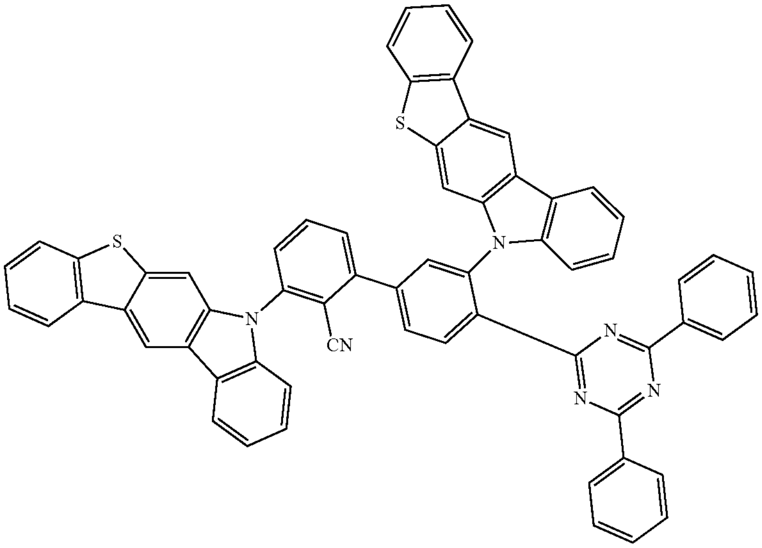
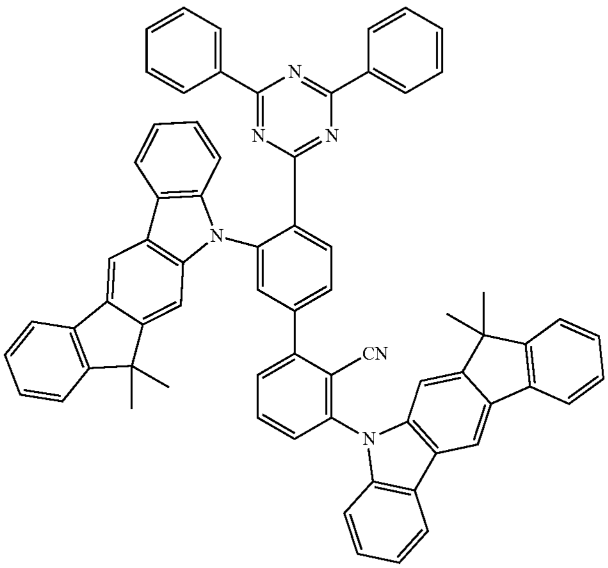

-continued
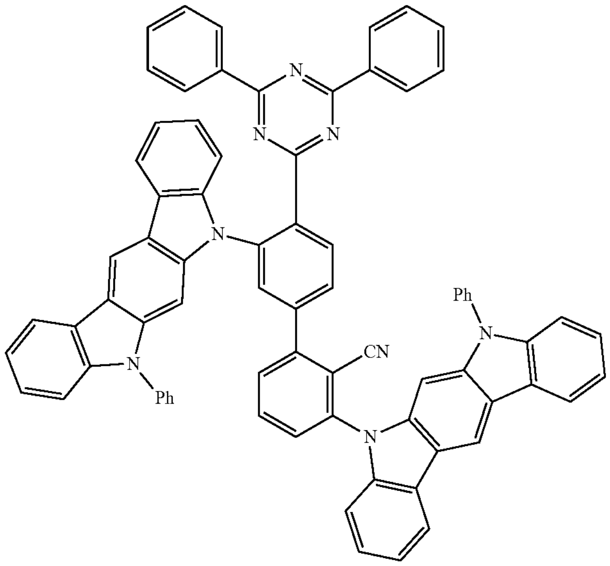
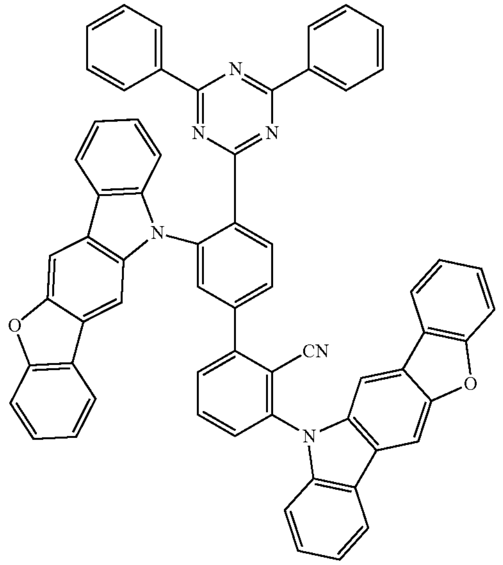
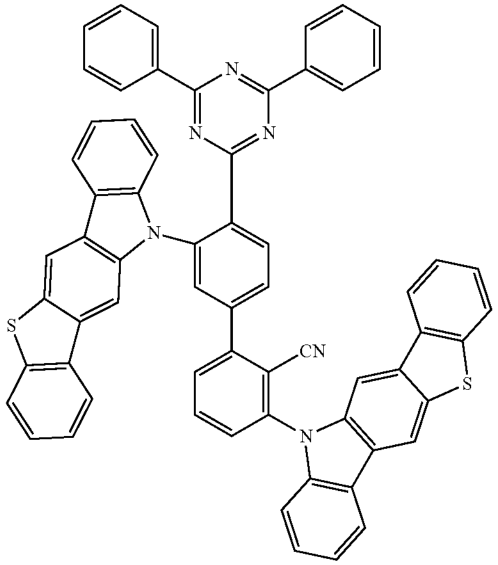
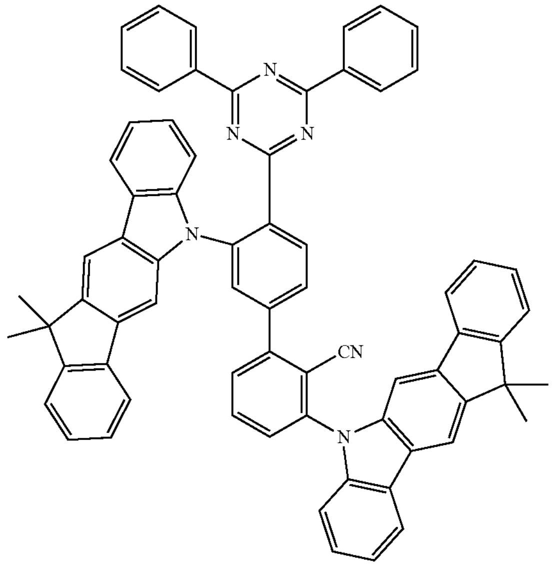
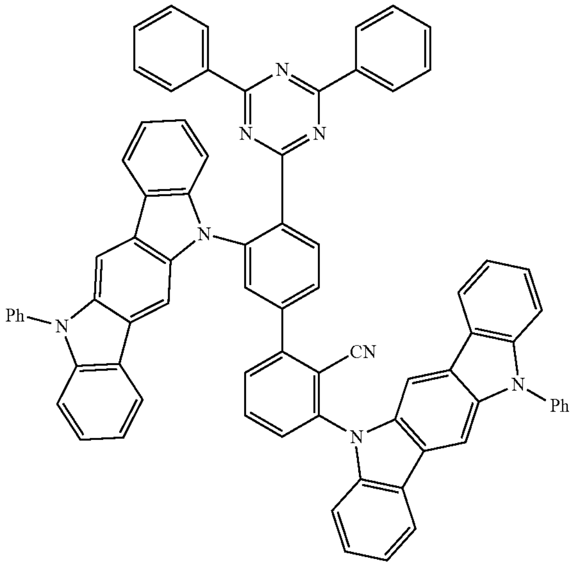

-continued
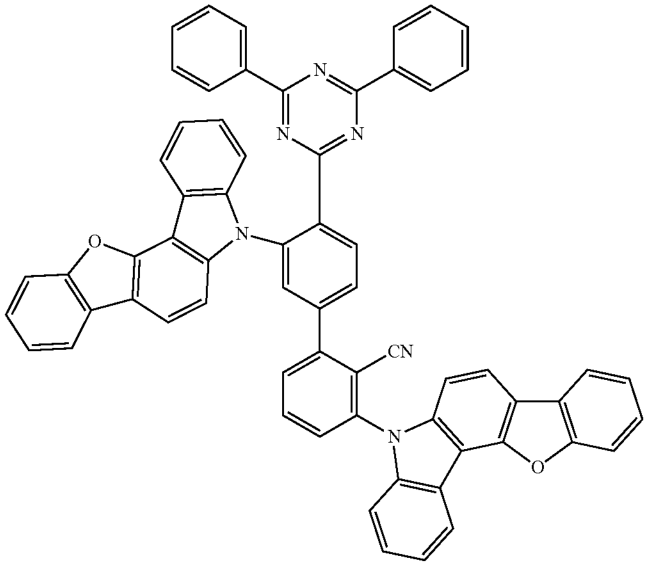
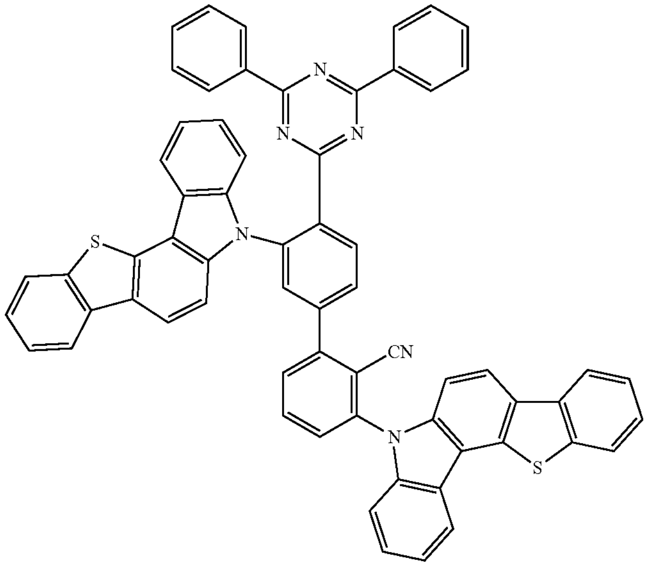
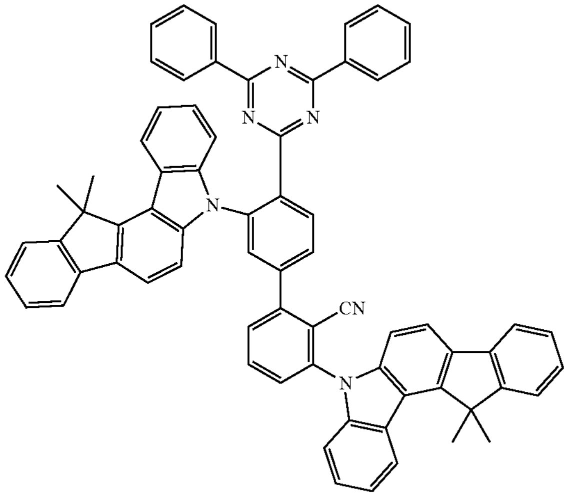
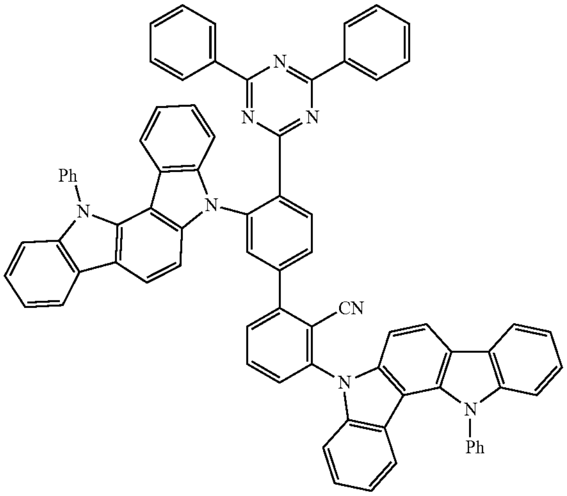

-continued
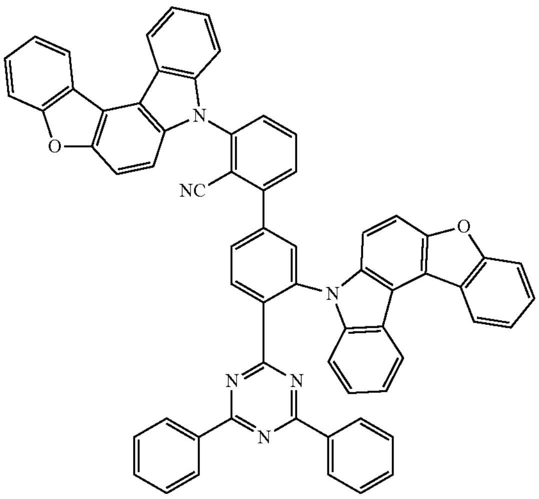
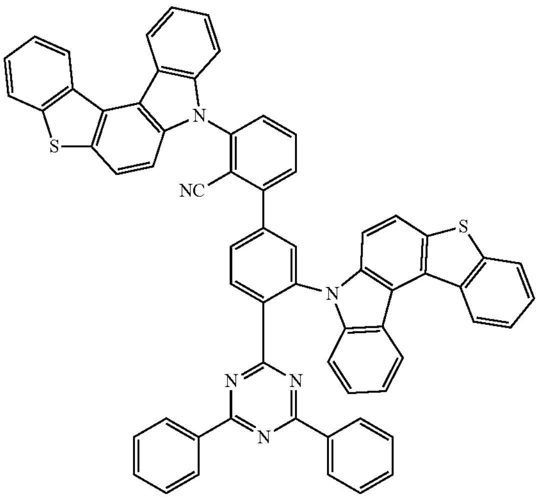
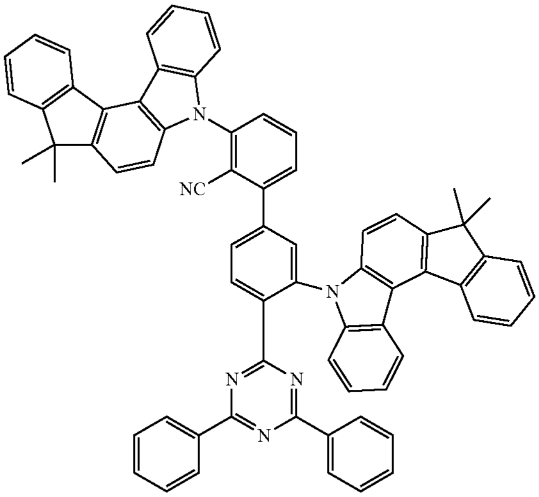
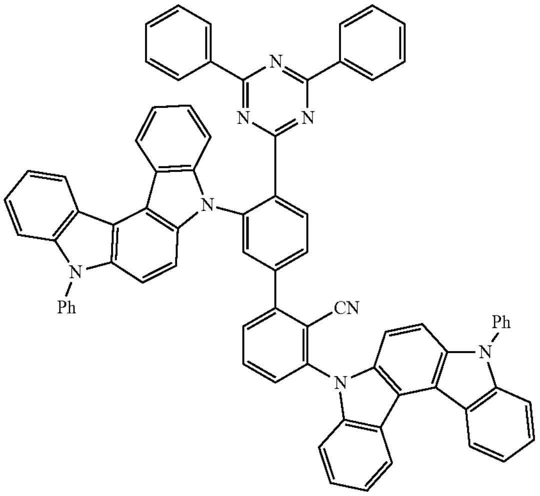
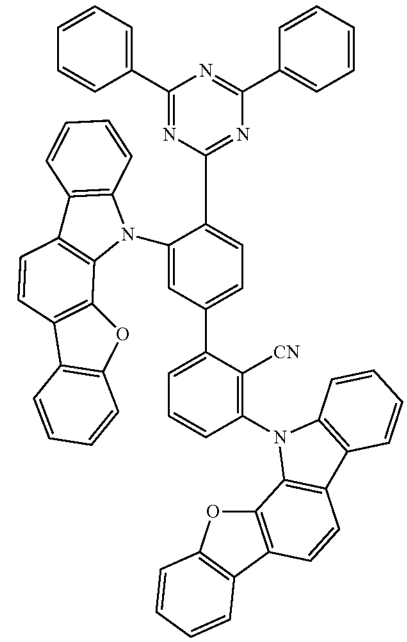
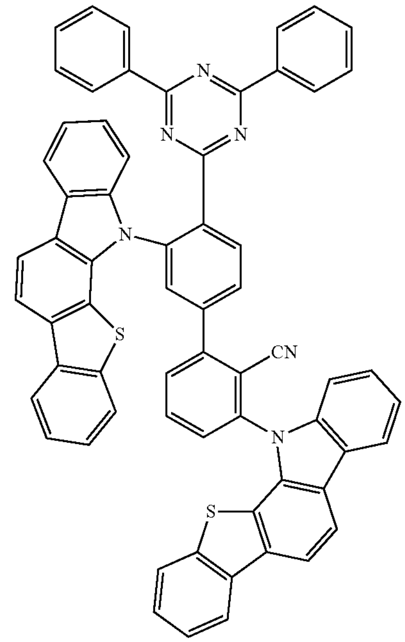

-continued
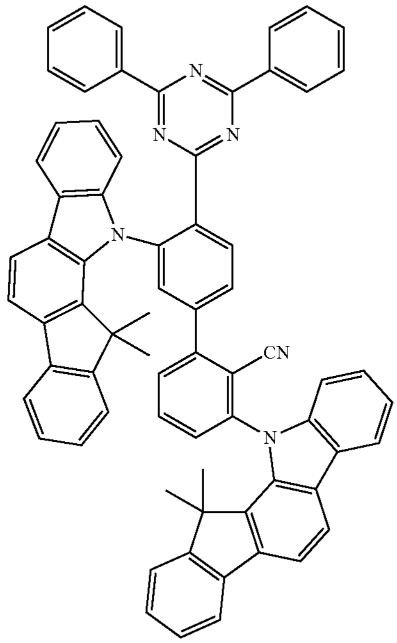
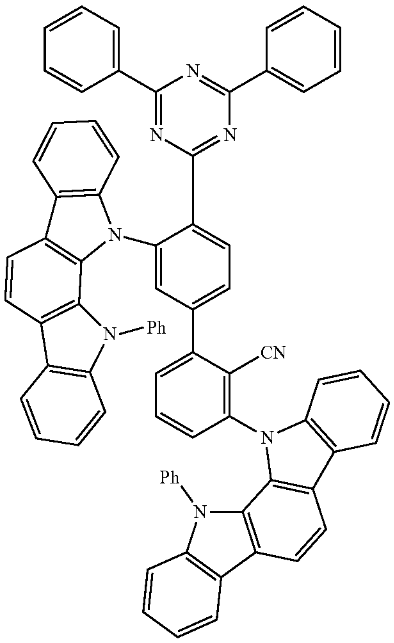
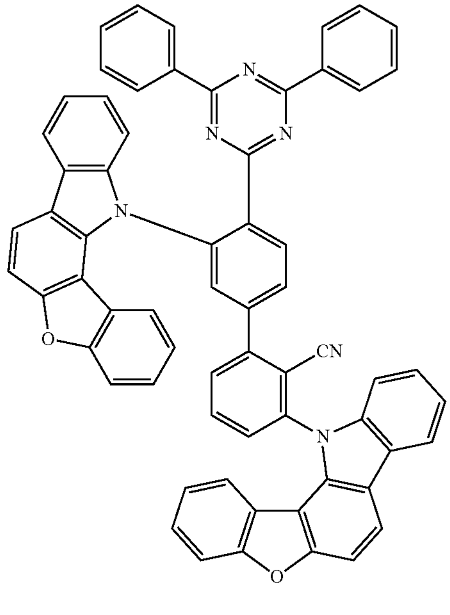
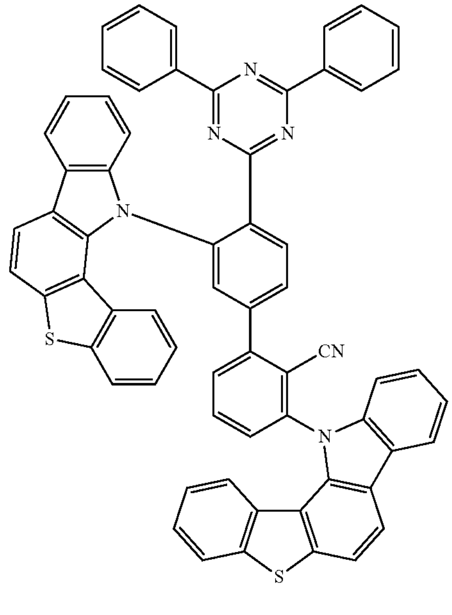

-continued
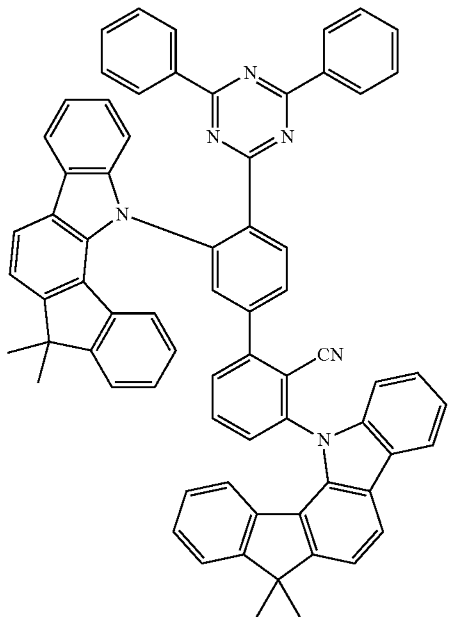
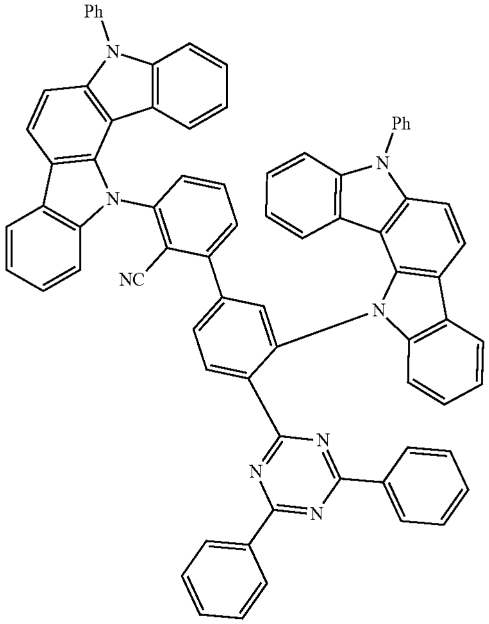
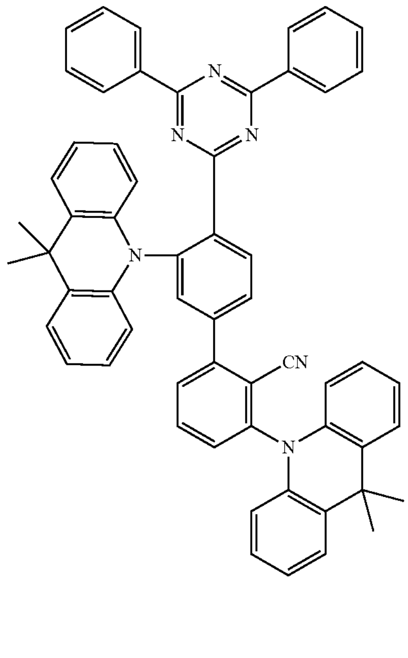
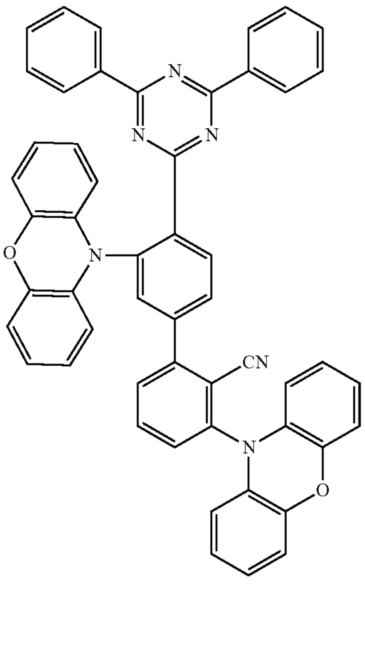

-continued
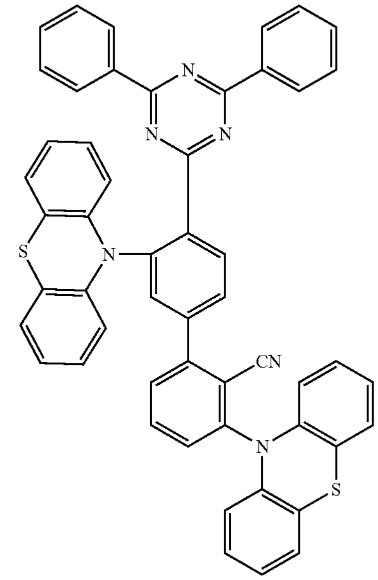
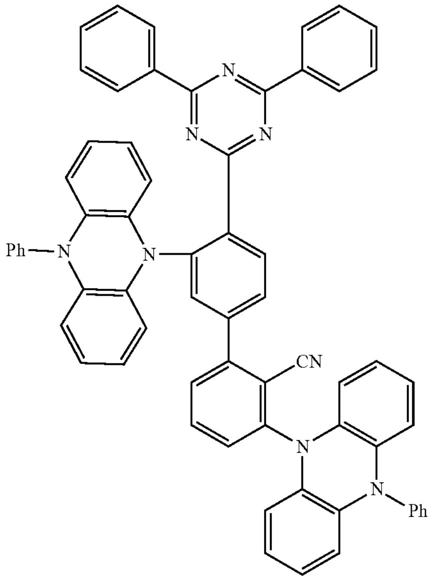
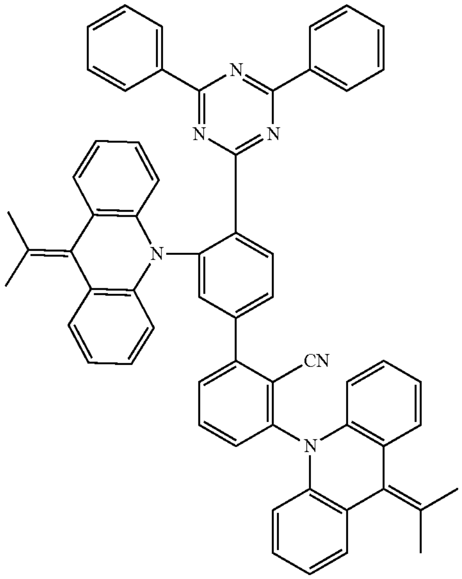
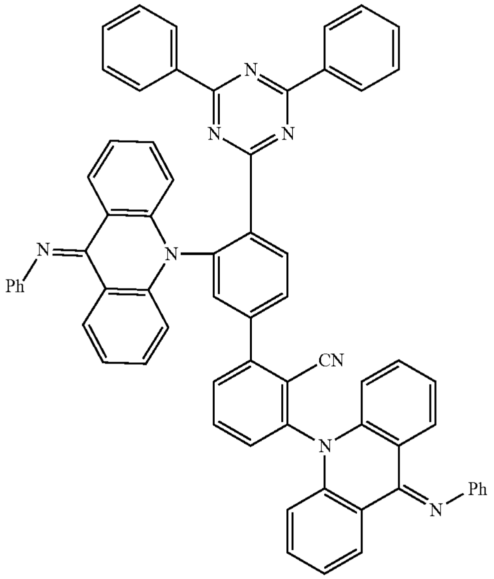

-continued
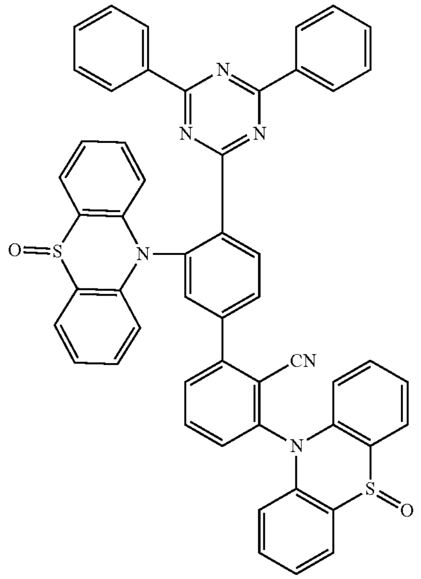
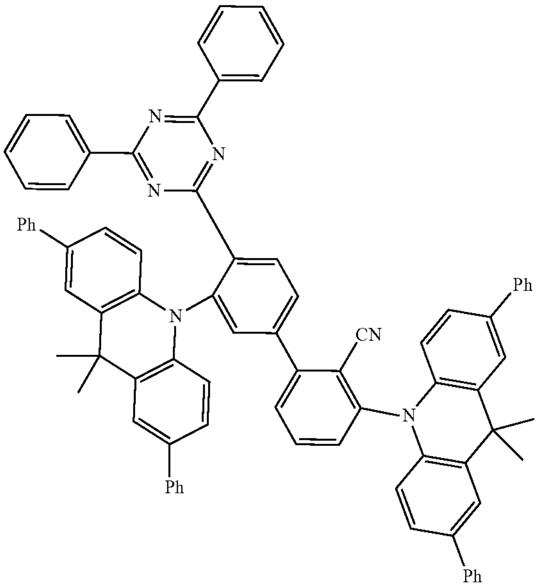
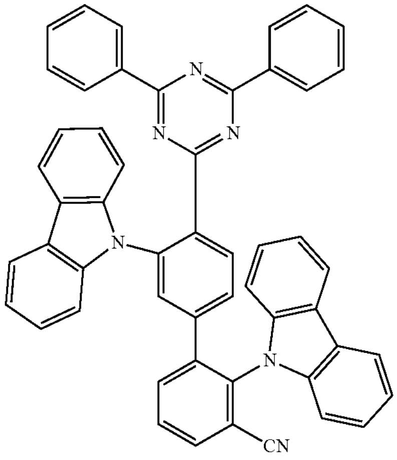
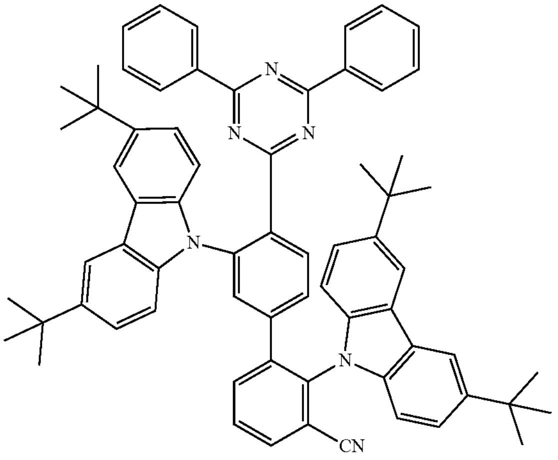
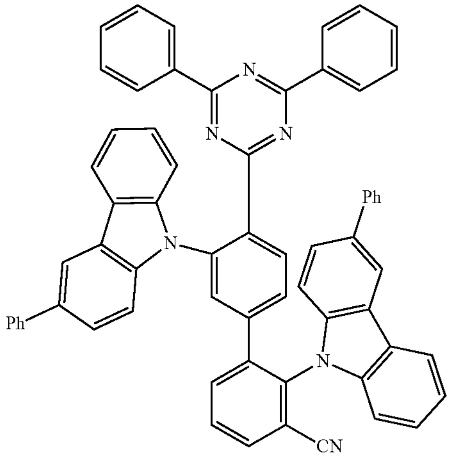
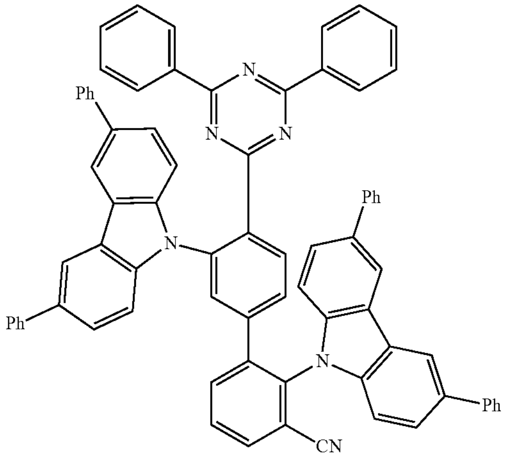

-continued
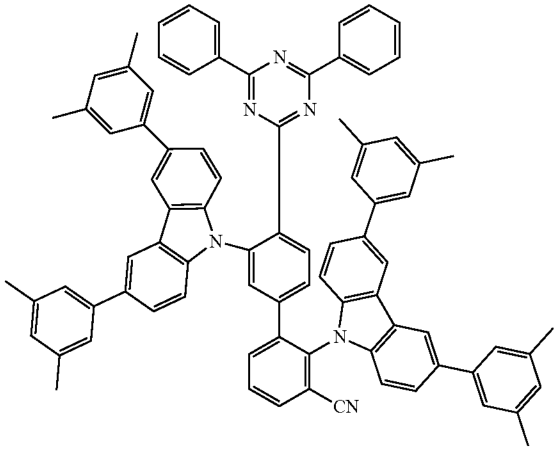
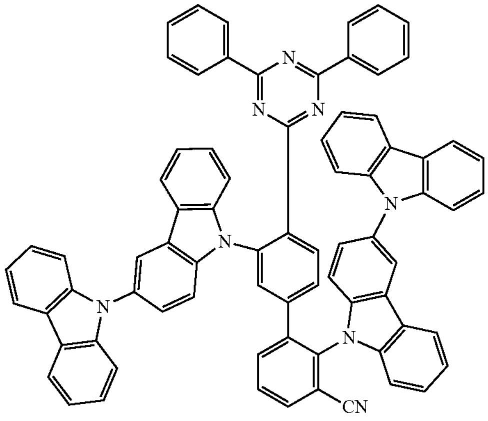
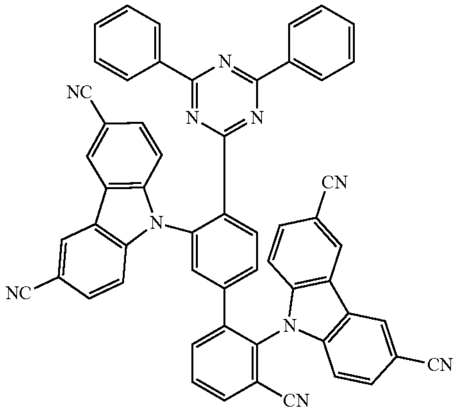
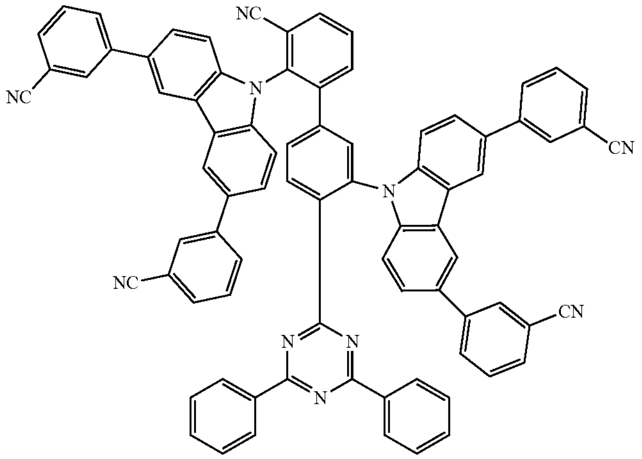
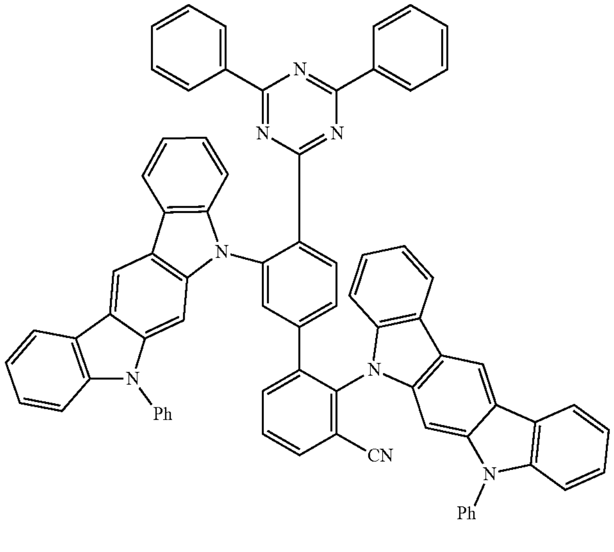
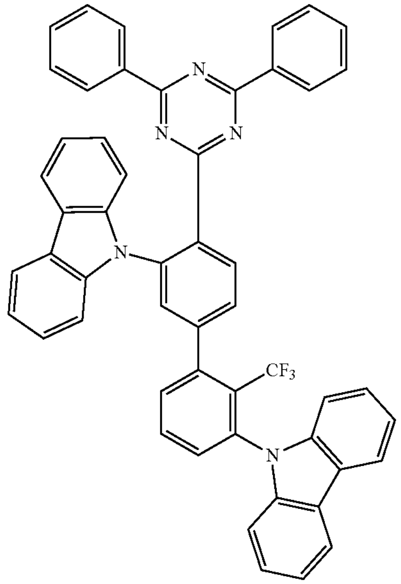

-continued
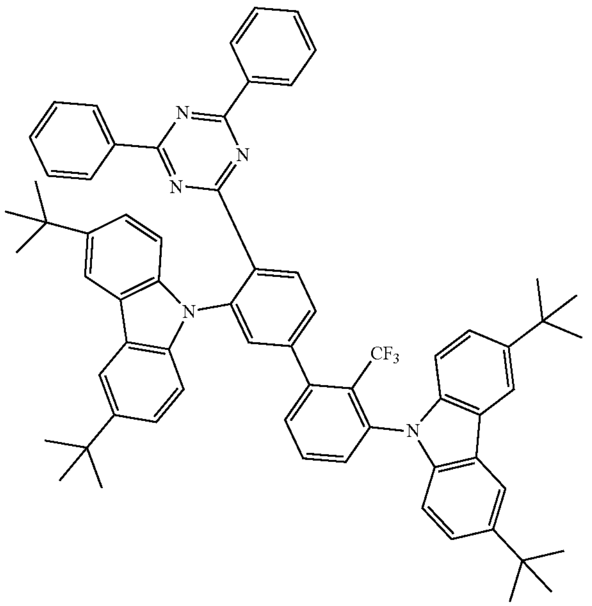
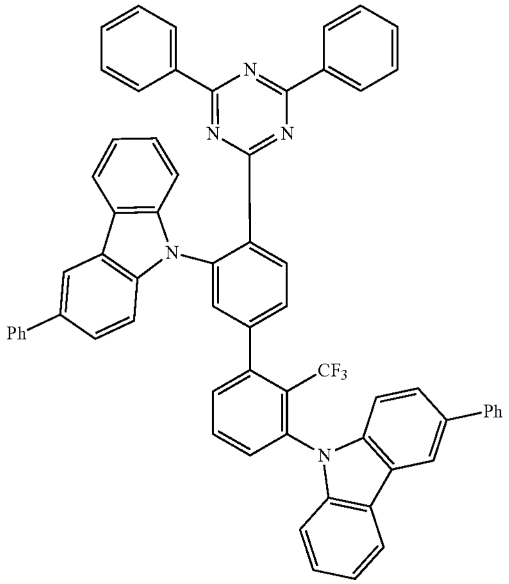
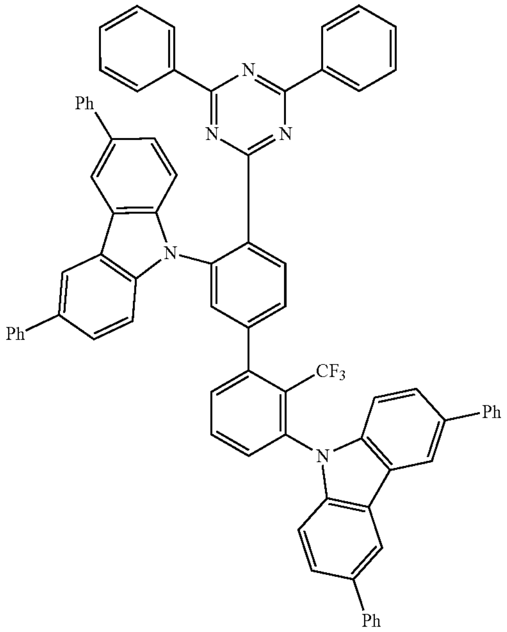
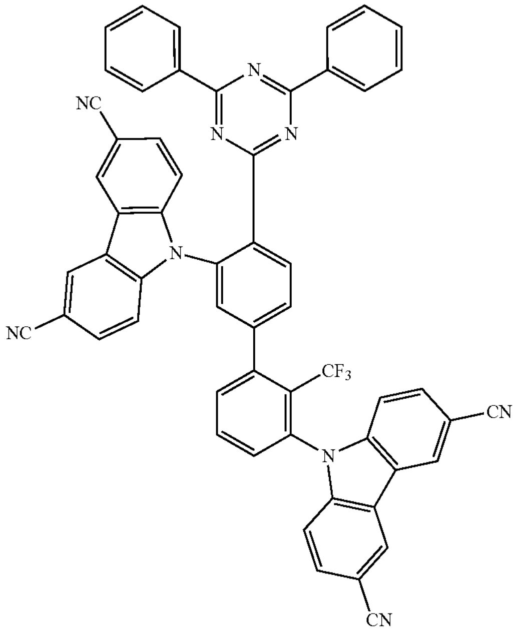

-continued
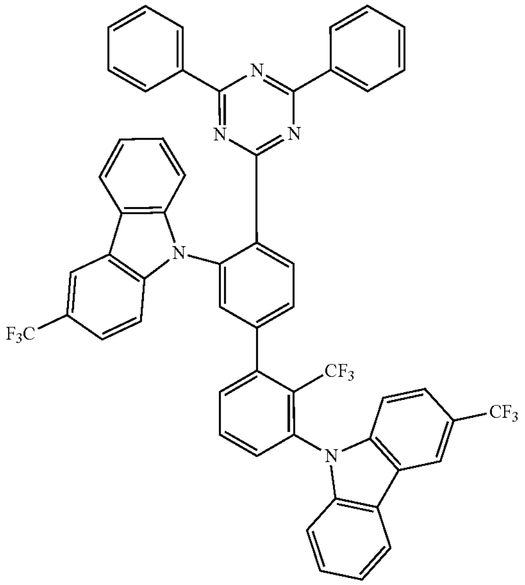
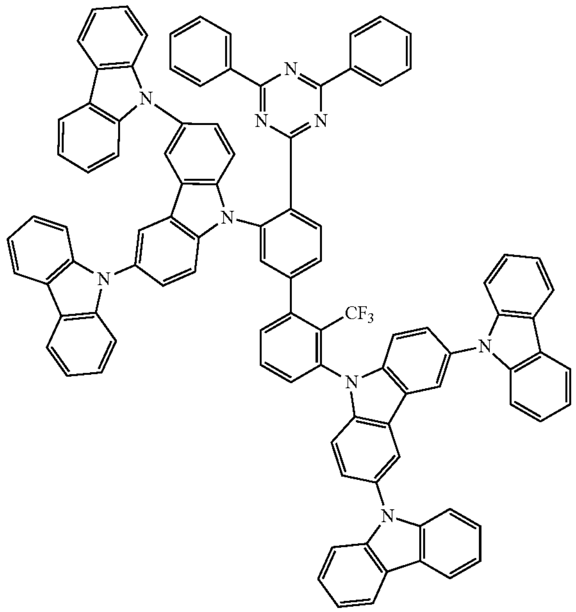
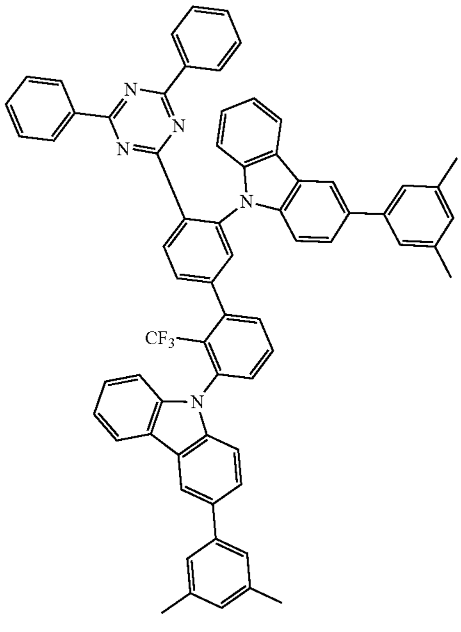
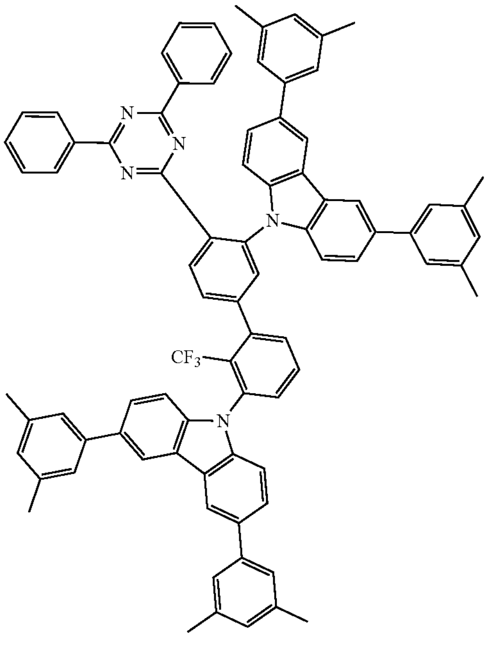

-continued
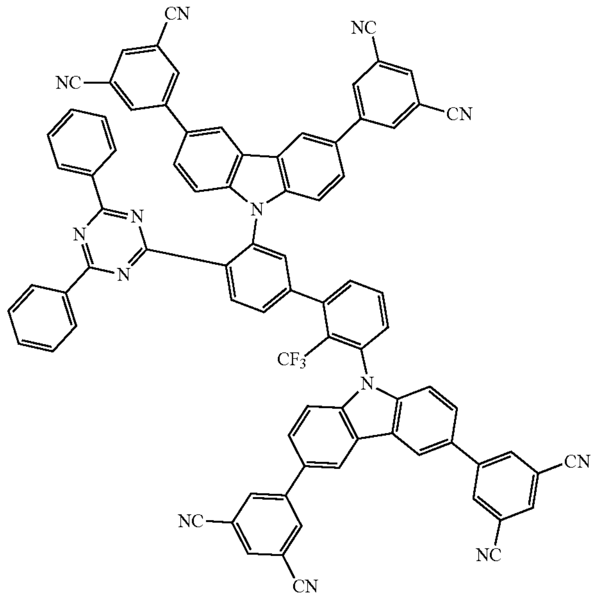
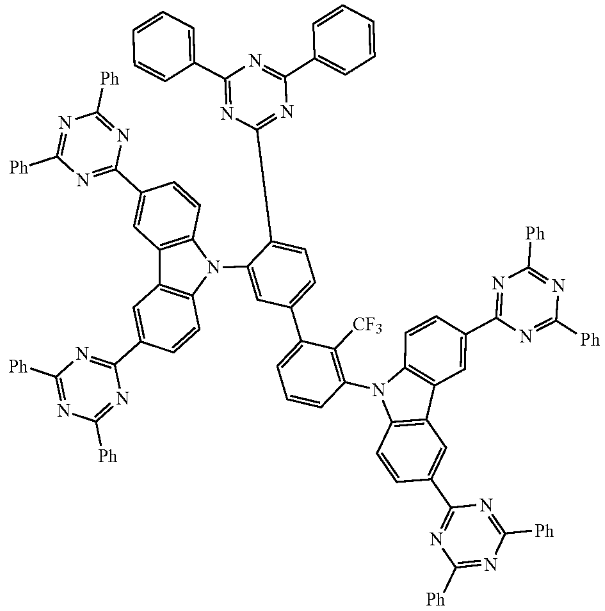

-continued
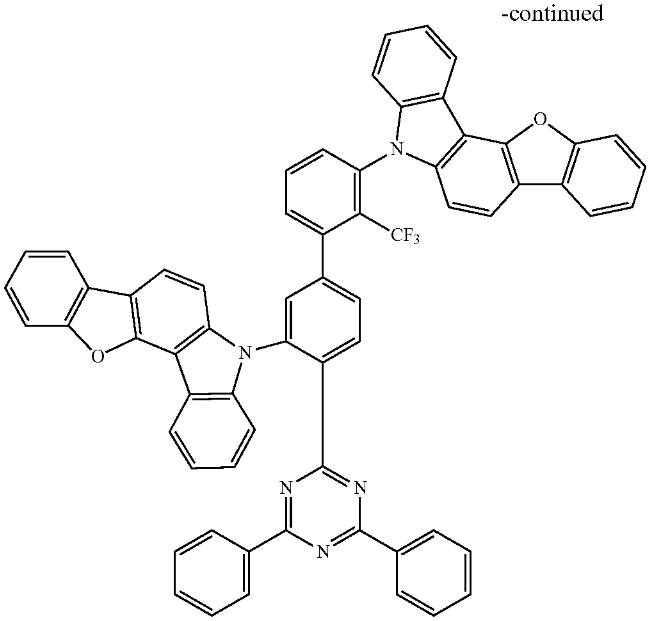
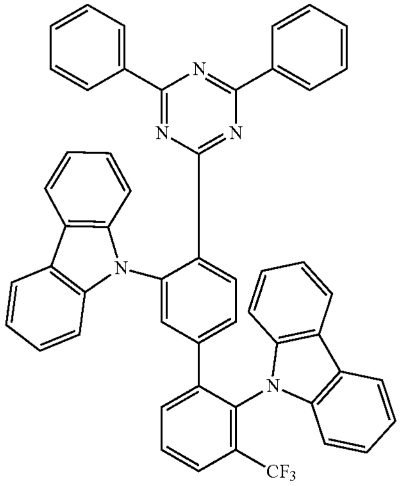
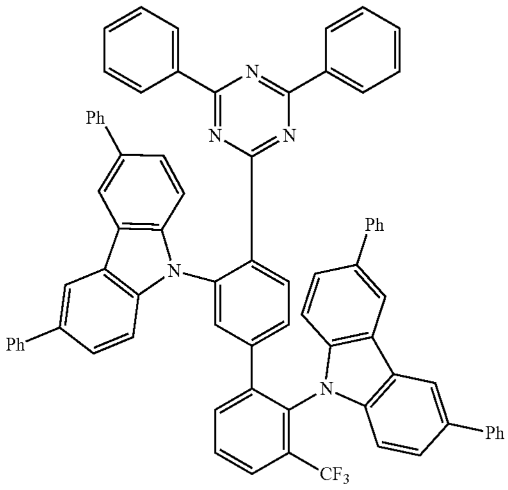
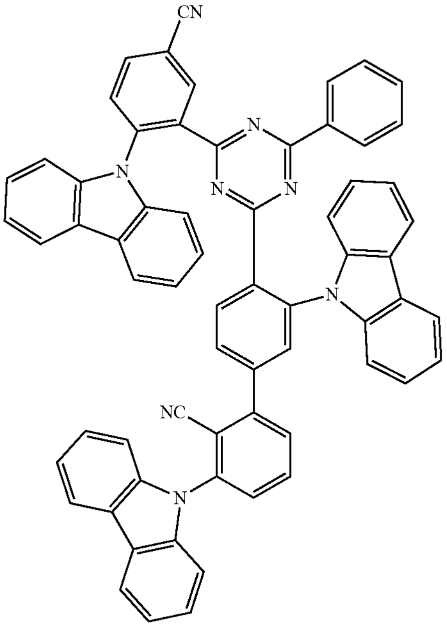

-continued
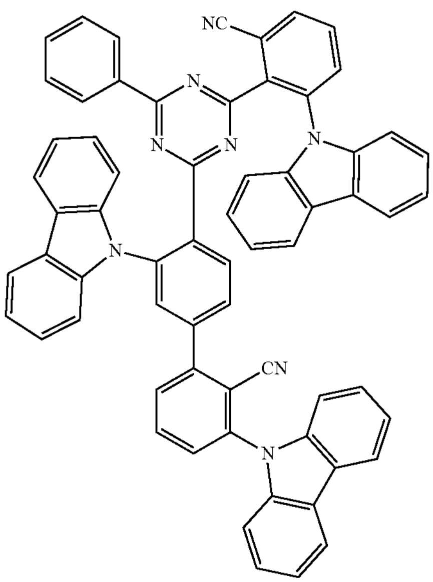
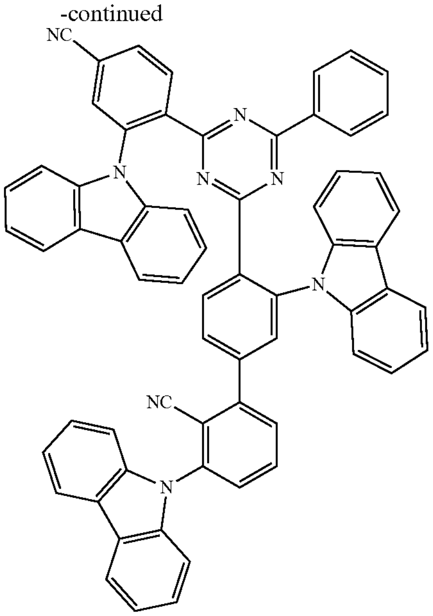
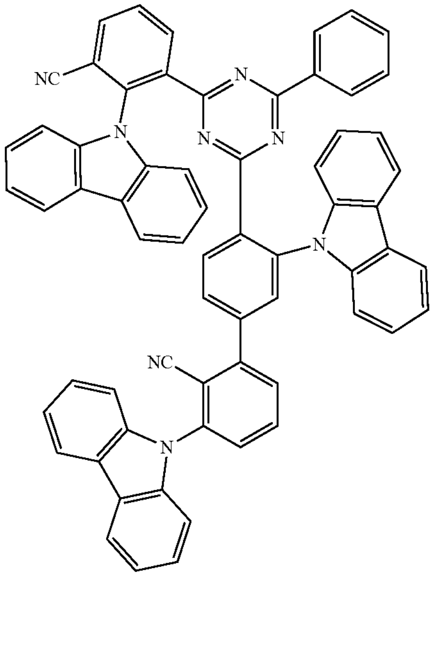
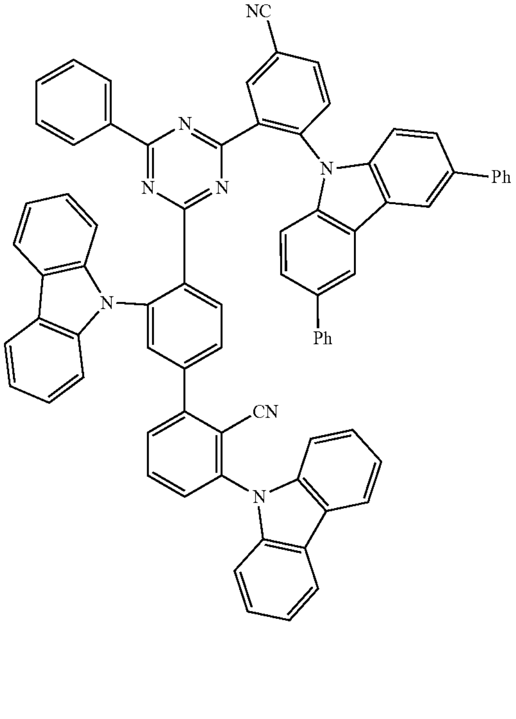

-continued
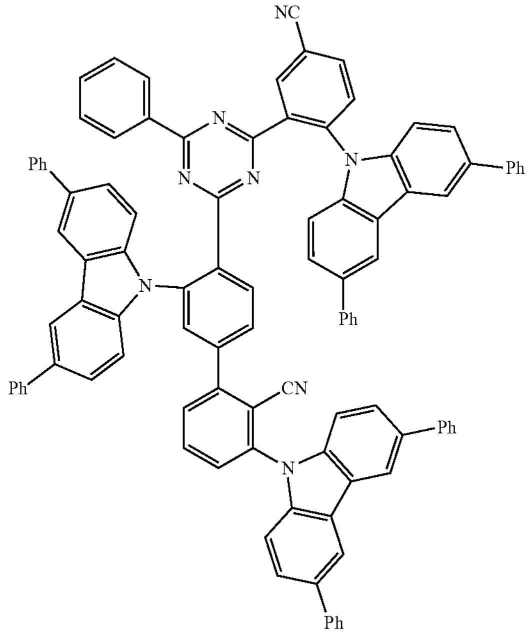
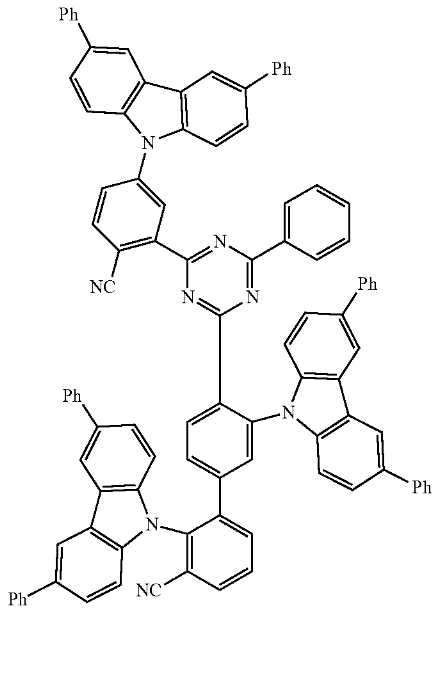
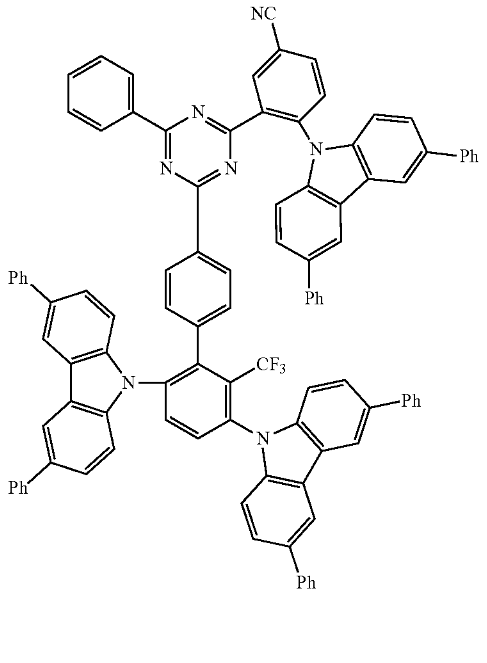

-continued
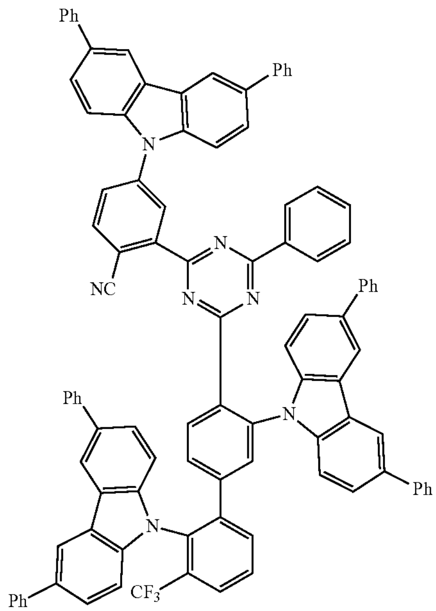
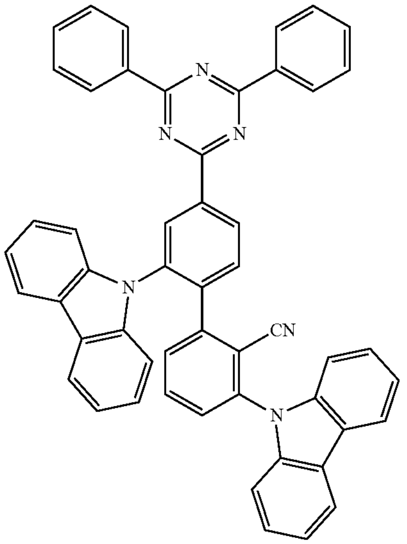
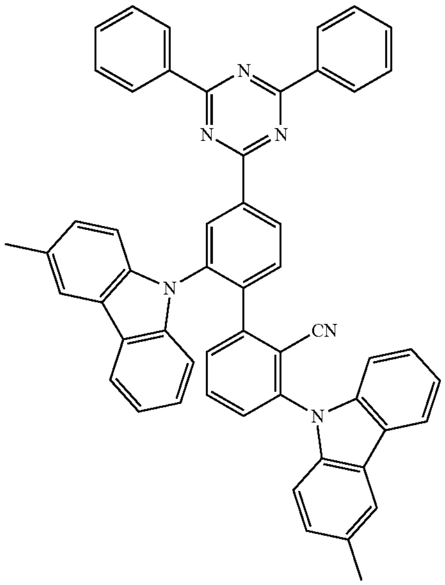
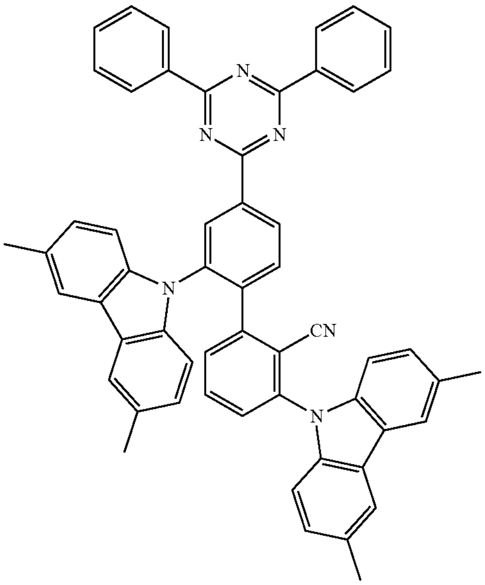

-continued
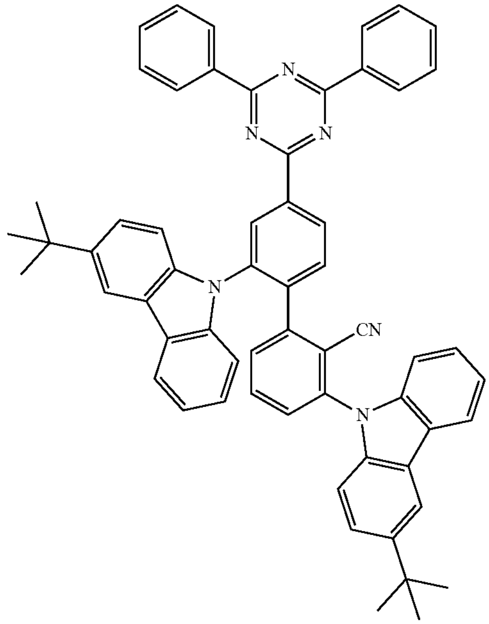
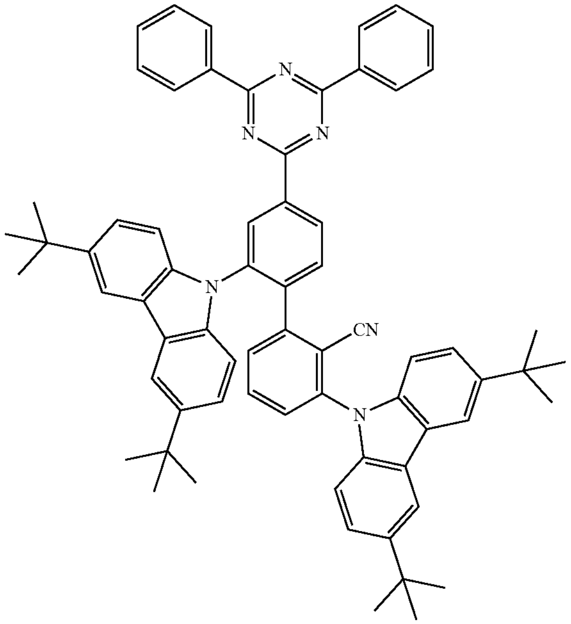
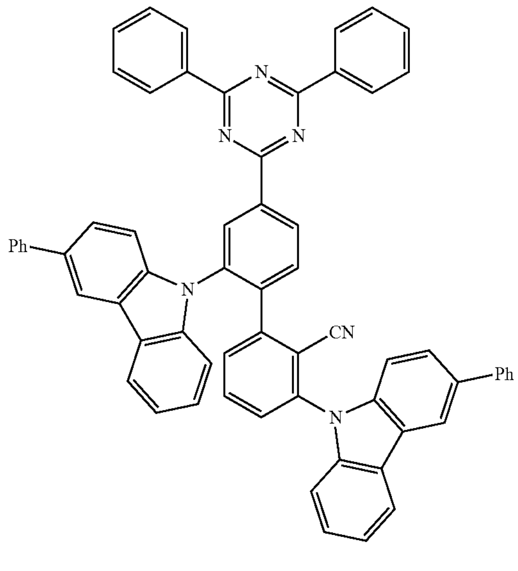
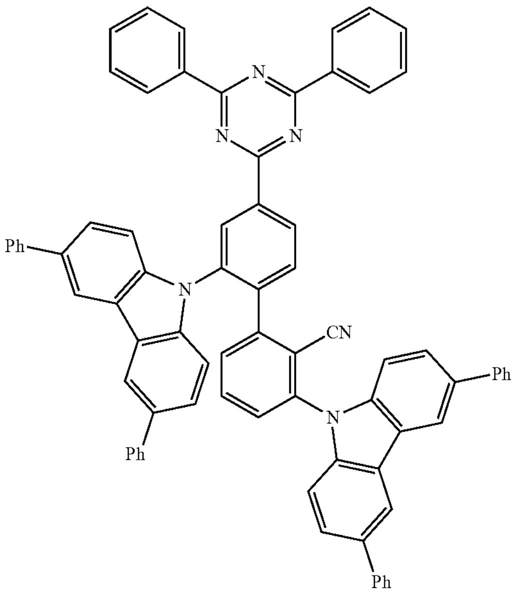

-continued
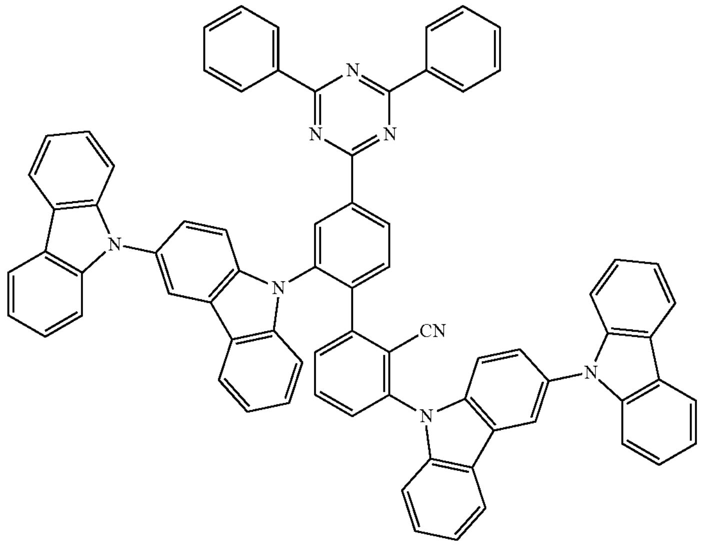
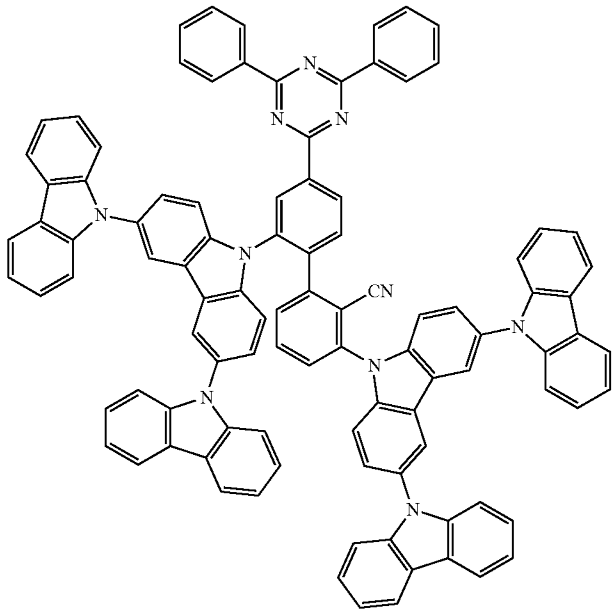

-continued
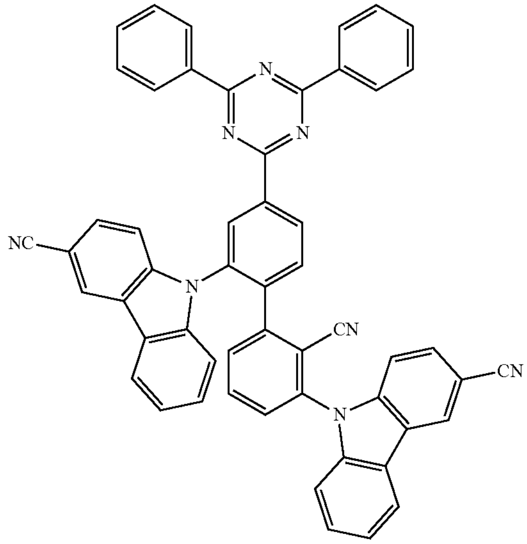
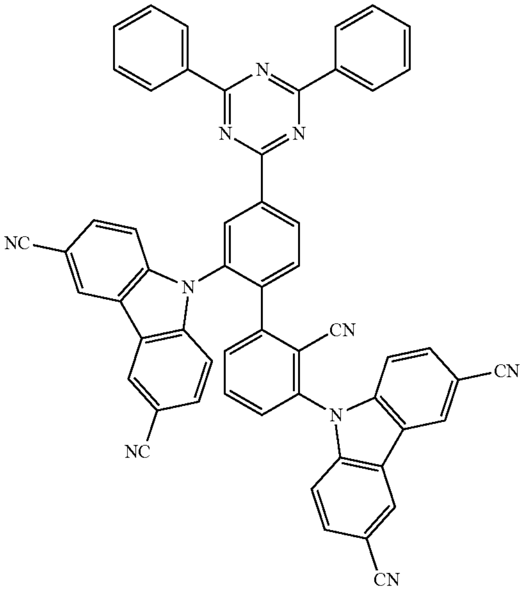
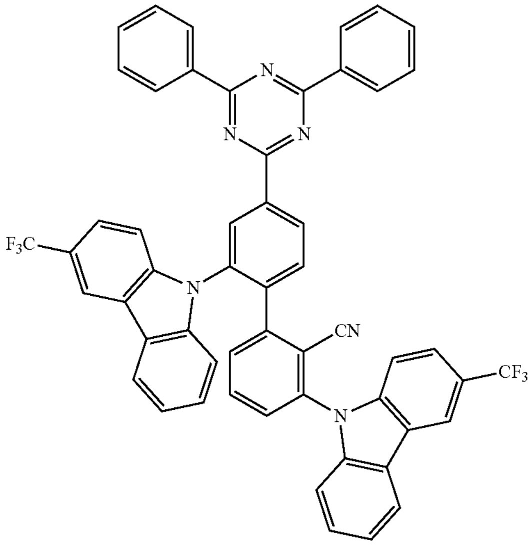
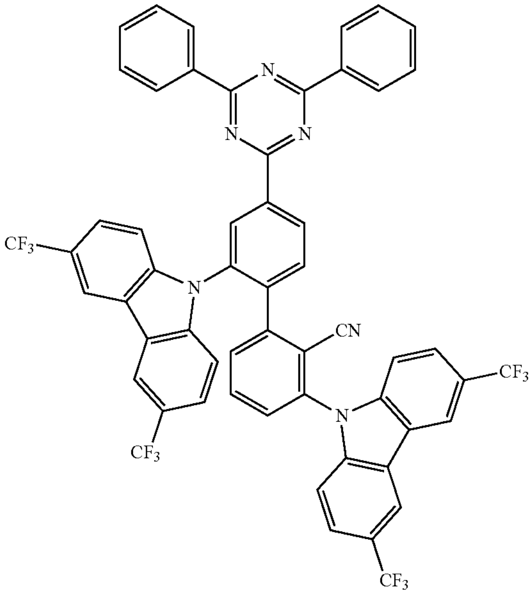
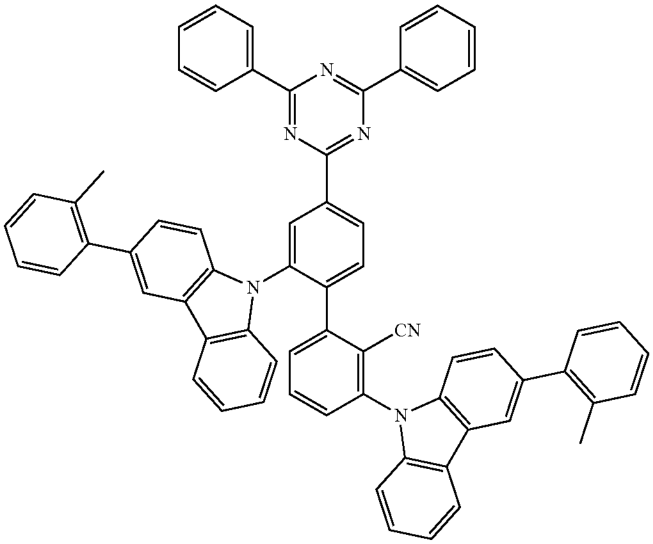

-continued
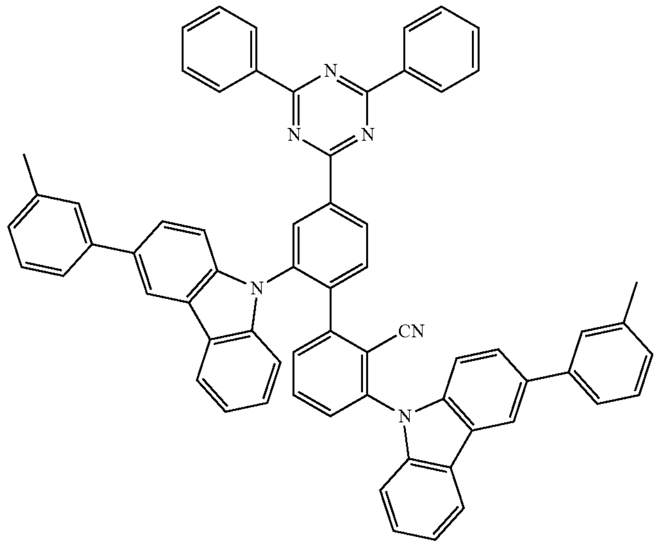
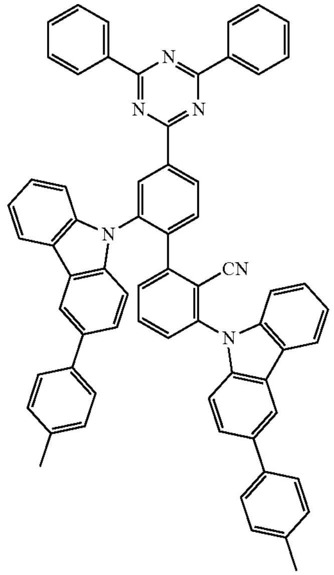
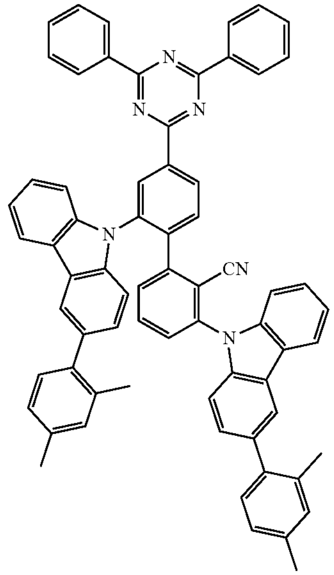
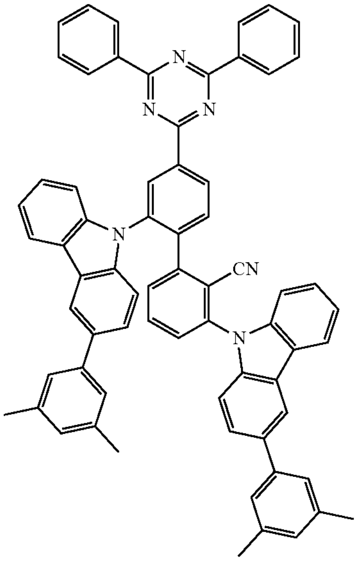
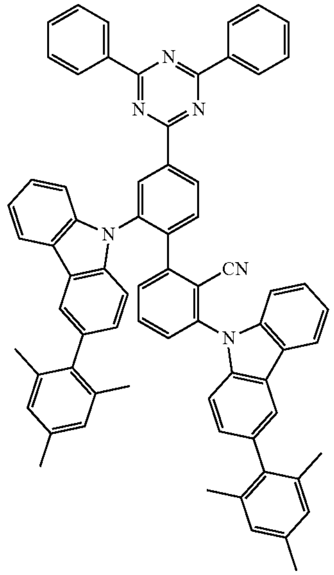
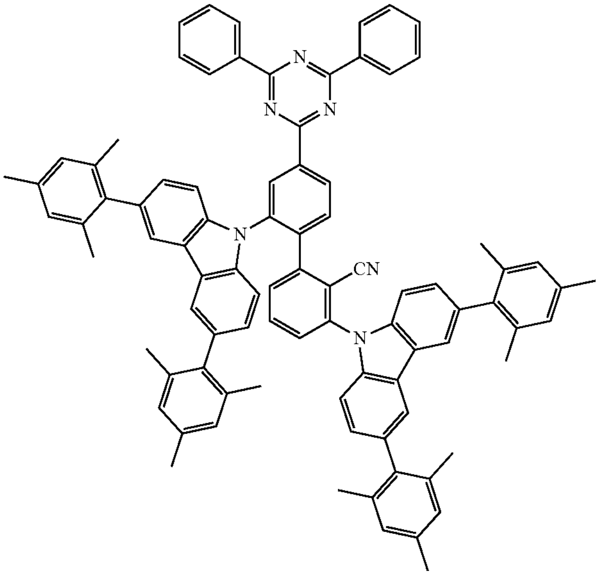

-continued
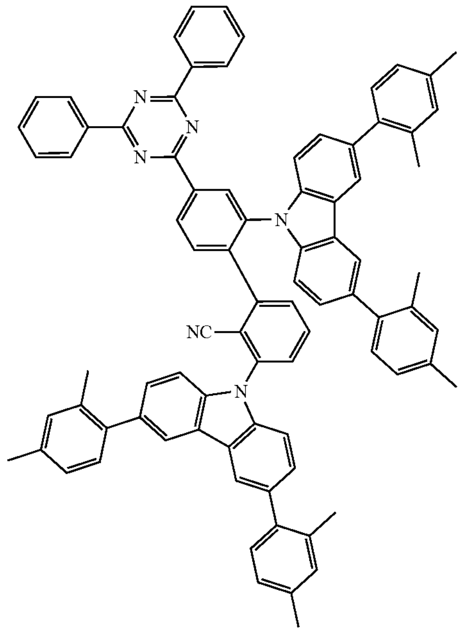
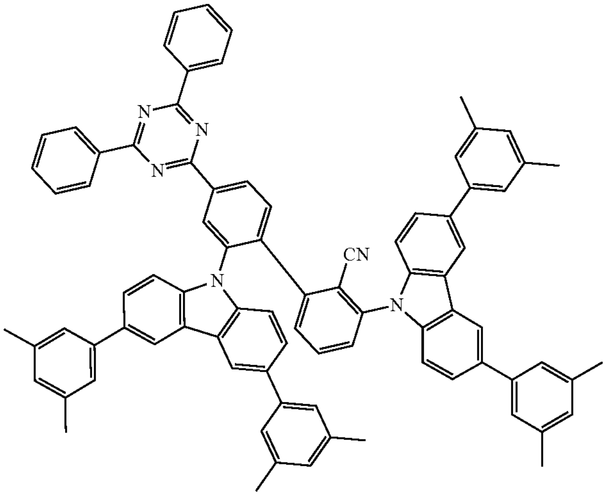
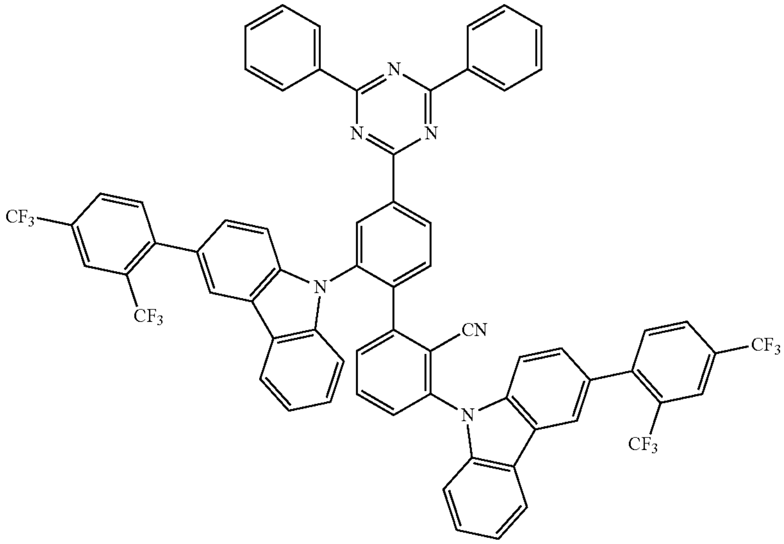

-continued
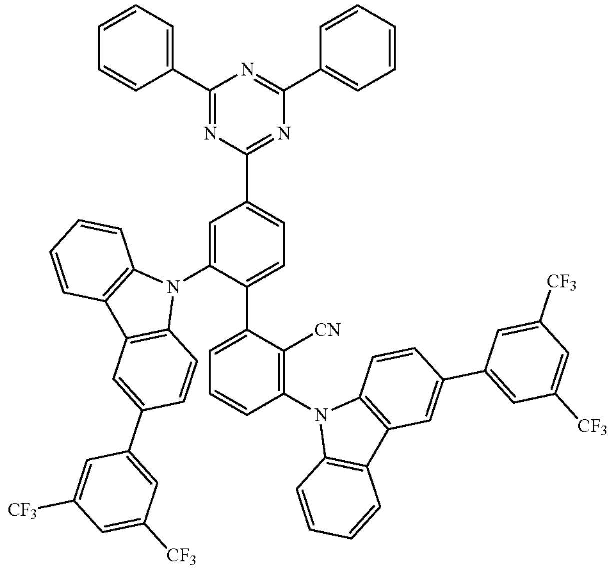
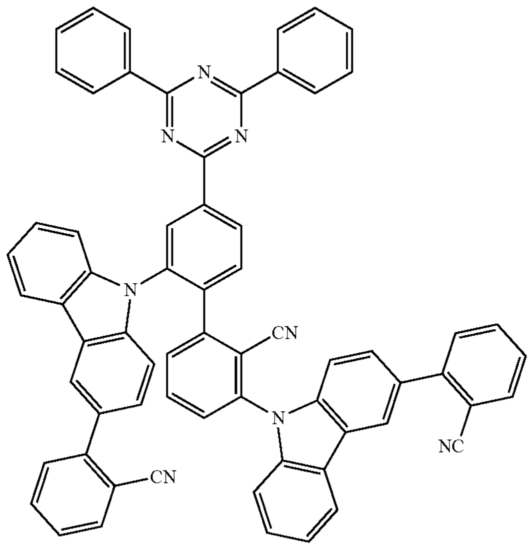
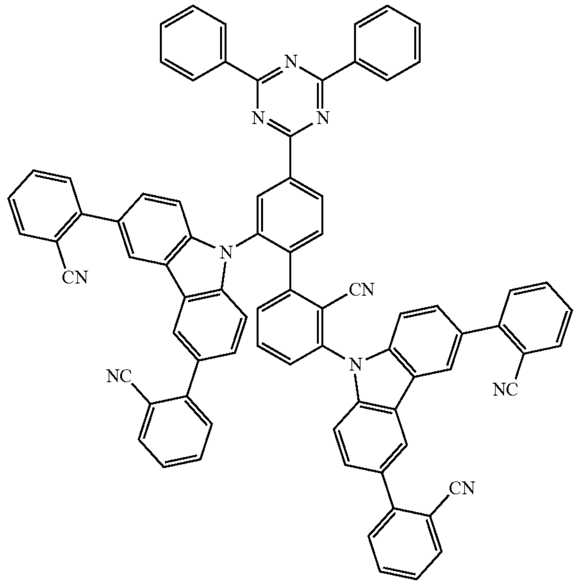
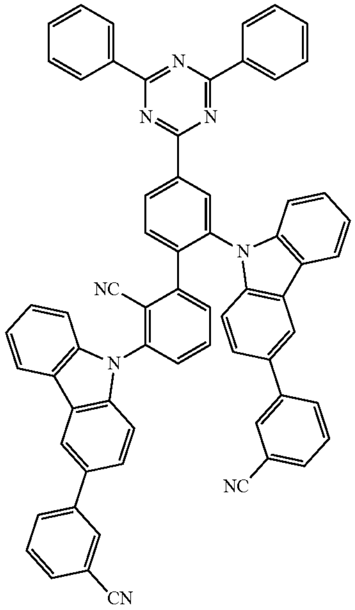
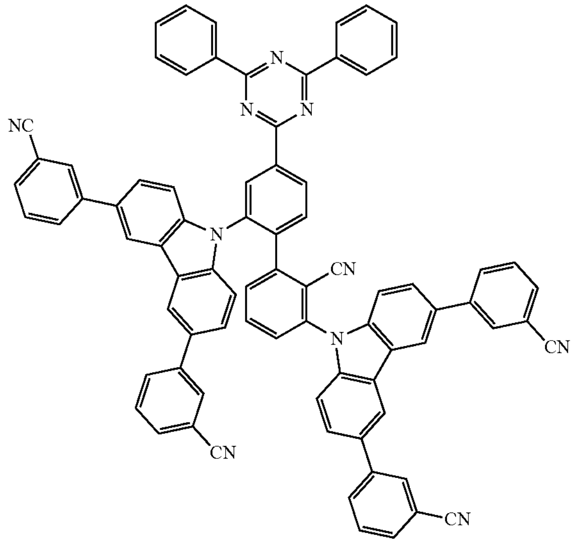
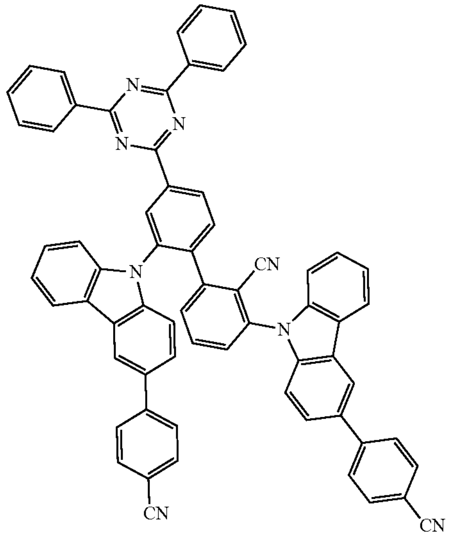

-continued
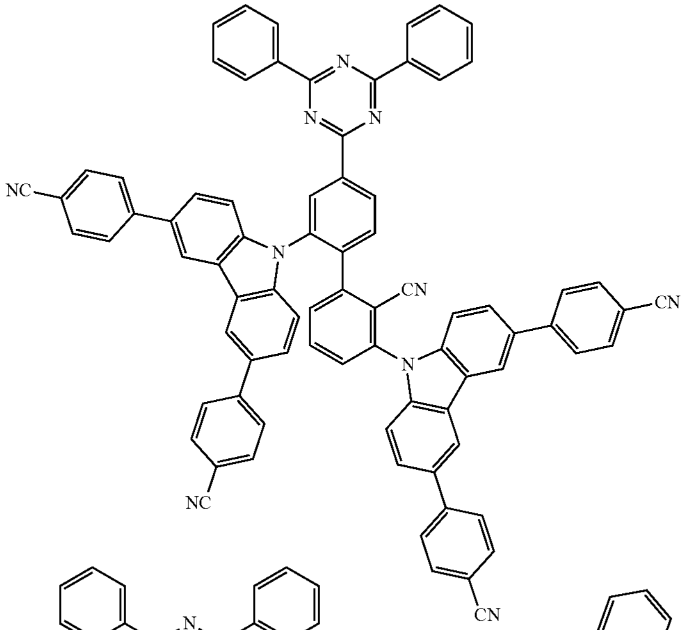
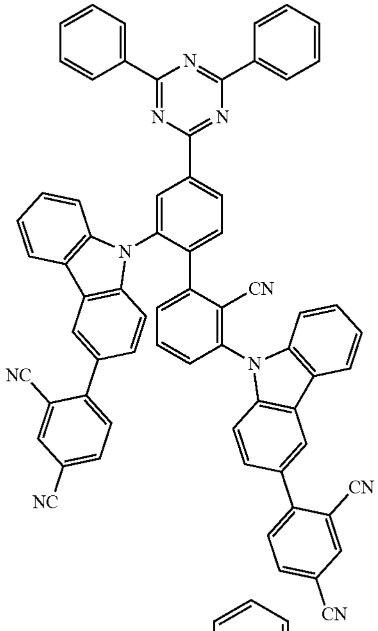
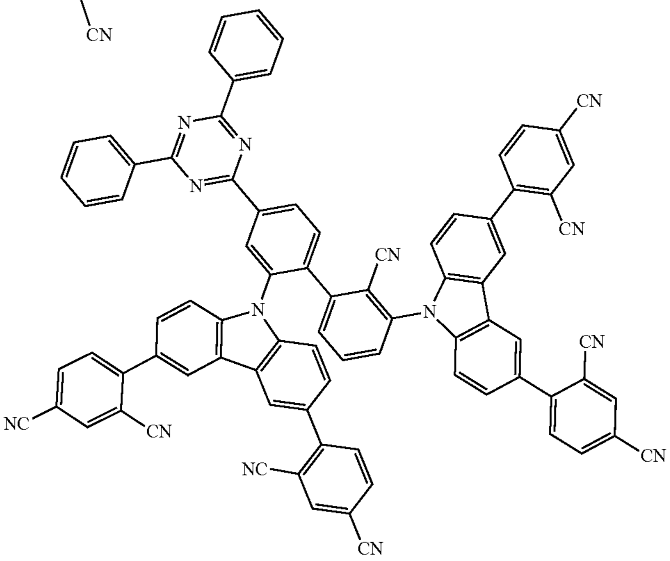
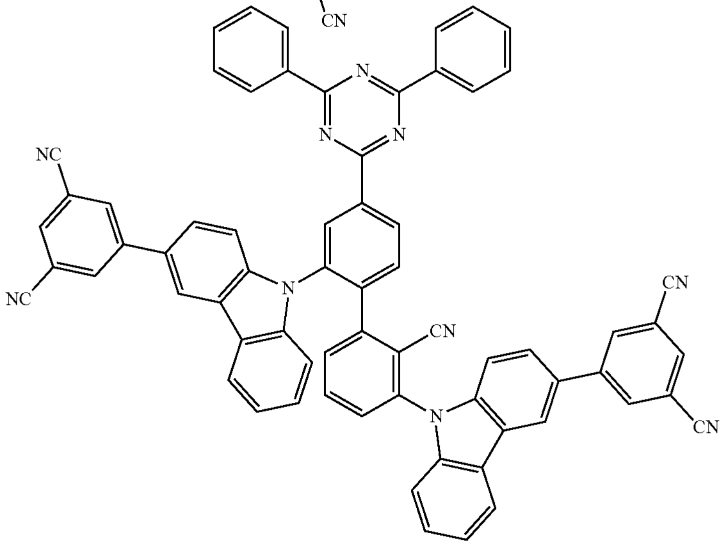

-continued
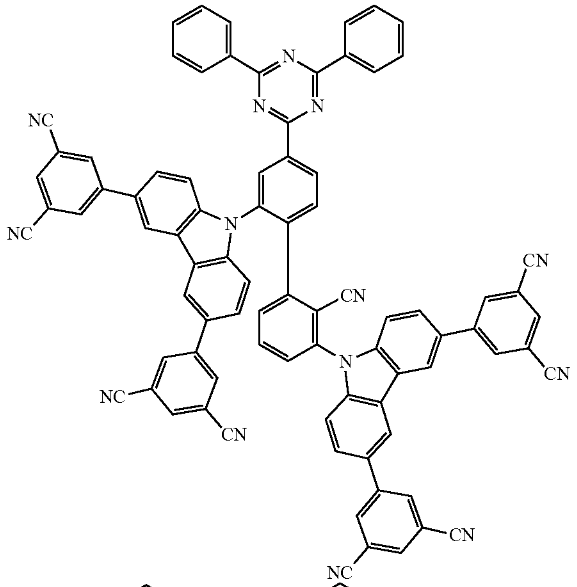
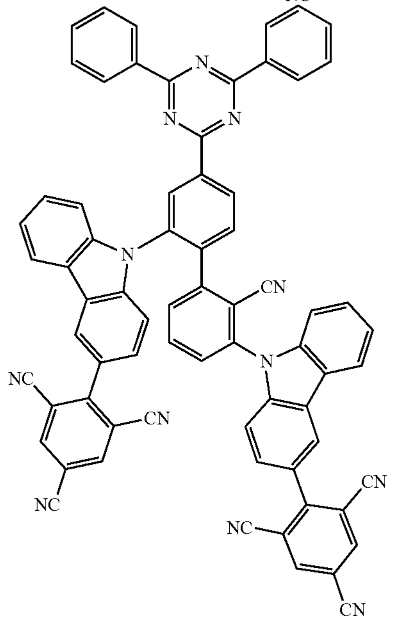
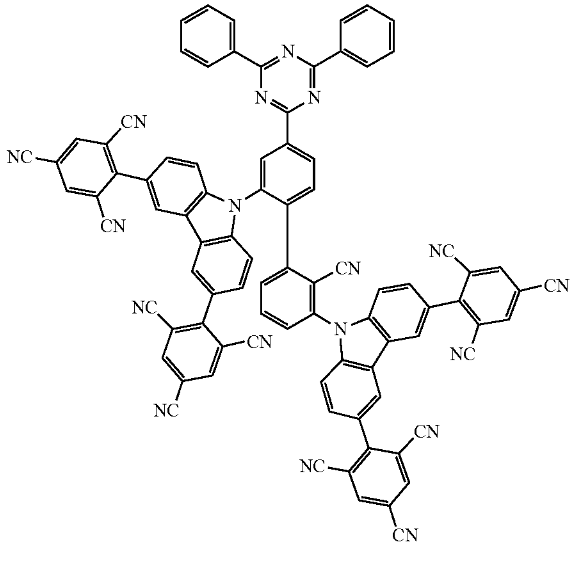
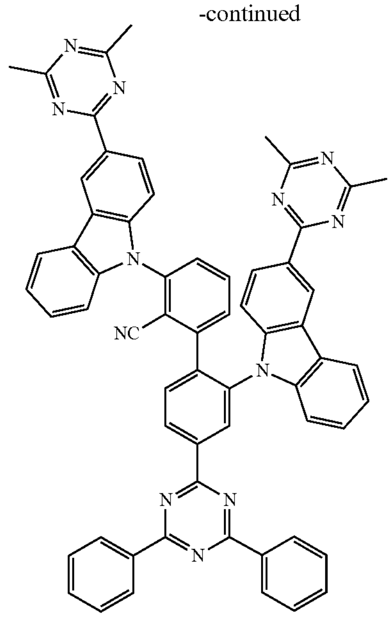
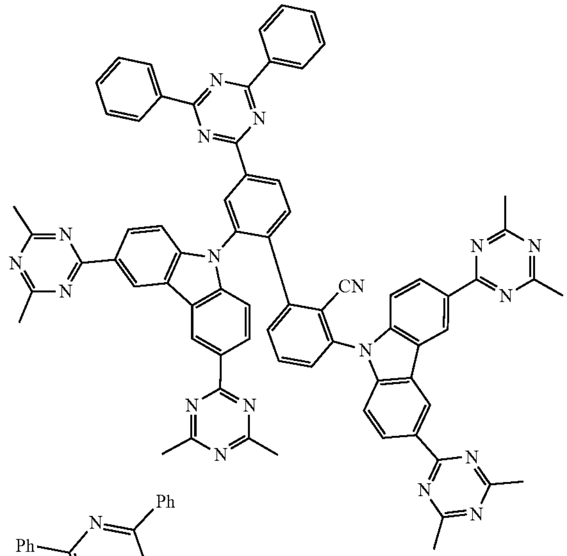
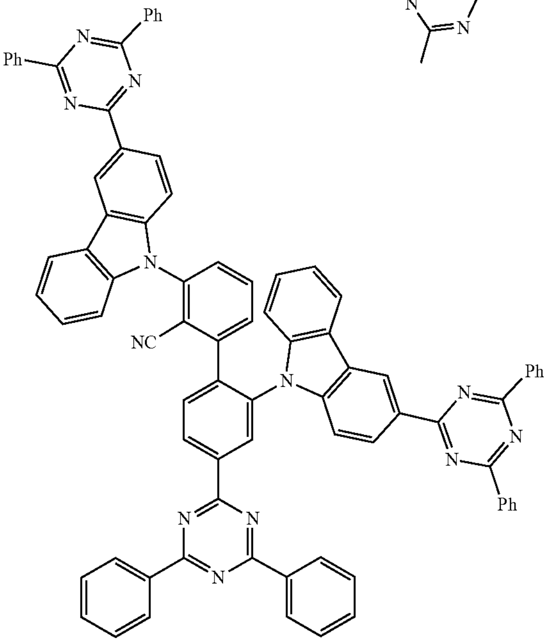

-continued
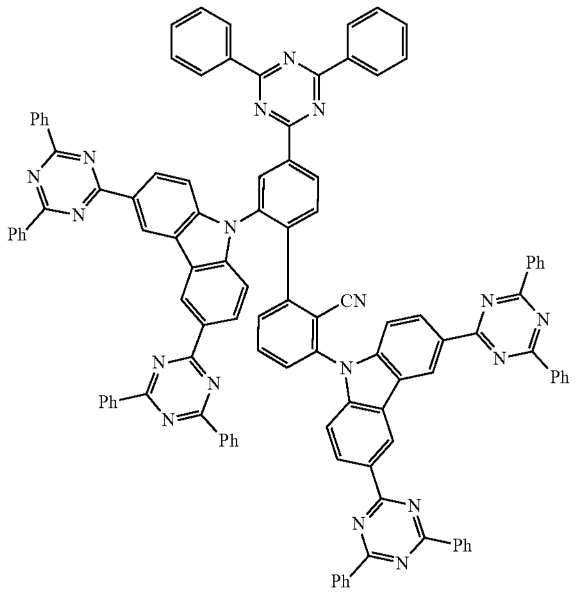
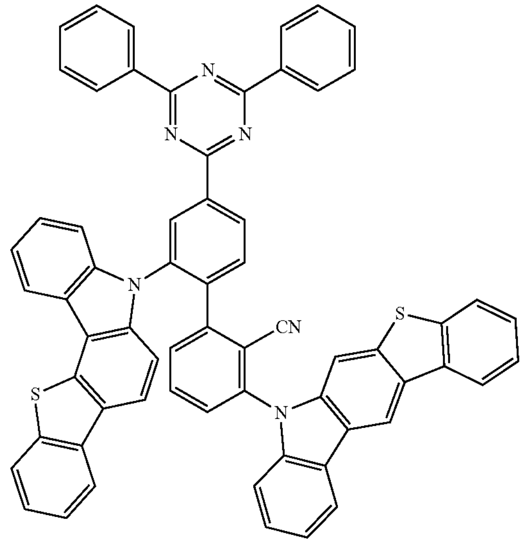
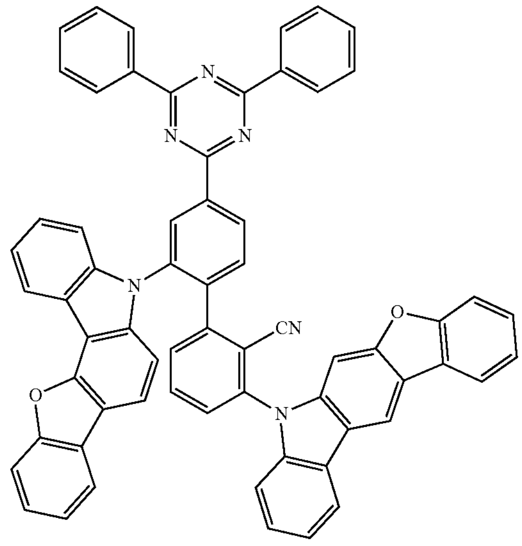
-continued
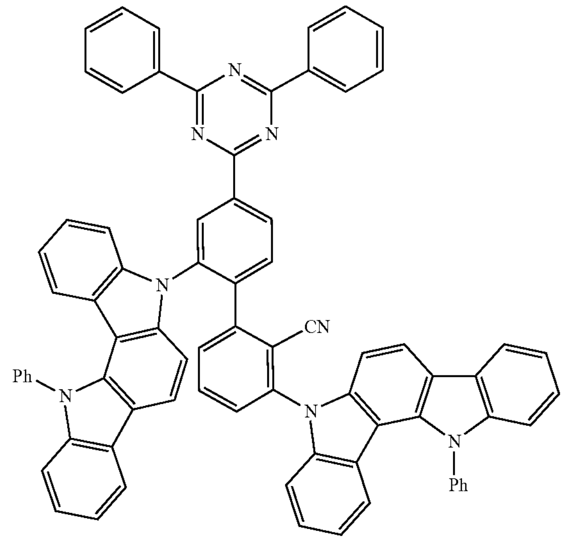
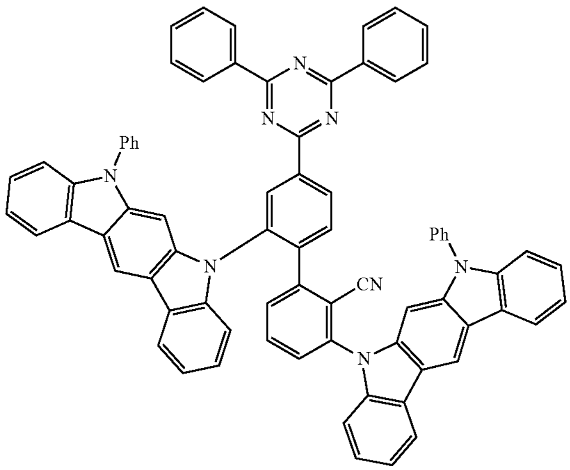
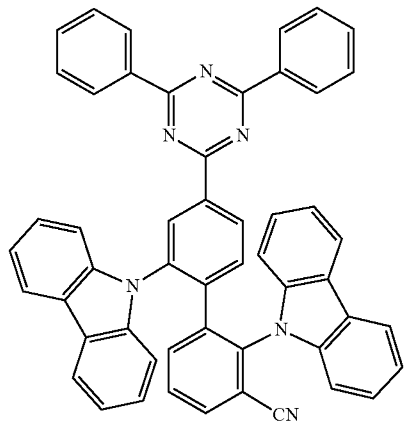

-continued
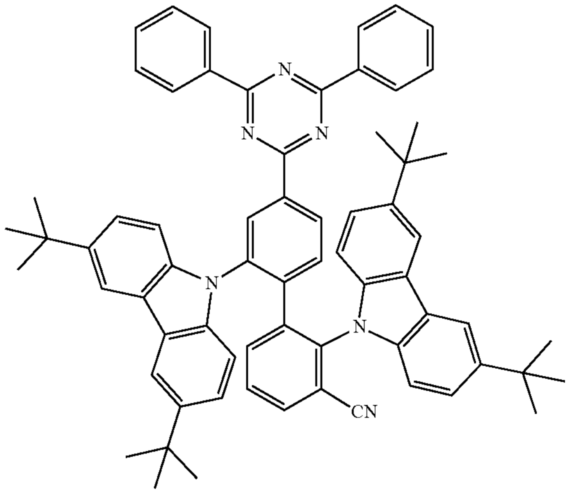
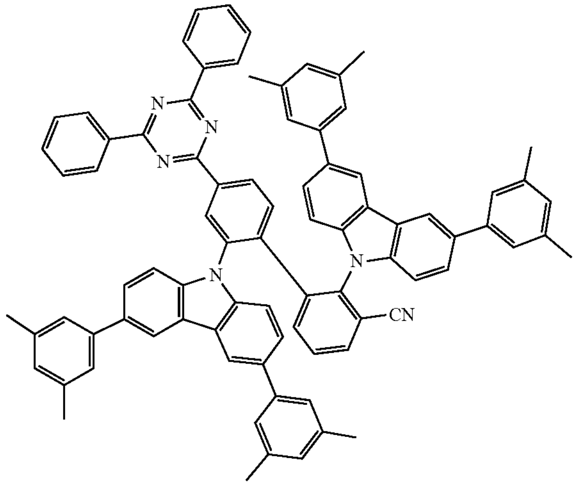
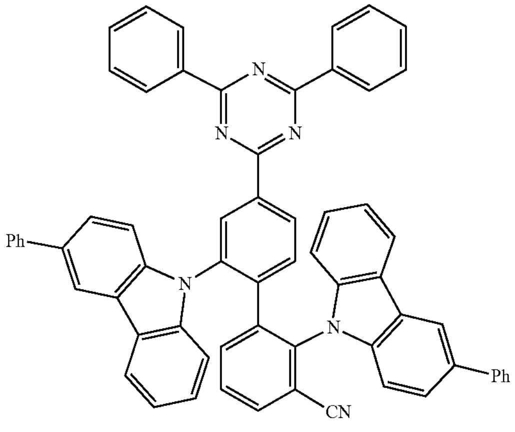
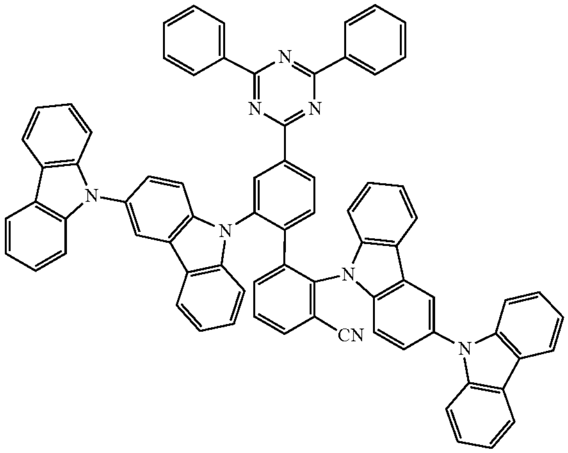
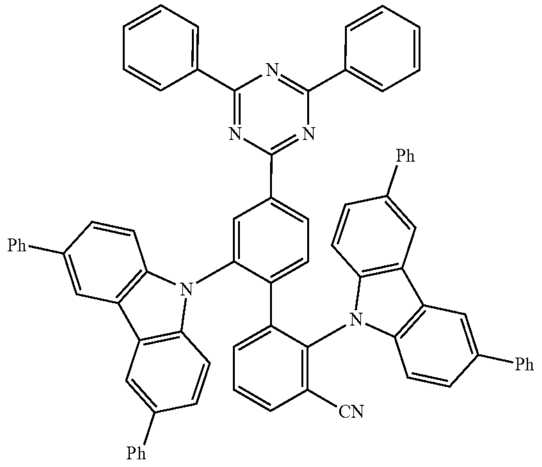
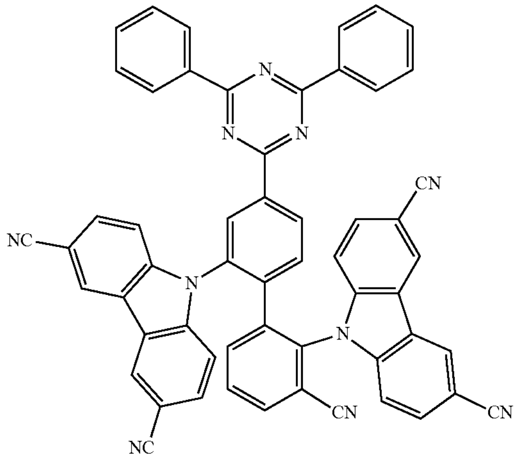

-continued
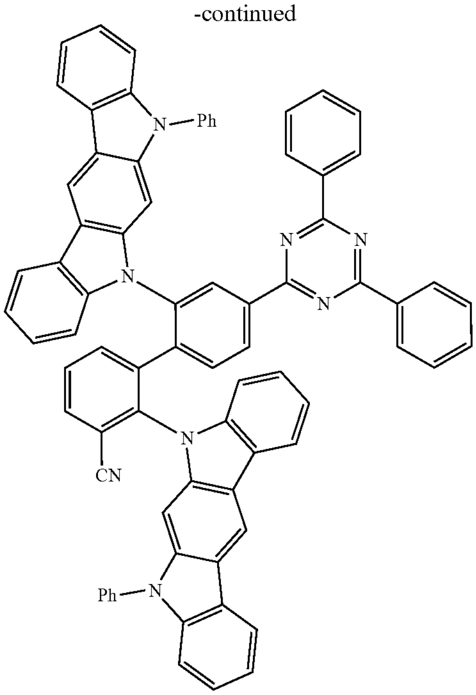
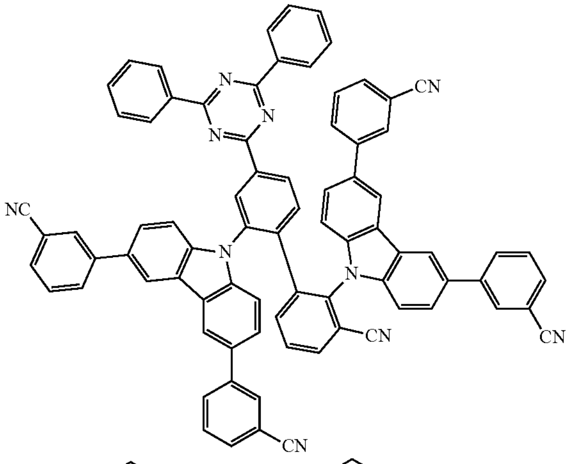
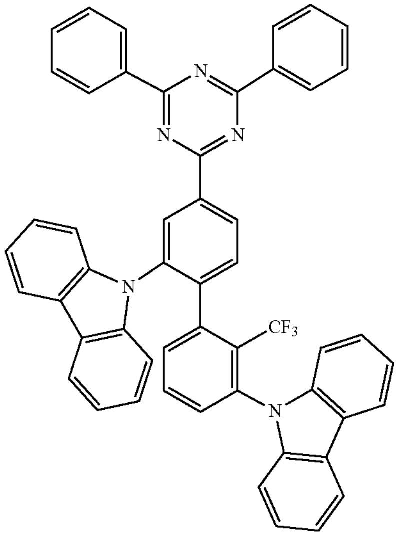
-continued
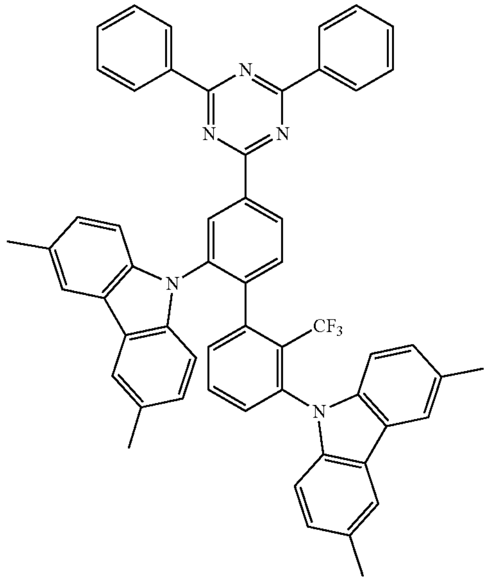
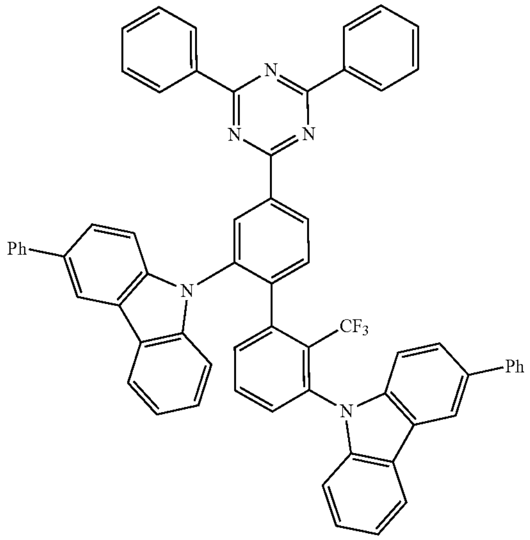
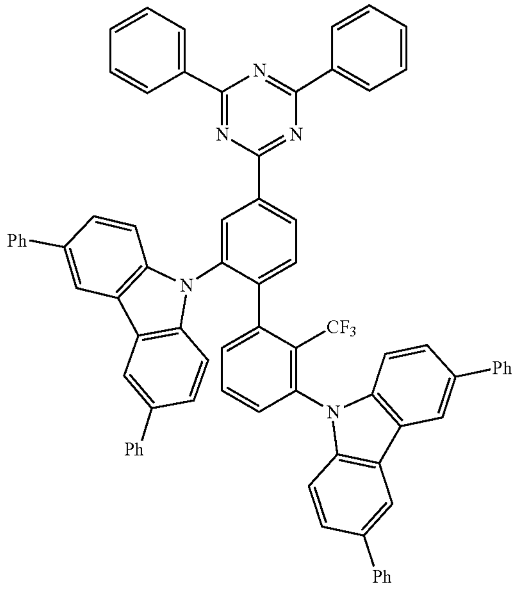

-continued
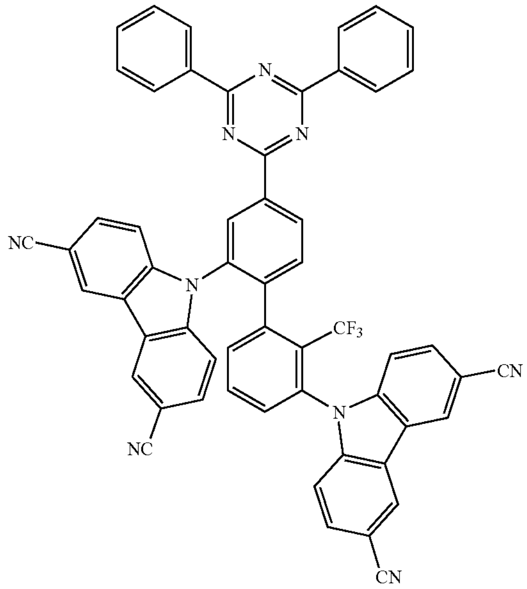
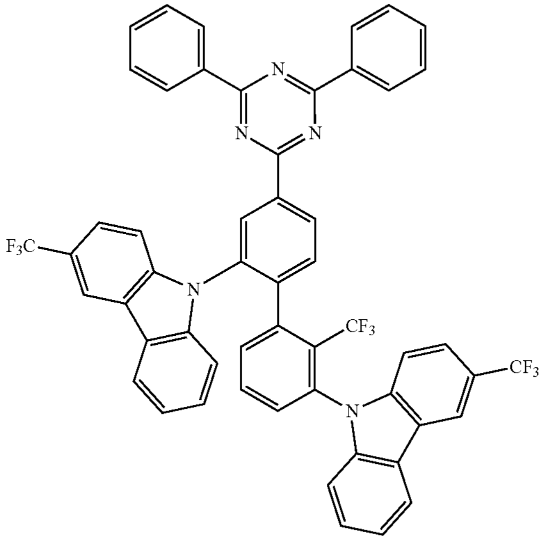
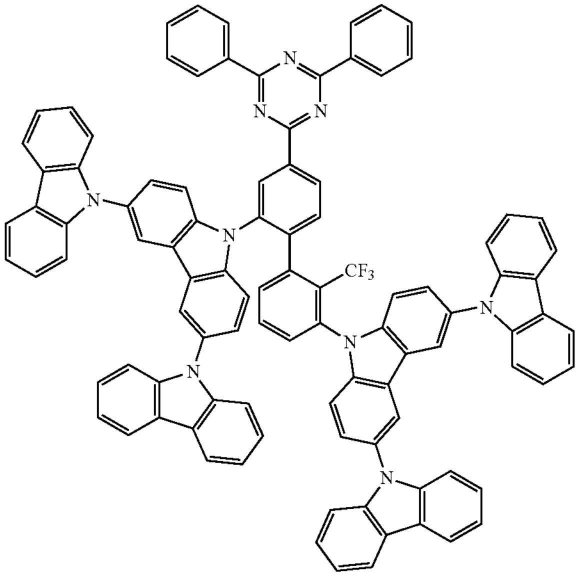
-continued
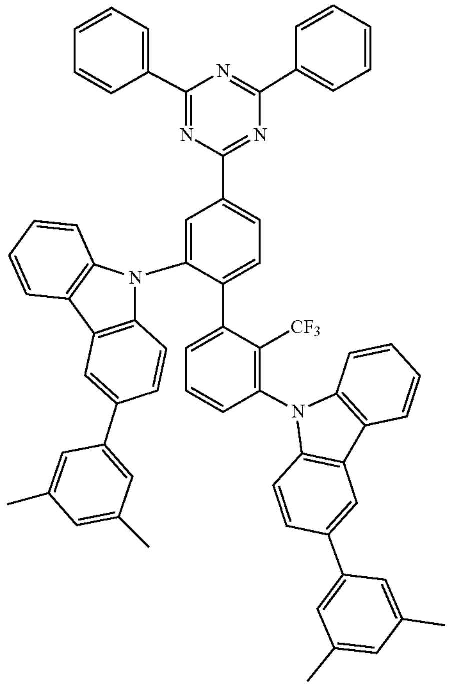
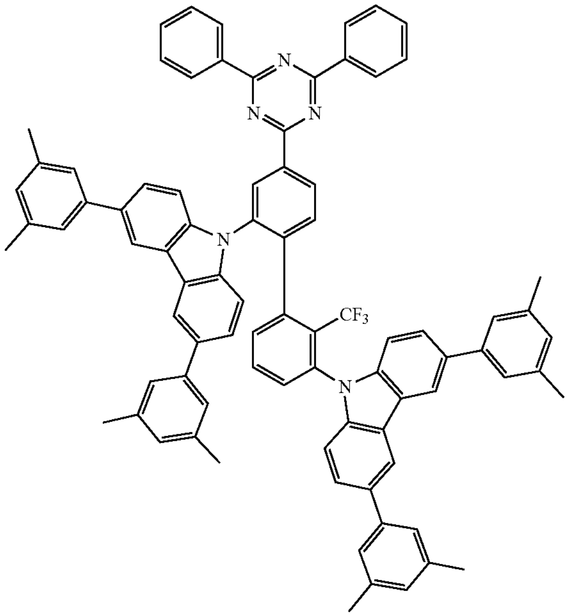

-continued
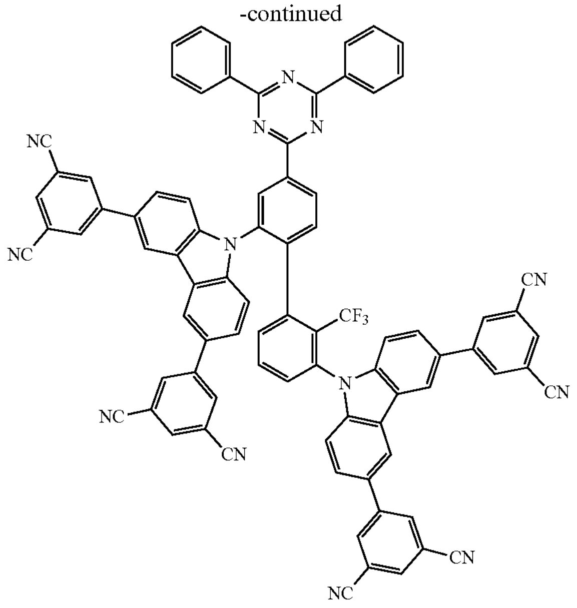
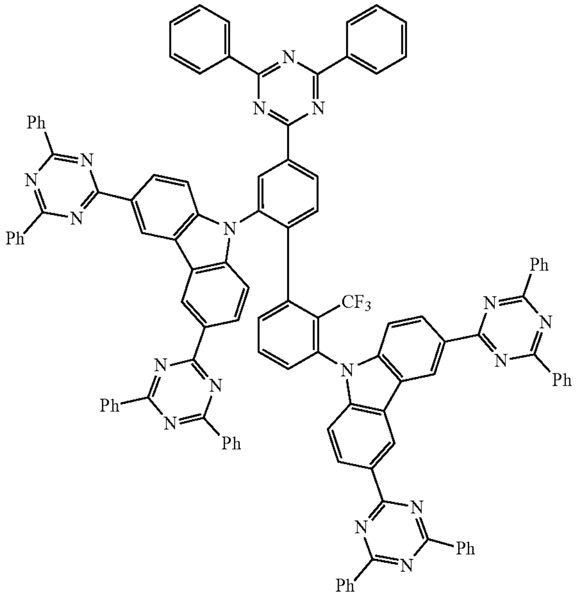
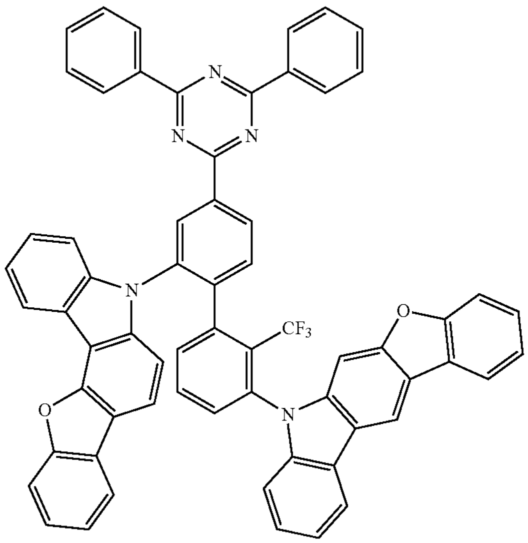
-continued
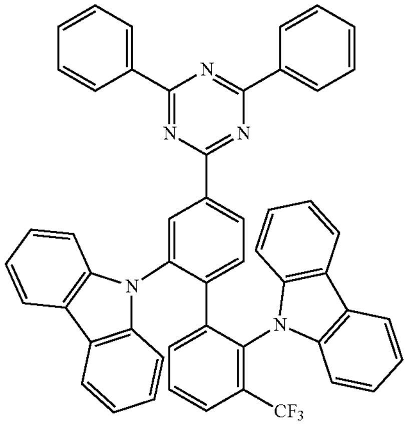
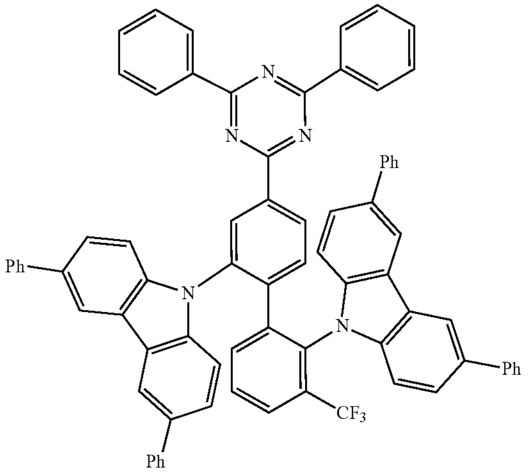
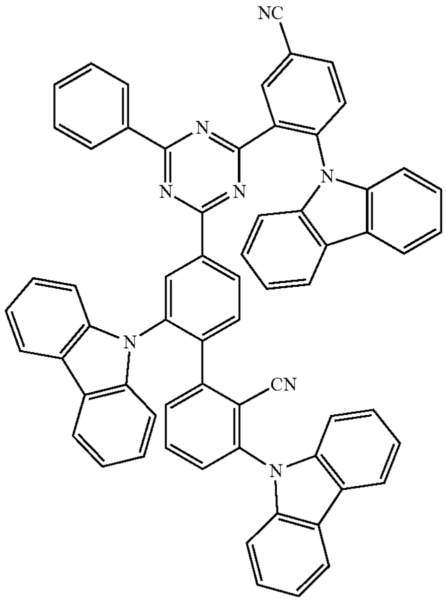

-continued
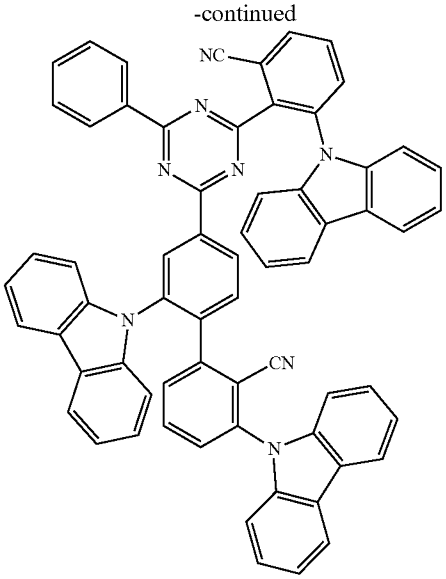
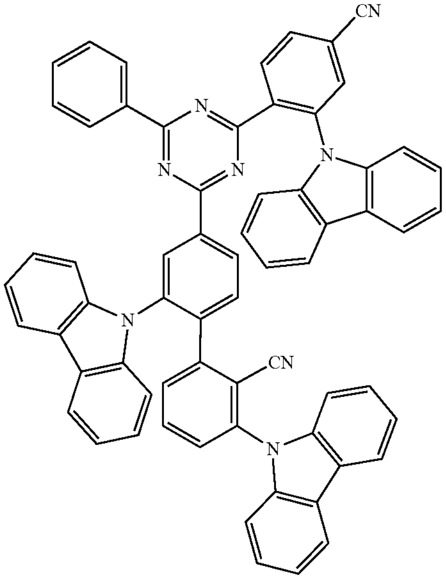
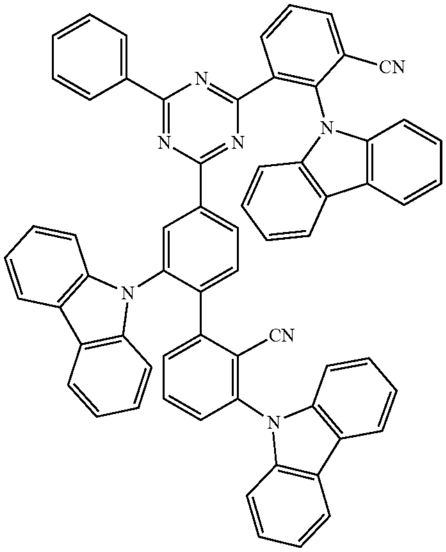
-continued
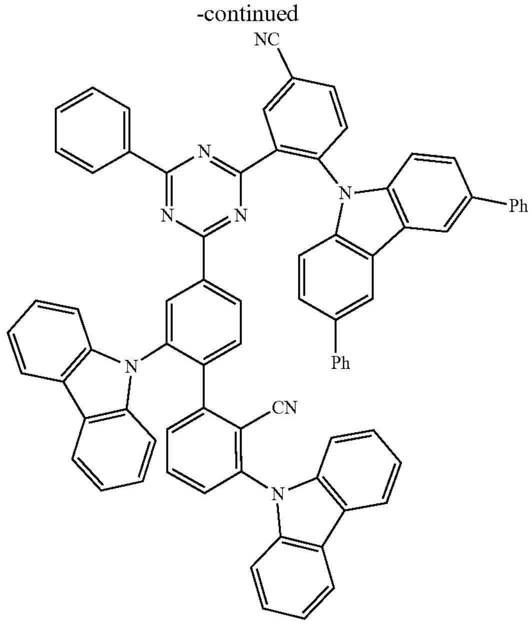
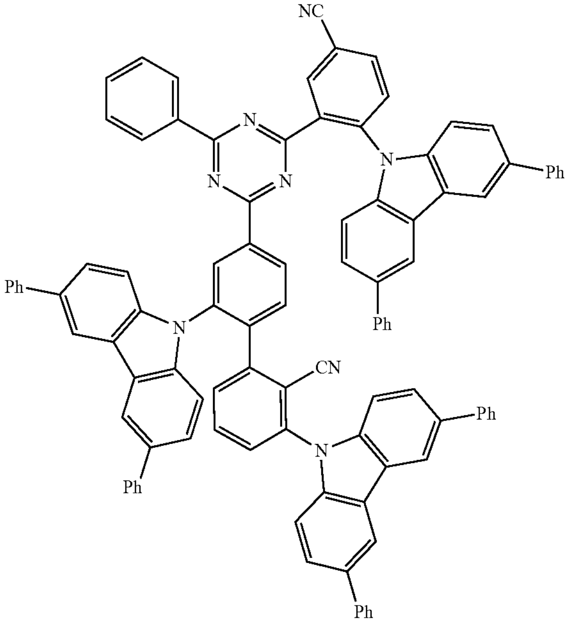

-continued
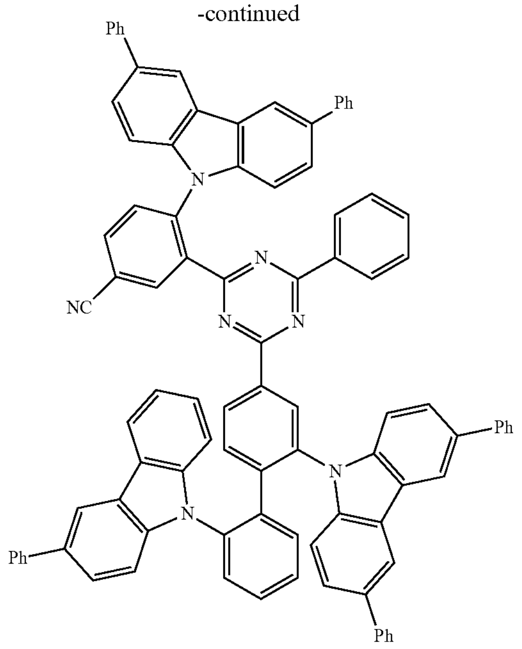
-continued
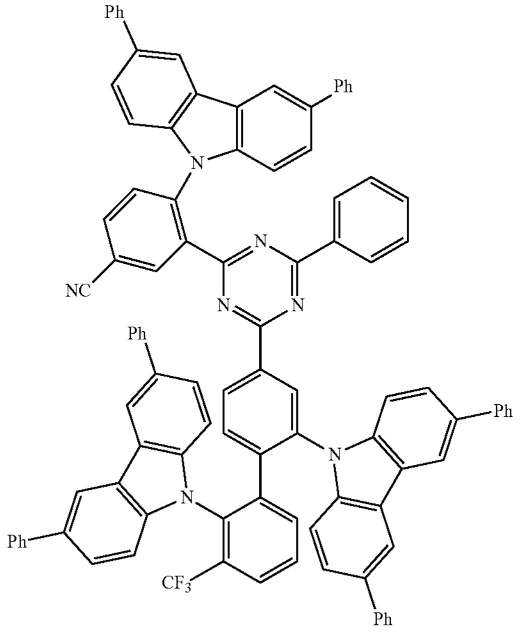
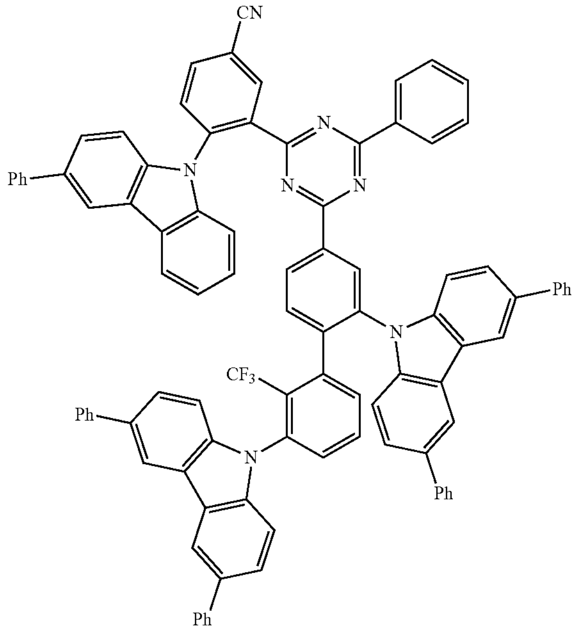
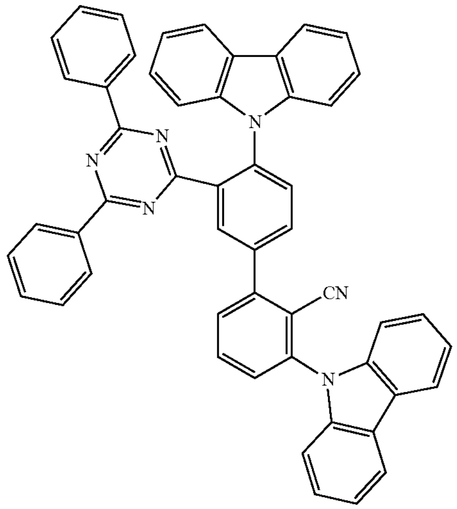

-continued
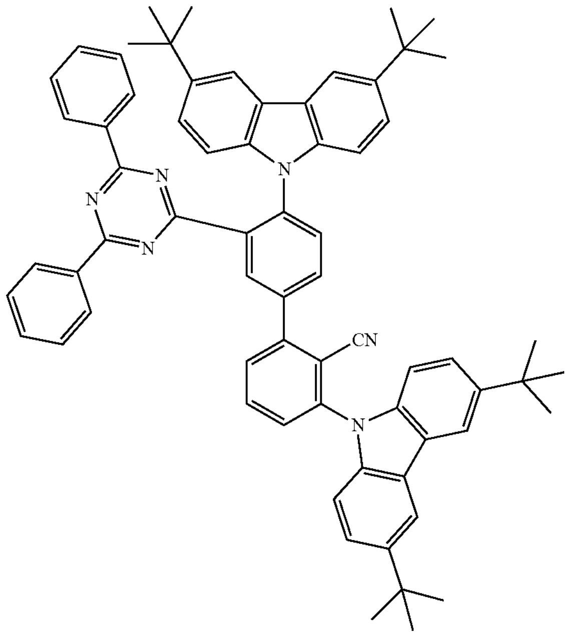
-continued
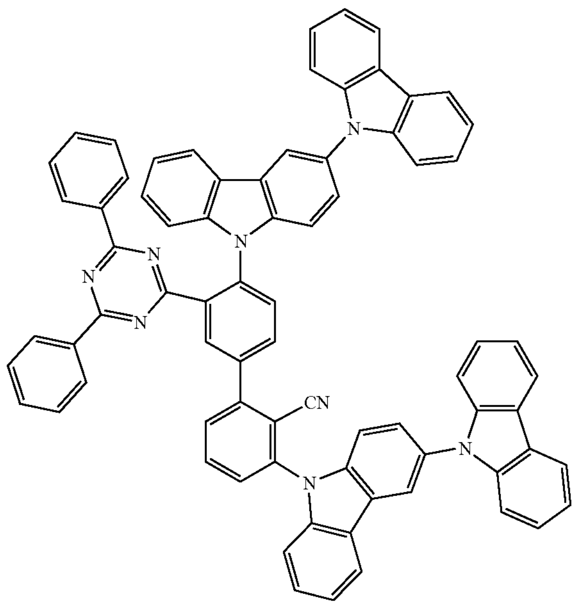
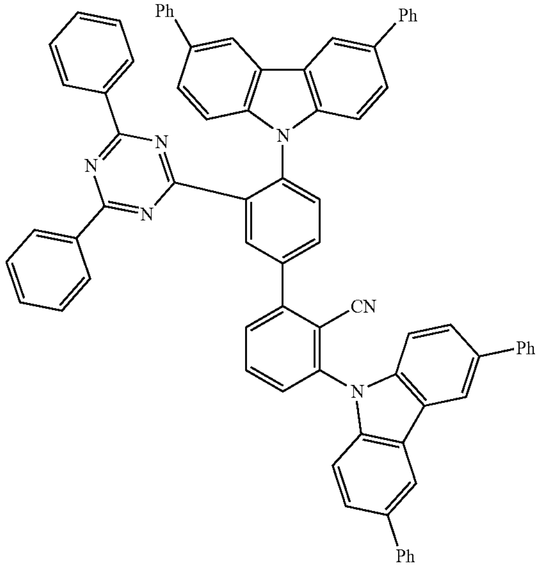
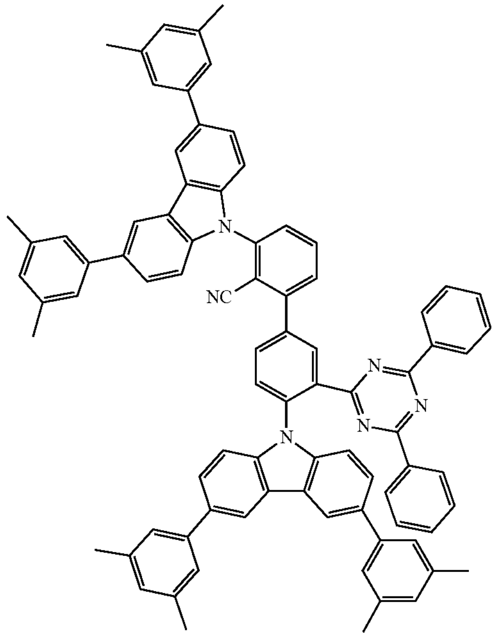

-continued
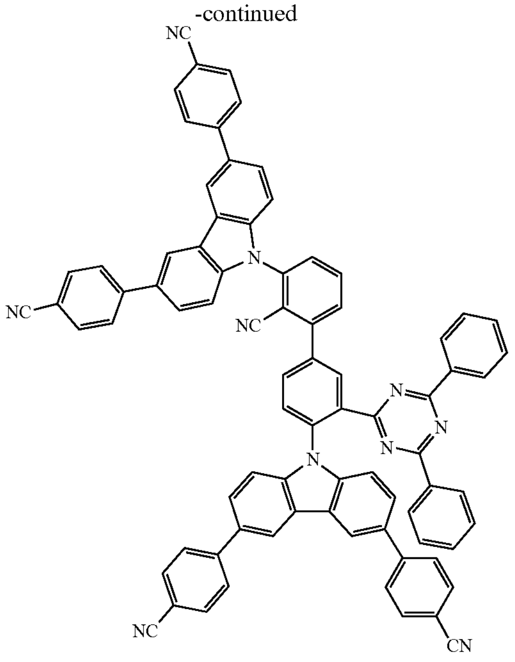
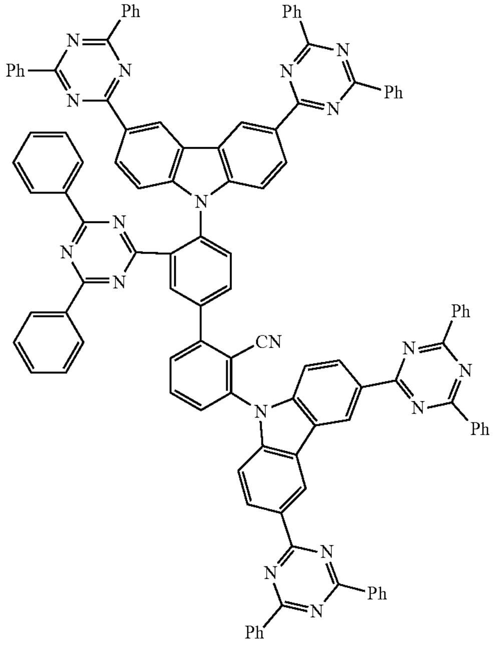
-continued
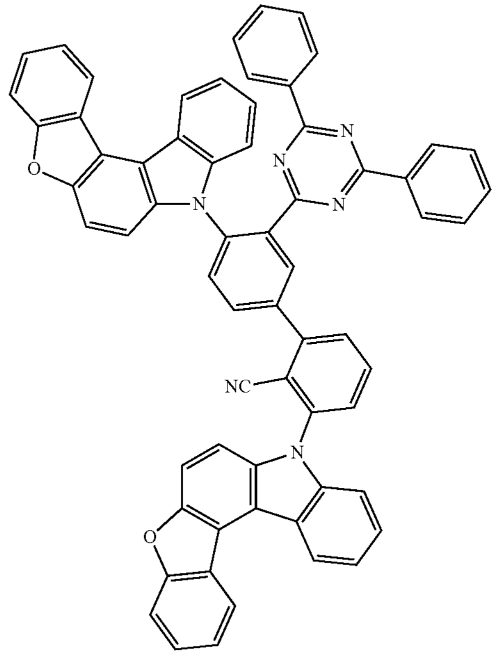
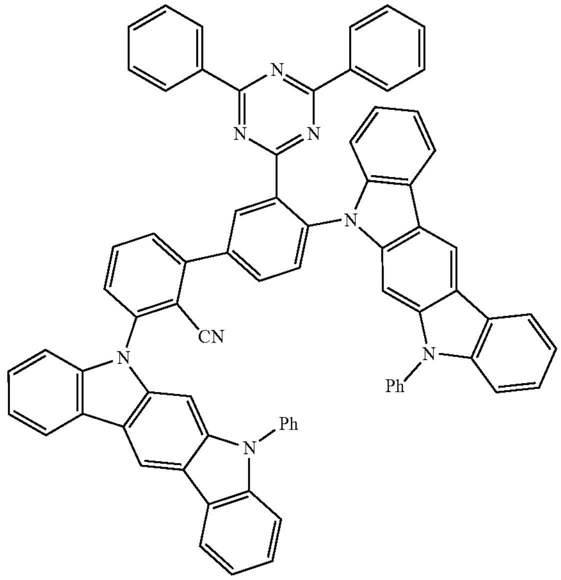
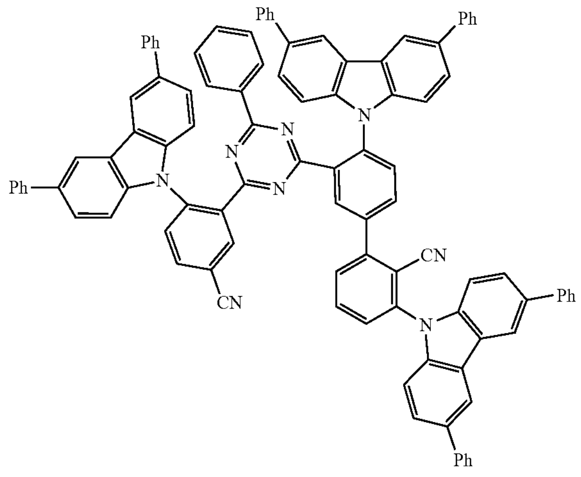

-continued
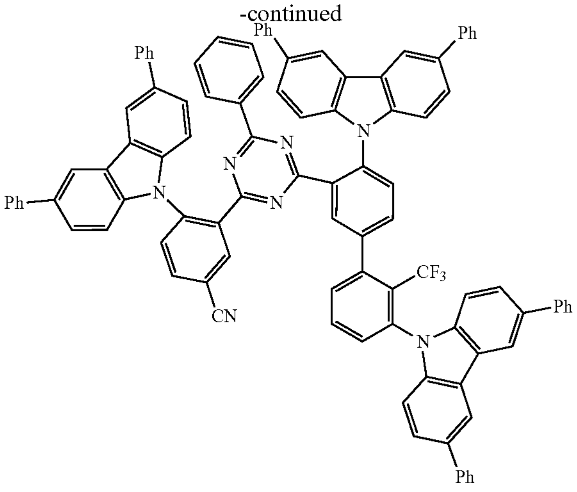
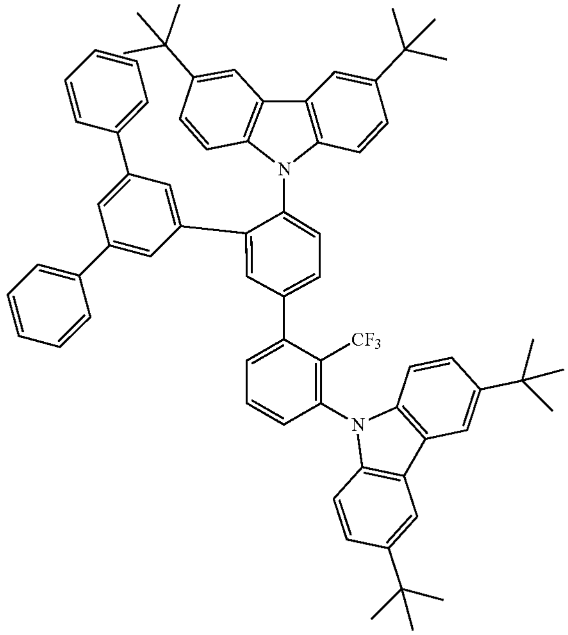
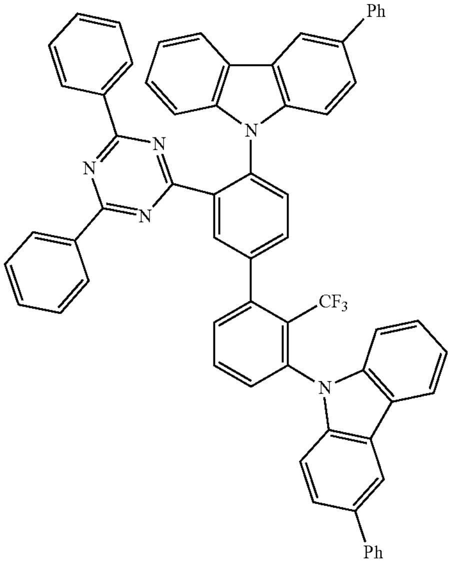
-continued
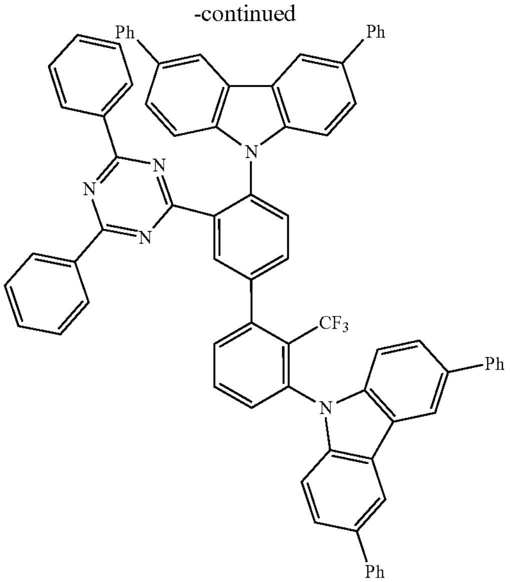
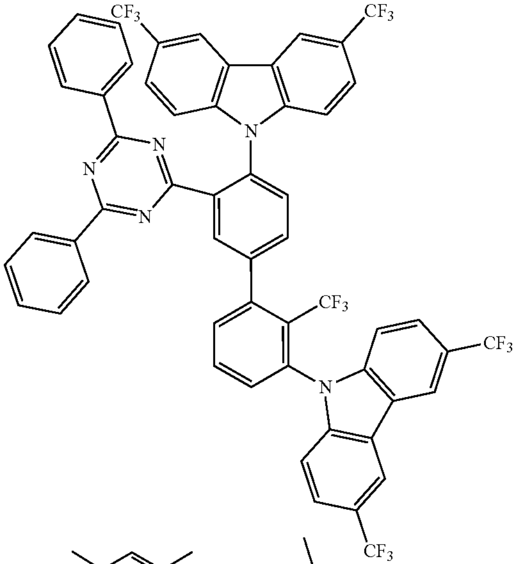
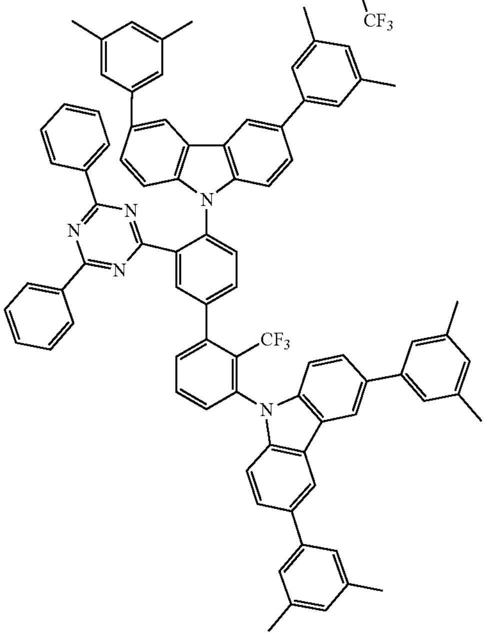

-continued
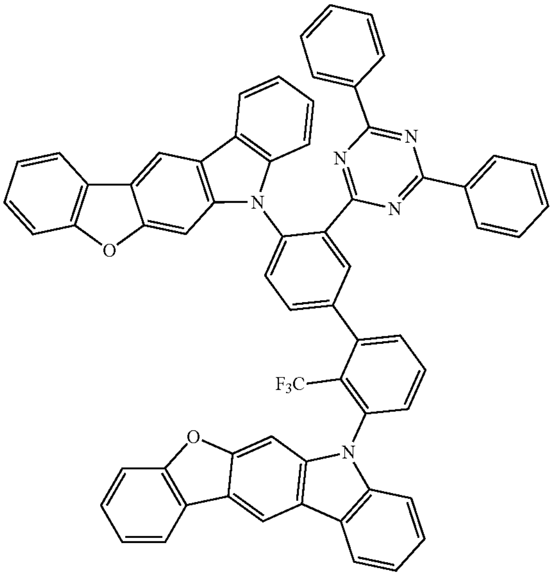
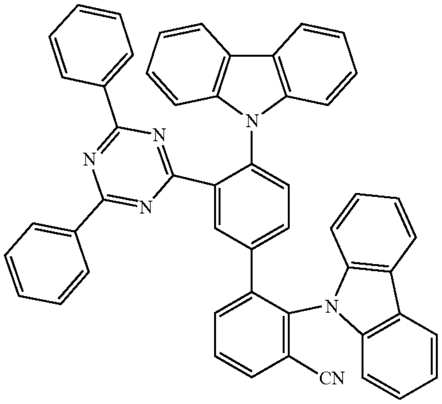
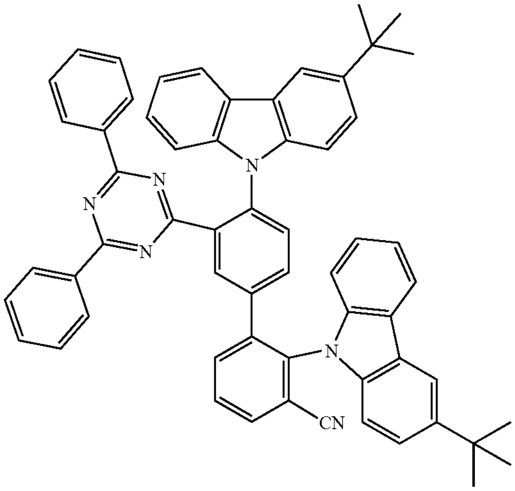
-continued
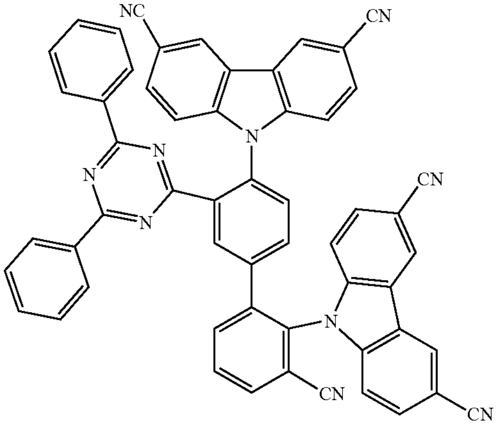
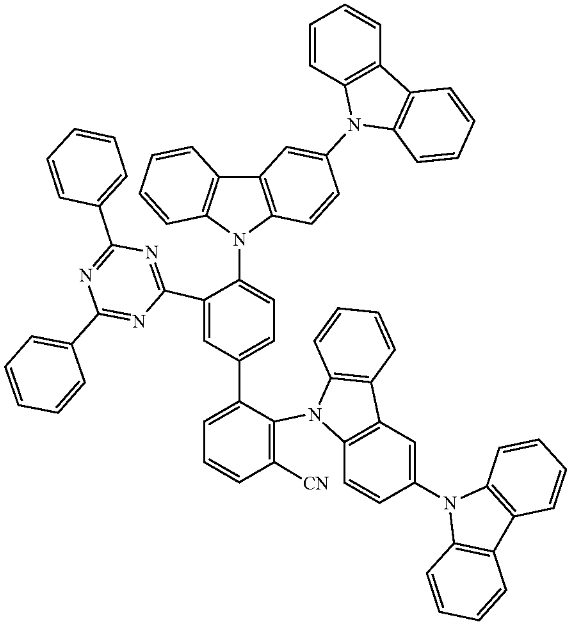
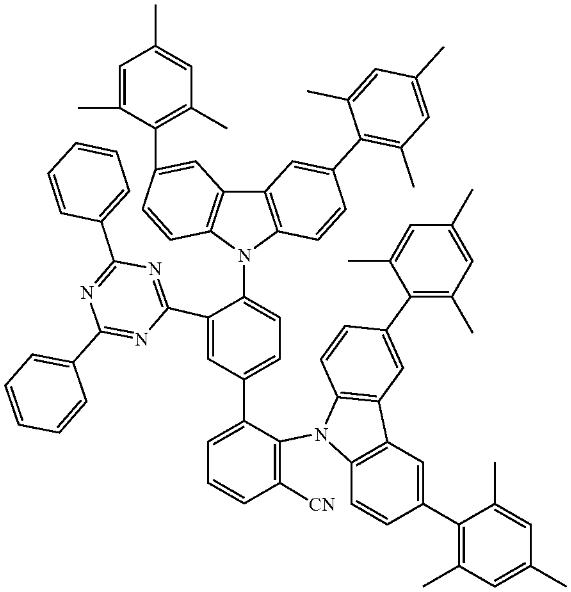

-continued
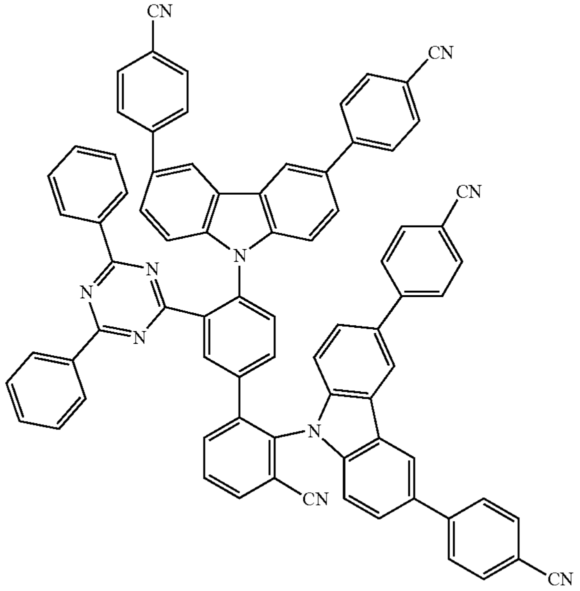
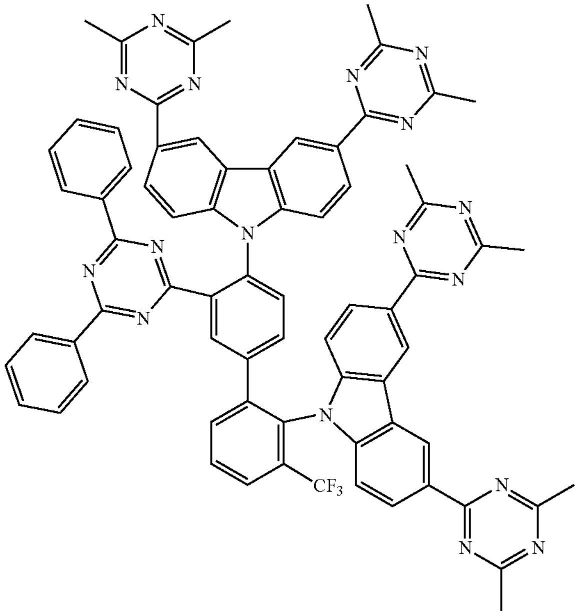
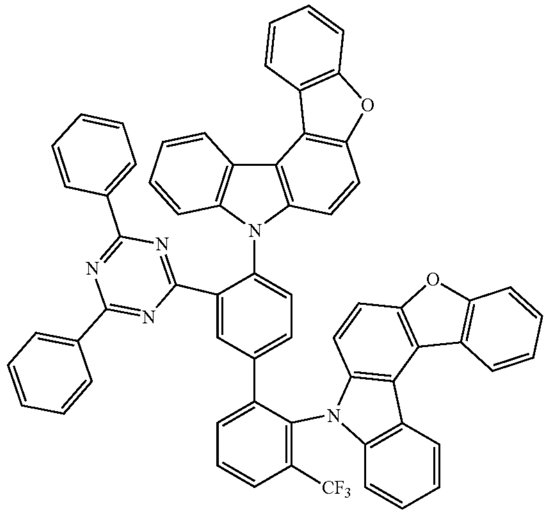
-continued
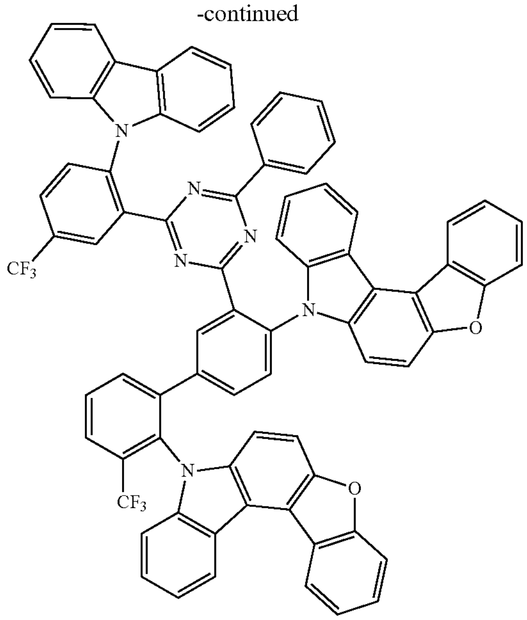
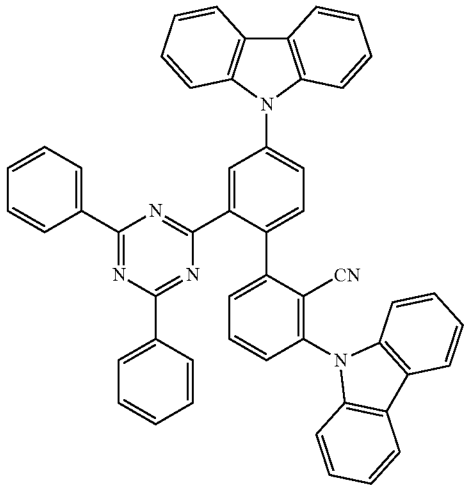
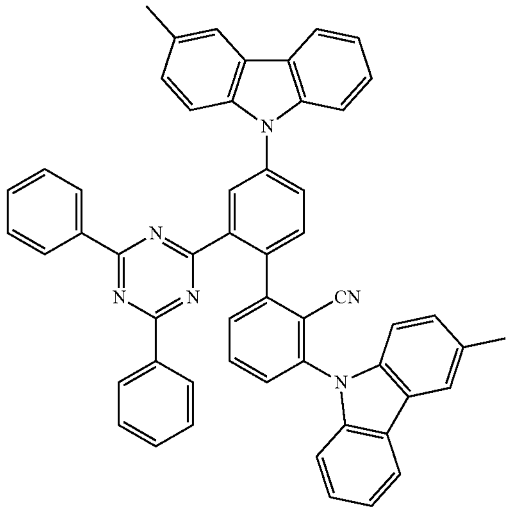

-continued
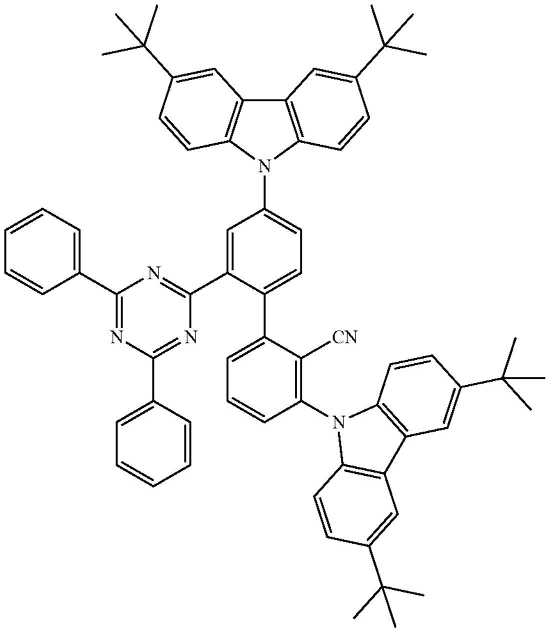
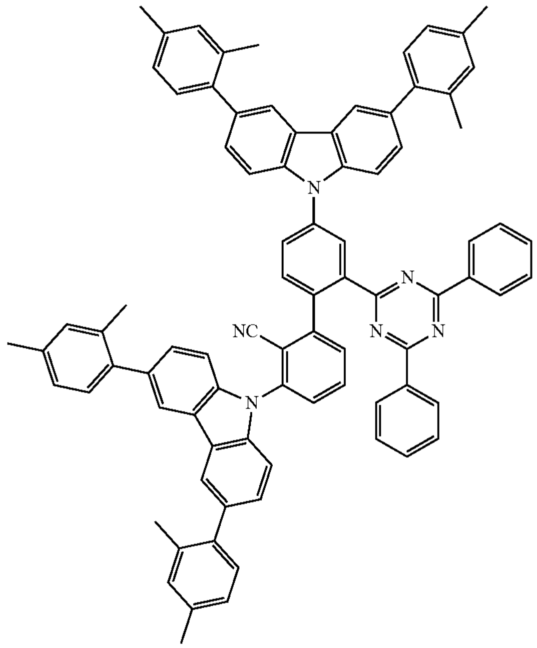
-continued
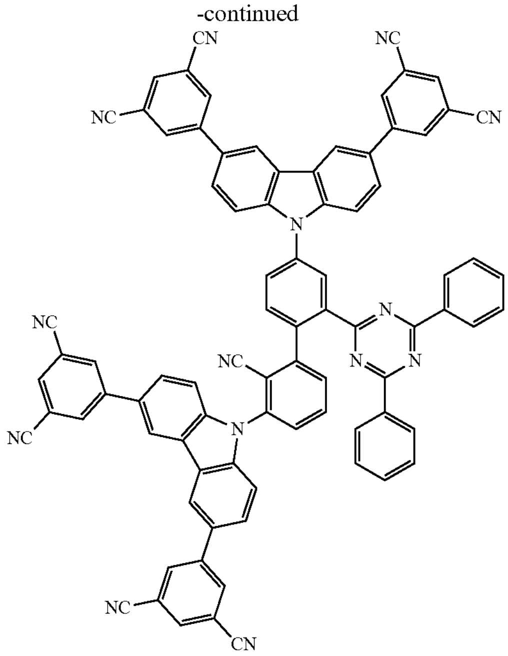
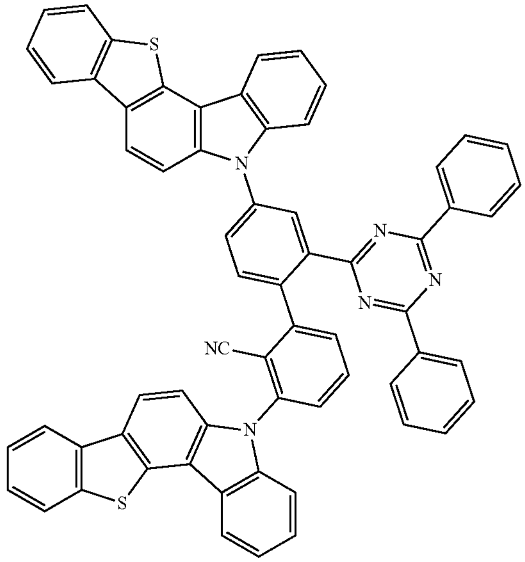
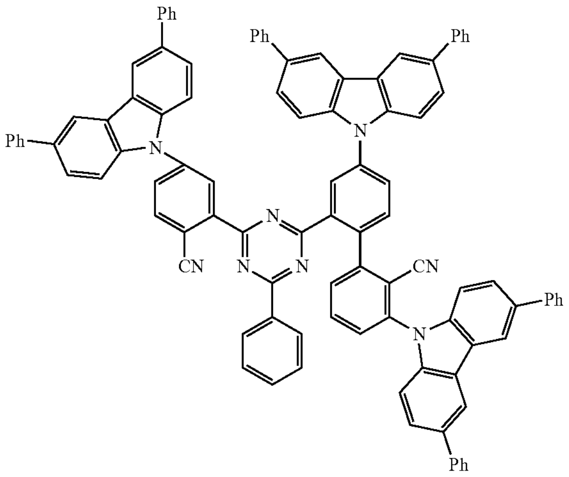

-continued
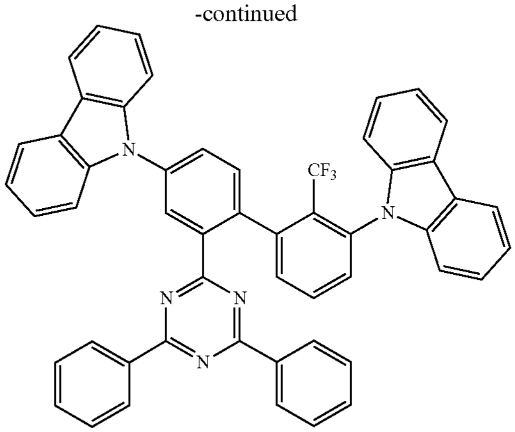
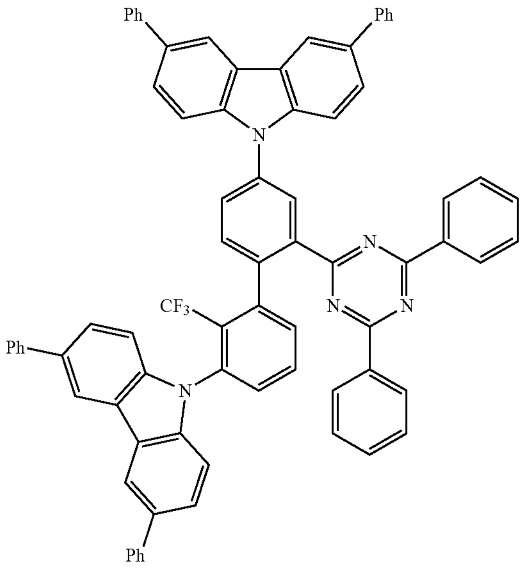
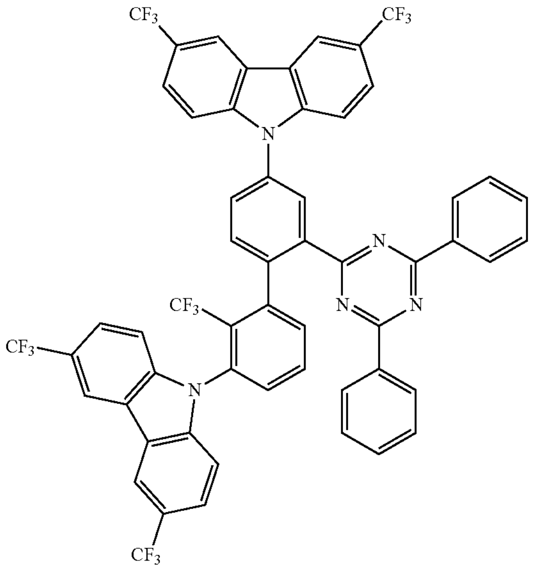
-continued
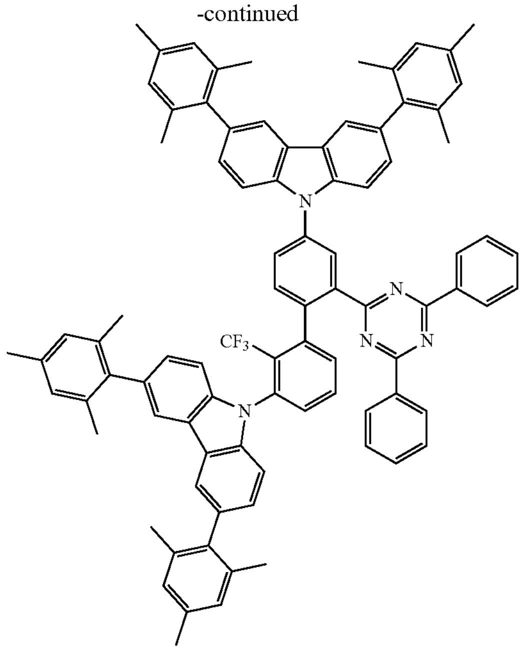
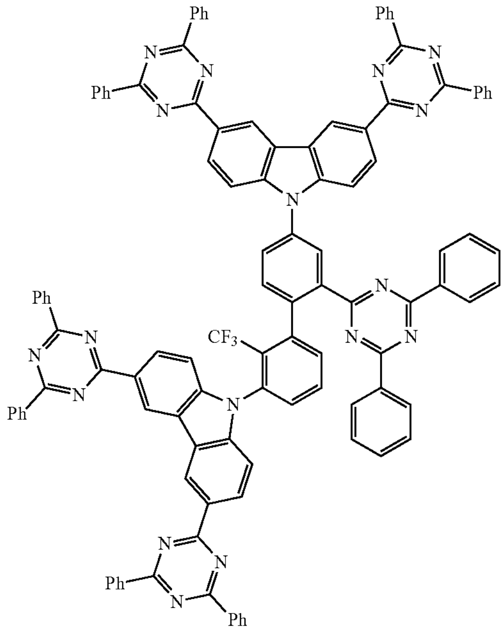

-continued
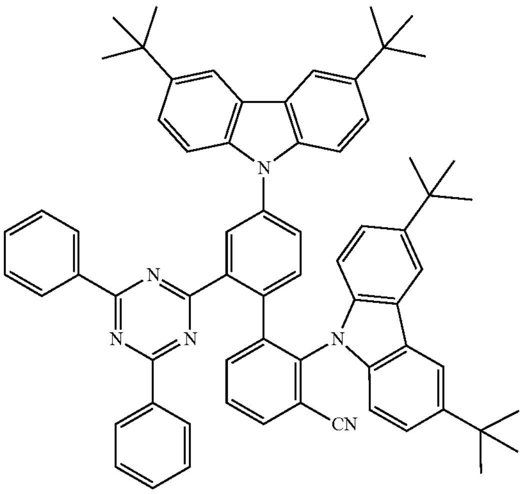
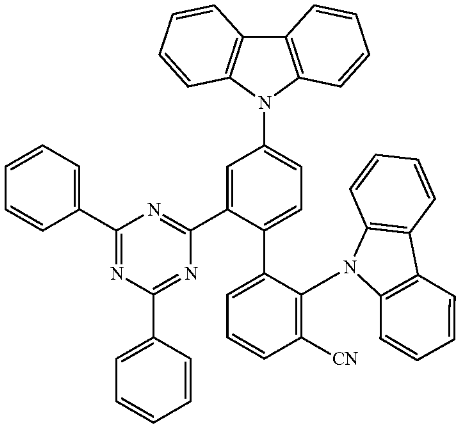
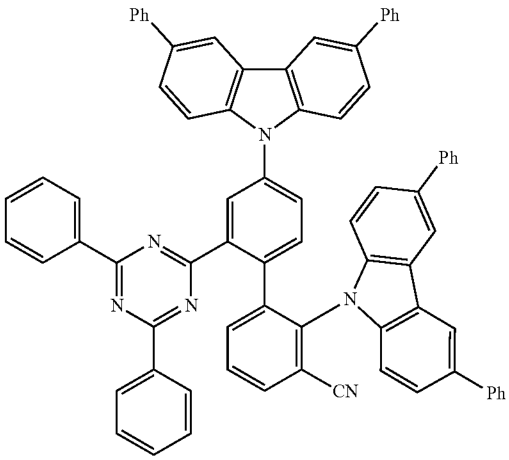
-continued
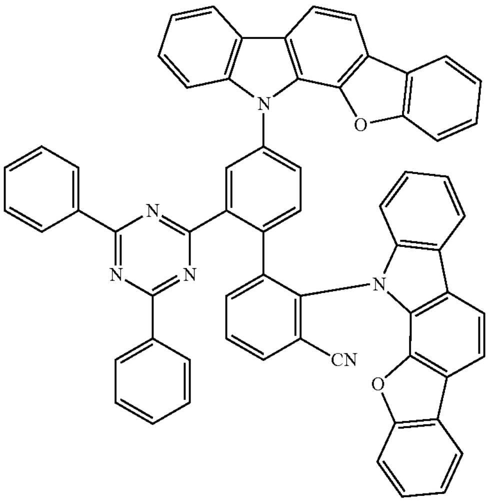
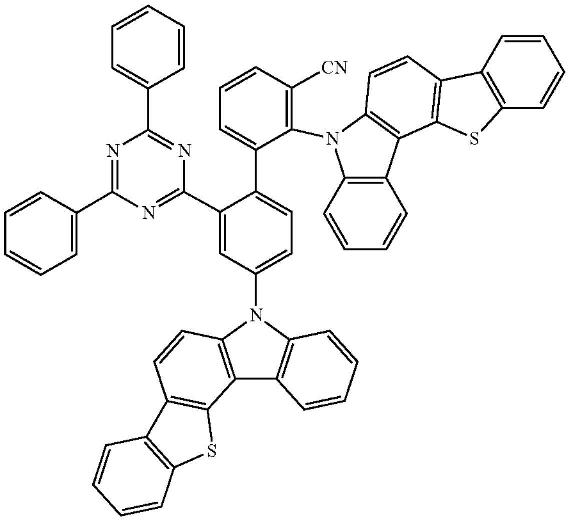
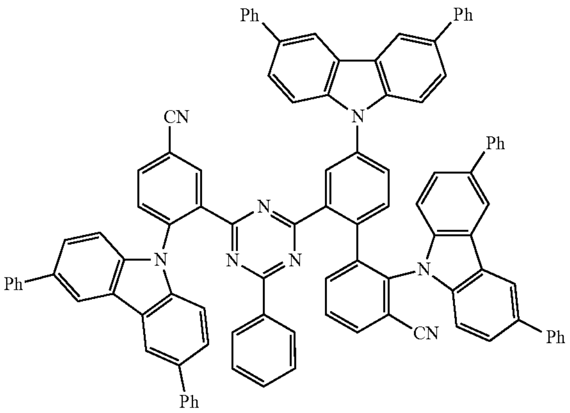

-continued
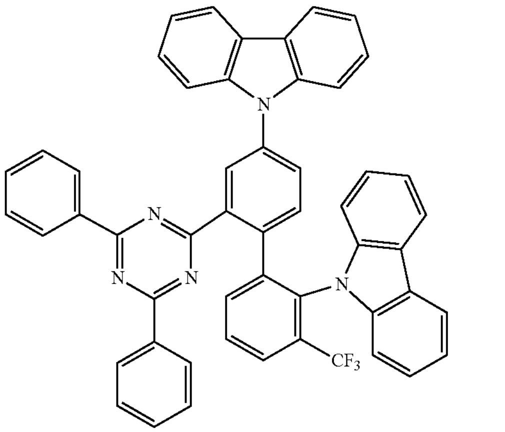
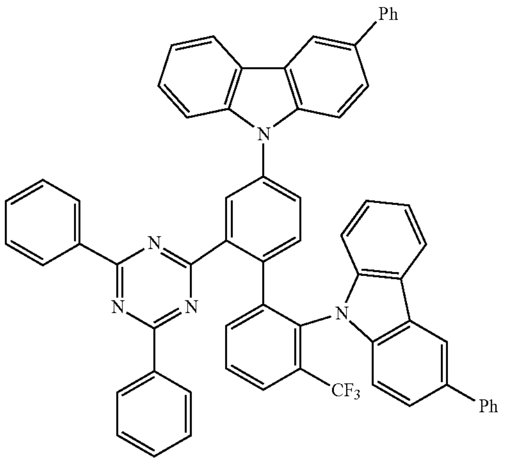
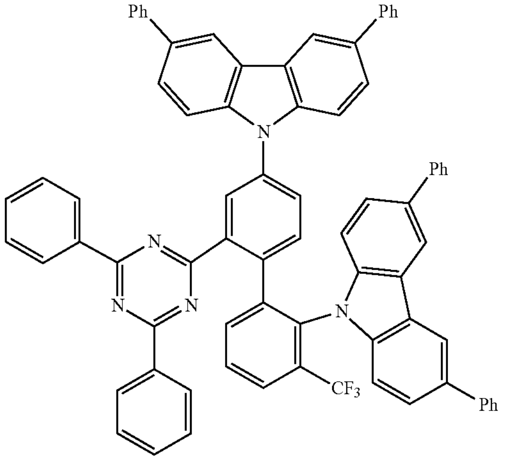
-continued
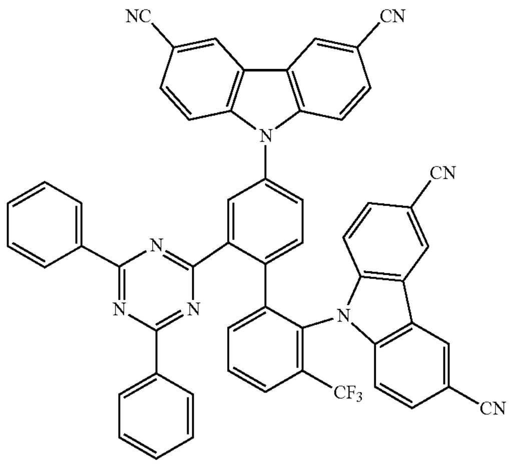
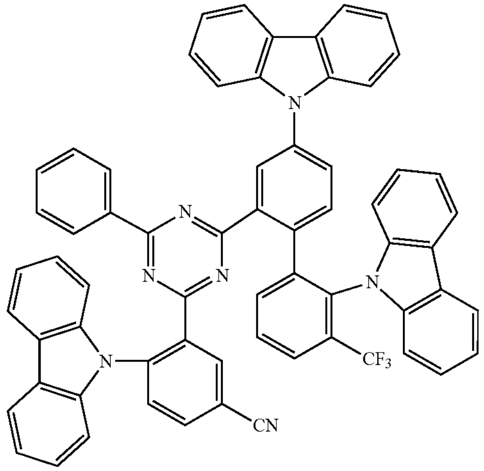
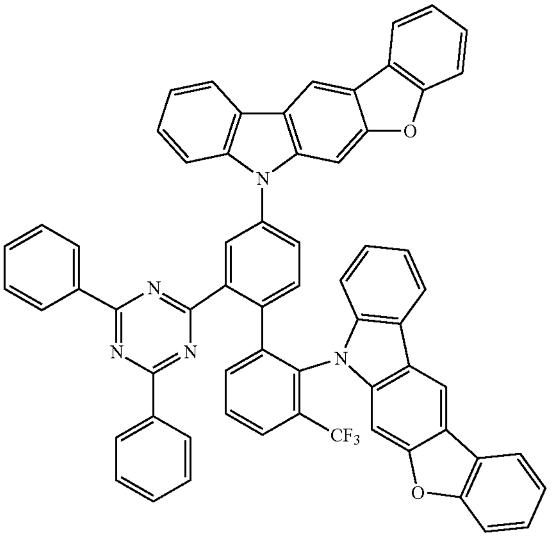

-continued
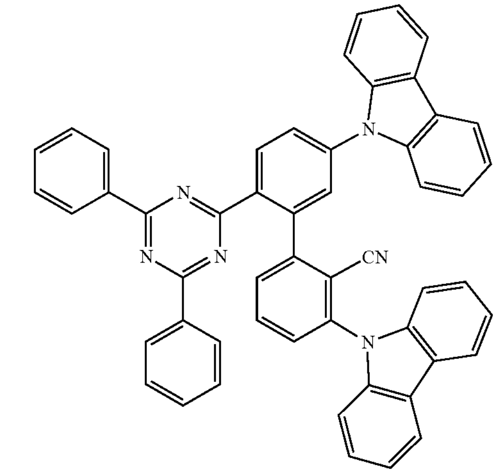
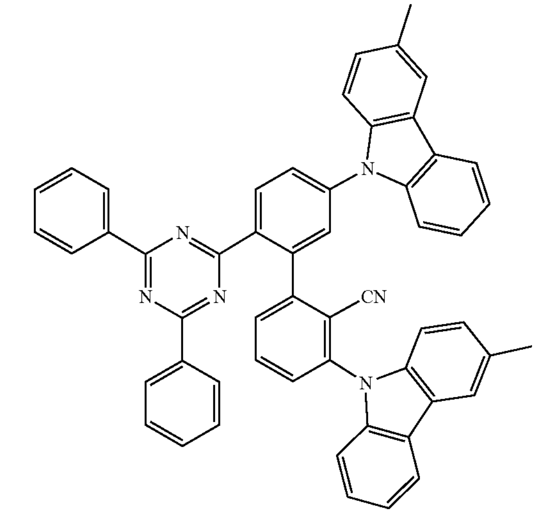
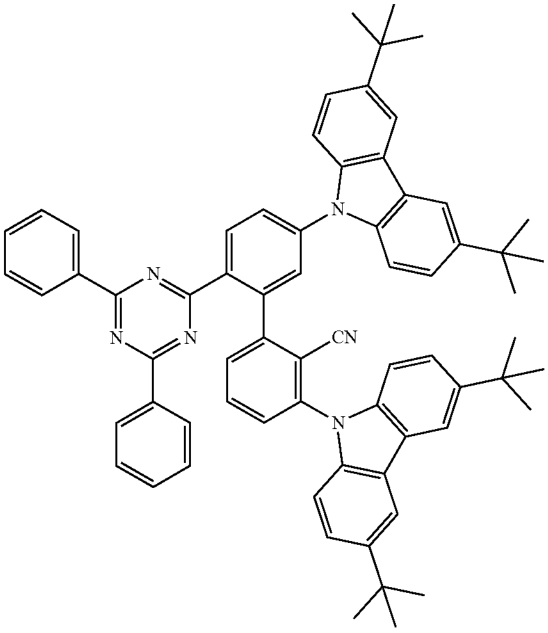
-continued
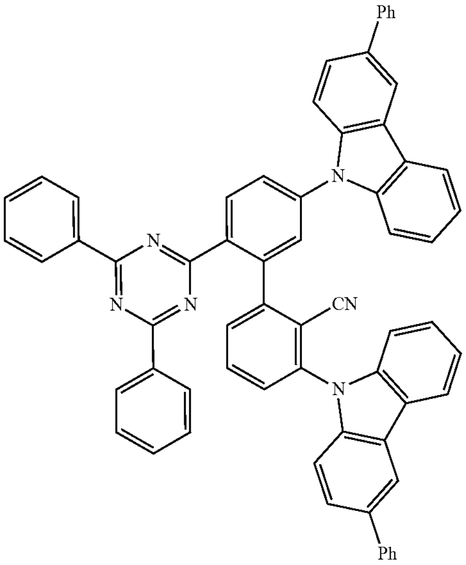
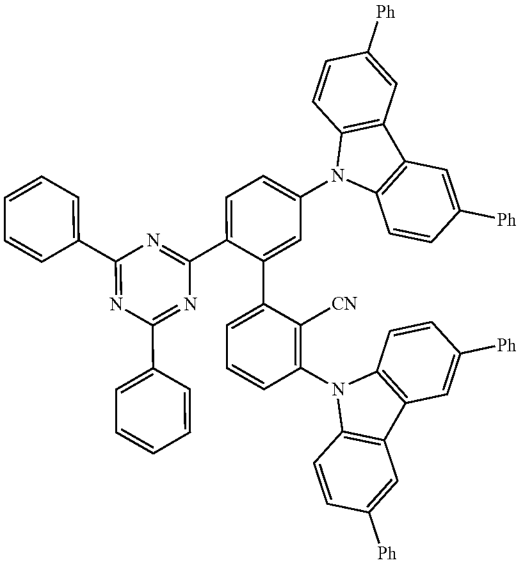
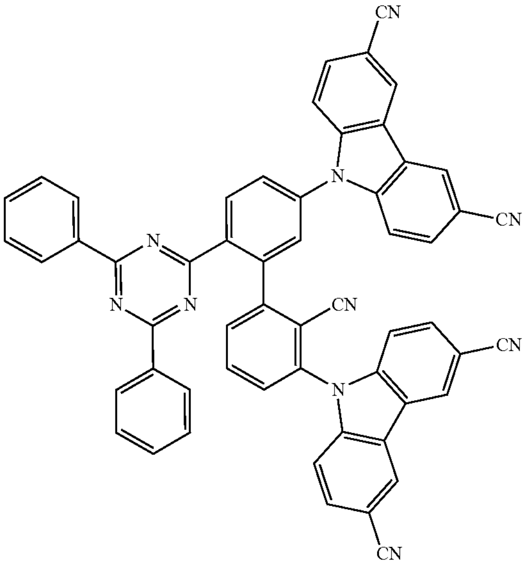

-continued
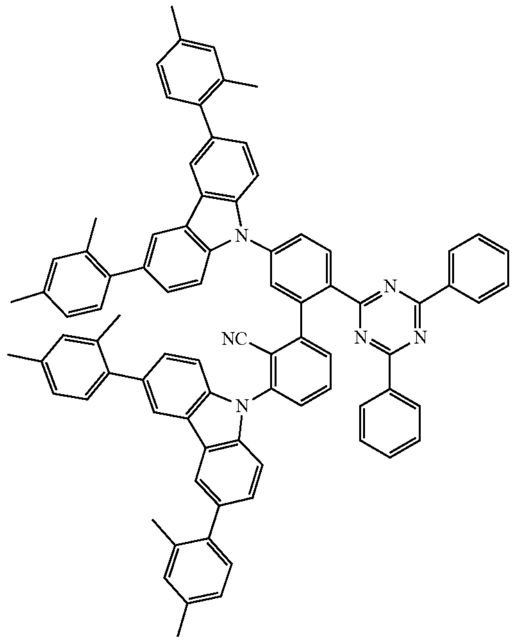
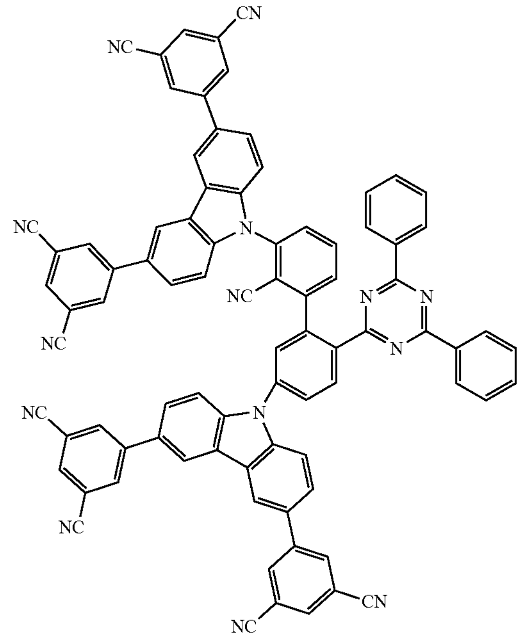
-continued
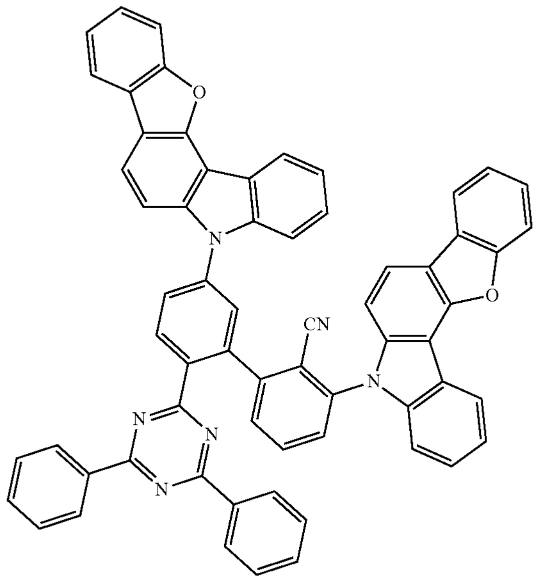
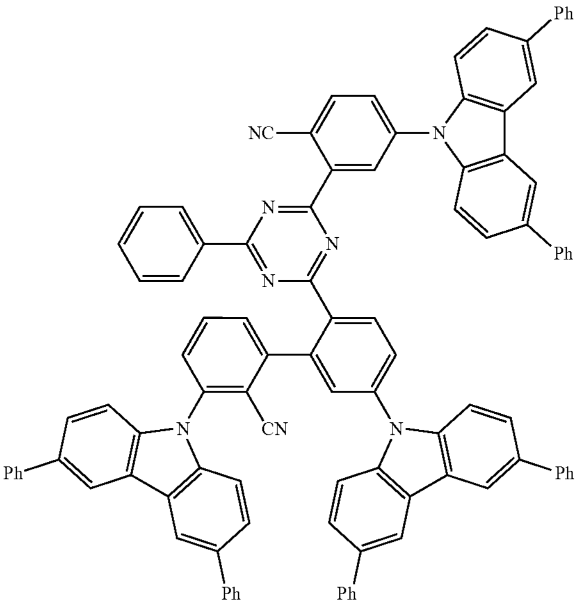
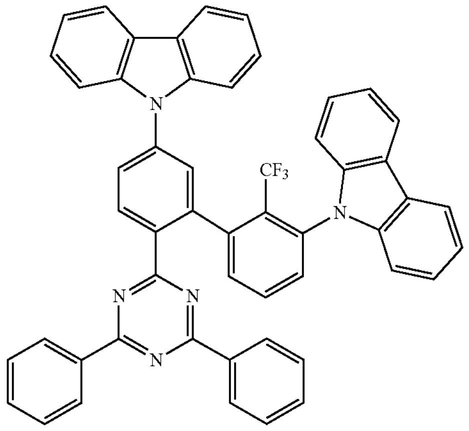

-continued
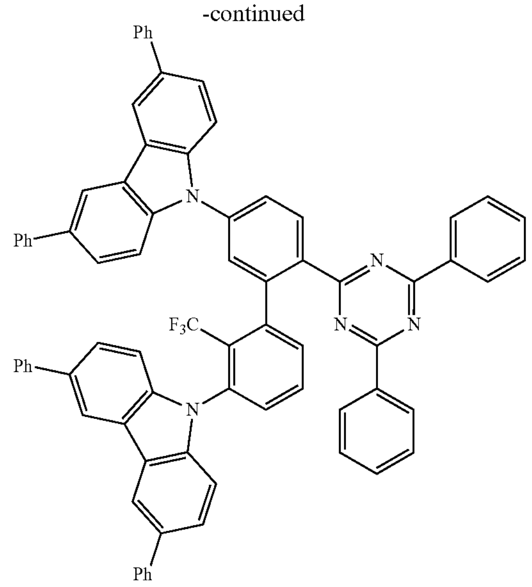
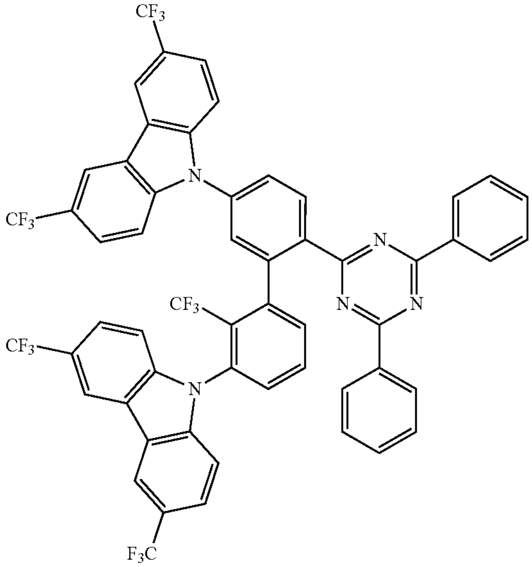
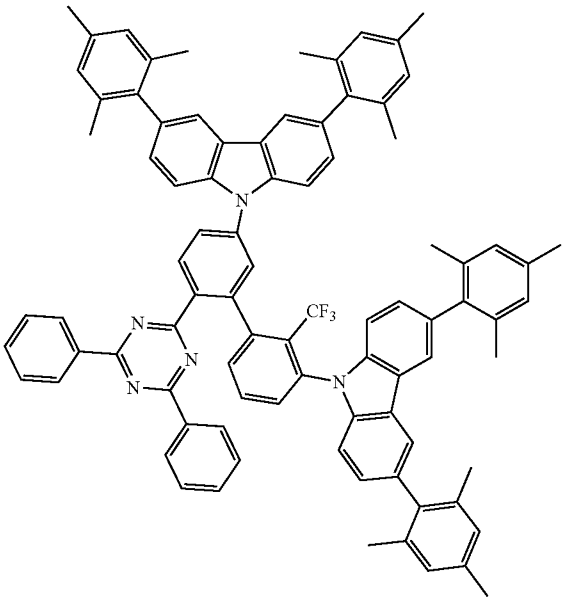
-continued
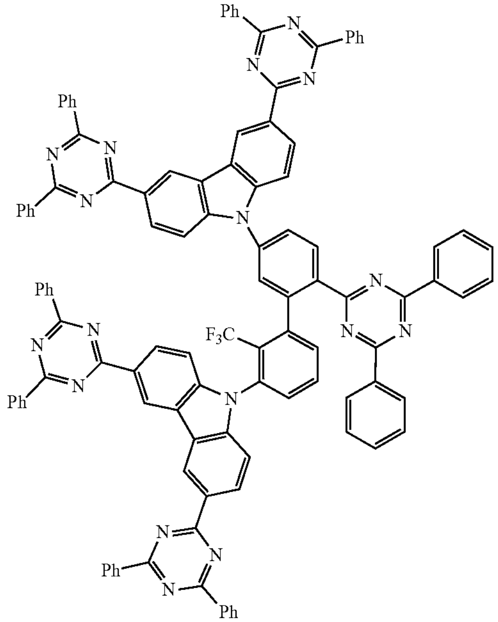
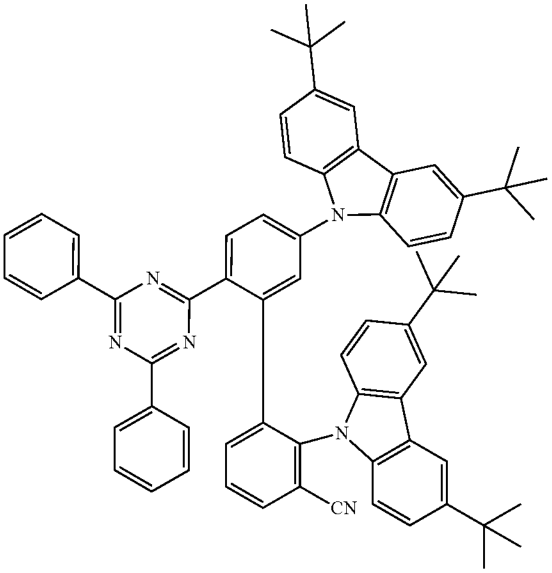
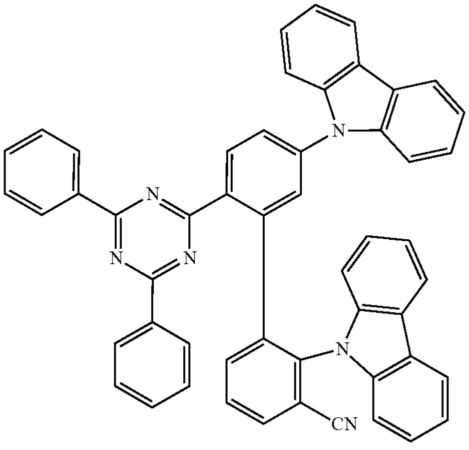

-continued
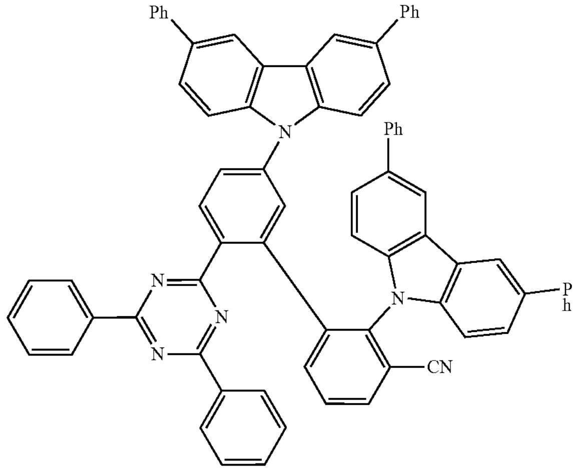
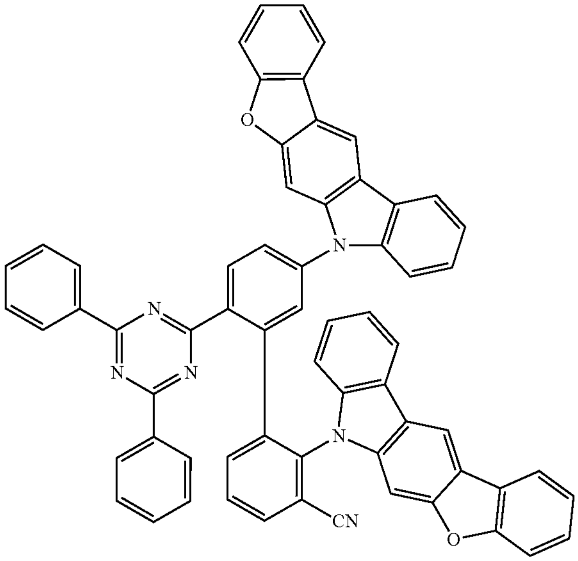
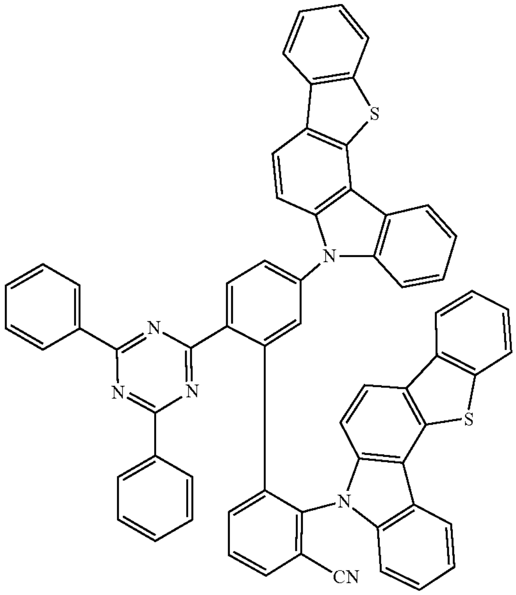
-continued
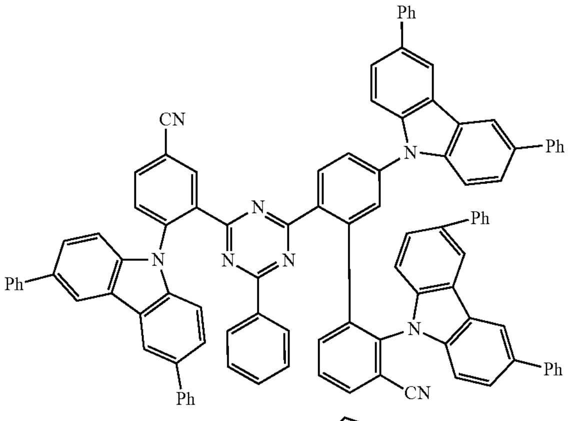
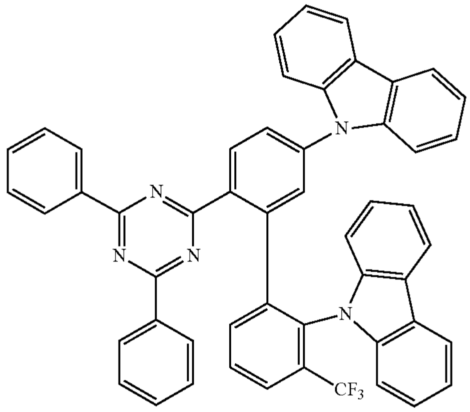
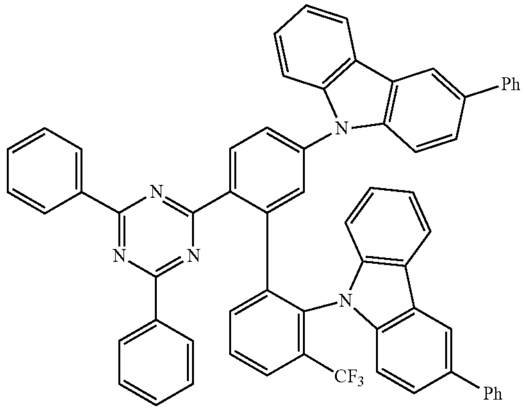
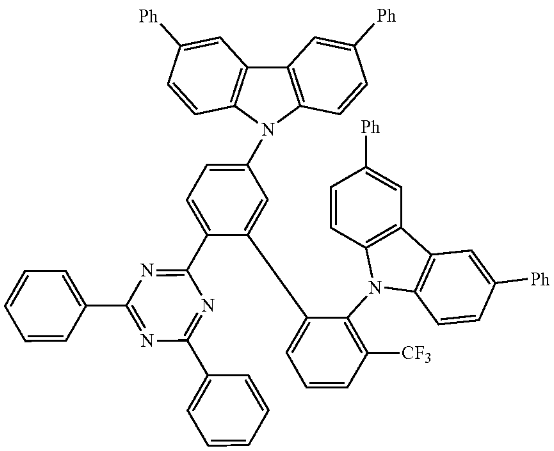

-continued
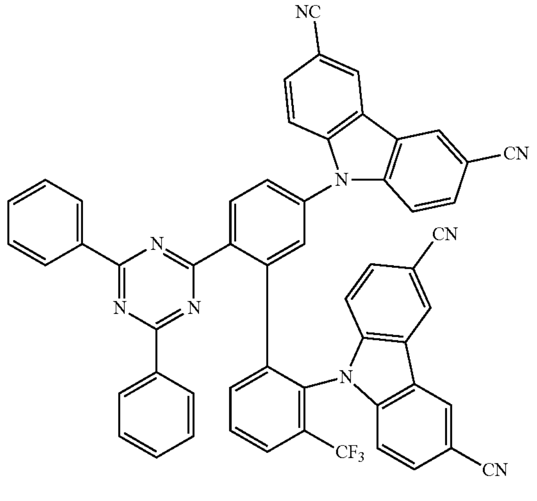
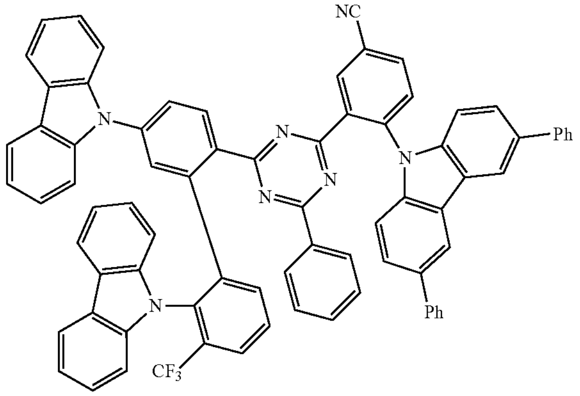
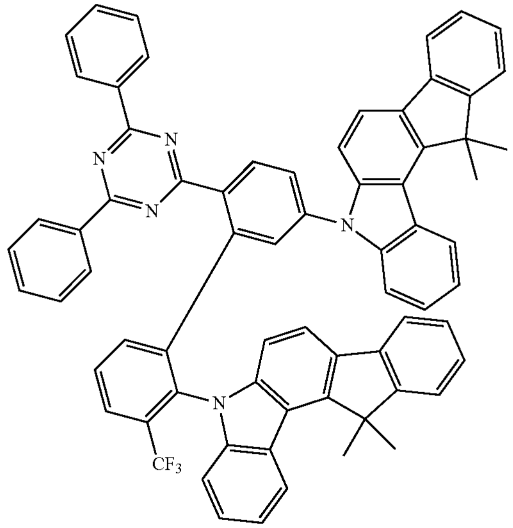
-continued
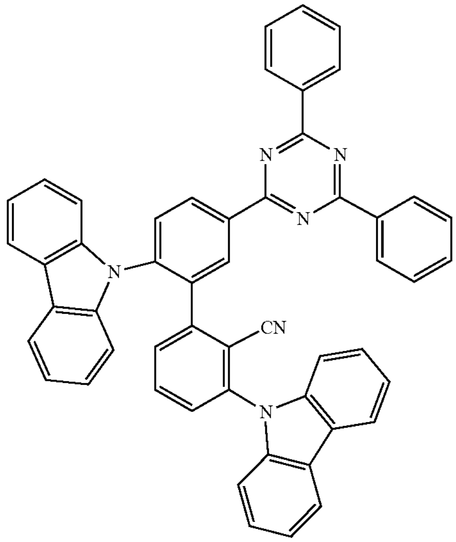
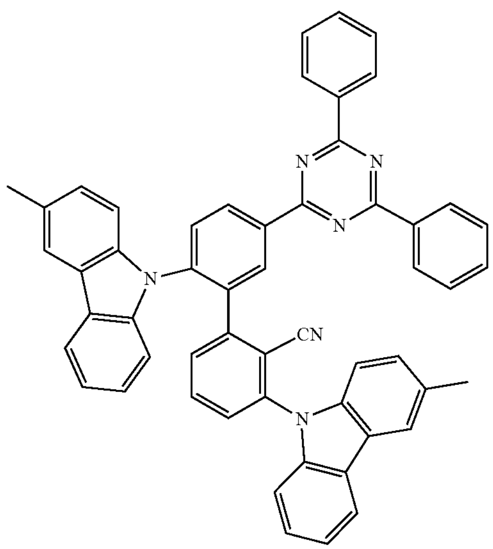
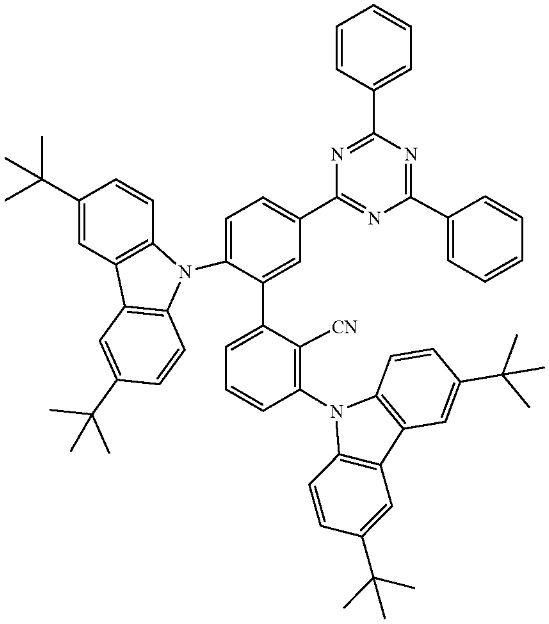

-continued
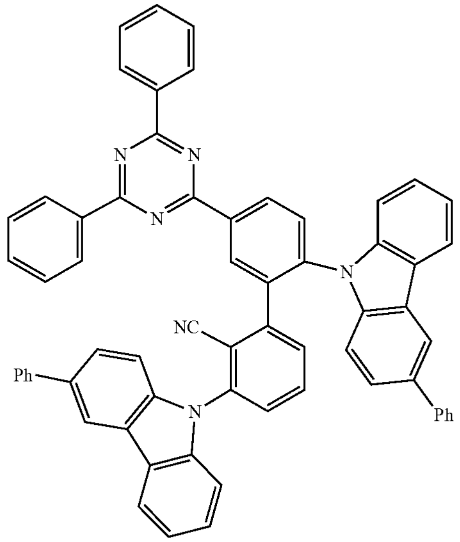
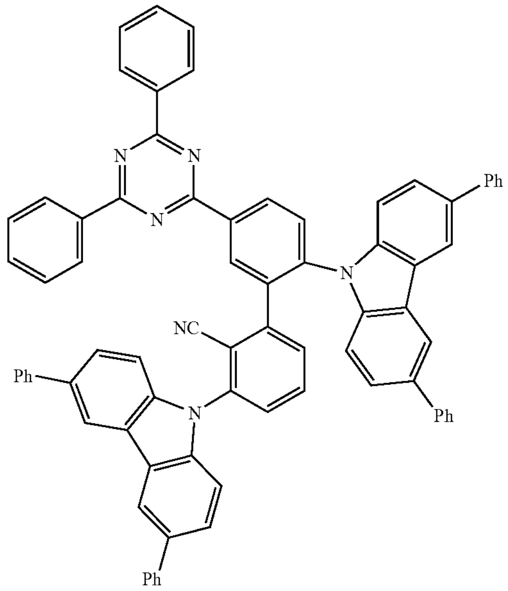
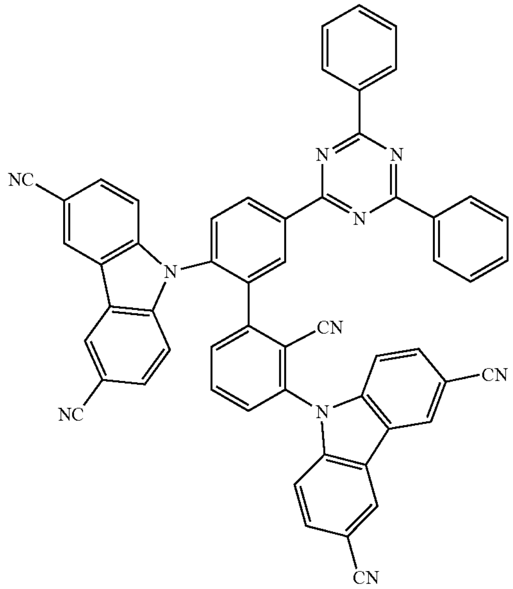
-continued
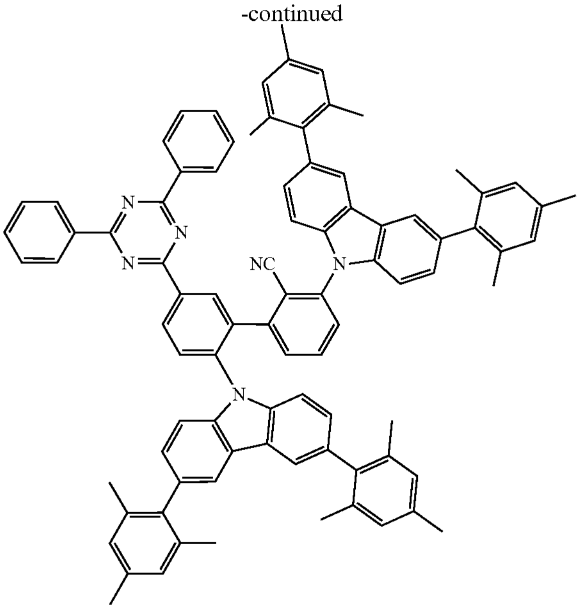
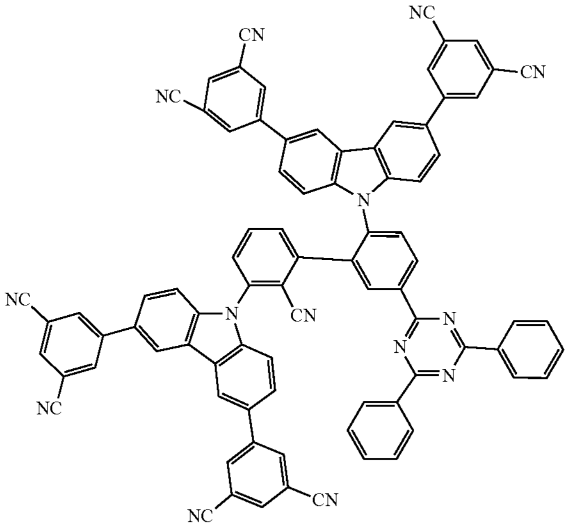
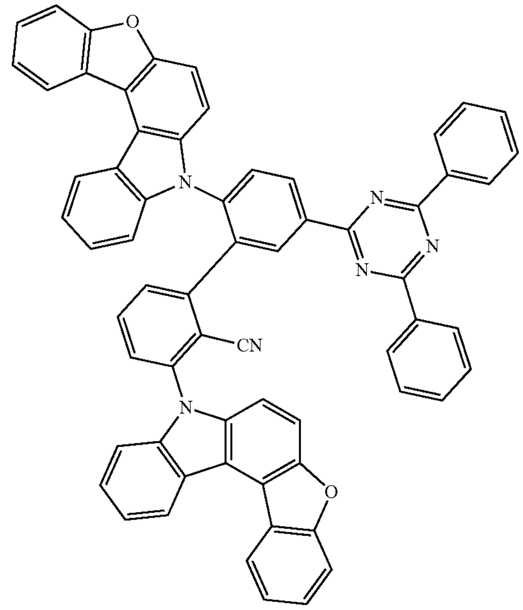

-continued
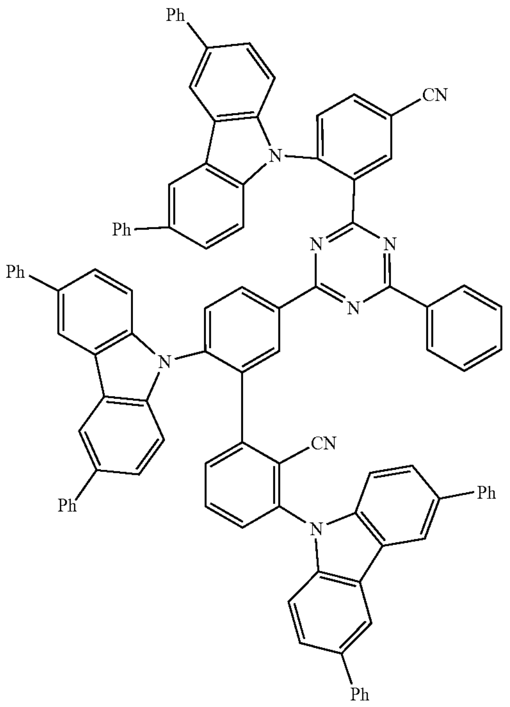
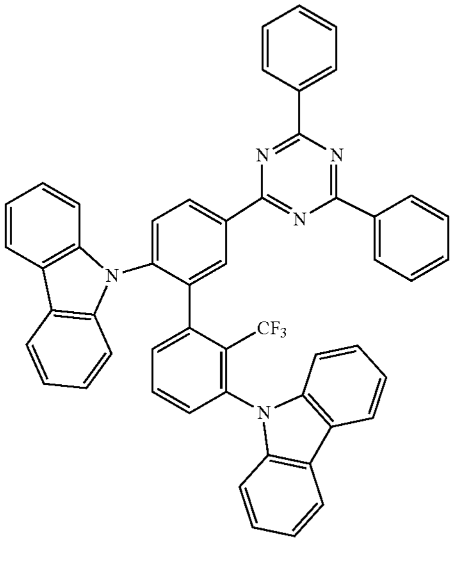
-continued
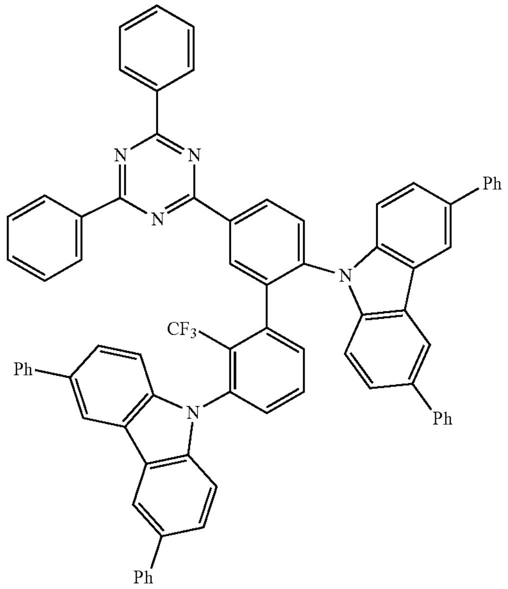
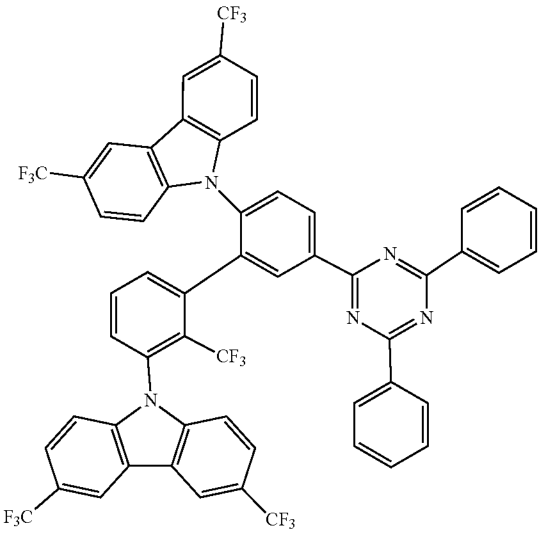
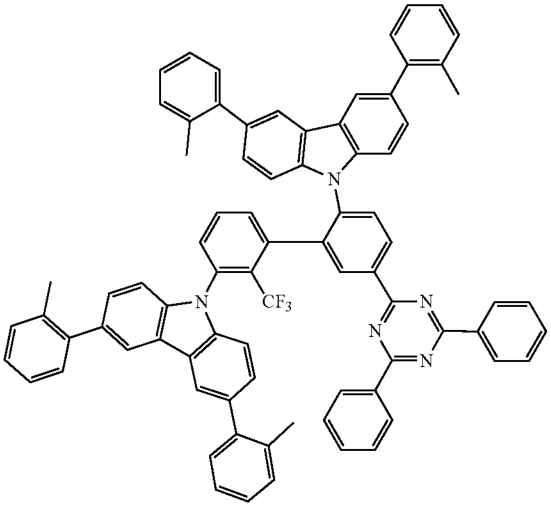

-continued
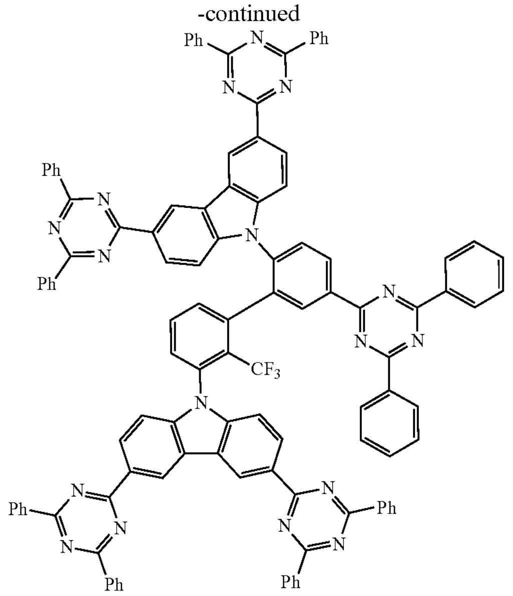
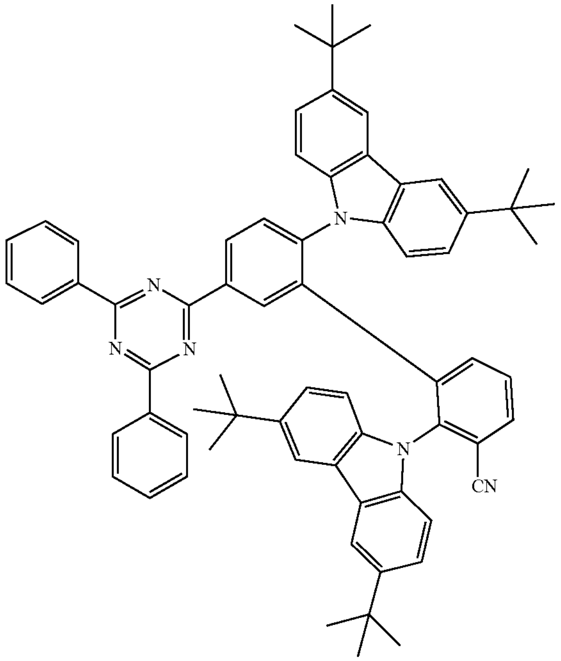
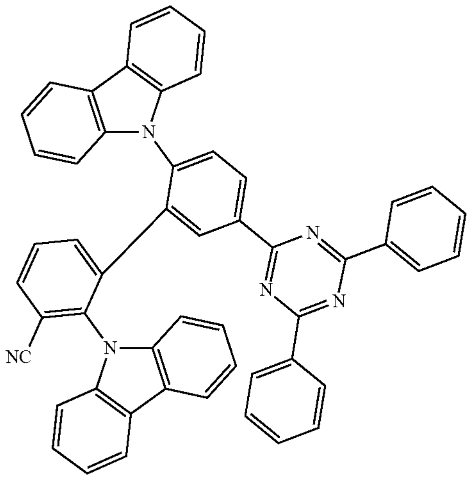
-continued
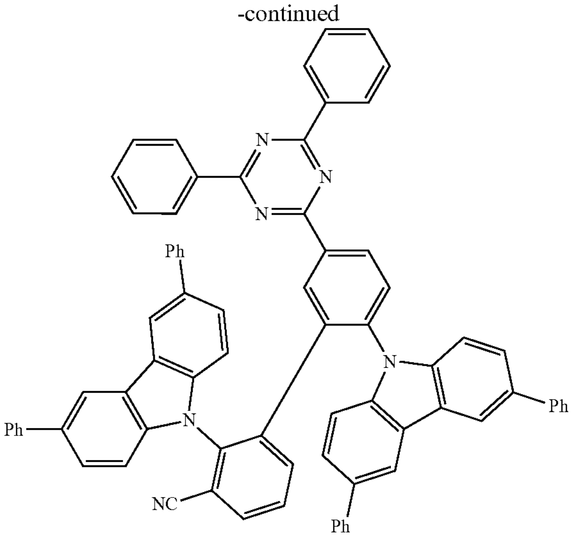
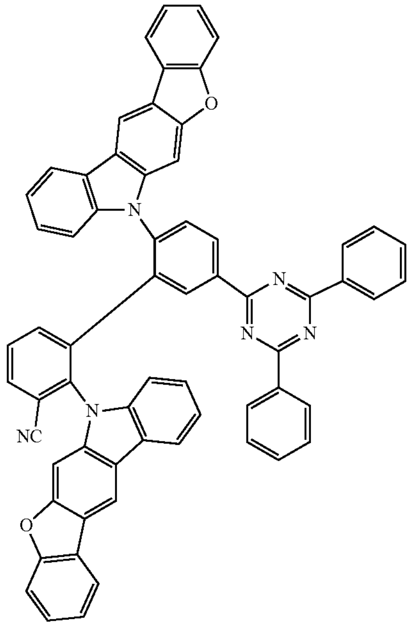

-continued
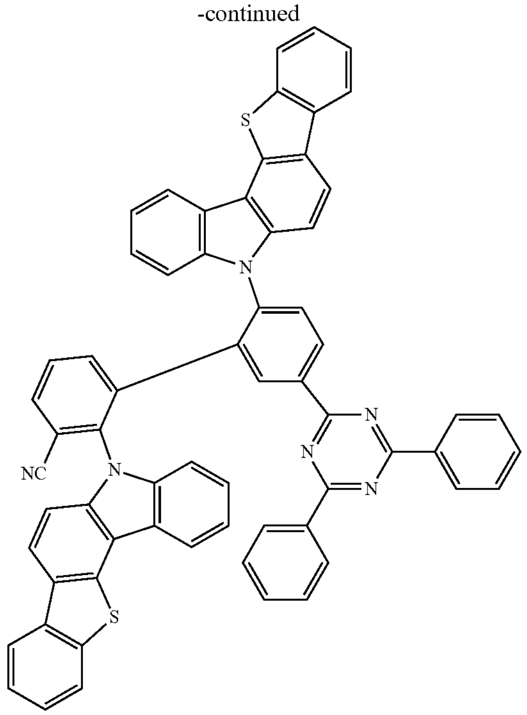
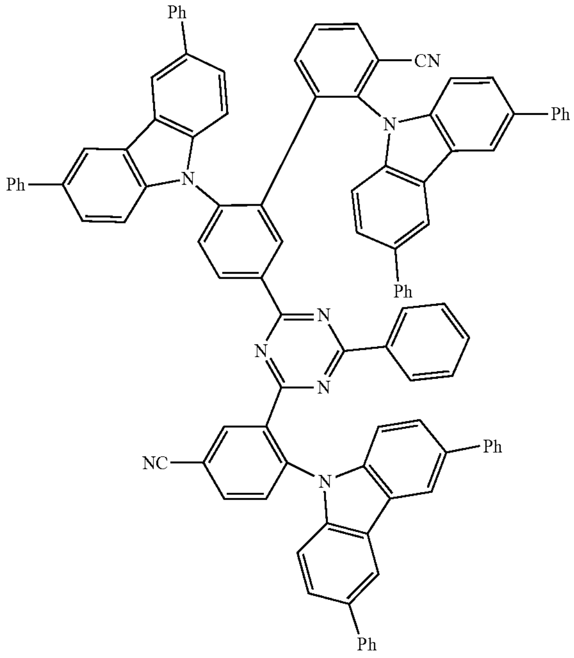
-continued
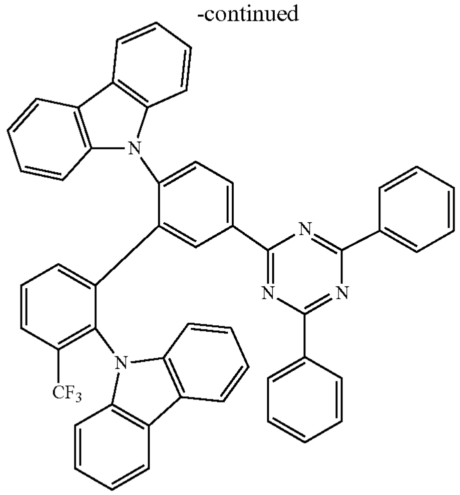
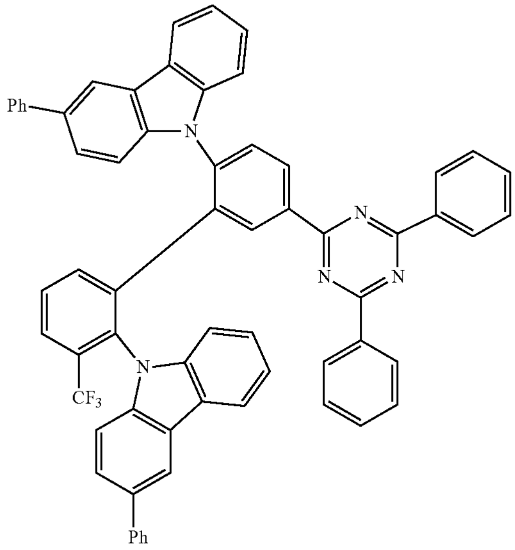
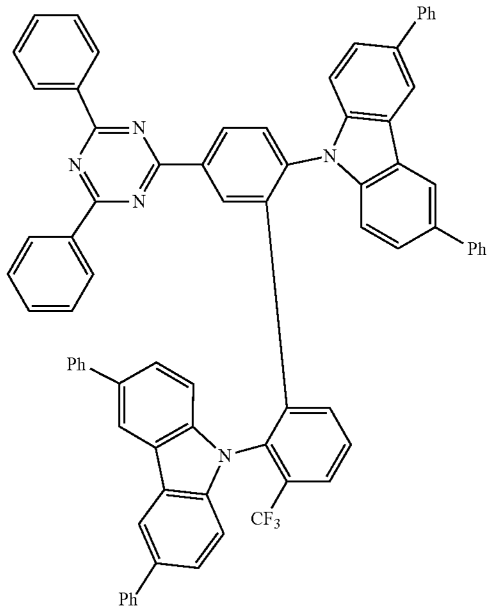

-continued

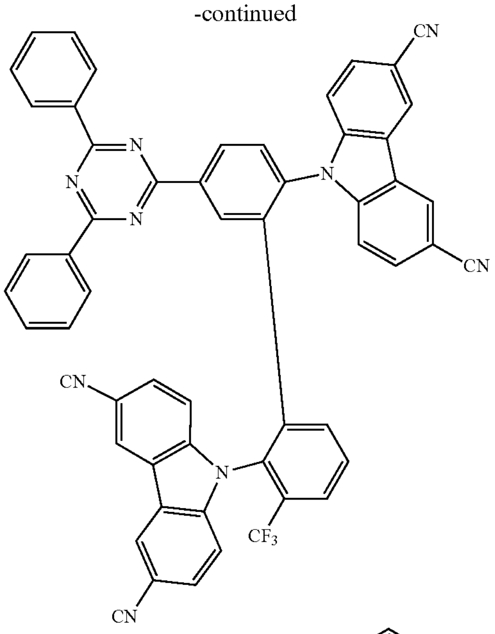

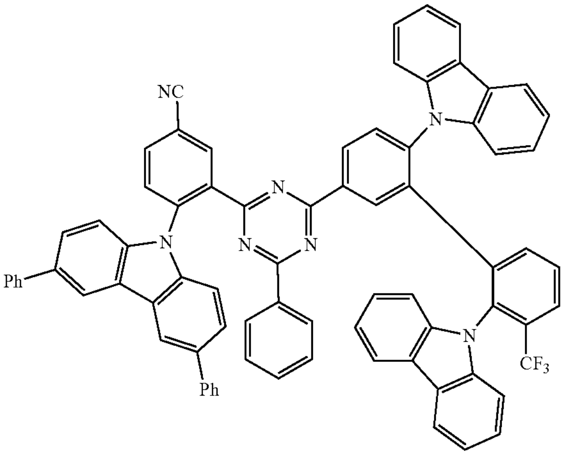

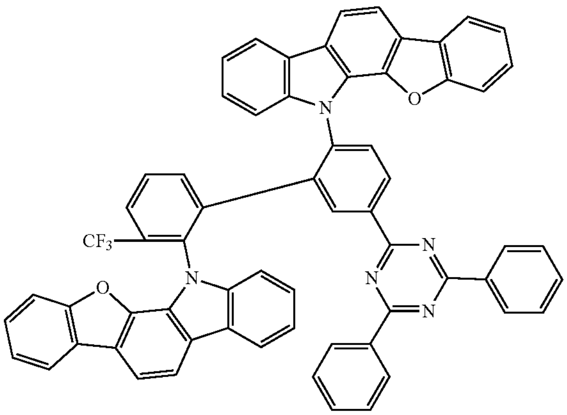

FIGURES

The drawing: Emission spectrum of example 1 (10% by weight) in PMMA.

The invention claimed is:

1. An organic molecule, comprising:

a first chemical moiety comprising or consisting of a structure of Formula I,

Formula I

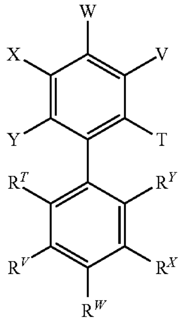

and two second chemical moieties, each independently from one another comprising or consisting of a structure of Formula II, Formula II

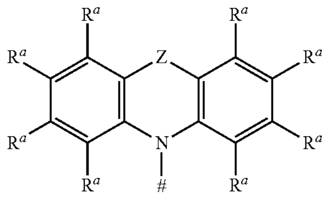

wherein each of the two second chemical moieties is linked to the first chemical moiety via a single bond;

wherein

T is selected from the group consisting of $R^A$ and $R^1$

V is selected from the group consisting of $R^A$ and $R^1$

W is a binding site of the single bond linking the first chemical moiety to one of the two second chemical moieties or is selected from the group consisting of $R^A$ and $R^2$ X is the binding site of the single bond linking the first chemical moiety to one of the two second chemical moieties or is $R^2$;

Y is the binding site of the single bond linking the first chemical moiety to one of the two second chemical moieties or is $R^2$;

$R^A$ is 1,3,5-triazinyl substituted with two substituents $R^{TZ}$:

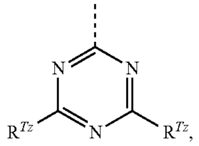

which is bonded to the structure of Formula I via a position marked by the dotted line;

$R^T$ is the binding site of the single bond linking the first chemical moiety to one of the two second chemical moieties or is selected from the group consisting of CN and $CF_3$;

$R^V$ is the binding site of the single bond linking the first chemical moiety to one of the two second chemical moieties or is selected from the group consisting of CN and $CF_3$;

$R^W$ is $R^I$;

$R^X$ is $R^I$;

$R^Y$ is $R_I$;

# represents the binding site of the single bond linking the second chemical moieties to the first chemical moiety;

Z is at each occurrence independently from one another selected from the group consisting of a direct bond, $CR^3R^4$, $C{=}CR^3R^4$, $C{=}O$, $C{=}NR^3$, $NR^3$, O, $SiR^3R^4$, S, S(O) and $S(O)_2$;

$R^1$ is at each occurrence independently from one another selected from the group consisting of:

hydrogen; deuterium;

$C_1$-$C_5$-alkyl, wherein one or more hydrogen atoms are optionally substituted by deuterium;

$C_2$-$C_8$-alkenyl, wherein one or more hydrogen atoms are optionally substituted by deuterium;

$C_2$-$C_8$-alkynyl, wherein one or more hydrogen atoms are optionally substituted by deuterium; and $C_6$-$C_{18}$-aryl, which is optionally substituted with one or more substituents $R^6$;

$R^2$ is at each occurrence independently from one another selected from the group consisting of:

hydrogen; deuterium;

$C_1$-$C_5$-alkyl, wherein one or more hydrogen atoms are optionally substituted by deuterium;

$C_2$-$C_8$-alkenyl, wherein one or more hydrogen atoms are optionally substituted by deuterium;

$C_2$-$C_8$-alkynyl, wherein one or more hydrogen atoms are optionally substituted by deuterium; and $C_6$-$C_{18}$-aryl, which is optionally substituted with one or more substituents $R^6$;

$R^I$ is at each occurrence independently from one another selected from the group consisting of:

hydrogen; deuterium;

$C_1$-$C_5$-alkyl, wherein one or more hydrogen atoms are optionally substituted by deuterium;

$C_2$-$C_8$-alkenyl, wherein one or more hydrogen atoms are optionally substituted by deuterium;

$C_2$-$C_8$-alkynyl, wherein one or more hydrogen atoms are optionally substituted by deuterium; and $C_6$-$C_{18}$-aryl comprising only carbon atoms as ring forming atoms, which is optionally substituted with one or more substituents $R^6$;

$R^{TZ}$ is at each occurrence independently from one another selected from the group consisting of:

hydrogen;

deuterium;

$C_1$-$C_5$-alkyl, wherein one or more hydrogen atoms are optionally substituted by deuterium;

$C_6$-$C_{18}$-aryl, which is optionally substituted with one or more substituents $R^6$; and $C_3$-$C_{17}$-heteroaryl, which is optionally substituted with one or more substituents $R^6$;

$R^a$, $R^3$, and $R^4$ are at each occurrence independently from one another selected from the group consisting of:

hydrogen, deuterium, $N(R^5)_2$, $OR^5$, $Si(R^5)_3$, $B(OR^5)_2$, $OSO_2R^5$, $CF_3$, CN, F, Br, I;

$C_1$-$C_{40}$-alkyl, which is optionally substituted with one or more substituents $R^5$ and wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;

$C_1$-$C_{40}$-alkoxy, which is optionally substituted with one or more substituents $R^5$ and wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;

$C_1$-$C_{40}$-thioalkoxy, which is optionally substituted with one or more substituents $R^5$ and wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;

$C_2$-$C_{40}$-alkenyl, which is optionally substituted with one or more substituents $R^5$ and wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;

$C_2$-$C_{40}$-alkynyl, which is optionally substituted with one or more substituents $R^5$ and wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;

$C_6$-$C_{60}$-aryl, which is optionally substituted with one or more substituents $R^5$; and $C_3$-$C_{57}$-heteroaryl, which is optionally substituted with one or more substituents $R^5$;

$R^5$ is at each occurrence independently from one another selected from the group consisting of;

hydrogen, deuterium, $N(R^6)_2$, $OR^6$, $Si(R^6)_3$, $B(OR^6)_2$, $OSO_2R^6$, $CF_3$, CN, F, Br, I;

$C_1$-$C_{40}$-alkyl, which is optionally substituted with one or more substituents $R^6$ and wherein one or more non-adjacent $CH_2$-groups are optionally substituted by $R^6C{=}CR^6$, $C{\equiv}C$, $Si(R^6)_2$, $Ge(R^6)_2$, $Sn(R^6)_2$, $C{=}O$, $C{=}S$, $C{=}Se$, $C{=}NR^6$, $P({=}O)(R^6)$, SO, $SO_2$, $NR^6$, O, S or $CONR^6$;

$C_1$-$C_{40}$-alkoxy, which is optionally substituted with one or more substituents $R^6$ and wherein one or more non-adjacent $CH_2$-groups are optionally substituted by $R^6C{=}CR^6$, $C{\equiv}C$, $Si(R^6)_2$, $Ge(R^6)_2$, $Sn(R^6)_2$, $C{=}O$, $C{=}S$, $C{=}Se$, $C{=}NR^6$, $P({=}O)(R^6)$, SO, $SO_2$, $NR^6$, O, S or $CONR^6$;

$C_1$-$C_{40}$-thioalkoxy, which is optionally substituted with one or more substituents $R^6$ and wherein one or more non-adjacent $CH_2$-groups are optionally substituted by $R^6C{=}CR^6$, $C{\equiv}C$, $Si(R^6)_2$, $Ge(R^6)_2$, $Sn(R^6)_2$, C═O, C═S, C═Se, $C═NR^6$, $P(═O)(R^6)$, SO, $SO_2$, $NR^6$, O, S or $CONR^6$;

$C_2$-$C_{40}$-alkenyl, which is optionally substituted with one or more substituents $R^6$ and wherein one or more non-adjacent $CH_2$-groups are optionally substituted by $R^6C═CR^6$, C≡C, $Si(R^6)_2$, $Ge(R^6)_2$, $Sn(R^6)_2$, C═O, C═S, C═Se, $C═NR^6$, $P(═O)(R^6)$, SO, $SO_2$, $NR^6$, O, S or $CONR^6$;

$C_2$-$C_{40}$-alkynyl, which is optionally substituted with one or more substituents $R^6$ and wherein one or more non-adjacent $CH_2$-groups are optionally substituted by $R^6C═CR^6$, C≡C, $Si(R^6)_2$, $Ge(R^6)_2$, $Sn(R^6)_2$, C═O, C═S, C═Se, $C═NR^6$, $P(═O)(R^6)$, SO, $SO_2$, $NR^6$, O, S or $CONR^6$;

$C_6$-$C_{60}$-aryl, which is optionally substituted with one or more substituents $R^6$; and $C_3$-$C_{57}$-heteroaryl, which is optionally substituted with one or more substituents $R^6$;

$R^6$ is at each occurrence independently from one another selected from the group consisting of:

hydrogen; deuterium; OPh; $CF_3$; CN; F;

$C_1$-$C_5$-alkyl, wherein one or more hydrogen atoms are optionally, independently from each other substituted by deuterium, CN, $CF_3$, or F;

$C_1$-$C_5$-alkoxy, wherein one or more hydrogen atoms are optionally, independently from each other substituted by deuterium, CN, $CF_3$, or F;

$C_1$-$C_5$-thioalkoxy, wherein one or more hydrogen atoms are optionally, independently from each other substituted by deuterium, CN, $CF_3$, or F;

$C_2$-$C_5$-alkenyl, wherein one or more hydrogen atoms are optionally, independently from each other substituted by deuterium, CN, $CF_3$, or F;

$C_2$-$C_5$-alkynyl, wherein one or more hydrogen atoms are optionally, independently from each other substituted by deuterium, CN, $CF_3$, or F;

$C_6$-$C_{18}$-aryl, which is optionally substituted with one or more $C_1$-$C_5$-alkyl or $C_6$-$C_{18}$-aryl substituents;

$C_3$-$C_{17}$-heteroaryl, which is optionally substituted with one or more $C_1$-$C_5$-alkyl or $C_6$-$C_{18}$-aryl substituents;

$N(C_6$-$C_{18}$-aryl$)_2$;

$N(C_3$-$C_{17}$-heteroaryl$)_2$; and $N(C_3$-$C_{17}$-heteroaryl$)(C_6$-$C_{18}$-aryl);

wherein optionally, $R^a$, $R^3$, $R^4$ or $R^5$ independently from each other forms a mono- or polycyclic, aliphatic, aromatic and/or benzo-fused ring system with one or more other substituents $R^a$, $R^3$, $R^4$ and/or $R^5$;

wherein exactly one substituent selected from the group consisting of T, V and W is $R^A$ exactly one substituent selected from the group consisting of W, X, and Y represents the binding site of the single bond linking the first chemical moiety and one of the two second chemical moieties, exactly one substituent selected from $R^T$ and $R^V$ is the binding site of the single bond linking the first chemical moiety to one of the two second chemical moieties, and the remaining substituent selected from $R^T$ and $R^V$ is selected from the group consisting of CN and $CF_3$.

2. The organic molecule according to claim 1, wherein the first chemical moiety comprises a structure of Formula Ia:

Formula Ia

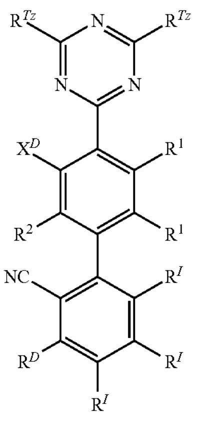

wherein $X^D$ is the binding site of the single bond linking the first chemical moiety to one of the two second chemical moieties; and $R^D$ is the binding site of the single bond linking the first chemical moiety to one of the two second chemical moieties.

3. An organic molecule, comprising:

a first chemical moiety comprising or consisting of a structure of Formula I,

Formula I

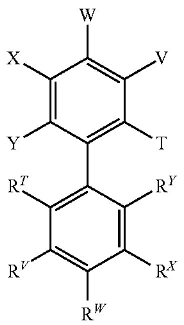

and two second chemical moieties, each independently from one another comprising or consisting of a structure of Formula II, Formula II

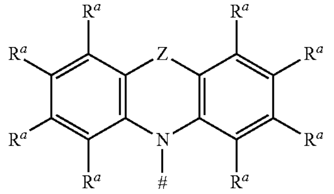

wherein each of the two second chemical moieties is linked to the first chemical moiety via a single bond;

wherein

T is selected from the group consisting of $R^A$ and $R^1$:

V is selected from the group consisting of $R^A$ and $R^1$:

W is a binding site of the single bond linking the first chemical moiety to one of the two second chemical moieties or is selected from the group consisting of $R^A$ and $R^2$;

X is the binding site of the single bond linking the first chemical moiety to one of the two second chemical moieties or is $R^2$;

Y is the binding site of the single bond linking the first chemical moiety to one of the two second chemical moieties or is $R^2$;

$R^A$ is 1,3,5-triazinyl substituted with two substituents $R^{Tz}$:

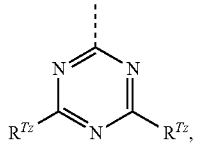

which is bonded to the structure of Formula I via a position marked by the dotted line;

$R^T$ is the binding site of the single bond linking the first chemical moiety to one of the two second chemical moieties or is selected from the group consisting of CN and $CF_3$;

$R^V$ is the binding site of the single bond linking the first chemical moiety to one of the two second chemical moieties or is selected from the group consisting of CN and $CF_3$;

$R^W$ is $R^I$;

$R^X$ is $R^I$;

$R^Y$ is $R^I$;

# represents the binding site of the single bond linking the second chemical moieties to the first chemical moiety:

Z is at each occurrence independently from one another selected from the group consisting of a direct bond, $CR^3R^4$, $C{=}CR^3R^4$, C=O, $C{=}NR^3$, $NR^3$, O, $SiR^3R^4$, S, S(O) and $S(O)_2$;

$R^{Tz}$ is at each occurrence independently from one another selected from the group consisting of:

hydrogen;

deuterium;

$C_1$-$C_5$-alkyl, wherein one or more hydrogen atoms are optionally substituted by deuterium;

$C_6$-$C_{18}$-aryl, which is optionally substituted with one or more substituents $R^6$; and $C_3$-$C_{17}$-heteroaryl, which is optionally substituted with one or more substituents $R^6$;

$R^a$, $R^3$, and $R^4$ are at each occurrence independently from one another selected from the group consisting of:

hydrogen, deuterium, $N(R^5)_2$, $OR^5$, $Si(R^5)_3$, $B(OR^5)_2$, $OSO_2R^5$, $CF_3$, CN, F, Br, I;

$C_1$-$C_{40}$-alkyl, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_1$-$C_{40}$-alkoxy, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_1$-$C_{40}$-thioalkoxy, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_2$-$C_{40}$-alkenyl, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_2$-$C_{40}$-alkynyl, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_6$-$C_{40}$-aryl, which is optionally substituted with one or more substituents $R^5$; and $C_3$-$C_{57}$-heteroaryl, which is optionally substituted with one or more substituents $R^5$;

$R^5$ is at each occurrence independently from one another selected from the group consisting of:

hydrogen, deuterium, $N(R^6)_2$, $OR^6$, $Si(R^6)_3$, $B(OR^6)_2$, $OSO_2R^6$, $CF_3$, CN, F, Br, I;

$C_1$-$C_{40}$-alkyl, which is optionally substituted with one or more substituents $R^6$ and wherein one or more non-adjacent $CH_2$-groups are optionally substituted by $R^6C{=}CR^6$, C≡C, $Si(R^6)_2$, $Ge(R^6)_2$, $Sn(R^6)_2$, C=O, C=S, C=Se, $C{=}NR^6$, $P({=}O)(R^6)$, SO, $SO_2$, $NR^6$, O, S or $CONR^6$;

$C_1$-$C_{40}$-alkoxy, which is optionally substituted with one or more substituents $R^6$ and wherein one or more non-adjacent $CH_2$-groups are optionally substituted by $R^6C{=}CR^6$, C≡C, $Si(R^6)_2$, $Ge(R^6)_2$, $Sn(R^6)_2$, C=O, C=S, C=Se, $C{=}NR^6$, $P({=}O)(R^6)$, SO, $SO_2$, $NR^6$, O, S or $CONR^6$;

$C_1$-$C_{40}$-thioalkoxy, which is optionally substituted with one or more substituents $R^6$ and wherein one or more non-adjacent $CH_2$-groups are optionally substituted by $R^6C{=}CR^6$, C≡C, $Si(R^6)_2$, $Ge(R^6)_2$, $Sn(R^6)_2$, C=O, C=S, C=Se, $C{=}NR^6$, $P({=}O)(R^6)$, SO, $SO_2$, $NR^6$, O, S or $CONR^6$;

$C_2$-$C_{40}$-alkenyl, which is optionally substituted with one or more substituents $R^6$ and wherein one or more non-adjacent $CH_2$-groups are optionally substituted by $R^6C{=}CR^6$, C≡C, $Si(R^6)_2$, $Ge(R^6)_2$, $Sn(R^6)_2$, C=O, C=S, C=Se, $C{=}NR^6$, $P({=}O)(R^6)$, SO, $SO_2$, $NR^6$, O, S or $CONR^6$;

$C_2$-$C_{40}$-alkynyl, which is optionally substituted with one or more substituents $R^6$ and wherein one or more non-adjacent $CH_2$-groups are optionally substituted by $R^6C{=}CR^6$, C≡C, $Si(R^6)_2$, $Ge(R^6)_2$, $Sn(R^6)_2$, C=O, C=S, C=Se, $C{=}NR^6$, $P({=}O)(R^6)$, SO, $SO_2$, $NR^6$, O, S or $CONR^6$;

$C_6$-$C_{60}$-aryl, which is optionally substituted with one or more substituents $R^6$; and $C_3$-$C_{57}$-heteroaryl, which is optionally substituted with one or more substituents $R^6$;

$R^6$ is at each occurrence independently from one another selected from the group consisting of:

hydrogen; deuterium; OPh; $CF_3$; CN; F;

$C_1$-$C_5$-alkyl, wherein one or more hydrogen atoms are optionally, independently from each other substituted by deuterium, CN, $CF_3$, or F;

$C_1$-$C_5$-alkoxy, wherein one or more hydrogen atoms are optionally, independently from each other substituted by deuterium, CN, $CF_3$, or F;

$C_1$-$C_5$-thioalkoxy, wherein one or more hydrogen atoms are optionally, independently from each other substituted by deuterium, CN, $CF_3$, or F;

$C_2$-$C_5$-alkenyl, wherein one or more hydrogen atoms are optionally, independently from each other substituted by deuterium, CN, $CF_3$, or F;

$C_2$-$C_5$-alkynyl, wherein one or more hydrogen atoms are optionally, independently from each other substituted by deuterium, CN, $CF_3$, or F;

$C_6$-$C_{18}$-aryl, which is optionally substituted with one or more $C_1$-$C_5$-alkyl or $C_6$-$C_{18}$-aryl substituents;

$C_3$-$C_{17}$-heteroaryl, which is optionally substituted with one or more $C_1$-$C_5$-alkyl or $C_6$-$C_{18}$-aryl substituents;

$N(C_6$-$C_{18}$-aryl$)_2$:

$N(C_3$-$C_{17}$-heteroaryl$)_2$; and $N(C_3$-$C_{17}$-heteroaryl$)(C_6$-$C_{18}$-aryl$)$;

wherein optionally, $R^a$, $R^3$, $R^4$ or $R^5$ independently from each other forms a mono- or polycyclic, aliphatic, aromatic and/or benzo-fused ring system with one or more other substituents $R^a$, $R^3$, $R^4$ and/or $R^5$;

wherein exactly one substituent selected from the group consisting of T, V and W is $R^A$, exactly one substituent selected from the group consisting of W, X, and Y represents the binding site of the single bond linking the first chemical moiety and one of the two second chemical moieties, exactly one substituent selected from $R^T$ and $R^V$ is the binding site of the single bond linking the first chemical moiety to one of the two second chemical moieties, and exactly one substituent selected from $R^T$ and $R^V$ is selected from the group consisting of CN and $CF_3$, and at each occurrence, $R^1$, $R^2$ and $R^I$ are independently from each other selected from the group consisting of H, methyl, mesityl, tolyl, and phenyl.

4. The organic molecule according to claim 1, wherein $R^{Tz}$ is independently from each other selected from the group consisting of H, methyl and phenyl; and wherein in case that at least one substituent $R^{Tz}$ is a phenyl group, it is substituted with one or more substituents $R^6$.

5. The organic molecule according to claim 1, wherein the two second chemical moieties independently comprise a structure of Formula IIa:

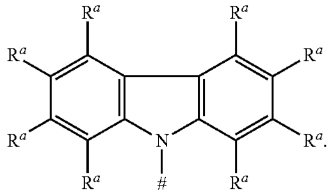

Formula IIa

6. The organic molecule according to claim 1, wherein the two second chemical moieties independently comprise a structure of Formula IIb:

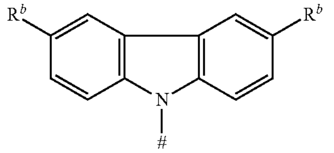

Formula IIb wherein $R^b$ is at each occurrence independently from one another selected from the group consisting of:

deuterium; $N(R^5)_2$; $OR^5$; $Si(R^5)_3$; $B(OR^5)_2$; $OSO_2R^5$; $CF_3$; CN, F, Br, I, $C_1$-$C_{40}$-alkyl, which is optionally substituted with one or more substituents $R^5$ and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_1$-$C_{40}$-alkoxy, which is optionally substituted with one or more substituents $R^5$, and wherein one or more non-adjacent $CH_2$-groups are optionally substituted by $R^5C{=}CR^5$, C≡C, $Si(R^5)_2$, $Ge(R^5)_2$, $Sn(R^5)_2$, C=O, C=S, C=Se, $C{=}NR^5$, $P({=}O)(R^5)$, SO, $SO_2$, $NR^5$, O, S or $CONR^5$;

$C_1$-$C_{40}$-thioalkoxy, which is optionally substituted with one or more substituents $R^5$, and wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;

$C_2$-$C_{40}$-alkenyl, which is optionally substituted with one or more substituents $R^5$, and wherein one or more non-adjacent $CH_2$-groups are optionally substituted by $R^5C{=}CR^5$, $C{=}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;

$C_2$-$C_{40}$-alkynyl, which is optionally substituted with one or more substituents $R^5$, and wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;

$C_6$-$C_{60}$-aryl, which is optionally substituted with one or more substituents $R^5$; and $C_3$-$C_{57}$-heteroaryl, which is optionally substituted with one or more substituents $R^5$.

7. The organic molecule according to claim 1, wherein the two second chemical moieties independently comprise a structure of Formula IIc:

Formula IIc

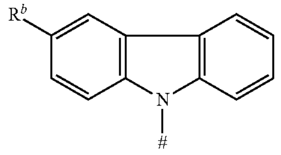

wherein $R^b$ is at each occurrence independently from one another selected from the group consisting of:

deuterium; $N(R^5)_2$; $OR^5$; $Si(R^5)_3$; $B(OR^5)_2$; $OSO_2R^5$; $CF_3$; CN; F; Br; I;

$C_1$-$C_{40}$-alkyl, which is optionally substituted with one or more substituents $R^5$, and wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;

$C_1$-$C_{40}$-alkoxy, which is optionally substituted with one or more substituents $R^5$ and wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;

$C_1$-$C_{40}$-thioalkoxy, which is optionally substituted with one or more substituents $R^5$ and wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;

$C_2$-$C_{40}$-alkenyl, which is optionally substituted with one or more substituents $R^5$ and wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;

$C_2$-$C_{40}$-alkynyl, which is optionally substituted with one or more substituents $R^5$ and wherein one or more non-adjacent $CH_2$-groups are optionally substituted by $R^5C{=}CR^5$, $C{\equiv}C$, $Si(R^5)_2$, $Ge(R^5)_2$, $Sn(R^5)_2$, $C{=}O$, $C{=}S$, $C{=}Se$, $C{=}NR^5$, $P({=}O)(R^5)$, SO, $SO_2$, $NR^5$, O, S or $CONR^5$;

$C_6$-$C_{60}$-aryl, which is optionally substituted with one or more substituents $R^5$; and $C_3$-$C_{57}$-heteroaryl, which is optionally substituted with one or more substituents $R^5$.

8. The organic molecule according to claim 6, wherein $R^b$ is at each occurrence independently from one another selected from the group consisting of:

Me; $^i$Pr; $^t$Bu; CN; $CF_3$;

Ph, which is optionally substituted with one or more substituents independently from each other selected from the group consisting of Me, $^i$Pr, $^t$Bu, CN, $CF_3$ and Ph;

pyridinyl, which is optionally substituted with one or more substituents independently from each other selected from the group consisting of Me, $^i$Pr, $^t$Bu, CN, $CF_3$ and Ph;

pyrimidinyl, which is optionally substituted with one or more substituents independently from each other selected from the group consisting of Me, $^i$Pr, $^t$Bu, CN, $CF_3$ and Ph;

carbazolyl, which is optionally substituted with one or more substituents independently from each other selected from the group consisting of Me, $^i$Pr, $^t$Bu, CN, $CF_3$ and Ph;

triazinyl, which is optionally substituted with one or more substituents independently from each other selected from the group consisting of Me, $^i$Pr, $^t$Bu, CN, $CF_3$, and Ph;

and $N(Ph)_2$.

9. A method for preparing the organic molecule according to claim 1, the method comprising providing a reactant selected from the group consisting of 2-bromo-6-fluorobenzonitrile, 3-bromo-2-fluorobenzonitrile, 1-bromo-3-fluoro-2-(trifluoromethyl)benzene, and 1-bromo-2-fluoro-3-(trifluoromethyl)benzene, each substituted with exactly three substituents $R^I$.

10. An optoelectronic device comprising the organic molecule according to claim 1, as a luminescent emitter and/or as a host material and/or as an electron transport material and/or as a hole transport material and/or as a hole injection material and/or as a hole blocking material.

11. The optoelectronic device according to claim 10, wherein the optoelectronic device is at least one selected from the group consisting of:

organic light-emitting diodes (OLEDs),
light-emitting electrochemical cells,
OLED-sensors,
organic diodes,
organic solar cells,
organic transistors,
organic field-effect transistors,
organic lasers, and
down-conversion elements.

12. A composition, comprising:

(a) at least one organic molecule according to claim 1, as an emitter and/or a host, and (b) one or more emitter and/or host materials, which differ from the at least one organic molecule, and (c) optionally, one or more dyes and/or one or more solvents.

13. An optoelectronic device, comprising a layer formed from the composition according to claim 12, wherein the device is at least one selected from the group consisting of organic light-emitting diodes (OLEDs), light-emitting electrochemical cells, OLED-sensors in non-hermetically shielded gas and vapor sensors, organic diodes, organic solar cells, organic transistors, organic field-effect transistors, organic lasers, and down-conversion elements.

14. The optoelectronic device according to claim 10, comprising:

a substrate, an anode, and a cathode, wherein the anode or the cathode is on the substrate, and a light-emitting layer between the anode and the cathode and comprising the organic molecule.

15. A method for producing an optoelectronic device, the method comprising depositing the organic molecule according to claim 1 by a vacuum evaporation method or from a solution.

16. A method for producing an optoelectronic device, the method comprising depositing the composition according to claim 12 by a vacuum evaporation method or from a solution.

17. The optoelectronic device according to claim 13, comprising:

a substrate, an anode, and a cathode, wherein the anode or the cathode is on the substrate, and a light-emitting layer between the anode and the cathode and comprising the layer formed from the composition.

* * * * *